US008673932B2

(12) United States Patent
Kshirsagar et al.

(10) Patent No.: US 8,673,932 B2
(45) Date of Patent: *Mar. 18, 2014

(54) OXIME SUBSTITUTED IMIDAZO-CONTAINING COMPOUNDS

(75) Inventors: Tushar A. Kshirsagar, Woodbury, MN (US); David T. Amos, St. Paul, MN (US); Joseph F. Dellaria, Jr., Woodbury, MN (US); Philip D. Heppner, Forest Lake, MN (US); Scott E. Langer, Woodbury, MN (US); Bernhard M. Zimmermann, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 2003 days.

This patent is subject to a terminal disclaimer.

(21) Appl. No.: 10/595,065

(22) PCT Filed: Aug. 12, 2004

(86) PCT No.: PCT/US2004/026065
§ 371 (c)(1),
(2), (4) Date: Jan. 26, 2006

(87) PCT Pub. No.: WO2005/018551
PCT Pub. Date: Mar. 3, 2005

(65) Prior Publication Data
US 2007/0066639 A1 Mar. 22, 2007

Related U.S. Application Data

(60) Provisional application No. 60/494,608, filed on Aug. 12, 2003, provisional application No. 60/494,605, filed on Aug. 12, 2003.

(51) Int. Cl.
*C07D 487/04* (2006.01)
*C07D 487/06* (2006.01)
*A61K 31/437* (2006.01)

(52) U.S. Cl.
USPC ............................................ 514/290; 546/80

(58) Field of Classification Search
USPC ............................................ 546/80; 514/290
See application file for complete search history.

(56) References Cited

U.S. PATENT DOCUMENTS

| | | | |
|---|---|---|---|
| 3,314,941 A | 4/1967 | Littell et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster |
| 5,268,376 A | 12/1993 | Gerster |
| 5,274,113 A | 12/1993 | Kang et al. |
| 5,342,784 A | 8/1994 | Yamada et al. |
| 5,346,905 A | 9/1994 | Gerster |
| 5,352,680 A | 10/1994 | Portoghese et al. |

(Continued)

FOREIGN PATENT DOCUMENTS

AU 2004220534 A1 9/2004
AU 2004229478 A1 10/2004

(Continued)

OTHER PUBLICATIONS

Dorwald F. A. Side Reactions in Organic Synthesis, 2005, Wiley: VCH, Weinheim p. IX of Preface.*
Wozniak, et al, "The Amination of 3-nitro-1, 5-naphthyridines By Liquid Ammonia/Potassium Permanganate[1,2]. A New and Convenient Amination Method.", *Journal of the Royal Netherlands Chemical Society*, 102, pp. 511-513, Dec. 12, 1983.
Brennan, et al, "Automated Bioassay of Interferons in Micro-test Plates", *Biotechniques*, Jun./Jul., 78, 1983.
Testerman, et al., "Cytokine Induction by the Immunomodulators Imiquimod and S-27609", *Journal of Leukocyte Biology*, vol. 58, pp. 365-372, Sep. 1995.

(Continued)

*Primary Examiner* — Rita Desai

(57) ABSTRACT

Imidazo-containing compounds (e.g., imidazoquinolines, imidazonaphthyridines, and imidazopyridines) with an oxime substituent at the 1-position, pharmaceutical compositions containing the compounds, intermediates, and methods of use of these compounds as immunomodulators, for inducing cytokine biosynthesis in animals and in the treatment of diseases including viral and neoplastic diseases are disclosed.

19 Claims, No Drawings

(56) References Cited

U.S. PATENT DOCUMENTS

| | | |
|---|---|---|
| 5,352,784 A | 10/1994 | Nikolaides et al. |
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Llindstrom et al. |
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andre et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster et al. |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |

(56) References Cited

U.S. PATENT DOCUMENTS

| | | |
|---|---|---|
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2007/0060754 A1 | 3/2007 | Lindstrom et al. |
| 2007/0072893 A1 | 3/2007 | Krepski et al. |
| 2007/0099901 A1 | 5/2007 | Krepski et al. |
| 2007/0155767 A1 | 7/2007 | Radmer et al. |
| 2007/0167476 A1 | 7/2007 | Kshirsagar et al. |
| 2007/0208052 A1 | 9/2007 | Prince et al. |
| 2007/0213356 A1 | 9/2007 | Merrill et al. |
| 2007/0219196 A1 | 9/2007 | Krepski et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0042925 A1* | 2/2009 | Kshirsagar et al. ........... 514/293 |
| 2009/0062272 A1 | 3/2009 | Bonk et al. |
| 2009/0062328 A1* | 3/2009 | Kshirsagar et al. ........... 514/293 |

(56) References Cited

U.S. PATENT DOCUMENTS

| | | |
|---|---|---|
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0240055 A1 | 9/2009 | Krepski et al. |
| 2009/0253695 A1 | 10/2009 | Kshirsagar et al. |
| 2009/0270443 A1 | 10/2009 | Stoermer et al. |
| 2009/0318435 A1 | 12/2009 | Hays et al. |
| 2010/0113565 A1 | 5/2010 | Gorden et al. |

FOREIGN PATENT DOCUMENTS

| | | |
|---|---|---|
| AU | 2004264336 A1 | 2/2005 |
| AU | 2004268625 A1 | 3/2005 |
| AU | 2002239547 | 11/2006 |
| CA | 2 044 087 A1 | 12/1991 |
| CA | 2 158 996 A1 | 10/1994 |
| CN | 1 354 663 A | 6/2002 |
| EP | 0145340 A2 | 6/1985 |
| EP | 0223420 A1 | 5/1987 |
| EP | 0310950 A1 | 4/1989 |
| EP | 0385630 A2 | 9/1990 |
| EP | 0389302 A1 | 9/1990 |
| EP | 0 394 026 | 10/1990 |
| EP | 0425306 A2 | 5/1991 |
| EP | 0510260 A2 | 10/1992 |
| EP | 0645389 A1 | 3/1995 |
| EP | 0778277 A1 | 6/1997 |
| EP | 0894797 A1 | 2/1999 |
| EP | 0940629 A2 | 9/1999 |
| EP | 1082960 A2 | 3/2001 |
| EP | 1097709 A2 | 5/2001 |
| EP | 1 104 764 | 6/2001 |
| EP | 1145340 A2 | 10/2001 |
| EP | 1256582 A1 | 11/2002 |
| EP | 1341791 A2 | 9/2003 |
| EP | 1495758 A2 | 1/2005 |
| HU | 34479 A2 | 3/1985 |
| HU | 190109 A2 | 3/1985 |
| HU | 210051 A2 | 6/1991 |
| HU | 218950 A2 | 9/1995 |
| IL | 73534 A | 12/1990 |
| JP | 53-050197 A | 5/1978 |
| JP | 63-010787 A | 1/1988 |
| JP | 4-066571 A | 3/1992 |
| JP | 4-327587 A | 11/1992 |
| JP | 5-286973 A | 11/1993 |
| JP | 9-208584 | 8/1997 |
| JP | 11-080156 A | 3/1999 |
| JP | 11-222432 | 8/1999 |
| JP | 2000-247884 | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO-91/06682 A1 | 5/1991 |
| WO | WO-92/01305 A1 | 1/1992 |
| WO | WO-92/06093 A1 | 4/1992 |
| WO | WO-92/15581 A1 | 9/1992 |
| WO | WO-92/15582 A1 | 9/1992 |
| WO | WO-93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO-95/02598 A1 | 1/1995 |
| WO | WO-9611199 A1 | 4/1996 |
| WO | WO-96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304 A1 | 12/2000 |
| WO | WO-00/76505 A1 | 12/2000 |
| WO | WO-00/76518 A1 | 12/2000 |
| WO | WO-00/76519 A1 | 12/2000 |
| WO | WO-01/34709 A1 | 5/2001 |
| WO | WO-01/51486 A2 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO 02/36592 | 5/2002 |
| WO | WO-02/46188 A2 | 6/2002 |
| WO | WO-02/46189 A2 | 6/2002 |
| WO | WO-02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/09852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A1 | 6/2003 |
| WO | WO-03/050118 A1 | 6/2003 |
| WO | WO 03/050119 A2 | 6/2003 |
| WO | WO-03/050121 A1 | 6/2003 |
| WO | WO-03/077944 A1 | 9/2003 |
| WO | WO-03/080114 A2 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A2 | 11/2003 |
| WO | WO-03/101949 A2 | 12/2003 |
| WO | WO-03/103584 A2 | 12/2003 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004-091500 A2 | 10/2004 |
| WO | WO-2004-096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO-2005/023190 A2 | 3/2005 |
| WO | WO-2005/025614 A2 | 3/2005 |

(56) References Cited

FOREIGN PATENT DOCUMENTS

| WO | WO-2005/029037 A2 | 3/2005 |
| WO | WO 2005/032484 | 4/2005 |
| WO | WO-2005/041891 A2 | 5/2005 |
| WO | WO 2005/048933 | 6/2005 |
| WO | WO 2005/048945 | 6/2005 |
| WO | WO-2005/049076 A1 | 6/2005 |
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO-2005/065678 A1 | 7/2005 |
| WO | WO 2005/066169 | 7/2005 |
| WO | WO 2005/066170 | 7/2005 |
| WO | WO 2005/066172 | 7/2005 |
| WO | WO-2005/067500 A2 | 7/2005 |
| WO | WO 2005/076783 | 8/2005 |
| WO | WO 2005/079195 | 9/2005 |
| WO | WO 2005/094531 | 10/2005 |
| WO | WO-2005/110013 A2 | 11/2005 |
| WO | WO 2005/123079 | 12/2005 |
| WO | WO 2005/123080 | 12/2005 |
| WO | WO-2006/004737 A2 | 1/2006 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO-2006/063072 A2 | 6/2006 |
| WO | WO-2006/063152 A2 | 6/2006 |
| WO | WO-2006/065280 A2 | 6/2006 |
| WO | WO-2006/073940 A2 | 7/2006 |
| WO | WO-2006/074003 A2 | 7/2006 |
| WO | WO-2006/074045 A2 | 7/2006 |
| WO | WO-2006/083440 A2 | 8/2006 |
| WO | WO-2006/084251 A2 | 8/2006 |
| WO | WO-2006/086449 A2 | 8/2006 |
| WO | WO-2006/086633 A2 | 8/2006 |
| WO | WO-2006/086634 A2 | 8/2006 |
| WO | WO-2006/091394 A2 | 8/2006 |
| WO | WO-2006/091567 A2 | 8/2006 |
| WO | WO-2006/091568 A2 | 8/2006 |
| WO | WO-2006/091647 A2 | 8/2006 |
| WO | WO-2006/093514 A2 | 9/2006 |
| WO | WO-2006/098852 A2 | 9/2006 |
| WO | WO-2006/107753 A2 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Bachman, et al, "Synthesis of Substituted Quinolylamines. Derivatives of 4-Amino-7-Chloroquinoline", *J. Org. Chem*, 15, pp. 1278-1284 (1950).

Jain, et al, "Chemical and Pharmacological Investigations of Some ω-Substituted Alkylamino-3-aminopyridines", *J. Med. Chem.*, 11, pp. 87-92 (1968).

Baranov, et al., *Chem. Abs.* 85, 94362, (1976).

Berényi, et al, "Ring Transformation of Condensed Dihydro-as-triazines", *J. Heterocyclic Chem.*, 18, pp. 1537-1540 (1981).

Chollet, et al, "Development of a Topically Active Imiquimod Formulation", *Pharmaceutical Development and Technology*, 4(1), pp. 35-43 (1999).

Izumi, et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines", *Bioorganic & Medicinal Chemistry*, 11, pp. 2541-2550 (2003).

Macchia et al., Synthesis and antiviral properties of 9-[(2-methyleneaminoxyethoxy)methyl]guanine derivatives as novel Acyclovir analogues. Farmaco. Feb. 2000;55(2):104-8.

[No Author Listed] "Comparative Tests." Filed Apr. 8, 2005 during prosecution for EP 00938205.2, EP 00950215.4 and EP 00938211.0 in the name of 3M Innovative Properties Co.

[No Author Listed] Chemical Abstracts. 1964;61(1):6060g.

[No Author Listed] Encyclopedia of Pharmaceutical Technology. 2nd Ed. Marcel Dekker, Inc. 2002:856-60.

Agrawal et al., Synthetic agonists of Toll-like receptors 7, 8 and 9. Biochem Soc Trans. Dec. 2007;35(Pt 6):1461-7.

Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.

Akira et al., Recognition of pathogen-associated molecular patterns by TLR family. Immunol Lett. 2003;85:85-95.

Akira et al., Toll-like receptors: critical proteins linking innate and acquired immunity. Nature Immunol. 2001;2(8):675-80.

Alexopoulou et at., Recognition of double-stranded RNA and activation of NF-kappaB by Toll-like receptor 3. Nature. Oct. 18, 2001;413(6857):732-8.

Assuma et al., IL-1 and TNF Antagonists Inhibit the Inflammatory Response and Bone Loss in Experimental Periodontitis. J Immunol. 2000;160:403-09.

Au et al., Virus-mediated induction of interferon A gene requires cooperation between multiple binding factors in the interferon alpha promoter region. J Biol Chem. Nov. 15, 1993;268(32):24032-40.

Auerbach et al., Erythema nodosum following a jellyfish sting. J Emerg Med. Nov.-Dec. 1987;5(6):487-91.

Auwers, [Uber die Isomerie-Verhaltnisse in der Pyrazol-Reihe. Berichte. VI.] 1926;601-607. German.

Baffis et al., Use of interferon for prevention of *Hepatocellular carcinoma* in cirrhotic patients with hepatitis B or hepatitis C virus infection. Ann Intern Med. Nov. 2, 1999;131(9):696-701.

Baker et al., Oral infection with Porphyromonas gingivalis and induced alveolar bone loss in immunocompetent and severe combined immunodeficient mice. Arch Oral Biol. Dec. 1994;39(12):1035-40.

Baldwin et al., Amino Acid Synthesis via Ring Opening of N-Sulphonyl Aziridine-2-Carboxylate Esters with Organometallic Reagents. Tetrahedron. 1993;49:6309-30.

Bártová et al., Th1 and Th2 cytokine profile in patients with early onset periodontitis and their healthy siblings. Mediators Inflamm. 2000;9(2):115-20.

Beck et al., Dental Infections and Atherosclerosis. Am Heart J. 1999;13:528-33.

Beckett et al., Configurational Studies in Synthetic Analgesics: the Synthesis of (−)—Methadone from D-(−)—Alanine. J Chem Soc. 1957;1:858-61.

(56) References Cited

OTHER PUBLICATIONS

Beilman et al., Experimental brown spider bite in the guinea pig: Results of treatment with dapsone or hyperbaric oxygen. J Wilderness Medicine. 1994;5:287-94.

Belikov, Abbreviated Guide to Synthetic and Natural Medications. Pharmaceutical Chemistry. Higher School. 1993;1:43-47. Russian.

Beltrami et al., Some Methylhydrazonium Salts; An Improved Synthesis of Tetramethylhydrazine. J Am Chem Soc. 1956;1956:2467-68.

Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.

Bertino et al., Principles of Cancer Therapy. Cecil Textbook of Medicine. Goldman et al., eds. 21th Ed. W.B. Saunders Company. 2000:1:1060-74.

Beutler et al., Tumor necrosis factor in the pathogenesis of infectious diseases. Crit Care Med. Oct. 1993;21(10 Suppl):S423-35.

Beutner et al., Therapeutic response of basal cell carcinoma to the immune response modifier imiquimod 5% cream. J Am Acad Dermatol. Dec. 1999;41(6):1002-7.

Beutner et al., Treatment of genital warts with an immune-response modifier (imiquimod). J Am Acad Dermatol. Feb. 1998;38(2 Pt 1):230-9.

Binder, Acute arthropod envenomation. Incidence, clinical features and management. Med Toxicol Adverse Drug Exp. May-Jun. 1989;4(3):163-73.

Bishop et al., Molecular mechanisms of B lymphocyte activation by the immune response modifier R-848. J Immunol. Nov. 15, 2000;165(10):5552-7.

Bitterman-Deutsch et al., [Brown spider bite]. Harefuah. Sep. 1990;119(5-6):137-9. Hebrew.

Booth et al., Dapsone suppresses integrin-mediated neutrophil adherence function. J Invest Dermatol. Feb. 1992;98(2):135-40.

Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and *Borrelia burgdorferi* outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of lmmunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chuang et al., Toll-like receptor 9 mediates CpG-DNA signaling. J Leukoc Biol. Mar. 2002;71(3):538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Colotta et al., Synthesis and structure:activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

Davis, Current therapy for chronic hepatitis C. Gastroenterology. Feb. 2000;118(2 Suppl 1):S104-14.

De Clerq, Synthetic interferon inducers. Top Curr Chem. 1974;52:173-208.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Di Carlo et al., Neutrophils in anti-cancer immunological strategies: old players in new games. J Hematother Stem Cell Res. Dec. 2001;10(6):739-48.

Diaz-Arrastia et al., Clinical and molecular responses in high-grade intraepithelial neoplasia treated with topical imiquimod 5%. Clin Cancer Res. Oct. 2001;7(10):3031-3.

Dicken et al., Reactions at High Pressures. [3 + 2] Dipolar Cycloaddition of Nitrones with Vinyl Ethers. J Org Chem. 1982;47:2047-51.

(56) References Cited

OTHER PUBLICATIONS

Dockrell et al., Imiquimod and resiquimod as novel immunomodulators. J Antimicrob Chemother. Dec. 2001;48(6):751-5.

Douglas, Introduction to Viral Diseases. In: Cecil Textbook of Medicine. Bennet et al., eds. 20th Ed. W.B. Saunders Company. 1996:2:1739-47.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et W., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-αProducing Cells in Human Blood and Tonsil Are CD11C/CD123+Cells Identical to Precursors of Type Two Dendritic Cells (pDC2). J Interferon Cytokine Res. 1999;19(1):S117.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fontenau et al., Human Immunodeficiency Virus Type 1 Activates Plasmacytoid Dendritic Cells and Concomitantly Induces the Bystander Maturation of Myeloid Dendritic Cells. J Virol. 2003;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-39.

Galose, Dapsone (diaminodiphenylsulphone DDS). Clinidal Toxicology Review. 1999:21(9). 3 pages.

Gendron, Loxosceles reclusa Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-loxosceles Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gürsel et al., Differential and competitive activation of human immune cells by distinct classes of CpG oligodeoxynucleotide. J Leukoc Biol. May 2002;71(5):813-20.

Gunning et al., Chemoprevention by lipoxygenase and leukotriene pathway inhibitors of vinyl carbamate-induced lung tumors in mice. Cancer Res. Aug. 1, 2002;62(15):4199-201.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-9. Epub Jun. 26, 2003.

Hayes et al., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for loxosceles envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides_ignaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Jacobs, The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

(56) References Cited

OTHER PUBLICATIONS

Jurk et al. Human TLR7 and TLR8 independently confer responsiveness to the antiviral compound R-848. Nat Immunol. Jun. 2002;3(6):499.
Juweid, Radioimmunotherapy of B-Cell Non-Hodgkin's Lymphoma: From Clinical Trials to Clinical Practice. J Nuclear Med. 2002;43(11):1507-29.
Katritsky et al., Comprehensive Heterocyclic Chemistry: The Structure, Reactions, Synthesis and Uses of Heterocyclic Compounds. 1984;2:586-587.
Keating et al., Long-term follow-up of patients with chronic lymphocytic leukemia treated with fludarabine as a single agent. Blood. Jun. 1, 1993;81(11):2878-84.
Klausen et al., Two complementary methods of assessing periodontal bone level in rats. Scand J Dent Res. Dec. 1989;97(6):494-9.
Klinman, Immunotherapeutic uses of CpG oligodeoxynucleotides. Nat Rev Immunol. Apr. 2004;4(4):249-58.
Kloek et al., An improved method for the synthesis of stabilized primary enamines and imines. J Org Chem. 1978;43:1460-62.
Kloetzel, Reactions of nitroparaffins. I. Synthesis and reduction of some γ-nitrokenes. J Am Chem Soc. 1947;69:2271-2275.
Kornman, Host modulation as a therapeutic strategy in the treatment of periodontal disease. Clin Infect Dis. Mar. 1999;28(3):520-6.
Kourafalos et al., Synthesis of 7-aminopyrazolo[3,4-c]pyridine as a probe for the preparation of compounds of pharmacological interest. Heterocycles. 2002;57(12):2335-2343.
Krause et al., Autoimmune aspects of cytokine and anticytokine therapies. Am J Med. Oct. 1, 2003;115(5):390-7.
Krenitsky et al., Imidazo[4,5-c]pyridines (3-deazapurines) and their nucleosides as immunosuppressive and _nti-inflammatory agents. J Med Chem. Jan. 1986;29(1):138-43.
Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.
Lall et al., Serine and threonine beta-lactones: a new class of hepatitis A virus 3C cysteine proteinase inhibitors. J Org Chem. Mar. 8, 2002;67(5):1536-47.
Lee et al., p38 mitogen-activated protein kinase inhibitors—mechanisms and therapeutic potentials. Pharmacol Ther. 1999;82:389-97.
Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.
Lehner et al., The role of γσcells and β-chemokines in mucosal protection against SIV infection. Immunology Lett. 1999;69:25-192. Abstract 2.1.
Levy et al., Unique efficacy of Toll-like receptor 8 agonists in activating human neonatal antigen-presenting cells. Blood. Aug. 15, 2006;108(4):1284-90. Epub Apr. 25, 2006.
Leynadier et al., Allergic reactions to North African scorpion venom evaluated by skin test and specific IgE. J Allergy Clin Immunol. Jun. 1997;99(6 Pt 1):851-3. 4 pages.
Li et al., An improved protocol for the preparation of 3-pyridyl- and some arylboronic acids. J Org Chem. Jul. 26, 2002;67(15):5394-7.
Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.
Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.
Litt et al., Mucosal delivery of vaccine antigens displayed on the surface of *Lactococcus lactis*. Immunology Lett. 1999;69(1):61. Abstract #11.26.
Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.
Loesche et al., Treatment paradigms in periodontal disease. Compend Contin Educ Dent. Mar. 1997;18(3):221-6, 228-30, 232 passim; quiz 234. Review.
Luger et al., Evidence for an epidermal cytokine network. J Invest Dermatol. Dec. 1990;95(6 Suppl):100S-104S.
Luskin et al., Olefinic Derivatives of 2,4-Diamino-s-triazines. J Org Chem. 1958;23:1032-37.
Majeski et al., Action of venom from the brown recluse spider (*Loxosceles reclusa*) on human neutrophils. Toxicon. 1977;15(5):423-7.
Makarenkova et al., Identification of delta- and mu- type opioid receptors on human and murine dendritic cells. J Neuroimmunol. 2001;117:68-77.
Masihi, Progress on novel immunomodulatory agents for HIV-1 infection and other infectious diseases. Expert Opin Ther Patents. 2003;13(6):867-82.
Masiukiewicz et al., Scalable Syntheses of $N^{\alpha}$-Benzyloxy carbonyl-$_L$-Ornithine and of $N^{\alpha}$-(9-Fluorenylmethoxy)Carbonyl-$_L$-Ornithine. Org Prep Proced Int. 2002;34:531-37.
Mataka et al., Condensation reaction of 3,4-Dibenzoyl-1-methyl-2,5-diphenylpyrrole and -1-phenylpyrazole with methylamine derivatives affording pyrrolo[3,4-c]pyridine and 2H-pyrazolo[3,4-c]- and [4,3-c]pyridines. Journal of Heterocyclic Chemistry. 1981;18(6):1073-5.
Mathur et al., Cell-mediated immune system regulation in periodontal diseases. Crit Rev Oral Biol Med. 1997;8(1):76-89.
Maynor et al., Brown recluse spider envenomation: a prospective trial of hyperbaric oxygen therapy. Acad Emerg Med. Mar. 1997;4(3):184-92.
Mbow et al., Small molecule and biologic modulators of the immune response to hepatitis C virus. Mini Rev Med Chem. May 2006;6(5):527-31.
McCarthy et al., Opioids, opioid receptors, and the immune response. Drug & Alcohol Dependence. 2001;62:111-23.
McKennon et al., A Convenient Reduction of Amino Acids and Their Derivatives. J Org Chem. 1993;58:3568-71.
McLaughlin et al., Opioid growth factor (OGF) inhibits the progression of human squamous cell carcinoma of the head and neck transplanted into nude mice. Cancer Lett. 2003;199:209-17.
Medzhitov, Toll-Like Receptors and Innate Immunity. Nature Rev Immunol. 2001;1:135-45.
Mee et al., Stille coupling made easier—the synergic effect of copper(I) salts and the fluoride ion. Angew Chem. 2004;116:1152-56.
Merigian et al., Envenomation From the Brown Recluse Spider. Review of Mechanism and Treatment Options. Am J Ther. Oct. 1996;3(10):724-734.
Miller et al., Imiquimod applied topically: a novel immune response modifier and new class of drug. Int J Immunopharmacol. Jan. 1999;21(1):1-14.
Minakawa et al., Nucleosides and Nucleotides. 184. Synthesis and Conformational Investigation of Anti-Fixed 3-Deaza-3-halopurine Ribonucleosides. J Org Chem. 1999;64:7158-72.
Moebius et al., The mysteries of sigma receptors: new family members reveal a role in cholesterol synthesis. Trends Pharmacol Sci. Mar. 1997;18(3):67-70.
Moldoveanu et al., Poly-L-lysine as a potential mucosal adjuvant. Immunology Lett. 1999;69(1):62. Abstract #11.28.
Mollick et al., MUC1-like tandem repeat proteins are broadly immunogenic in cancer patients. Cancer Immun. Mar. 17, 2003;3:3. 17 pages.
Moody et al., Lipoxygenase inhibitors prevent lung carcinogenesis and inhibit non-small cell lung cancer growth. Exp Lung Res. Jul.-Aug. 1998;24(4):617-28.
Moraczewski et al., Using Hydrogen Bonding to Control Carbamate C-N Rotamer Equilibria. Org Chem. Oct. 16, 1998;63(21):7258-7262.
Mosbech et al., [Allergy to insect stings] Ugeskr Laeger. Oct. 28, 1991;153(44):3067-71. Danish.
Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.

(56) References Cited

OTHER PUBLICATIONS

Muller et al., An improved one-pot procedure for the synthesis of alkynes from aldehydes. Synlett. 1996;6:521-522.
Mutschler et al., 9.2 Anti-infectives. In: Drug Actions: Basic Principles and Therapeutic Aspects. 1995:515-80.
Muzio et al., Differential expression and regulation of toll-like receptors (TLR) in human leukocytes: selective expression of TLR3 in dendritic cells. J Immunol. Jun. 1, 2000;164(11):5998-6004.
Nagarajan et al., Condensed heterotricycles: synthesis of pyrazolo[3,4-c]quinoline derivatives. Indian Journal of Chemistry. 1992;31B:316-321.
Nagase et al., Expression and function of Toll-like receptors in eosinophils: activation by Toll-like receptor 7 ligand. J Immunol. Oct. 15, 2003;171(8):3977-82.
Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.
Ohana et al., Differential effect of adenosine on tumor and normal cell growth: focus on the A3 adenosine receptor. Journal of Cellular Physiology. Jan. 2001;186(1):19-23. Review.
O'Mahony et al., New patient-applied therapy for anogenital warts is rated favourably by patients. Intl J STD & AIDS. 2001;12:565-70.
Osol et al., Chapter 27: Structure-Activtiy Relationship and Drug Design. In: Remington's Pharmaceutical Sciences. 16th Ed. Mach Publishing. 1980:420-35.
Ottonello et al., Sulphonamides as anti-inflammatory agents: old drugs for new therapeutic strategies in neutrophilic inflammation? Clin Sci (Lond). Mar. 1995;88(3):331-6.
Ozinsky et al., The repertoire for pattern recognition of pathogens by the innate immune system is defined by cooperation between Toll-like receptors. Proc. Nat. Acad. Sci. 2000; 97(25):13766-71.
Page et al., Advances in the pathogenesis of periodontitis: summary of developments, clinical implications and future directions. Periodontol 2000. Jun. 1997;14:216-48.
Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.
Park et al., Sodium Dithionite Reduction of Nitroarenes Using Viologen as an Electron Phase-Transfer Catalyst. Tetrahedron Lett. 1993;34(46):7445-46.
Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.
Patrick et al., Paragraph 10.3: Drug optimization: strategies in drug design. In: An Introduction to Medicinal Chemistry. Oxford: Oxford University Press. Jan. 2005. 200-218.
Pavletic et al., Outcome of allogeneic stem cell transplantation for B cell chronic lymphocytic leukemia. Bone Marrow Transplant. Apr. 2000,25(7):717-22.
Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.
Payvandi et al., Exogenous and Endogenous IL-10 Regulate IFN-α Production by Peripheral Blood Mononuclear Cells in Response to Viral Stimulation. J Immunol. 1998;160:5861-68.
Peschke et al., Synthesis and in vitro characterization of new growth hormone secretagogues derived from ipamorelin with dipeptidomimetic N-terminals. Eur J Med Chem. 1999;34:363-380.
Peterson et al., The opioid-cytokine connection. J Neuroimmunol. 1998;83:63-69.
Phillips et al., Therapy of brown spider envenomation: a controlled trial of hyperbaric oxygen, dapsone, and cyproheptadine. Ann Emerg Med. Mar. 1995;25(3):363-8.

Pickersgill et al., Preparation of functionalized, conformationally constrained DTPA analogues from L—or D-serine and trans-4-hydroxy-L-proline. Hydroxymethyl substituents on the central acetic acid and on the backbone. J Org Chem. Jun. 30, 2000;65(13):4048-57.
Poljakovic et al., iNOS and COX-2 immunoreactivity in the mice bladder and kidney after bacterial instillation. Immunology Lett. 1999;69(1):122. Abstract #31.5.
Powell et al., Compendium of excipients for parenteral formulations. PDA J Pharm Sci Technol. Sep.-Oct. 1998;52(5):238-311.
Prelog et al., Cycloalkeno-pyridine. Hely Chem Acta. 1945;28:1684-93. German.
Rees et al., Brown recluse spider bites. A comparison of early surgical excision versus dapsone and delayed surgical excision. Ann Surg. Nov. 1985;202(5):659-63.
Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.
Rhodes, Discovery of immunopotentiatory drugs: current and future strategies. Clin Exp Immunol. Dec. 2002;130(3):363-9.
Ribera et al., "Spontaneous" complete remissions in chronic lymphocytic leukemia: report of three cases and review of the literature. Blood Cells. 1987;12(2):471-83.
Ritter et al., A new reaction of nitriles; amides from alkenes and mononitriles. J Am Chem Soc. Dec. 1948;70(12):4045-8.
Rocca et al., Carbolines. Part VII. Ansidines, Convenient tools to synthesize_fficien-β-carbolines. J Heterocyclic Chem. 1995;32:1171-1175.
Rocca et al., Connection between metalation and cross-coupling strategies. A new convergent route to azacarbazoles. Tetrahedron Lett. 1993;49(1):49-64.
Rollins et al., Chemokines. Blood. Aug. 1, 1997;90(3):909-28. Review.
Rosenberg et al., Treatment of 283 consecutive patients with metastatic melanoma or renal cell cancer using high-dose bolus interleukin 2. JAMA. Mar. 23-30, 1994;271(12):907-13.
Rothel et al., The use of recombinant ovine IL-1beta and TNF-alpha as natural adjuvants and their physiological effects in vivo. Immunol Cell Biol. Apr. 1998;76(2):167-72.
Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.
Royals et al., Studies in mixed ester condensations. IV. Acylations with methyl dimethoxyacetate. J Am Chem Soc. 1956;78:4161-4164.
Rozman et al., Chronic lymphocytic leukemia. N Engl J Med. Oct. 19, 1995;333(16):1052-7.
Sakthivel et al. Direct SnAr amination of fluorinated imizazo[4,5-c]pyridine nucleosides:_fficient synthesis of 3-fluoro-3-3-deazaadenosine analogs. Tetrahedron Letters. May 2005;46(22):3883-3887.
Salaun et al., TLR3 Can Directly Trigger Apoptosis in Human Cancer Cells. J of Immunology. 2006;176:4894-901.
Salemink, Uber 2-Propyl-1—Und 2-Propyl-Desaza-Adenin. Recueil. 1961;80:545-56. German.
Sambhi et al., Local production of tumor necrosis factor encoded by recombinant *Vaccinia* virus is effective in controlling viral replication in vivo. Proc Natl Acad Sci U S A. May 1, 1991;88(9):4025-9.
Sams et al., Necrotic arachnidism. J Am Acad Dermatol. Apr. 2001;44(4):561-73; quiz 573-6.
Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.
Scheerlinck, Genetic adjuvants for DNA vaccines. Vaccine. Mar. 21, 2001;19(17-19):2647-56.
Scheuer et al., Application of the Ritter reaction to mesityl oxide and chalcone. J Am Chem Soc. 1957;22:674-676.
Schofield et al., Reply. Low-Dose Interferon-alpha in Chronic Myeloid Leukemia. Ann Internal Med. 1995;122(9):728-29. 1 page.

(56) References Cited

OTHER PUBLICATIONS

Schwandner et al., Peptidoglycan- and lipoteichoic acid-induced cell activation is mediated by toll-like receptor 2. J Biol Chem. Jun. 18, 1999;274(25):17406-9.
Seeman et al., Steric and Conformational Effects in Nicotine Chemistry. J Org Chem. 1981;46:3040-48.
Serrat et al., A highly efficient and straightforward stereoselective synthesis of novel chiral α-acetylenic ketones. Tetrahedron: Assymmetry. 1999;10:3417-30.
Severa et al., Sensitization to TLR7 agonist in IFN-beta-preactivated dendritic cells. J Immunol. May 15, 2007;178(10):6208-16.
Seymour et al., Cellular immunity and hypersensitivity as components of periodontal destruction. Oral Dis. Mar. 1996;2(1):96-101. Review.
Shelbourne et al., Quantitation of Bacteroids forsythus in subgingival plaque comparison on immunoassay and quantitative polymerase chain reaction. J Microbiol Methods. 2000;39:97-107.
Sidky et al., Inhibition of murine tumor growth by an interferon-inducing imidazoquinolinamine. Cancer Res. Jul. 1, 1992;52(13):3528-33.
Siegal et al., The nature of the principal type 1 interferon-producing cells in human blood. Science. Jun. 11, 1999;284(5421):1835-7.
Sletzinger et al., The Synthesis of Isomethadone. J Am Chem Soc. 1952;74:5619-20.
Smith et al., The role of polymorphonuclear leukocytes in the lesion caused by the venom of the brown spider, Loxosceles_ecluse. Lab Invest. Jan. 1970;22(1):90-3.
Sofina et al., Experimental evaluation of antitumor drugs in the USA and USSR and clinical correlations. NCI Monograph 55. NIH Publication No. 80/1933. 1980:76-8.
Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.
Soria et al., Effect of food on the pharmacokinetics and bioavailability of oral imiquimod relative to a subcutaneous dose. Int J Clin Pharmacol Ther. Oct. 2000;38(10):476-81. Abstract Only.
Spaner et al., A phase I/II trial of TLR-7 agonist immunotherapy in chronic lymphocytic leukemia. Leukemia. 2010; 24:222-26.
Spaner et al., Immunomodulatory effects of Toll-like receptor-7 activation on chronic lymphocytic leukemia cells. Leukemia. Feb. 2006;20(2):286-95.
Spaner et al., Toll-like receptor agonists in the treatment of chronic lymphocytic leukemia. Leukemia. Jan. 2007;21(1):53-60. Epub Oct. 26, 2006.
Spivey et al., Configurationally stable biaryl analogues of 4-(dimethylamino)pyridine: A novel class of chiral nucleophilic catalysts. J Org Chem. 1999;64 9430-9443.
Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.
Stack, Images in clinical medicine. *Latrodectus mactans*. N Engl J Med. Jun. 5, 1997;336(23):1649.
Stanley, Imiquimod and the imidazoquinolones: mechanism of action and therapeutic potential. Clin Exp Dermatol. Oct. 2002;27(7):571-7. Review.
Stashenko et al., Periapical inflammatory responses and their modulation. Crit Rev Oral Biol Med. 1998;9(4):498-521.
Steele et al., Lipoxygenase inhibitors as potential cancer chemopreventives. Cancer Epidemiol Biomarkers Prev. May 1999;8(5):467-83.
Steele et al., Potential use of lipoxygenase inhibitors for cancer chemoprevention. Expert Opin Investig Drugs. Sep. 2000;9(9):2121-38.
Steinmann et al., Topical imiquimod treatment of a cutaneous melanoma metastasis. J Am Acad Dermatol. Sep. 2000;43(3):555-6.
Stewart et al., Synthesis of a Carba-analog of S-Acetyl Coenzyme A, Acetonyl-dethio Coenzyme A; an Effective Inhibitor of Citrate Synthase. Liebigs Ann Chem. 1978:57-65.
Stillings et al., Substituted 1,3,4-thiadiazoles with anticonvulsant activity. 2. Aminoalkyl derivatives. J Med Chem. Nov. 1986;29(11):2280-4.
Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.
Stringfellow, Induction of interferon with low molecular weight compounds: fluorenone esters, ethers (tilorone), and pyrimidinones. Methods Enzymol. 1981;78(Pt A):262-84.
Ströher et al., Progress towards the treatment of Ebola haemorrhagic fever. Expert Opin Investig Drugs. Dec. 2006;15(12):1523-35.
Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475:Abstract 3030.
Surrey et al., The Synthesis of Some 3-Nitro- and 3-Amino-4-dialkylaminoalkylaminoquinoline Derivatives. J Am Chem Soc. 1951;73:2413-16.
Takeichi et al., Cytokine profiles of T-lymphocytes from gingival tissues with pathological pocketing. J Dent Res. Aug. 2000;79(8):1548-55.
Takeshita et al., Signal transduction pathways mediated by the interaction of CpG DNA with Toll-like receptor 9. Semin Immunol. Feb. 2004;16(1):17-22.
Takeuchi et al., Discrimination of bacterial lipoproteins by Toll-like receptor 6. Int Immunol. Jul. 2001;13(7):933-40.
Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.
Thesing et al., [Darstellung und Eigenschaften des $\Delta^1$-Pyrrolin-$N$-oxyds.]. Chem Ber. 1959;92:1748-55. German.
Thiruvikraman et al., Synthesis and reactions of pyrazolo-[3,4-c]quinoline derivatives. Indian Journal of Chemistry. 1987;26B:695-696.
Tomai et al., Imiquimod: in vivo and in vitro characteristics and toxicology. In: Cutaneous Infection and Therapy. Aly et al., eds. Marcel Dekkar, Inc., New York. 1997:406-15.
Tomic et al., Sensitization of IL-2 Signaling through TLR-7 Enhances B Lymphoma Cell Immunogenicity. J Immunol. 2006;176:3830-39.
Tomioka et al., Asymmetric Alkylation of α-Alkyl β-Keto Esters. J Am Chem Soc. 1984;106:2718-19.
Totterman et al., Phorbol ester-induced differentiation of chronic lymphocytic leukaemia cells. Nature. Nov. 13, 1980;288(5787):176-8.
Tracy et al., Studies in the Pyridine Series. II. Synthesis of 2-Methyl-3-(βHydroxyethyl)pyridine and of the Pyridine Analog of Thiamine (Vitamin B2). J Org Chem. 1941;6:54-62.
Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.
Urosevic et al., Imiquimod treatment induces expression of opioid growth factor receptor: a novel tumor antigen induced by interferon-alpha? Clin Cancer Res. Aug. 1, 2004;10(15):4959-70.
Van De Kerhof, New Immunomodulatory Drugs. In: Skin and Environment: Perception and Protection. Ring et al., eds., 10th EADV Congress, Oct. 10-14, Munich, Germany. 2001:1:343-8.
Vasilakos et al., Adjuvant Activities of Immune Response Modifier R-848: Comparison with CoG ODN. Cell Immunol. 2000;204:64-74.
Vieweg et al., Tumor vaccines: from gene therapy to dendritic cells-the emerging frontier. Urol Clin North Am. Aug. 2003;30(3):633-43.
Vilcek, The cytokines: An overview. In: The Cytokine Handbook, Fourth Ed. M. Lotze and A.W. Thompson (eds.), 2003;1:3-14.
Volhardt, 18-5. Amides: The Least-Reactive Carboxylic Acid Derivatives. Organic Chemistry. 1987:813.
Vollmer et al., Highly immunostimulatory CpG-free oligodeoxynucleotides for activation of human leukocytes. Antisense Nucleic Acid Drug Dev. Jun. 2002;12(3):165-75.

(56) References Cited

OTHER PUBLICATIONS

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wermuth, Molecular Variations Based on Isosteric Replacements. Practice of Medicinal Chemistry.1996:203-37.

Wexler et al., Accurate identification of experimental pulmonary metastases. J Natl Cancer Inst. Apr. 1966;36(4):641-5.

Wibaut et al., Syntheses of 3,4-Dimethylpyridine, 2,3-Dimethylpridine and 2-Methyl-3-Ethylpyridine. Rec Tray Chim. 1944;63:231-38.

Wierda et al., CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22.

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., The biology of the opioid growth factor receptor (OGFr). Brain Res Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zagon et al., Opioids and the apoptotic pathway in human cancer cells. Neuropeptides. 2003;37:79-88.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and *Drosophila* nicotinic receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

Supplementary European Search Report mailed Jun. 25, 2009 in connection with European Application No. EP 04780922.3.

\* cited by examiner

OXIME SUBSTITUTED IMIDAZO-CONTAINING COMPOUNDS

RELATED APPLICATIONS

The is application is the National Stage of International Application No. PCT/US2004/026065, filed Aug. 12, 2004, which claims priority to U.S. Provisional Application Ser. No. 60/494608, filed Aug. 12, 2003, and U.S. Provisional Application Ser. No. 60/494605, filed Aug. 12, 2003, both of which are incorporated herein by reference.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c] pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers (IRMs), rendering them useful in the treatment of a variety of disorders.

There continues to be interest in and a need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula I:

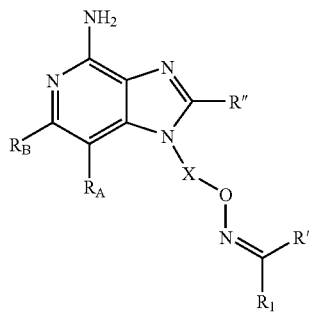

and, more specifically of the following Formula II:

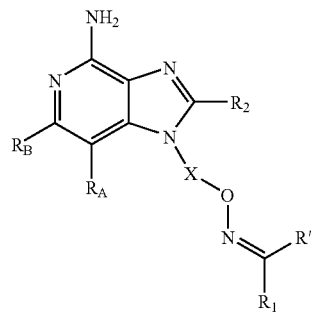

wherein: X, $R_A$, $R_B$, $R_1$, $R_2$, R', and R" are as defined below.

Examples of such compounds include imidazoquinolines of the following Formulas III, IV, and V, and imidazotetrahydroquinolines of Formula VII:

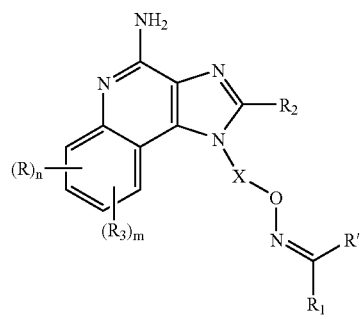

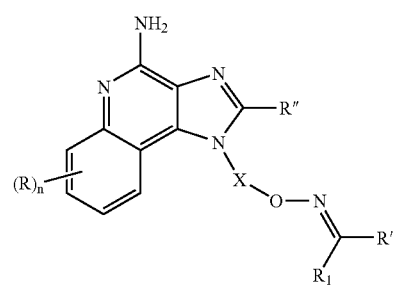

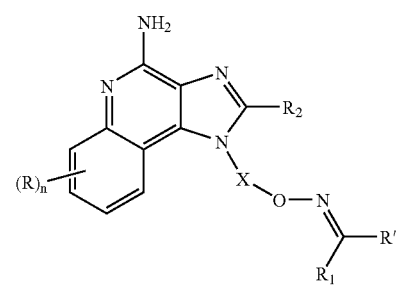

VII

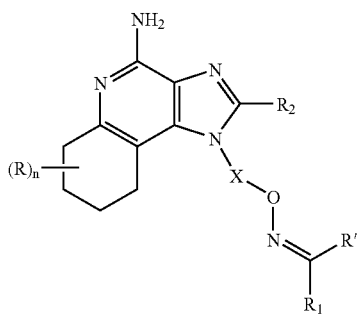

wherein: X, R, R', R", n, mn, $R_1$, $R_2$, and $R_3$ are as defined below.

Examples of such compounds also include imidazopyridines of the following Formula VI:

VI

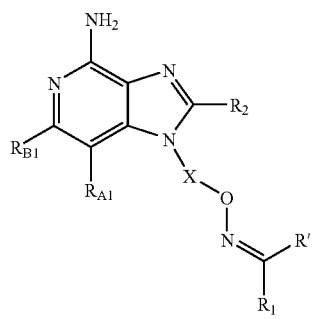

wherein: X, R', $R_1$, $R_2$, $R_{A1}$, and $R_{B1}$ are as defined below.

Examnples of such compounds also include imidazonaphthyridines of the following Formula VIII and imidazotetrahydronaphthyridines of the following Formula IX:

VIII

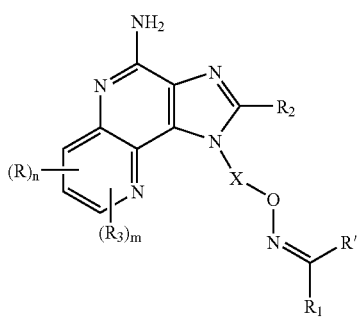

IX

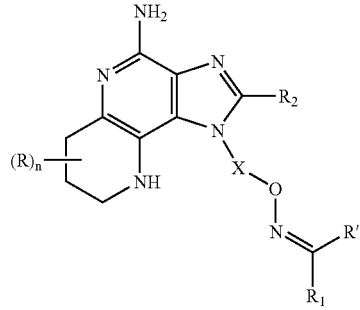

wherein: X, n, m, R, R', $R_1$, $R_2$, and $R_3$ are as defined below.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through IX:

I

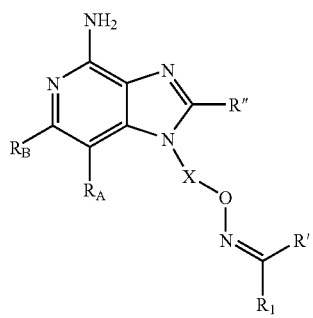

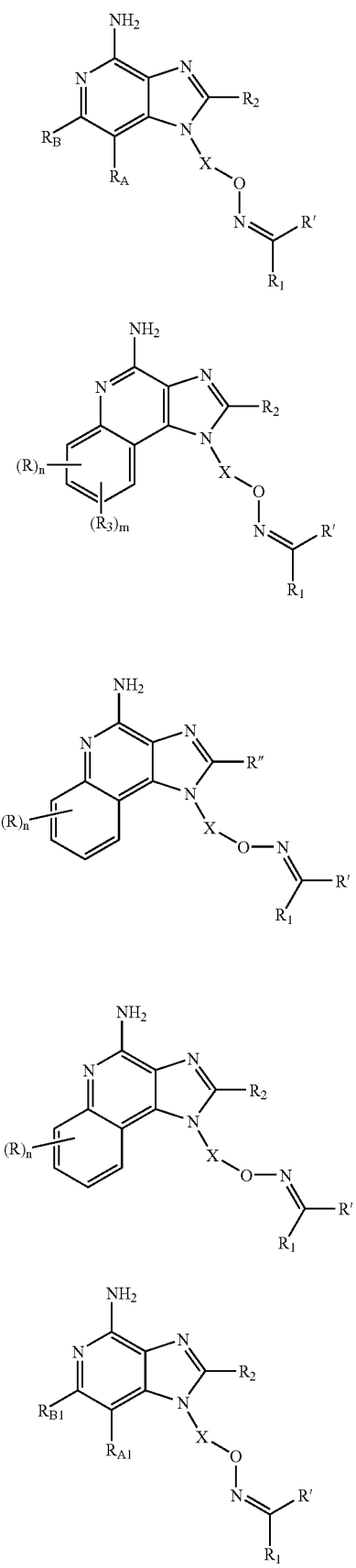
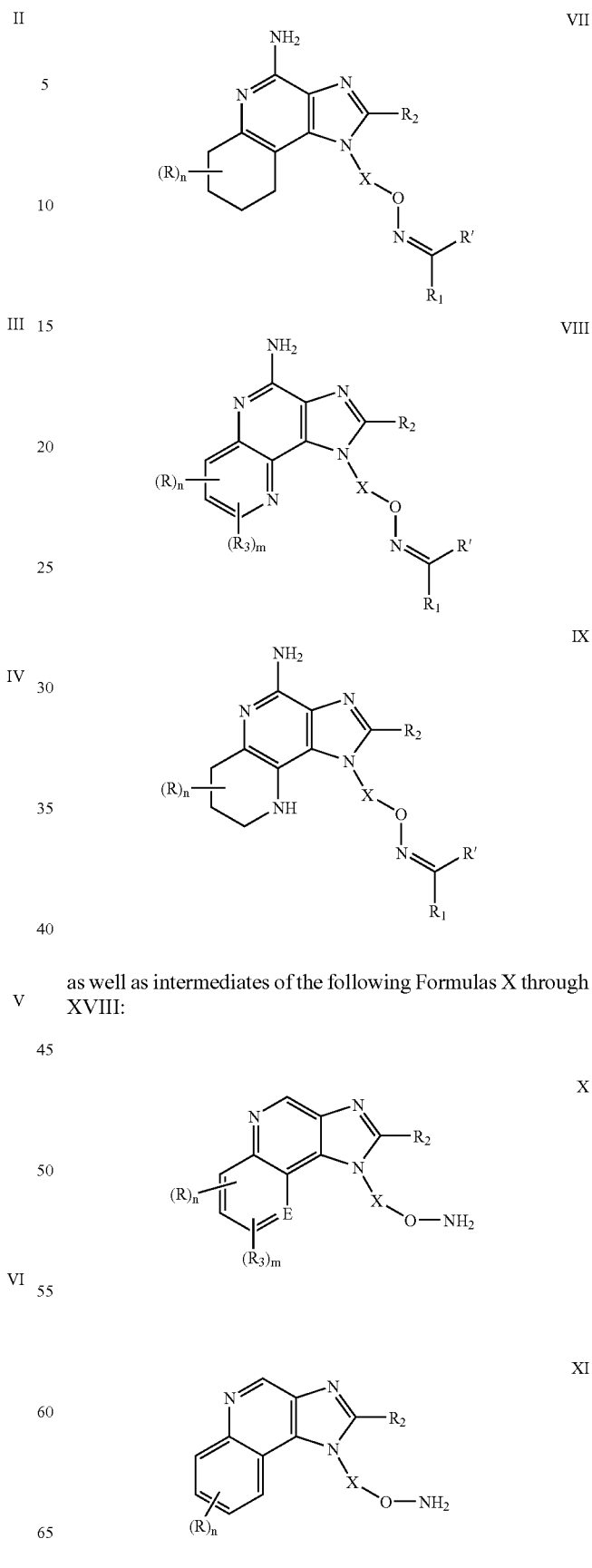
as well as intermediates of the following Formulas X through XVIII:
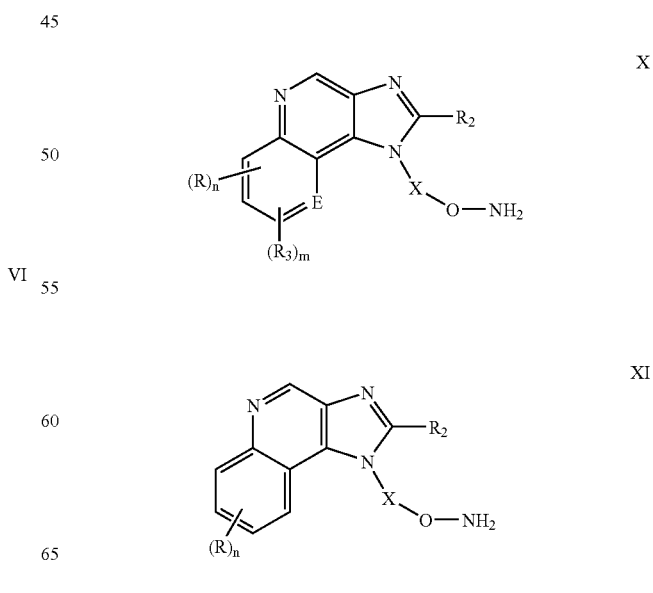

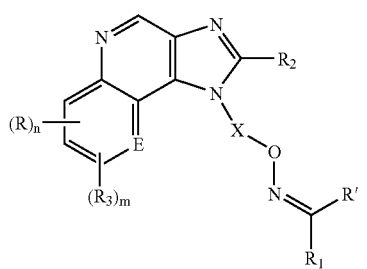
XII

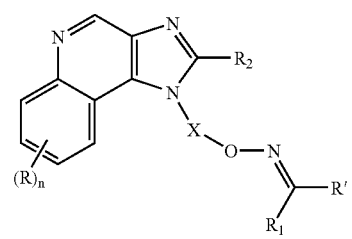
XIII

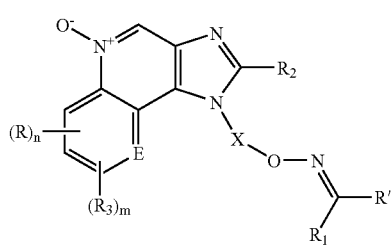
XIV

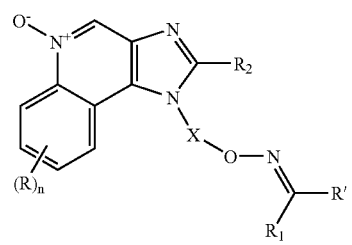
XV

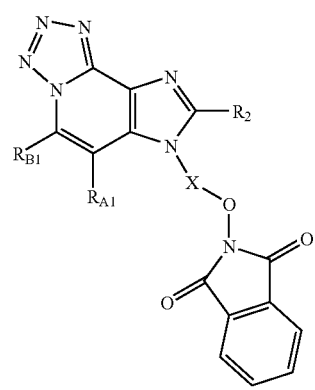
XVI

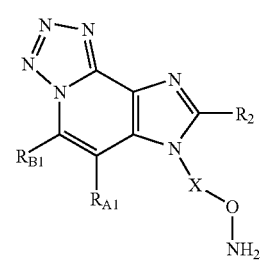
XVII

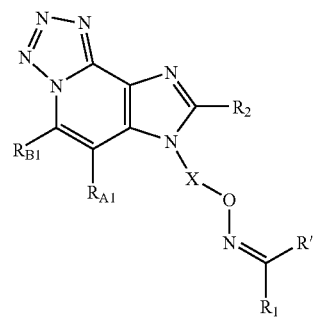
XVIII wherein: E, X, R, R', R", n, m, $R_1$, $R_2$, $R_3$, $R_4$, $R_B$, $R_{A1}$, and $R_{B1}$ are as defined below.

In one embodiment, the present invention provides a compound of Formula I:

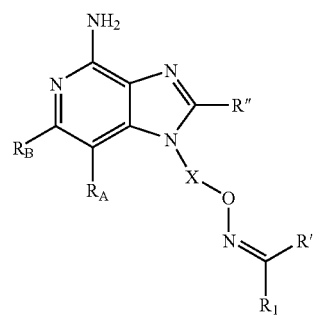
I wherein:
X is selected from the group consisting of —CH($R_{9a}$)-alkyiene- and —CH($R_{9a}$)-alkenylene-, wherein the allylene and alkenylene are optionally interrupted by one or more —O— groups;
$R_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen, nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;
or R$_1$ and R' can join together to form a ring system selected from the group consisting of:

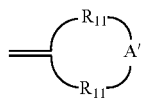

wherein the total number of atoms in the ring is 4 to 9, and

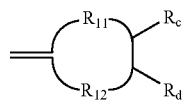

wherein the total number of atoms in the ring is 4 to 9; R$_A$ and R$_B$ are each independently selected from the group consisting of: hydrogen,
halogen,
alkyl,
alkenyl,
alkoxy,
alkylthio, and
—N(R$_9$)$_2$;
or when taken together, R$_A$ and R$_B$ form a fused aryl ring or heteroaryl ring containing one heteroatom selected from the group consisting of N and S, wherein the aryl or heteroaryl ring is unsubstituted or substituted by one or more R''' groups;
or when taken together, R$_A$ and R$_B$ form a fused 5 to 7 membered saturated ring, optionally containing one heteroatom selected from the group consisting of N and S, and unsubstituted or substituted by one or more R groups;
R is selected from the group consisting of:
halogen,
hydroxyl,
alkyl,
alkenyl,
haloalkyl,
alkoxy,
alkylthio, and
—N(R$_9$)$_2$;
A' is selected from the group consisting of —O—, —S(O)$_{0-2}$—, —N(—Q—R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
W is selected from the group consisting of a bond, —C(O)—, and —S(O)$_2$—;
R$_c$ and R$_d$ are independently selected from the group consisting of hydrogen, halogen, hydroxyl, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms;
R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (diaLlylamino)alkyleneoxy, and in the case of alkyl, alkenyl, alkynyl, and heterocyclyl, oxo;
each R$_6$ is independently selected from the group consisting of =O and =S;
each R$_8$ is independently selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;
each R$_9$ is independently selected from the group consisting of hydrogen and alkyl;
R$_{9a}$ is selected from the group consisting of hydrogen and alkyl which is optionally interrupted by one or more —O— groups;
each R$_{11}$ is independently C$_{1-6}$ alkylene or C$_{2-6}$ alkenylene, wherein the alkylene or alkenylene is optionally interrupted by one heteroatom;
R$_{12}$ is selected from the group consisting of a bond, C$_{1-5}$ alkylene, and C$_{2-5}$ alkenylene, wherein the alkylene or alkenylene is optionally interrupted by one heteroatom;
R'' is hydrogen or a non-interfering substituent; and
each R''' is a non-interfering substituent; or a pharmaceutically acceptable salt thereof.

In one embodiment, the present invention provides a compound of Formula II:

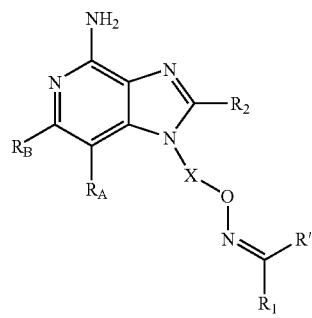

wherein:
X is selected from the group consisting of —CH(R$_{9a}$)-alkylene- and —CH(R$_{9a}$)-alkenylene-, wherein the alkylene and alkenylene are optionally interrupted by one or more —O— groups;
R$_1$ and R' are independently selected from the group consisting of:
hydrogen,
alkyl,
alkenyl,
aryl,
arylalkylenyl,
heteroaryl, heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrite,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;
or R$_1$ and R' can join together to form a ring system selected from the group consisting of:

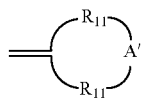

wherein the total number of atoms in the ring is 4 to 9, and

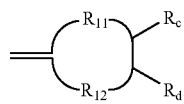

wherein the total number of atoms in the ring is 4 to 9;
R$_A$ and R$_B$ are each independently selected from the group consisting of:
hydrogen,
halogen,
alkyl,
alkenyl,
alkoxy,
alkylthio, and
—N(R$_9$)$_2$;
or when taken together, R$_A$ and R$_B$ form a fused aryl ring or heteroaryl ring containing one heteroatom selected from the group consisting of N and S, wherein the aryl or heteroaryl ring is unsubstituted or substituted by one or more R groups, or substituted by one R$_3$ group, or substituted by one R$_3$ group and one R group;
or when taken together, R$_A$ and R$_B$ form a fused 5 to 7 membered saturated ring, optionally containing one heteroatom selected from the group consisting of N and S, and unsubstituted or substituted by one or more R groups;
R is selected from the group consisting of:
halogen,
hydroxyl,
alkyl,
alkenyl,
haloalkyl,
alkoxy,
alkylthio, and
—N(R$_9$)$_2$;
R$_2$ is selected from the group consisting of:
—R$_4$,
—X'—R$_4$,
—X'—Y—R$_4$, and
—X'—R$_5$;
R$_3$ is selected from the group consisting of:
—Z—R$_4$,
—Z—X'—R$_4$,
—Z—X'—Y—R$_4$, and
—Z—X'—R$_5$;
each X' is independently selected from the group consisting of alkylene, alkenylene, alkynylene, arylene, heteroarylene, and heterocyclylene, wherein the alkylene, alkenylene, and allynylene groups can be optionally interrupted or terminated with arylene, heteroarylene, or heterocyclylene, and optionally interrupted by one or more —O— groups;
each Y is independently selected from the group consisting of:

—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)—Q—,
—C(R$_6$)—N(R$_8$)—,
—O—C(R$_6$)—N(R$_8$)—,
—C(R$_6$)—N(OR$_9$)—,

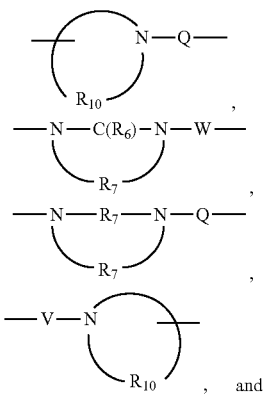

, and

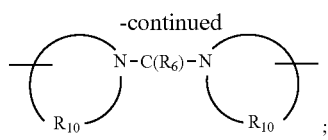

Z is a bond or —O—;

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

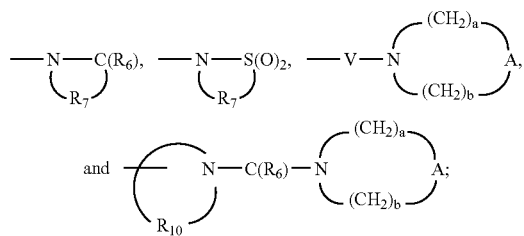

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

$R_c$ and $R_d$ are independently selected from the group consisting of hydrogen, halogen, hydroxyl, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

each $R_{11}$ is independently $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

each A is independently selected from the group consisting of —O—, —C(O)—, —CH$_2$—, —S(O)$_{0-2}$—, and —N(R$_4$)—;

A' is selected from the group consisting of —O—, —S(O)$_{0-2}$—, —N(—Q—R$_4$)—, and —CH$_2$—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

each V is independently selected from the group consisting of —C(R$_6$)—, —O—C(R$_6$)—, —N(R$_8$)—C(R$_6$)—, and —S(O)$_2$—;

each W is independently selected from the group consisting of a bond, —C(O)—, and S(O)$_2$—; and a and b are independently integers from 1 to 6 with the proviso that a+b is ≤7;

or a pharmaceutically acceptable salt thereof.

In one embodiment, the present invention provides a compound of Formula III:

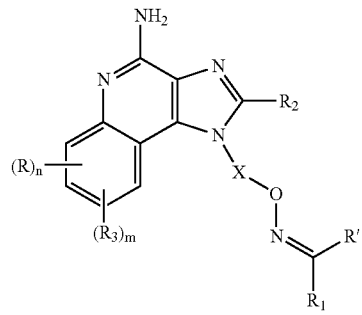

wherein:

X is selected from the group consisting of —CH(R$_{9a}$)-alkylene- and —CH(R$_{9a}$)-alkenylene-, wherein the alkylene and alkenylene are optionally interrupted by one or more —O— groups;

each R is independently selected from the group consisting of:
halogen,
hydroxyl,
alkyl,
alkenyl,
haloalkyl,
alkoxy,
alkylthio, and
—N(R$_9$)$_2$;

R$_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl, —NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;

or R$_1$ and R' can join together to form a ring system selected from the group consisting of:

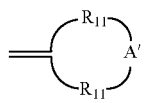

wherein the total number of atoms in the ring is 4 to 9, and

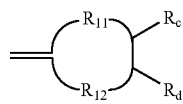

wherein the total number of atoms in the ring is 4 to 9;

R$_2$ is selected from the group consisting of:
—R$_4$,
—X'—R$_4$,
—X'—Y—R$_4$, and
—X'—R$_5$;

R$_3$ is selected from the group consisting of:
—Z—R$_4$,
—Z—X'—R$_4$,
—Z—X'—Y—R$_4$, and
—Z—X'—R$_5$;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:

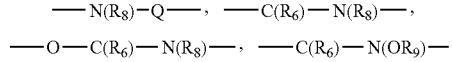

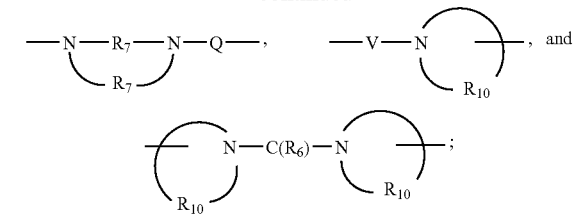

Z is a bond or —O—;

each R$_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each R$_5$ is independently selected from the group consisting of:

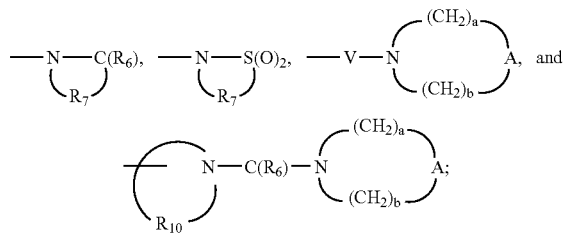

each R$_6$ is independently selected from the group consisting of =O and =S;

each R$_7$ is independently C$_{2-7}$ alkylene;

each R$_8$ is independently selected from the group consisting of hydrogen, C$_{1-10}$ alkyl, C$_{2-10}$ alkenyl, C$_{1-10}$ alkoxy-C$_{1-10}$ alkylenyl, and aryl-C$_{-10}$ alkylenyl;

each R$_9$ is independently selected from the group consisting of hydrogen and alkyl;

R$_{9a}$ is selected from the group consisting of hydrogen and alkyl which is optionally interrupted by one or more —O— groups;

each R$_{10}$ is independently C$_{3-8}$ alkylene;

R$_c$ and R$_d$ are independently selected from the group consisting of hydrogen, halogen, hydroxyl, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms;

each R$_{11}$ is independently C$_{1-6}$ alkylene or C$_{2-6}$ alkenylene, wherein the alkylene or alkenylene is optionally interrupted by one heteroatom;

R$_{12}$ is selected from the group consisting of a bond, C$_{1-5}$ alkylene, and C$_{2-5}$ alkenylene, wherein the alkylene or alkenylene is optionally interrupted by one heteroatom;

each A is independently selected from the group consisting of —O—, —C(O)—, —CH$_2$—, —S(O)$_{0-2}$—, and —N(R$_4$)—;

A' is selected from the group consisting of —O—, —S(O)$_{0-2}$—, —N(—Q—R$_4$)—, and —CH$_2$—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—, each V is independently selected from the group consisting of —C(R$_6$)—, —O—C(R$_6$)—, —N(R$_8$)—C(R$_6$)—, and —S(O)$_2$—;

each W is independently selected from the group consisting of a bond, —C(O)—, and —(O)$_2$—;

a and b are independently integers from 1 to 6 with the proviso that a+b is ≤7;

n is an integer from 0 to 4; and m is 0 or 1, with the proviso that when m is 1, n is 0 or 1;

or a pharmaceutically acceptable salt thereof.

In one embodiment, the present invention provides a compound of Formula IV:

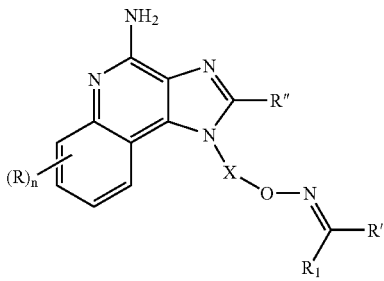

IV wherein:
X is selected from the group consisting of —CH(R$_{9a}$)-alkylene- and —CH(R$_{9a}$)-alkenylene-;

R$_1$ and R' are independently selected from the group consisting of:
hydrogen,
alkyl,
alkenyl,
aryl,
alkylene-aryl,
heteroaryl,
heterocyclyl, and
alkyl, alkenyl, aryl, arylalkylenyl, heteroaryl or heterocyclyl substituted by one or more substituents selected from the group consisting of:
hydroxyl,
alkyl,
haloalkyl,
hydroxyalkyl,
—O-alkyl,
—S-alkyl,
—O-haloalkyl,
halogen,
nitrile,
aryl,
heteroaryl,
heterocyclyl,
—O-aryl,
—O-alkylene-aryl,
—C(O)—O-alkyl,
—C(O)—N(R$_{8a}$)$_2$, and
—N(R$_{8a}$)—C(O)-alkyl;

or R$_1$ and R' can join together to form a ring system containing one or two saturated or unsaturated rings optionally including one or more heteroatoms;

n is an integer from 0 to 4;

each R and R" are independently selected from the group consisting of hydrogen and non-interfering substituents;

R$_{9a}$ is selected from the group consisting of hydrogen and alkyl which may be optionally interrupted by one or more —O— groups; and each R$_{8a}$ is independently selected from the group consisting of hydrogen, C$_{1-10}$ alky, and C$_{2-10}$ alkenyl;

or a pharmaceutically acceptable salt thereof.

In one embodiment, the present invention provides a compound of Formula V:

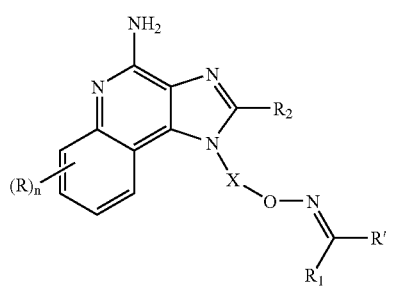

V wherein:
X is selected from the group consisting of —CH(R$_{9a}$)-alkylene- and —CH(R$_{9a}$)-alkenylene-;

R$_1$ and R' are independently selected from the group consisting of:
hydrogen,
alkyl,
alkenyl,
aryl,
alkylene-aryl,
heteroaryl,
heterocyclyl, and
alkyl, alkenyl, aryl, arylalkylenyl, heteroaryl or heterocyclyl substituted by one or more substituents selected from the group consisting of:
hydroxyl,
alkyl,
haloalkyl,
hydroxyalkyl,
—O-alkyl,
—S-alkyl,
—O-haloalkyl,
halogen,
nitrile,
aryl,
heteroaryl,
heterocyclyl,
—O-aryl,
—O-alkylene-aryl,
—C(O)—O-alkyl,
—C(O)—N(R$_{8a}$)$_2$, and
—N(R$_{8a}$)—C(O)-alkyl;

or R$_1$ and R' can join together to form a ring system containing one or two saturated or unsaturated rings optionally including one or more heteroatoms;

n is an integer from 0 to 4;

each R is independently selected from the group consisting of alkyl, alkoxy, halogen, hydroxyl, and trifluoromethyl;

$R_2$ is selected from the group consisting of:
hydrogen,
alkyl,
alkenyl,
aryl,
heteroaryl,
heterocyclyl,
alkylene-Y"-alkyl,
alkylene-Y"-alkenyl,
alkylene-Y"-aryl, and
alkyl or alkenyl substituted by one or more substituents selected from the group consisting of:
hydroxyl,
halogen,
—N($R_{8a}$)$_2$,
—C(O)—$C_{1-10}$ alkyl,
—C(O)—O—$C_{1-10}$ alkyl,
—$N_3$,
aryl,
heteroaryl,
heterocyclyl,
—C(O)-aryl, and
—C(O)-heteroaryl;
Y" is —O— or —O—S(O)$_{0-2}$—;
$R_{9a}$ is selected from the group consisting of hydrogen and alkyl which may be optionally interrupted by one or more —O— groups; and
each $R_{8a}$ is independently selected from the group consisting of hydrogen, $C_{1-10}$ alkyl, and $C_{2-10}$ alkenyl;
or a pharmaceutically acceptable salt thereof.

In one embodiment, the present invention provides a compound of Formula VI:

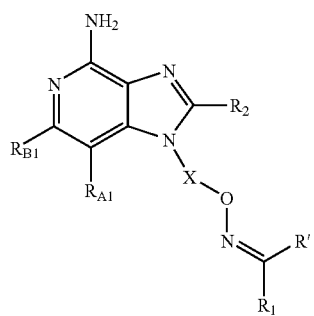

VI wherein:
X is selected from the group consisting of —CH($R_{9a}$)-alkylene- and —CH($R_{9a}$)-alenylene-, wherein the alkylene and alkenylene are optionally interrupted by one or more —O— groups;
$R_1$ and R' are independently selected from the group consisting of:
hydrogen,
alkyl
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N($R_8$)$_2$,
—N($R_8$)—C(O)-alkyl,
—O—C(O)-alkyl, and
—C(O)-alkyl;
or $R_1$ and R' can join together to form a ring system selected from the group consisting of:

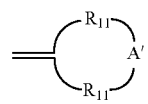

wherein the total number of atoms in the ring is 4 to 9, and

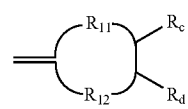

wherein the total number of atoms in the ring is 4 to 9;
$R_2$ is selected from the group consisting of:
—$R_4$,
—X'—$R_4$,
—X'—Y—$R_4$, and
—X'—$R_5$;
$R_{A1}$ and $R_{B1}$ are each independently selected from the group consisting of:
hydrogen,
halogen,
alkyl,
alkenyl,
alkoxy,
alkylthio, and
—N($R_9$)$_2$;
X' is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

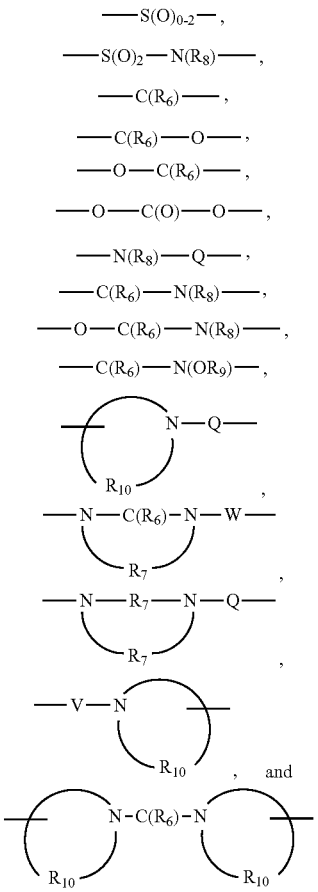

each R₄ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloaOlyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

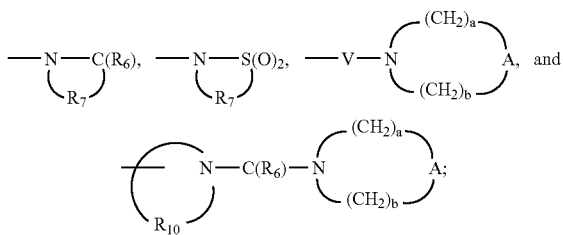

each R is independently selected from the group consisting of =O and =S;

each R₇ is independently C$_{2-7}$ alkylene;

each R₈ is independently selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

each R₉ is independently selected from the group consisting of hydrogen and alkyl;

R$_{9a}$ is selected from the group consisting of hydrogen and alkyl which is optionally interrupted by one or more —O— groups;

each R₁₀ is independently C$_{3-8}$ alkylene;

R$_c$ and R$_d$ are independently selected from the group consisting of hydrogen, halogen, hydroxyl, alkyl, alkenyl, aryl, haloalkyl, alkoxy, alkylthio, and —N(R₉)₂; or R$_c$ and R$_d$ can join to form a fused aryl ring or fused 5-10 membered heteroaryl ring containing one to four heteroatoms;

each R₁₁ is independently C$_{1-6}$ alkylene or C$_{2-6}$ alkenylene, wherein the alkylene or alkenylene is optionally interrupted by one heteroatom;

R₁₂ is selected from the group consisting of a bond, C$_{1-5}$ alkylene, and C$_{2-5}$ alkenylene, wherein the alkylene or alkenylene is optionally interrupted by one heteroatom;

A is selected from the group consisting of —O—, —C(O)—, —CH₂—, —S(O)$_{0-2}$—, and —N(R₄)—;

A' is selected from the group consisting of —O—, —S(O)$_{0-2}$—, —N(—Q—R₄)—, and —CH₂—;

each Q is independently selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, and —C(R₆)—N(OR₉)—;

V is selected from the group consisting of —C(R₆)—, —O—C(R₆)—, —N(R₈)—C(R₆)—, and —S(O)₂—;

each W is independently selected from the group consisting of a bond, —C(O)—, and —S(O)₂—; and a and b are independently integers from 1 to 6 with the proviso that a+b is≤7;

or a pharmaceutically acceptable salt thereof.

In one embodiment, the present invention provides a compound of Formula VII:

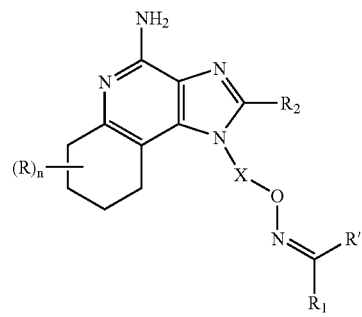

VII wherein:

X is selected from the group consisting of —CH(R$_{9a}$)-alkylene- and —CH(R$_{9a}$)-alkenylene-, wherein the alkylene and alkenylene are optionally interrupted by one or more —O— groups;

each R is independently selected from the group consisting of:
halogen,
hydroxyl,
alklyl, alkenyl,
haloalkyl,
alkoxy,
alkylthio, and
—N($R_9$)$_2$;
$R_1$ and R' are independently selected from the group consisting of:
hydrogen,
alkyl,
alkenyl,
aryl,
arylalkylenyl,
heteroaryl,
heteroarylakylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N($R_8$)$_2$,
—N($R_8$)—C(O)-alkyl,
—O—C(O)-alkyl, and
—C(O)-alkyl;
or $R_1$ and R' can join together to form a ring system selected from the group consisting of:

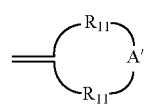

wherein the total number of atoms in the ring is 4 to 9, and

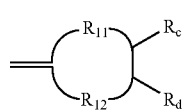

wherein the total number of atoms in the ring is 4 to 9;
$R_2$ is selected from the group consisting of:
—$R_4$,
—X'—$R_4$,
—X'—Y—$R_4$, and
—X'—$R_5$;

X' is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

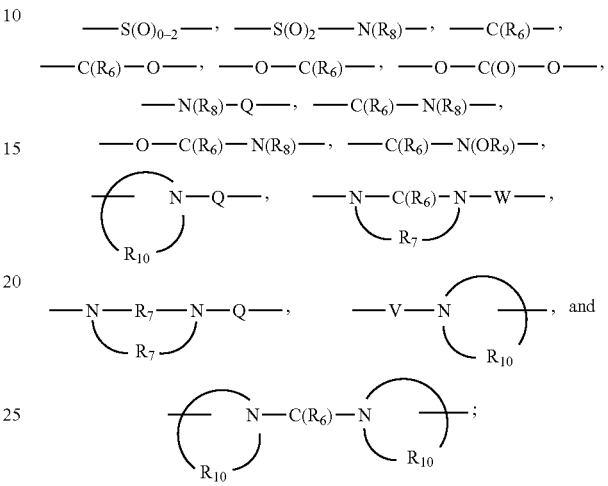

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, allynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_5$ is selected from the group consisting of:

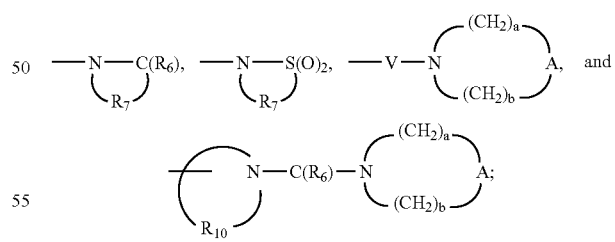

each $R_6$ is independently selected from the group consisting of =O and =S;
each $R_7$ is independently $C_{2-7}$ alkylene;
each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;
each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

$R_c$ and $R_d$ are independently selected from the group consisting of hydrogen, halogen, hydroxyl, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

each $R_{11}$ is independently $C_{1-6}$ alylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

A is selected from the group consisting of —O—, —C(O)—, —CH$_2$—, —S(O)$_{0-2}$—, and —N(R$_4$)—;

A' is selected from the group consisting of —O—, —S(O)$_{0-2}$—, —N(—Q—R$_4$)—, and —CH$_2$—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

each W is independently selected from the group consisting of a bond, —C(O)—, and —S(O)$_2$—;

a and b are independently integers from 1 to 6 with the proviso that a+b is ≤7; and n is an integer from 0 to 4;

or a pharmaceutically acceptable salt thereof.

In one embodiment, the present invention provides a compound of Formula VIII:

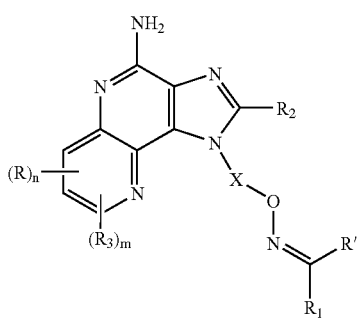

VIII wherein:

X is selected from the group consisting of —CH(R$_{9a}$)-alkylene- and —CH(R$_{9a}$)-alkenylene-, wherein the alkylene and alkenylene are optionally interrupted by one or more —O— groups;

each R is independently selected from the group consisting of:
halogen,
hydroxyl,
alkyl,
alkenyl,
haloalkyl,
alkoxy,
alkylthio, and
—N(R$_9$);

$R_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;

or $R_1$ and R' can join together to form a ring system selected from the group consisting of:

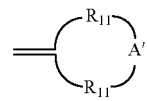

wherein the total number of atoms in the ring is 4 to 9, and

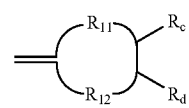

wherein the total number of atoms in the ring is 4 to 9;

$R_2$ is selected from the group consisting of:
—R$_4$,
—X'—R$_4$,
—X'—Y—R$_4$, and
—X'—R$_5$;

$R_3$ is selected from the group consisting of:
—Z—$R_4$,
—Z—X'—$R_4$,
—Z—X'—Y—$R_4$, and
—Z—X'—$R_5$;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:

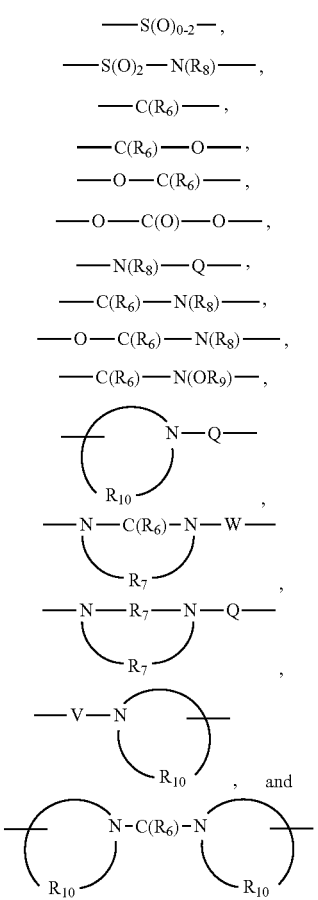

Z is a bond or —O—;

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylanmino)alkyleneoxy, and in the case of alkyl, alkenyl, alkynyl, and heterocyclyl, oxo;

each $R_5$ is independently selected from the group consisting of:

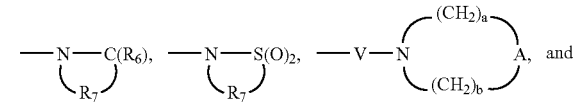

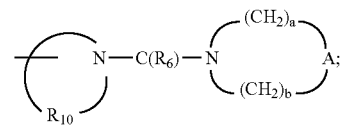

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

$R_c$ and $R_d$ are independently selected from the group consisting of hydrogen, halogen, hydroxyl, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

each $R_{11}$ is independently $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

each A is independently selected from the group consisting of —O—, —C(O)—, —CH$_2$—, —S(O)$_{0-2}$—, and —N($R_4$)—;

A' is selected from the group consisting of —O—, —S(O)$_{0-2}$—, —N(—Q—$R_4$)—, and —CH$_2$—;

each Q is independently selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(OR$_9$)—;

each V is independently selected from the group consisting of —C($R_6$)—, —O—C($R_6$)—, —N($R_8$)—C($R_6$)—, and —S(O)$_2$—;

each W is independently selected from the group consisting of a bond, —C(O)—, and —S(O)$_2$—;

a and b are independently integers from 1 to 6 with the proviso that a+b is ≤7;

n is an integer from 0 to 3; and m is 0 or 1, with the proviso that when m is 1, n is 0 or 1;

or a pharmaceutically acceptable salt thereof.

In one embodiment, the present invention provides a compound of Formula IX:

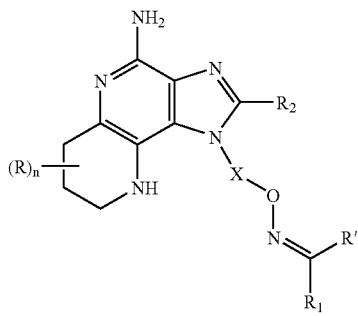

wherein:
X is selected from the group consisting of —CH(R$_{9a}$)-alkylene- and —CH(R$_{9a}$)-alkenylene-, wherein the alkylene and alkenylene are optionally interrupted by one or more —O— groups;
each R is independently selected from the group consisting of:
halogen,
hydroxyl,
alkyl,
alkenyl,
haloalkyl,
alkoxy,
alkylthio, and
—N(R$_9$)$_2$;
R$_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;
or R$_1$ and R' can join together to form a ring system selected from the group consisting of:

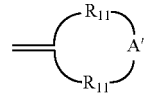

wherein the total number of atoms in the ring is 4 to 9, and

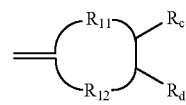

wherein the total number of atoms in the ring is 4 to 9;
R$_2$ is selected from the group consisting of:
—R$_4$,
—X'—R$_4$,
—X'—Y—R$_4$, and
—X'—R$_5$;
X' is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

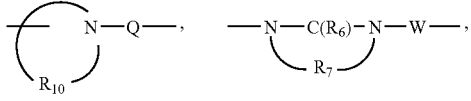

each R$_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

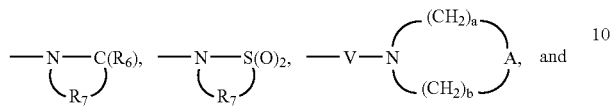

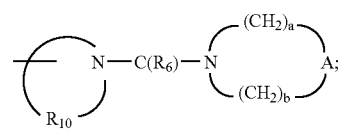

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

$R_c$ and $R_d$ are independently selected from the group consisting of hydrogen, halogen, hydroxyl, alkyl, alkenyl, aryl, haloalkyl, alkoxy, alkylthio, and —$N(R_9)_2$; or $R_c$ and $R_d$ can join to form a fused aryl ring or fused 5-10 membered heteroaryl ring containing one to four heteroatoms;

each $R_{11}$ is independently $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

A is selected from the group consisting of —O—, —C(O)—, —CH$_2$—, —S(O)$_{0-2}$—, and —N(R$_4$)—;

A' is selected from the group consisting of —O—, —S(O)$_{0-2}$—, —N(—Q—R$_4$)—, and —CH$_2$—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

each W is independently selected from the group consisting of a bond, —C(O)—, and S(O)$_2$—;

a and b are independently integers from 1 to 6 with the proviso that a+b is ≤7; and n is an integer from 0 to 3;

or a pharmaceutically acceptable salt thereof.

In one embodiment, the present invention provides a compound of Formula X:

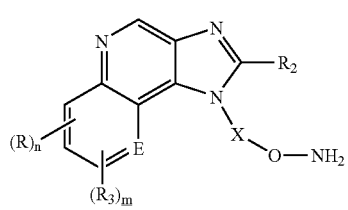

wherein:

E is selected from the group consisting of CH, CR, CR$_3$, and N, with the proviso that when E is CR$_3$, m is 0, and n is 0 or 1, and with the further proviso that when E is CR and m is 1, n is 0;

X is selected from the group consisting of —CH(R$_{9a}$)-alkylene- and —CH(R$_{9a}$)-alkenylene-, wherein the alkylene and alkenylene are optionally interrupted by one or more —O— groups;

n is an integer from 0 to 3;

m is 0 or 1, with the proviso that when m is 1, n is 0 or 1;

each R is independently selected from the group consisting of:
halogen,
hydroxyl,
alkyl,
alkenyl,
haloalkyl,
alkoxy,
alkylthio, and
—N(R$_9$)$_2$;

$R_2$ is selected from the group consisting of:
—R$_4$,
—X'—R$_4$,
—X'—Y—R$_4$, and
—X'—R$_5$;

$R_3$ is selected from the group consisting of:
—Z—X'—R$_4$,
—Z—X'—Y—R$_4$, and
—Z—X'—R$_5$;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:

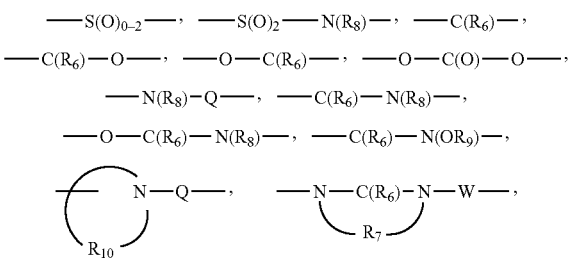

-continued

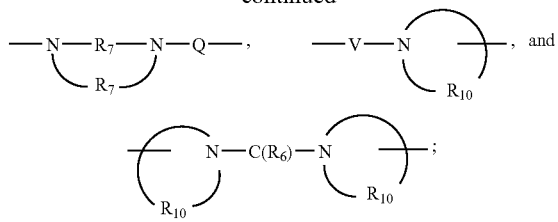

Z is a bond or —O—;

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

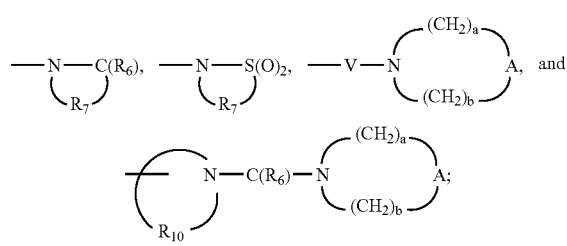

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ aalkenyl, $C_{1-10}$ alkoxy-$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

each A is independently selected from the group consisting of —O—, —C(O)—, —CH$_2$—, —S(O)$_{0-2}$—, and —N(R$_4$)—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

each V is independently selected from the group consisting of —C(R$_6$)—, —O—C(R$_6$)—, —N(R$_8$)—C(R$_6$)—, and —S(O)$_2$—;

each W is independently selected from the group consisting of a bond, —C(O)—, and —S(O)$_2$—; and a and b are independently integers from 1 to 6 with the proviso that a+b is ≤7;

or a pharmaceutically acceptable salt thereof.

In one embodiment, the present invention provides a compound of Formula XI:

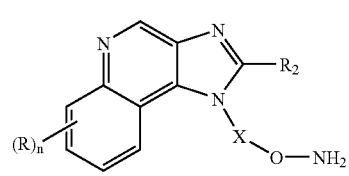

XI wherein:

X is selected from the group consisting of —CH(R$_{9a}$)-alkylene- and —CH(R$_{9a}$)-alkenylene-;

n is an integer from 0 to 4;

each R is independently selected from the group consisting of alkyl, alkoxy, halogen, hydroxyl, and trifluoromethyl;

$R_2$ is selected from the group consisting of;

hydrogen, alkyl, alkenyl, aryl, heteroaryl, heterocyclyl, alkylene-Y"-alkyl, alkylene-Y"-alkenyl, alkylene-Y"-aryl, and alkyl or alkenyl substituted by one or more substituents selected from the group consisting of:

hydroxyl, halogen,

—N(R$_{8a}$)$_2$,

—C(O)—C$_{1-10}$ alkyl,

—C(O)—O—C$_{1-10}$ alkyl,

—N$_3$, aryl, heteroaryl, heterocyclyl,

—C(O)-aryl, and

—C(O)-heteroaryl;

Y" is 0 or —S(O)$_{0-2}$—;

each $R_{8a}$ is independently selected from the group consisting of hydrogen, $C_{1-10}$ alkyl, and $C_{2-10}$ alkenyl; and $R_{9a}$ is selected from the group consisting of hydrogen and alkyl which may be optionally interrupted by one or more —O— groups;

or a pharmaceutically acceptable salt thereof.

In one embodiment, the present invention provides a compound of Formula XII:

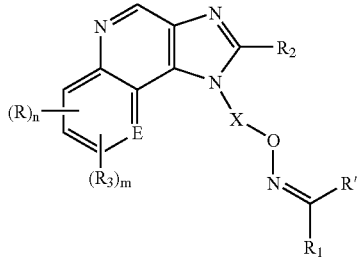

wherein:

E is selected from the group consisting of CH, CR, CR$_3$, and N, with the proviso that when E is CR$_3$, m is 0, and n is 0 or 1, and with the further proviso that when E is CR and m is 1, n is 0;

X is selected from the group consisting of —CH(R$_{9a}$)-alkylene- and —CH(R$_{9a}$)-alkenylene-, wherein the alkylene and alkenylene are optionally interrupted by one or more —O— groups;

each R is independently selected from the group consisting of:
halogen,
hydroxyl,
alkyl,
alkenyl,
haloalkyl,
alkoxy,
alkylthio, and
—N(R$_9$)$_2$;

R$_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkyienyl, heterocyclyl, or heterocylylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;

or R$_1$ and R' can join together to form a ring system selected from the group consisting of:

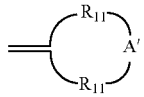

wherein the total number of atoms in the ring is 4 to 9, and

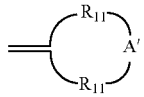

wherein the total number of atoms in the ring is 4 to 9;

R$_2$ is selected from the group consisting of:
—R$_4$,
—X'—Y—R$_4$, and
—X'—R$_5$;

R$_3$ is selected from the group consisting of:
—Z—R$_4$,
—Z—X'—R$_4$,
—Z—X'—Y—R$_4$, and
—Z—X'—R$_5$;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:

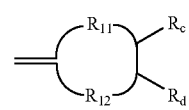

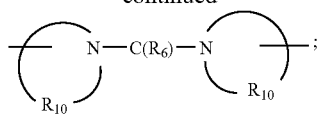

Z is a bond or —O—;

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the aRyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

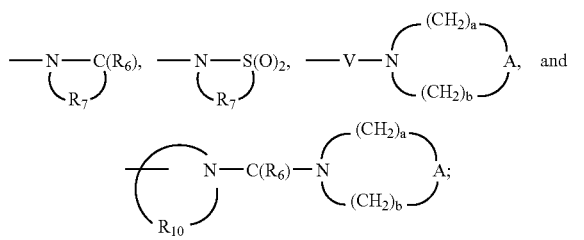

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

$R_c$ and $R_d$ are independently selected from the group consisting of hydrogen, halogen, hydroxyl, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

each $R_{11}$ is independently $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

each A is independently selected from the group consisting of —O—, —C(O)—, —CH$_2$—, —S(O)$_{0-2}$—, and —N(R$_4$)—;

A' is selected from the group consisting of —O—, —S(O)$_{0-2}$—, —N(—Q—R$_4$)—, and —CH$_2$—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

each V is independently selected from the group consisting of —C(R$_6$)—, —O—C(R$_6$)—, —N(R$_8$)—C(R$_6$)—, and —S(O)$_2$—;

each W is independently selected from the group consisting of a bond, —C(O)—, and —S(O)$_2$—;

a and b are independently integers from 1 to 6 with the proviso that a+b is ≤7;

n is an integer from 0 to 3; and m is 0 or 1, with the proviso that when m is 1, n is 0 or 1;

or a pharmaceutically acceptable salt thereof.

In one embodiment, the present invention provides a compound of Formula XIII:

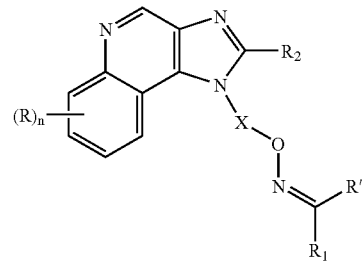

wherein:

X is selected from the group consisting of —CH(R$_{9a}$)-alkylene- and —CH(R$_{9a}$)-alkenylene-;

n is an integer from 0 to 4;

each R is independently selected from the group consisting of alkyl, alkoxy, halogen, hydroxyl, and trifluoromethyl;

$R_1$ and R' are independently selected from the group consisting of:

hydrogen,
alkyl,
alkenyl,
aryl,
alkylene-aryl,
heteroaryl,
heterocyclyl, and
alkyl, alkenyl, aryl, arylalkylenyl, heteroaryl or heterocyclyl substituted by one or more substituents selected from the group consisting of:
hydroxyl,
alkyl,
haloalkyl,
hydroxyalkyl,
—O-alkyl,
—S-alkyl,
—O-haloalkyl,
halogen,
nitrile,
aryl,
heteroaryl,
heterocyclyl,
—O-aryl,
—O-alkylene-aryl,
—C(O)—O-alkyl,
—C(O)—N(R$_{8a}$)$_2$, and
—N(R$_{8a}$)—C(O)-alkyl;

or $R_1$ and R' can join together to form a ring system containing one or two saturated or unsaturated rings optionally including one or more heteroatoms;

$R_2$ is selected from the group consisting of:
hydrogen,
alkyl,
alkenyl,
aryl,
heteroaryl,
heterocyclyl,
alkylene-Y"-alkyl,
alkylene-Y"-alkenyl,
alkylene-Y"-aryl, and
alkyl or alkenyl substituted by one or more subsfituents selected from the group consisting of:
hydroxyl,
halogen,
—$N(R_{8a})_2$,
—$C(O)$—$C_{1-10}$ alkyl,
—$C(O)$—O—$C_{1-10}$ alkyl,
—$N_3$,
aryl,
heteroaryl,
heterocyclyl,
—C(O)-aryl, and
—C(O)-heteroaryl;

Y" is 0 or —$S(O)_{0-2}$—;

each $R_{8a}$ is independently selected from the group consisting of hydrogen, $C_{1-10}$ alkyl, and $C_{2-10}$ alkenyl; and $R_{9a}$ is selected from the group consisting of hydrogen and alkyl which may be optionally interrupted by one or more —O— groups;

or a pharmaceutically acceptable salt thereof.

In one embodiment, the present invention provides a compound of Formula XIV:

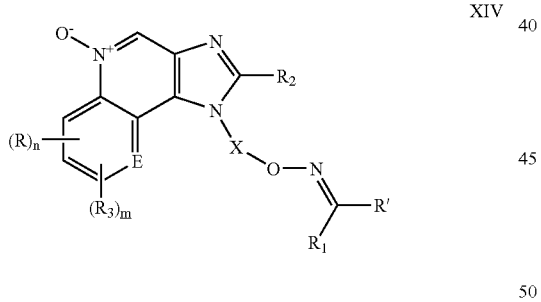

XIV wherein:

E is selected from the group consisting of CH, CR, $CR_3$, and N, with the proviso that when E is $CR_3$, m is 0, and n is 0 or 1, and with the further proviso that when E is CR and m is 1, n is 0;

X is selected from the group consisting of —$CH(R_{9a})$-alkylene- and —$CH(R_{9a})$-alkenylene-, wherein the alkylene and alkenylene are optionally interrupted by one or more —O— groups;

each R is independently selected from the group consisting of:
halogen,
hydroxyl,
alkyl,
alkenyl,
haloalkyl,
alkoxy,
alkylthio, and
—$N(R_9)_2$;

$R_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—$S(O)_{0-2}$-alkyl,
—$S(O)_{0-2}$-aryl,
—NH—$S(O)_2$-alkyl,
—NH—$S(O)_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—$N(R_8)_2$,
—$N(R_8)$—C(O)-alkyl,
—O—C(O)-alkyl, and
—C(O)-alkyl;

or $R_1$ and R' can join together to form a ring system selected from the group consisting of:

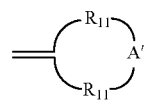

wherein the total number of atoms in the ring is 4 to 9, and

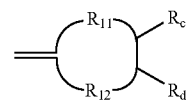

wherein the total number of atoms in the ring is 4 to 9;

$R_2$ is selected from the group consisting of:
—$R_4$,
—X'—$R_4$,
—X'—Y—$R_4$, and
—X'—$R_5$;

$R_3$ is selected from the group consisting of:
—Z—$R_4$,

—Z—X'—R₄,
—Z—X'—Y—R₄, and
—Z—X'—R₅;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:

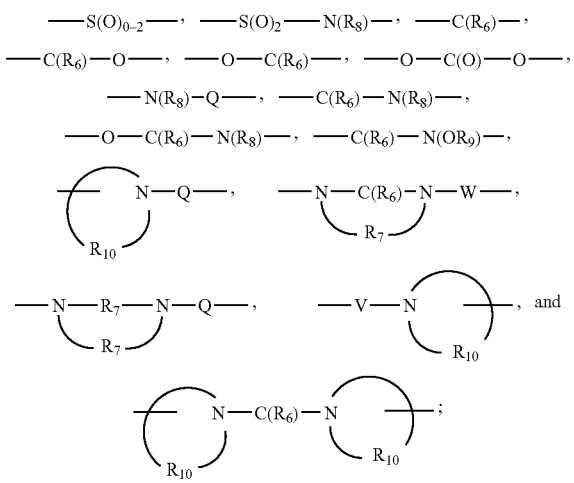

Z is a bond or —O—;

each R₄ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each R₅ is independently selected from the group consisting of:

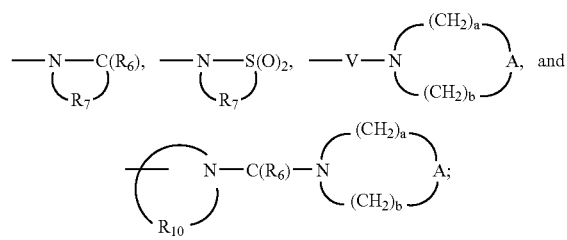

each R₆ is independently selected from the group consisting of =O and =S;

each R₇ is independently C₂₋₇ alkylene;
each R₈ is independently selected from the group consisting of hydrogen, C₁₋₁₀ alkyl, C₂₋₁₀ alkenyl, C₁₋₁₀ alkoxy-C₁₋₁₀ alkylenyl, and aryl-C₁₋₁₀ alkylenyl;
each R₉ is independently selected from the group consisting of hydrogen and alkyl;
R₉ₐ is selected from the group consisting of hydrogen and alkyl which is optionally interrupted by one or more —O— groups;
each R₁₀ is independently C₃₋₈ alllylene;
R_c and R_d are independently selected from the group consisting of hydrogen, halogen, hydroxyl, alkyl, alkenyl, aryl, haloalkyl, alkoxy, alkylthio, and —N(R₉)₂; or R_c and R_d can join to form a fused aryl ring or fused 5-10 membered heteroaryl ring containing one to four heteroatoms;
each R₁₁ is independently C₁₋₆ alkylene or C₂₋₄ alkenylene, wherein the alkylene or alkenylene is optionally interrupted by one heteroatom;
R₁₂ is selected from the group consisting of a bond, C₁₋₅ alkylene, and C₂₋₅ alkenylene, wherein the alkylene or alkenylene is optionally interrupted by one heteroatom;
each A is independently selected from the group consisting of —O—, —C(O)—, —CH₂—, —S(O)₀₋₂—, and —N(R₄)—;
A' is selected from the group consisting of —O—, —S(O)₀₋₂—, —N(—Q—R₄)—, and —CH₂—;
each Q is independently selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, and —C(R₆)—N(OR₉)—;
each V is independently selected from the group consisting of —C(R₆)—, —O—C(R₆)—, —N(R₈)—C(R₆)—, and —S(O)₂—;
each W is independently selected from the group consisting of a bond, —C(O)—, and —(O)₂—;
a and b are independently integers from 1 to 6 with the proviso that a+b is ≤7;
n is an integer from 0 to 3; and
m is 0 or 1, with the proviso that when m is 1, n is 0 or 1;
or a pharmaceutically acceptable salt thereof.

In one embodiment, the present invention provides a compound of Formula XV:

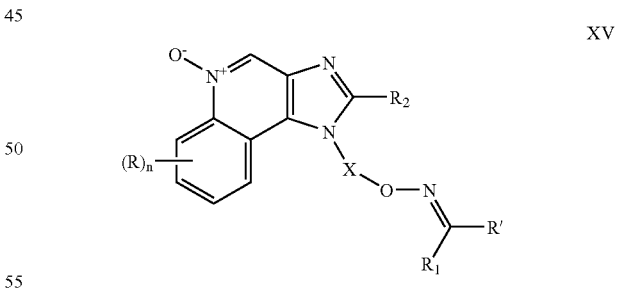

XV wherein:
X is selected from the group consisting of —CH(R₉ₐ)-alkylene- and —CH(R₉ₐ)-alkenylene-;
each R is independently selected from the group consisting of alkyl, alkoxy, halogen, hydroxyl, and trifluoromethyl;
n is an integer from 0 to 4;
R₁ and R' are independently selected from the group consisting of:
hydrogen,
alkyl,
alkenyl, aryl,
alkylene-aryl,
heteroaryl,
heterocyclyl, and
alkyl, alkenyl, aryl, arylalkylenyl, heteroaryl or heterocyclyl substituted by one or more substituents selected from the group consisting of:
hydroxyl,
alkyl,
haloalkyl,
hydroxyalkyl,
—O-alkyl,
—S-alkyl,
—O-haloalkyl,
halogen,
nitrile,
aryl,
heteroaryl,
heterocyclyl,
—O-aryl,
—O-alkylene-aryl,
—C(O)—O-alkyl,
—C(O)—N($R_{8a}$)$_2$, and
—N($R_{8a}$)—C(O)-alkyl;
or $R_1$ and R' can join together to form a ring system containing one or two saturated or unsaturated rings optionally including one or more heteroatoms;
$R_2$ is selected from the group consisting of:
hydrogen,
alkyl,
alkenyl,
aryl,
heteroaryl,
heterocyclyl,
alkylene-Y"-alkyl,
alkylene-Y"-alkenyl,
alkylene-Y"-aryl, and
alkyl or alkenyl substituted by one or more substituents selected from the group consisting of:
hydroxyl,
halogen,
—N($R_{8a}$)$_2$,
—C(O)—$C_{1-10}$ alkyl,
—C(O)—O—$C_{1-10}$ alkyl,
—$N_3$,
aryl,
heteroaryl,
heterocyclyl,
—C(O)-aryl, and
—C(O)-heteroaryl;
Y" is —O— or S(O)$_{0-2}$—;
$R_{9a}$ is selected from the group consisting of hydrogen and alkyl which may be optionally interrupted by one or more —O— groups; and
each $R_{8a}$ is independently selected from the group consisting of hydrogen, $C_{1-10}$ alkyl, and $C_{2-10}$ alkenyl;
or a pharmaceutically acceptable salt thereof.

In one embodiment, the present invention provides a compound of Formula XVI:

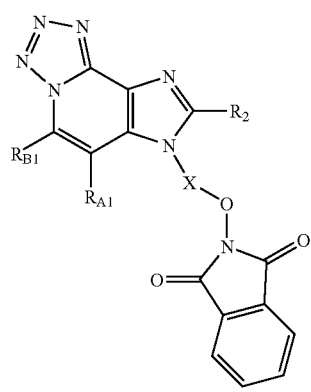

XVI wherein:
X is selected from the group consisting of —CH($R_{9a}$)-alkylene- and —CH($R_{9a}$)-alkenylene-, wherein the alkylene and alkenylene are optionally interrupted by one or more —O— groups;
$R_2$ is selected from the group consisting of:
—$R_4$,
—X'—$R_4$,
—X'—Y—$R_4$, and
—X'—$R_5$;
$R_{A1}$ and $R_{B1}$ are each independently selected from the group consisting of:
hydrogen,
halogen,
alkyl,
alkenyl,
alkoxy,
alkylthio, and
—N($R_9$)$_2$;
X' is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

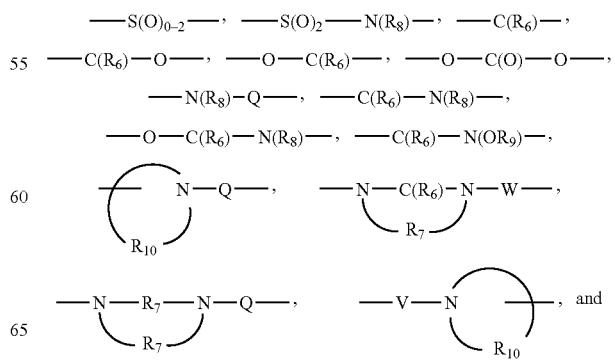

45
-continued

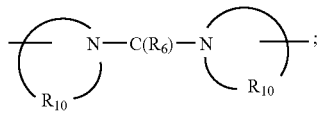

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

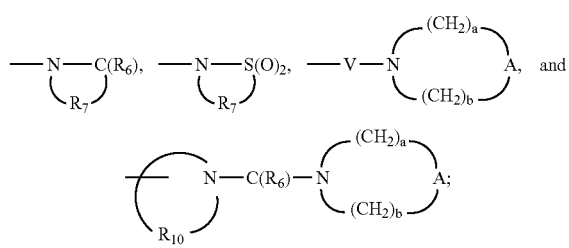

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

A is selected from the group consisting of —O—, —C(O)—, —CH$_2$—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_6$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof.

46
In one embodiment, the present invention provides a compound of Formula XVII:

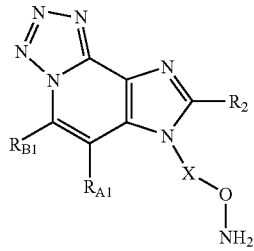

XVII wherein:

X is selected from the group consisting of —CH(R$_{9a}$)-alkylene- and —CH(R$_{9a}$)-alkenylene-, wherein the alkylene and alkenylene are optionally interrupted by one or more —O— groups;

$R_2$ is selected from the group consisting of:
—R$_4$,
—X'—R$_4$,
—X'—Y—R$_4$, and
—X'—R$_5$;

$R_{A1}$ and $R_{B1}$ are each independently selected from the group consisting of:
hydrogen,
halogen,
alkyl,
alkenyl,
alkoxy,
alkylthio, and
—N(R$_9$)$_2$;

X' is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—S(O)$_{0-2}$—, —S(O)$_2$—N(R$_8$)—, —C(R$_6$)—,
—C(R$_6$)—O—, —O—C(R$_6$)—, —O—C(O)—O—,
—N(R$_8$)-Q—, —C(R$_6$)—N(R$_8$)—,
—O—C(R$_6$)—N(R$_8$)—, —C(R$_6$)—N(OR$_9$)—,

[cyclic structures with N—Q, N—C(R$_6$)—N—W, N—R$_7$—N—Q, V—N, and N—C(R$_6$)—N groups containing R$_{10}$ and R$_7$];

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

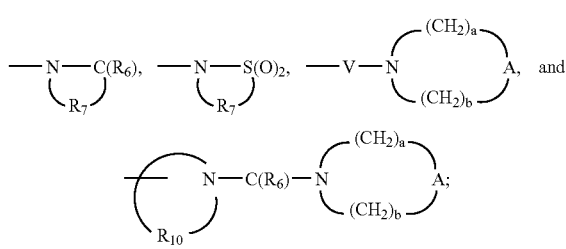

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

A is selected from the group consisting of —O—, —C(O)—, —CH$_2$—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_6$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is≤7; or a pharmaceutically acceptable salt thereof.

In one embodiment, the present invention provides a compound of Formula XVIII:

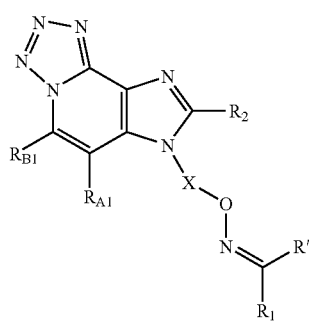

XVIII wherein:

X is selected from the group consisting of —CH(R$_{9a}$)-alkylene- and —CH(R$_{9a}$)-alkenylene-, wherein the alkylene and alkenylene are optionally interrupted by one or more —O— groups;

$R_{A1}$ and $R_{B1}$ are each independently selected from the group consisting of.
hydrogen,
halogen,
alkyl,
alkenyl,
alkoxy,
alkylthio, and
—N(R$_9$)$_2$;

$R_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;

or $R_1$ and R' can join together to form a ring system selected from the group consisting of:

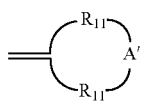

wherein the total number of atoms in the ring is 4 to 9, and

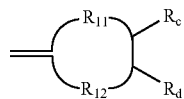

wherein the total number of atoms in the ring is 4 to 9;

$R_2$ is selected from the group consisting of:
—$R_4$,
—X'—$R_4$,
—X'—Y—$R_4$, and
—X'—$R_5$;

X' is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

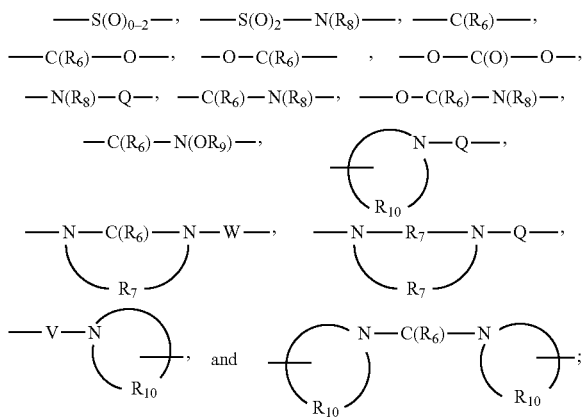

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

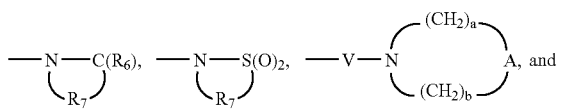

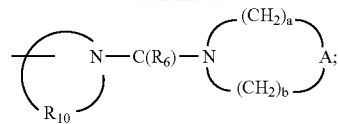

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

$R_c$ and $R_d$ are independently selected from the group consisting of hydrogen, halogen, hydroxyl, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

each $R_{11}$ is independently $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

A is selected from the group consisting of —O—, —C(O)—, —CH$_2$—, —S(O)$_{0-2}$—, and —N($R_4$)—;

A' is selected from the group consisting of —O—, —S(O)$_{0-2}$—, —N(—Q—$R_4$)—, and —CH$_2$—;

each Q is independently selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(OR$_9$)—;

V is selected from the group consisting of —C($R_6$)—, —O—C($R_6$)—, —N($R_8$)—C($R_6$)—, and —S(O)$_2$—;

each W is independently selected from the group consisting of a bond, —C(O)—, and —S(O)$_2$—; and a and b are independently integers from 1 to 6 with the proviso that a+b is ≤7; or a pharmaceutically acceptable salt thereof.

For any of the compounds presented herein, each one of the following variables (e.g., R, R', R", R''', $R_1$, $R_2$, $R_3$, m, n, A, and so on) in any of its embodiments can be combined with any one or more of the other variables in any of their embodiments as would be understood by one of slill in the art. Each of the resulting combinations of variables is an embodiment of the present invention.

For certain embodiments, each of R, R", and R''' is independently a non-interfering substituent. For certain embodiments, each R and R" is independently selected from the group consisting of hydrogen and non-interfering substituents. Herein, "non-interfering" means that the immunomodulator activity of the compound is not destroyed.

For certain embodiments, each R is independently selected from the group consisting of: halogen, hydroxyl, alkyl, alkenyl, haloalkyl, alkoxy, alkylthio, and —N($R_9$)$_2$. For certain embodiments, each R is independently selected from the group consisting of alkyl, alkoxy, halogen, hydroxyl, and trifluoromethyl.

For certain embodiments, $R_1$ and R' are independently selected from the group consisting of: hydrogen, alkyl, alkenyl, aryl, arylallylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of: hydroxyl, alkyl, haloalkyl, hydroxyalkyl, alkoxy, dialkylamino, —S(O)$_{0-2}$-alkyl, —S(O)$_{0-2}$-aryl, —NH—S(O)$_2$-alkyl, —NH—S(O)$_2$-aryl, haloalkoxy, halogen, nitrile, nitro, aryl, heteroaryl, heterocyclyl, aryloxy, arylalkyleneoxy, —C(O)—O-alkyl, —C(O)—N(R$_8$)$_2$, —N(R$_8$)—C(O)-alkyl, —O—C(O)-alkyl, and —C(O)-alkyl.

For certain embodiments, R$_1$ and R' join together to form a ring system. The size and components of the ring system are not imiting as long as they do not destroy the immunomodulator activity of the compound (i.e., they are non-interfering). Typically, this means that the ring system is a monocyclic ring system containing 5 to 8 atoms in the ring or a bicyclic ring system containing 9 to 11 atoms in the rings. For certain embodiments, the ring system contains one or two saturated or unsaturated rings. For certain embodiments, the ring system contains one or two heteroatoms (e.g., O, S, N).

The ring system is optionally substituted by one or more substituents selected from the group consisting of alkyl, aryl, alkylene-aryl, and —C(O)-alkyl. Also, one of skill in the art would understand that the ring system would not include an aromatic ring attached to the N═C moiety.

For certain embodiments, R$_1$ and R' join to form a ring system selected from the group consisting of cyclopentyl, cyclohexyl, cycloheptyl, piperidinyl, and indanyl.

For certain embodiments, R$_1$ and R' can join together to form a ring system selected from the group consisting of:

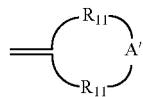

wherein the total number of atoms in the ring is 4 to 9, and

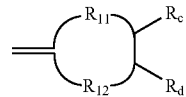

wherein the total number of atoms in the ring is 4 to 9.

For certain embodiments, at least one of R' or R$_1$ is hydrogen. For certain embodiments, at least one of R' or R$_1$ is selected from-the group consisting of aryl, heteroaryl, and alkyl, wherein the aryl, heteroaryl, and alkyl are optionally substituted. For certain embodiments, at least one of R' or R$_1$ is aryl or substituted aryl and at least one of R' or R$_1$ is hydrogen. For certain embodiments, at least one of R' or R$_1$ is heteroaryl or substituted heteroaryl and at least one of R' or R$_1$ is hydrogen.

For certain embodiments, R$_1$ and R' join together to form a ring system of the formula

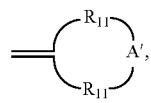

wherein A' is —N(—Q—R$_4$)— or —CH$_2$—, Q is a bond or —C(O)—, and R$_4$ is alkyl. For such embodiments, preferably, the ring system is

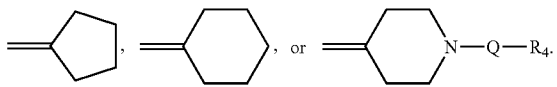

For certain embodiments, R$_1$ and R' are each methyl.

For certain embodiments, R" is hydrogen or a non-interfering substituent. For certain embodiments, R" is selected from the group consisting of: —R$_4$, —X'—R$_4$, —X'—Y—R$_4$, and —X'—R$_5$. For certain embodiments, R" is hydrogen, alkoxyalkylenyl, —R$_4$, —X—R$_4$, or —X'—Y—R$_4$. For certain of these embodiments, preferably, X' is C$_{1-2}$ alkylene; Y is —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)—Q—, —C(R$_6$)—N(R$_8$)—, —O—C(R$_6$)—N(R$_8$)—, or —C(R$_6$)—N(OR$_9$)—; and R$_4$ is alkyl.

For certain embodiments, R" is selected from the group consisting of: hydrogen, alkyl, alkenyl, aryl, heteroaryl, heterocyclyl, alkylene-Y"-alkyl, alkylene-Y"-alkenyl, alkylene-Y"-aryl, and alkyl or alkenyl substituted by one or more substituents selected from the group consisting of: hydroxyl, halogen, —N(R$_{8a}$)$_2$, —C(O)—C$_{1-10}$ alkyl, —C(O)—O—C$_{1-10}$ alkyl, —N$_3$, aryl, heteroaryl, heterocyclyl, —C(O)-aryl, and —C(O)-heteroaryl. For these embodiments, Y" is —O— or —S(O)$_{0-2}$—.

For certain embodiments, R" is selected from the group consisting of hydrogen, alkyl, and alkoxyalkylenyl (i.e., alkylene-O-alkyl). For certain embodiments, R" is selected from the group consisting of hydrogen, methyl, ethyl, propyl, butyl, ethoxymethyl, 2-methoxyethyl, and methoxymethyl.

For certain embodiments, R$_2$ is selected from the group consisting of: —R$_4$, —X'—R, —X'—Y—R$_4$, and —X'—R$_5$. For certain embodiments, R$_2$ is hydrogen, alkoxyalkylenyl, —R$_4$, —X'—R$_4$, or —X'—Y—R$_4$. For certain of these embodiments, preferably, X' is C$_{1-2}$ alkylene; Y is —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)—Q—, —C(R$_6$)—N(R$_8$)—, —O—C(R$_6$)—N(R$_8$)—, or —C(R$_6$)—N(OR$_9$)—; and R$_4$ is alkyl.

For certain embodiments, R$_2$ is selected from the group consisting of: hydrogen, alkyl, alkenyl aryl, heteroaryl, heterocyclyl, alkylene-Y"-alkyl, alkylene-Y"-alkenyl, alkylene-Y"-aryl, and alkyl or alkenyl substituted by one or more substituents selected from the group consisting of: hydroxyl, halogen, —N(R$_{8a}$)$_2$ —C(O)—C$_{1-10}$ alkyl, —C(O)—O—C$_{1-10}$ alkyl, —N$_3$, aryl, heteroaryl, heterocyclyl, —C(O)-aryl, and —C(O)-heteroaryl. For these embodiments, Y" is —O— or —S(O)$_{0-2}$—.

For certain embodiments, R$_2$ is selected from the group consisting of hydrogen, alkyl, and alkoxyalkylenyl (i.e., alkylene-O-alkyl). For certain embodiments, R$_2$ is selected from the group consisting of hydrogen, methyl, ethyl, propyl, butyl, ethoxymethyl, 2-methoxyethyl, and methoxymethyl.

For certain embodiments, R$_3$ is selected from the group consisting of: —Z—R$_4$, —Z—X—R$_4$, —Z—X'—Y—R$_4$, and —Z—X'—R$_5$. For certain embodiments, R$_3$ is phenyl, pyridin-3-yl, pyridin4-yl, 5-(hydroxymethyl)pyridin-3-yl, 2-ethoxyphenyl, 3-(morpholine4-carbonyl)phenyl, or 3-(N,N-dimethylaminocarbonyl)phenyl. For certain of these embodiments, m is 1.

For certain embodiments, each R$_4$ is independently selected from the group consisting of hydrogen, alkyl alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo. For certain embodiments, $R_4$ is alkyl.

For certain embodiments, each $R_5$ is independently selected from the group consisting of:

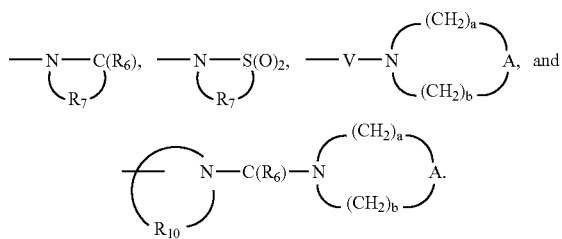

For certain embodiments, each R is independently selected from the group consisting of =O and =S.

For certain embodiments, each $R_7$ is independently $C_{2-7}$ alkylene.

For certain embodiments, each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl.

For certain embodiments, each $R_{8a}$ is independently selected from the group consisting of hydrogen, $C_{1-10}$ alkyl, and $C_{2-10}$ alkenyl.

For certain embodiments, each $R_9$ is independently selected from the group consisting of hydrogen and alkyl.

For certain embodiments, $R_{9a}$ is selected from the group consisting of hydrogen and alkyl which is optionally interrupted by one or more —O— groups.

For certain embodiments, each $R_{10}$ is independently $C_{3-8}$ alkylene.

For certain embodiments, each $R_{11}$ is independently $C_{1-6}$ alkylene or $C_{2-6}$ alkenylene, wherein the alkylene or alkenylene is optionally interrupted by one heteroatom.

For certain embodiments, $R_{12}$ is selected from the group consisting of a bond, $C_{1-5}$ alkylene, and $C_{2-5}$ alkenylene, wherein the alkylene or alkenylene is optionally interrupted by one heteroatom.

For certain embodiments, $R_A$ and $R_B$ are each independently selected from the group consisting of: hydrogen, halogen, alkyl, alkenyl, alkoxy, alkylthio, and —N($R_9$)$_2$; or when taken together, $R_A$ and $R_B$ form a fused aryl ring or heteroaryl ring containing one heteroatom selected from the group consisting of N and S, wherein the aryl or heteroaryl ring is unsubstituted or substituted by one or more R''' groups; or when taken together, $R_A$ and $R_B$ form a fused 5 to 7 membered saturated ring, optionally containing one heteroatom selected from the group consisting of N and S, and unsubstituted or substituted by one or more R groups.

For certain embodiments, $R_A$ and $R_B$ are each independently selected from the group consisting of: hydrogen, halogen, alkyl, alkenyl, alkoxy, alkylthio, and —N($R_9$)$_2$; or when taken together, $R_A$ and $R_B$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group; or when taken together, $R_A$ and $R_B$ form a fused 5 to 7 membered saturated ring, optionally containing one heteroatom selected from the group consisting of N and S, and unsubstituted or substituted by one or more R groups. In certain of these embodiments the fused aryl ring is a benzene ring. In certain of these embodiments the heteroaryl ring is a pyridine ring. In certain of these embodiments the saturated ring is a cyclohexane ring. In certain of these embodiments the saturated ring is a piperidine ring.

For certain embodiments, $R_A$ and $R_B$ form a fused aryl ring or heteroaryl ring containing one N, wherein the aryl ring or heteroaryl ring is unsubstituted. In certain of these embodiments the fused aryl ring is a benzene ring. In certain of these embodiments the heteroaryl ring is a pyridine ring. For certain embodiments, $R_A$ and $R_B$ form a fused 5 to 7 membered saturated ring, optionally containing one N, wherein the saturated ring is unsubstituted. In certain of these embodiments the saturated ring is a cyclohexane ring. In certain of these embodiments the saturated ring is a piperidine ring.

For certain embodiments, $R_{A1}$ and $R_{B1}$ are each independently selected from the group consisting of: hydrogen, halogen, alkyl, alkenyl, alkoxy, alkylthio, and —N($R_9$)$_2$. For certain embodiments, $R_{A1}$ and $R_{B1}$ are each methyl.

For certain embodiments, $R_c$ and $R_d$ are independently selected from the group consisting of hydrogen, halogen, hydroxyl, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

For certain embodiments, each A is independently selected from the group consisting of —O—, —C(O)—, —CH$_2$—, —S(O)$_{0-2}$—, and —N($R_4$)—.

For certain embodiments, A' is selected from the group consisting of —O—, —S(O)$_{0-2}$—, —N(—Q—$R_4$)—, and —CH$_2$—. For certain embodiments A' is —N(—Q—$R_4$)— or —CH$_2$—.

For certain embodiments, E is selected from the group consisting of CH, CR, CR$_3$, and N. In certain embodiments, when E is CR$_3$, then m is 0 and n is 0 or 1. In certain embodiments, when E is.CR and m is 1, n is 0. Preferably, E is CH or N.

For certain embodiments, Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—. For certain embodiments, Q is a bond or —C(O)—.

For certain embodiments, each V is independently selected from the group consisting of —C($R_6$)—, —O—C($R_6$)—, —N($R_8$)—C($R_6$)—, and —S(O)$_2$—.

For certain embodiments, W is selected from the group consisting of a bond, —C(O)—, and —S(O)$_2$—.

For certain embodiments, X is selected from the group consisting of —CH($R_{9a}$)-alkylene- and —CH($R_{9a}$)-alkenylene-, wherein the alkylene and alkenylene are optionally interrupted by one or more —O— groups. For certain embodiments, X is selected from the group consisting of —CH($R_{9a}$)-alkylene- and —CH($R_{9a}$)-alkenylene-. For certain embodiments, X is —CH($R_{9a}$)-alkylene-, wherein the alkylene is optionally interrupted by one or more —O— groups. For certain embodiments, X is —C$_{3-5}$ alkylene- or —CH$_2$CH$_2$OCH$_2$CH$_2$—. For certain embodiments, X is —CH(R$_{9a}$)—C$_{1-5}$ alkylene- and for other embodiments X is propylene or butylene.

For certain embodiments, each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups. For certain embodiments, each X' is independently C$_{1-2}$ alkylene.

For certain embodiments, each Y is independently selected from the group consisting of: —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)—Q—, —C(R$_6$)—N(R$_8$)—, —O—C(R$_6$)—N(R$_8$)—, —C(R$_6$)—N(OR$_9$)—,

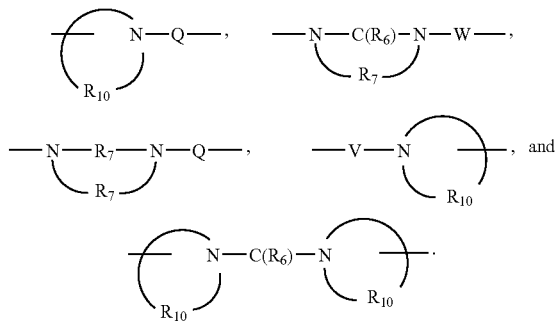

For certain embodiments, each Y is independently —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)—Q—, —C(R$_6$)—N(R$_8$)—, —O—C(R$_6$)—N(R$_8$)—, or —C(R$_6$)—N(OR$_9$)—.

For certain embodiments, Y" is —O— or —S(O)$_{0-2}$—.

For certain embodiments, Z is a bond or —O—. Preferably, Z is a bond.

For certain embodiments, n is an integer from 0 to 4. For certain embodiments, n is an integer from 0 to 3. For certain embodiments, n is 0 or 1. For certain embodiments, n is 0.

For certain embodiments, m is 0 or 1. For certain embodiments, m is 1.

For certain embodiments, when m is 1, n is 0 or 1.

For certain embodiments, when m is 0, n is 0 or 1.

For certain embodiments, m and n are each 0.

For certain embodiments, a and b are independently integers from 1 to 6 with the proviso that a+b is≤7.

As used herein, the terms "alkyl," "alkenyl," "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl, homopiperazinyl, and the like.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N(R$_9$)$_2$ each R$_9$ group is independently selected. In another example, when an R$_2$ and an R$_3$ group both contain an R$_4$ group, each R$_4$ group is independently selected. In a fllrher example, when more than one Y group is present (i.e., R$_2$ and R$_3$ both contain a Y group) and each Y group contains one or more R$_8$ groups, then each Y group is independently selected, and each R$_8$ group is independently selected.

The invention is inclusive of the compounds described herein and salts thereof in any of their pharmaceutically acceptable forms, including isomers such as diastereomers and enantiomers, solvates, polymorphs, and the like. In particular, if a compound is optically active, the invention specifically includes each of the compound's enantiomers as well as racemic mixtures of the enantiomers.

Preparation of the Compounds

Compounds of the invention can be prepared according to Reaction Scheme I where R, R', R$_1$, R$_2$, m, and X are as defined above; E' is carbon (imidazoquinoline ring) or nitrogen (imidazonaphthyridine ring); n is an integer from 0 to 4 (imidazoquinoline ring) or 0 to 3 (imidazonaphthyridine ring) with the proviso that when m is 1, n is 0 or 1; and D is —Br, —I, or —OCH$_2$Ph, wherein Ph is phenyl. In step (1) of Reaction Scheme I, an aniline or aminopyridine of Formula XX is treated with the condensation product generated from 2,2-dimethyl-1,3-dioxane4,6-dione (Meldrun's acid) and triethyl orthoformate to provide an imine of Formula XXI. The reaction is conveniently carried out by adding a solution of an aniline or amunopyridine of Formula XX to a heated rnixture of Meldrum's acid and triethyl orthoformate and heating the reaction at an elevated temperature. The product can be isolated using conventional methods. Many anilines and aminopyridines of Formula XX are commercially available; others can be prepared by known synthetic methods. For example, benzyloxypyridines of Formula XX can be prepared using the method of Holladay et al., *Biorg. Med. Chem. Lett.*, 8, pp. 2797-2802, (1998).

In step (2) of Reaction Scheme I, an imine of Formula XXI undergoes thermolysis and cyclization to provide a compound of Formula XXII. The reaction is conveniently carried out in a medium such as DOWTBERM A heat transfer fluid at a temperature between 200 and 250° C. The product can be isolated using conventional methods.

In step (3) of Reaction Scheme I, a compound of Formula XXII is nitrated under conventional nitration conditions to provide a compound of Formula XXIII. The reaction is conveniently carried out by adding nitric acid to the compound of Formula XXII in a suitable solvent such as propionic acid and heating the mixture at an elevated temperature. The product can be isolated using conventional methods.

In step (4) of Reaction Scheme I, a 3-nitro[1,5]naphthyridin-4-ol or 3-nitroquinolin-4-ol of Formula XXIII is chlorinated using conventional chlorination chemistry to provide a 4-chloro-3-nitro[1,5]naphthyridine or 4-chloro-3-nitroquinoline of Formula XXV. The reaction is conveniently carried out by treating the compound of Formula XXIII with phosphorous oxychloride in a suitable solvent such as NN-dimethylformamide (DMF). The reaction can be carried out at ambient temperature or at an elevated temperature such as 100° C., and the product can be isolated using conventional methods.

In step (5) of Reaction Scheme I, a 4-chloro-3-nitro[1,5]naphthyridine or 4-chloro-3-nitroquinoline of Formula XXIV is treated with an arnine of Formula HO—X—NH$_2$ to provide a compound of Formula XXV. Several amines of Formula HO—X—NH$_2$ are commercially available; others can be prepared by known synthetic methods. The reaction is conveniently carried out by adding the amine of Formula HO—X—NH$_2$ to a solution of the 4-chloro-3-nitro[1,5]naphthyridine or 4-chloro-3-nitroquinoline of Formula XXIV in a suitable solvent such as dichloromethane in the presence of a tertiary amine such as triethylamine. The reaction can be carried out at ambient temperature or at a sub-ambient temperature such as, for example, 0° C. The reaction product can be isolated using conventional methods.

In step (6) of Reaction Scheme I, a compound of Formula XXV is reduced to provide a diamine of Formula XXVI. The reaction can be carried out by hydrogenation using a heterogeneous hydrogenation catalyst such as palladium on carbon or platinum on carbon. The hydrogenation is conveniently carried out in a Parr apparatus in a suitable solvent such as toluene, methanol, acetonitrile, or ethyl acetate. The reaction can be carried out at ambient temperature, and the product can be isolated using conventional methods.

Alternatively, the reduction in step (6) can be carried out using a one- or two-phase sodium dithionite reduction. The reaction is conveniently carried out using the conditions described by Park, K. K.; Oh, C. H.; and Joung, W. K.; *Tetrahedron Lett.*, 34, pp. 7445-7446 (1993) by adding sodium dithionite to a compound of Formula XXV in a mixture of dichloromethane and water at ambient temperature in the presence of potassium carbonate and ethyl viologen dibromide, ethyl viologen diiodide, or 1,1'-di-n-octyl-4,4'-bipyridinium dibromide. The product can be isolated using conventional methods.

In step (7) of Reaction Scheme I, a diamine of Formula XXVI, is reacted with a carboxylic acid equivalent to provide a 1H-imidazo[4,5-c][1,5]naphthyridine or 1H-imidazo[4,5-c]quinoline of Formula XXVII. Suitable carboxylic acid equivalents include orthoesters of Formula R$_2$C(O-alkyl)$_3$, 1,1-dialkoxyalkyl alkanoates of Formula R$_2$C(O-alkyl)$_2$(O—C(O)-alkyl), and acid chlorides of Formula R$_2$C(O)Cl. The selection of the carboxylic acid equivalent is determined by the desired substituent at R$_2$. For example, triethyl orthoformate will provide a compound where R$_2$ is hydrogen, and trimethyl orthobutyrate will provide a compound where R$_2$ is a propyl group. Step (7) is conveniently carried out by adding the carboxylic acid equivalent to a diamine of Formula XXVI in a suitable solvent such as toluene or xylenes. Optionally, catalytic pyridine hydrochloride can be added. The reaction is carried out at a temperature high enough to drive off alcohol or water formed during the reaction. Conveniently, a Dean-Stark trap can be used to collect the volatiles. The 1H-imidazo [4,5-c][1,5]naphthyridine or 1H-imidazo[4,5-c]quinoline product of Formula XXVII can be isolated and optionally purified using conventional techniques.

Alternatively, step (7) of Reaction Scheme I can be carried out in two steps when an acid chloride of Formula R$_2$C(O)Cl is used as the carboxylic acid equivalent. Part (i) of step (7) is conveniently carried out by adding the acid chloride to a solution of a diamine of Formula XXVI in a suitable solvent such as dichloromethane or acetonitrile. Optionally, a tertiary amine such as triethylamine, pyridine, or 4-dimethylaminopyridine can be added. The reaction can be carried out at ambient temperature. The amide product can be isolated and optionally purified using conventional techniques. Part (ii) of step (7) involves heating the amide prepared in part (i) in the presence of base to provide a 1H-imidazo[4,5-c][1,5]naphthyridine or 1H-imidazo[4,5-c]quinoline of Formula XXVII. The reaction is conveniently carried out in a suitable solvent such as ethanol in the presence of a base such aqueous sodium hydroxide or aqueous potassium carbonate at elevated temperature. The product of Formula XXVII can be isolated using conventional methods.

In an alternative route to a compound of Formula XXVII, the alcohol group in a compound of Formula XXV is first protected with an appropriate protecting group such as an acetyl group. The protection reaction is conveniently carried out by adding acetic anhydride to a solution of a compound of Formula XXV in a suitable solvent such as dichloromethane in the presence of a tertiary amine such as triethylamine optionally with 4-dimethylaminopyridine as a catalyst. The reaction is carried out at a sub-ambient temperature such as, for example, 0° C. The reaction product can be isolated using conventional methods and is then subjected to the conditions described in steps (6) and (7) of Reaction Scheme I. If the two-step procedure employing an acid chloride as the carboxylic acid equivalent is used in step (7), the acetyl protecting group is cleaved under the conditions described in part (ii) of step (7) to afford a compound of the Formula XXVII. If the carboxylic acid equivalent is introduced using the one-step procedure described in step (7), the acetyl protecting group can be cleaved in a subsequent reaction to afford a compound of the Formula XXVII. Cleavage of the acetyl group is conveniently carried out using a base such as potassium carbonate in a suitable solvent such as methanol. The reaction is carried out at ambient temperature and the product of Formula XXVII can be isolated using conventional methods.

Several compounds of Formula XXVII, wherein m and n are both 0, are known and have been prepared by other related routes; see for example, U.S. Pat. No. 4,689,338 (Gerster), U.S. Pat. No. 6,194,425 (Gerster et al.), U.S. Pat. No. 5,605,899 (Gerster et al.), and U.S. Pat. No. 5,175,296 (Gerster).

In step (8) of Reaction Scheme I, a hydroxy-substituted compound of Formula XXVII is treated with N-hydroxyphthalimide under Mitsunobu reaction conditions to provide an N-phthalimide-protected hydroxylamine of Formula XXVIII. The reaction is conveniently carried out by adding triphenylphosphine and N-hydroxyphthalimide to a solution of the alcohol of Formula XXVII in a suitable solvent such as tetrahydrofuran or DMF and then slowly adding diisopropyl azodicarboxylate. The reaction can be carried out at ambient temperature or at an elevated temperature, such as 60° C. The product can be isolated using conventional methods.

In step (9) of Reaction Scheme I, an N-phthalimide-protected hydroxylamine of Formula XXVM is oxidized to provide a 1H-imidazo[4,5-c][1,5]naphthyridine-5N-oxide or 1H-irnidazo[4,5-c]quinoline-5N-oxide of Formula XXIX using a conventional oxidizing agent capable of forming N-oxides. The reaction is conveniently carried out by adding 3-chloroperoxybenzoic acid to a solution of a compound of Formula XXVIII in a solvent such as chloroform or dichloromethane. The reaction can be carried out at ambient temperature. The product can be isolated using conventional methods.

In step (10) of Reaction Scheme I, a 1H-imidazo[4,5-c][1,5]naphthyridine-5N-oxide, or 1H-imidazo[4,5-c]quinoline-5N-oxide of Formula XXIX is aminated to provide a 1H-imidazo[4,5-c][1,5]naphthyridinamine or 1H-imidazo[4,5-c]quinolin-4-amine of Formula XXX. Step (10) involves the activation of an N-oxide of Formula XXIX by conversion to an ester and then reacting the ester with an aminating agent. Suitable activating agents include alkyl- or arylsulfonyl chlorides such as benzenesulfonyl chloride, methanesulfonyl chloride, orp-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXX in a suitable solvent such as dichloromethane or chloroform and then adding p-toluenesulfonyl chloride. The reaction can be carried out at ambient temperature. Under these reaction conditions, the N-phthalimide protecting group is removed to provide the 1H-imidazo[4,5-c][1,5]naphthyridin4-amine or 1H-imidazo[4,5-c]quinolin-4-amine of Formula XXX or a pharmaceutically acceptable salt thereof, which can be isolated from the reaction mixture using conventional methods.

Steps (9) and (10) can alternatively be combined and carried out as a one-pot procedure by adding 3-chloroperoxybenzoic acid to a solution of a compound of Formula XXVIII in a solvent such as dichloromethane or chloroform and then adding ammonium hydroxide and p-toluenesulfonyl chloride without isolating the N-oxide of Formula XXIX. The product of Formula XXX or pharmaceutically acceptable salt thereof can be isolated using conventional methods.

In step (11) of Reaction Scheme I, the hydroxylamine group in a 1H-imidazo[4,5-c][1,5]naphthyridin-4-amine or 1H-imidazo[4,5-c]quinolin-4-amine of Formula XXX reacts with an aldehyde or ketone of Formula $R_1C(O)R'$ to provide an oxime of Formula XXXI, which is a subgenus of Formulas I and II. Numerous aldehydes and ketones of Formula $R_1C(O)R'$ are commercially available; others can be readily prepared using known synthetic methods. The reaction can be conveniently carried out by adding the aldehyde or ketone of Formula $R_1C(O)R'$ to a solution of the hydroxylamine of Formula XXX in a suitable solvent such as methanol. The reaction can be carried out at ambient temperature, or at elevated temperature. Optionally, an acid such as pyridine hydrochloride can be added. The product or pharmaceutically acceptable salt thereof can be isolated using conventional methods.

Compounds of the invention can also be prepared from the compound of Formula XXVII by an alternative route shown as Route 2 in Reaction Scheme I. In step (8a) of Reaction Scheme I an alcohol of Formula XXVII is converted to a hydroxylamine of Formula XXXII, which is a subgenus of Formula X. The reaction is carried out under Mitsunobu reaction conditions as described for step (8) of Route 1, and during the isolation of the reaction product, the N-phthalimide protecting group is removed by treatment with a strong base. Conveniently, an acidic aqueous solution of a N-phthalimide-protected hydroxylamine prepared from a compound of Formula XXVII is treated with sodium hydroxide until the pH of the solution is basic. The hydroxylamine of Formula XXXII can then be isolated using conventional methods.

In step (9a) of Reaction Scheme I, a hydroxylamine of Formula XXXII reacts with an aldehyde or ketone of Formula $R_1C(O)R'$ to provide an oxime of Formula XXIII, a subgenus of Formula XII. Numerous aldehydes and ketones of Formula $R_1C(O)R'$ are commercially available; others can be readily prepared using known synthetic methods. The reaction can be carried out as described above in step (11) of Route 1.

In step (10a) of Reaction Scheme I, a compound of Formula XXXIII is oxidized to provide an N-oxide of Formula XXXIV, a subgenus of Formula XIV, using a conventional oxidizing agent capable of forming N-oxides. The reaction can be carried out as described above in step (9) of Route 1.

In step (11a) of Reaction Scheme I, a N-oxide of Formula XXXIV is aminated to provide a 1H-imidazo[4,5-c][1,5]naphthyridin-4-amine or 1H-imidazo[4,5-c]quinolin-4-amine of Formula XXXI. The reaction can be carried out as described above in step (10) of Route 1. The product or pharmaceutically acceptable salt thereof can be isolated using conventional methods.

For some embodiments, compounds in Reaction Scheme I can be furter elaborated using known synthetic methods. For example, the acid chloride used in step (7) of Reaction Scheme I may contain a protected hydroxy or amino group. Some acid chlorides of this type, for example acetoxyacetyl chloride, are commercially available. Others can be prepared by known synthetic methods. The protected hydroxy or amino group may be deprotected and further functionalized before step (9) of Route 1 of Reaction Scheme I. For examples of this type of functionalization of an $R_2$ group, see U.S. Pat. No. 5,389,640 (Gerster et al.).

Reaction Scheme I
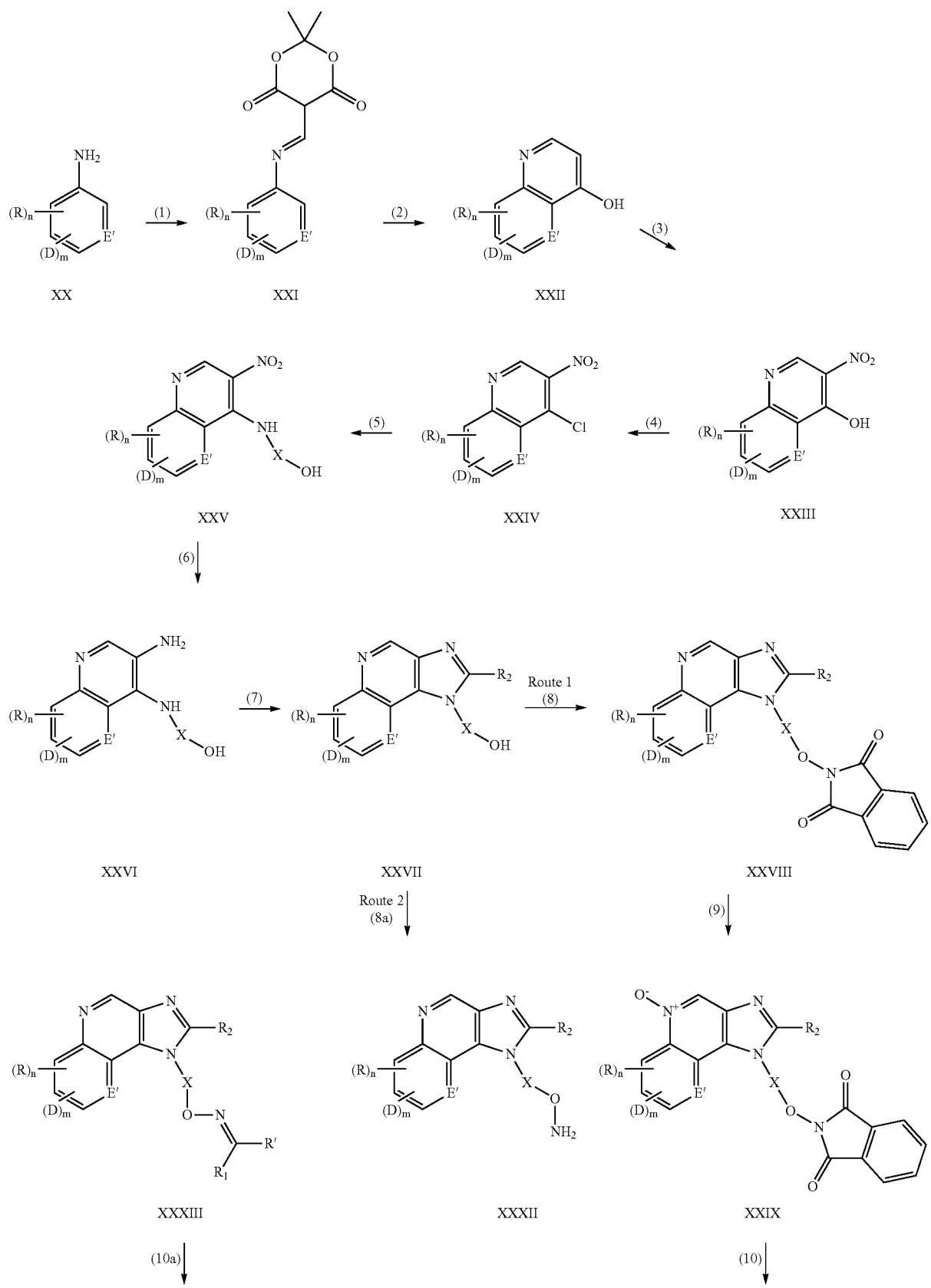

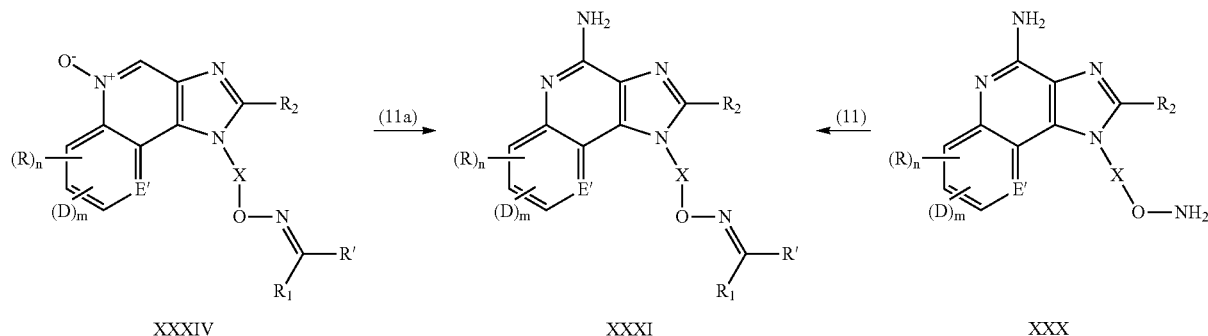

Compounds of the invention can also be prepared according to Reaction Scheme II, wherein R, R', $R_1$, $R_2$, E', and X are as defined above; n is 0 or 1; $R_{3a}$ is —O—$R_{4a}$, —O—X'—$R_4$, —O—X'—Y—$R_4$, or —O—X'—$R_5$; wherein $R_4$, $R_5$, X' and Y are as defined above, and $R_{4a}$ is aryl or heteroaryl where the aryl or heteroaryl groups can be unsubstituted or substituted as defined in $R_4$ above. Compounds of Formula XXXa are a subset of compounds of Formula XXX, defined in Reaction Scheme I, wherein D is —OCH$_2$Ph. In step (1) of Reaction Scheme II, the benzyl group in a benzyloxy-substituted 1H-imidazo[4,5-c][1,5]naphthyridin-4-amine or 1H-imidazo[4,5-c]quinolin-4-amine of Formula XXXa is cleaved to provide a compound of Formula XXXb. The cleavage is conveniently carried out on a Parr apparatus under hydrogenolysis conditions using a suitable heterogeneous catalyst such as palladium or platinum on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a compound of Formula XXXa in a suitable solvent such as ethanol in the presence of a catalyst such as palladium on carbon. The reaction is carried out at an elevated temperature, for example, the refluxing temperature of the solvent. The product or pharmaceutically acceptable salt thereof can be isolated using conventional methods.

In step (2) of Reaction Scheme II, the hydroxylamine group in a 1H-imidazo[4,5-c][1,5]naphthyridin-4-amine or 1H-imidazo[4,5-c]quinolin-4-amine of Formula XXXb reacts with an aldehyde or ketone of Formula $R_1C(O)R'$ to provide an oxime of Formula XXXIa, a subgenus of Formulas I and II. The reaction can be carried out as described above in step (11) of Reaction Scheme I. The product or pharmaceutically acceptable salt thereof can be isolated using conventional methods.

In step (3) of Reaction Scheme II, a hydroxy-substituted compound of Formula XXXIa is converted to an ether-substituted compound of Formula XXXIb using a Williamson-type ether synthesis. The reaction is effected by treating a compound of Formula XXXIa with an aryl or alkyl halide of Formula Halide-$R_{4a}$, Halide-alkylene-$R_4$, Halide-alkylene-Y-$R_4$ or Halide-alkylene-$R_5$ in the presence of a base. Numerous alkyl or aryl halides of these formulas are commercially available, including substituted benzyl bromides and chlorides, substituted or unsubstituted alkyl or arylalkylenyl bromides and chlorides, and substituted fluorobenzenes. Other alkyl or aryl halides of these Formulas can be prepared using conventional synthetic methods. The reaction is conveniently carried out by combining a reagent of Formula Halide-$R_{4a}$, Halide-alkylene-$R_4$, Halide-alkylene-Y-$R_4$ or Halide-alkylene-$R_5$ with a hydroxy-substituted compound of Formula XXXIa in a solvent such as DMF in the presence of a suitable base such as cesium carbonate. Optionally, catalytic tetrabutylammonium bromide can be added. The reaction can be carried out at ambient temperature or at an elevated temperature, for example 65° C. or 85° C., depending on the reactivity of the aryl or alkyl halide. The product of Formula XXXIB, which is a subgenus of Formulas I and II, or pharmaceutically acceptable salt thereof can be isolated using conventional methods.

Alternatively, step (3) may be carried out using the Ullmann ether synthesis, in which an alkali metal aryloxide of a compound of Formula XXXIa reacts with an aryl halide in the presence of copper salts, to provide a compound of Formula XXXIB, where $R_{3a}$ is —O—$R_{4a}$, —O—X'—$R_4$, or —O—X'—Y—$R_4$, wherein X' is an arylene or heteroarylene. Numerous substituted and unsubstituted aryl halides are commercially available; others can be prepared using conventional methods.

Compounds of the Formula XXXIb may also be obtained using an alternative five step procedure starting from a compound of Formula XXXII, shown in Reaction Scheme I. The methods described in steps (1), (2), and (3) of Reaction Scheme II can be sequentially carried out on a 1H-imidazo[4,5-c][1,5]naphthyridine or 1H-imidazo[4,5-c]quinoline of Formula XXII, wherein D is a benzyloxy group. The product can then be converted into a compound of Formula XXXIb according to the reaction conditions described in steps (9) and (10) of Reaction Scheme I.

Reaction Scheme II

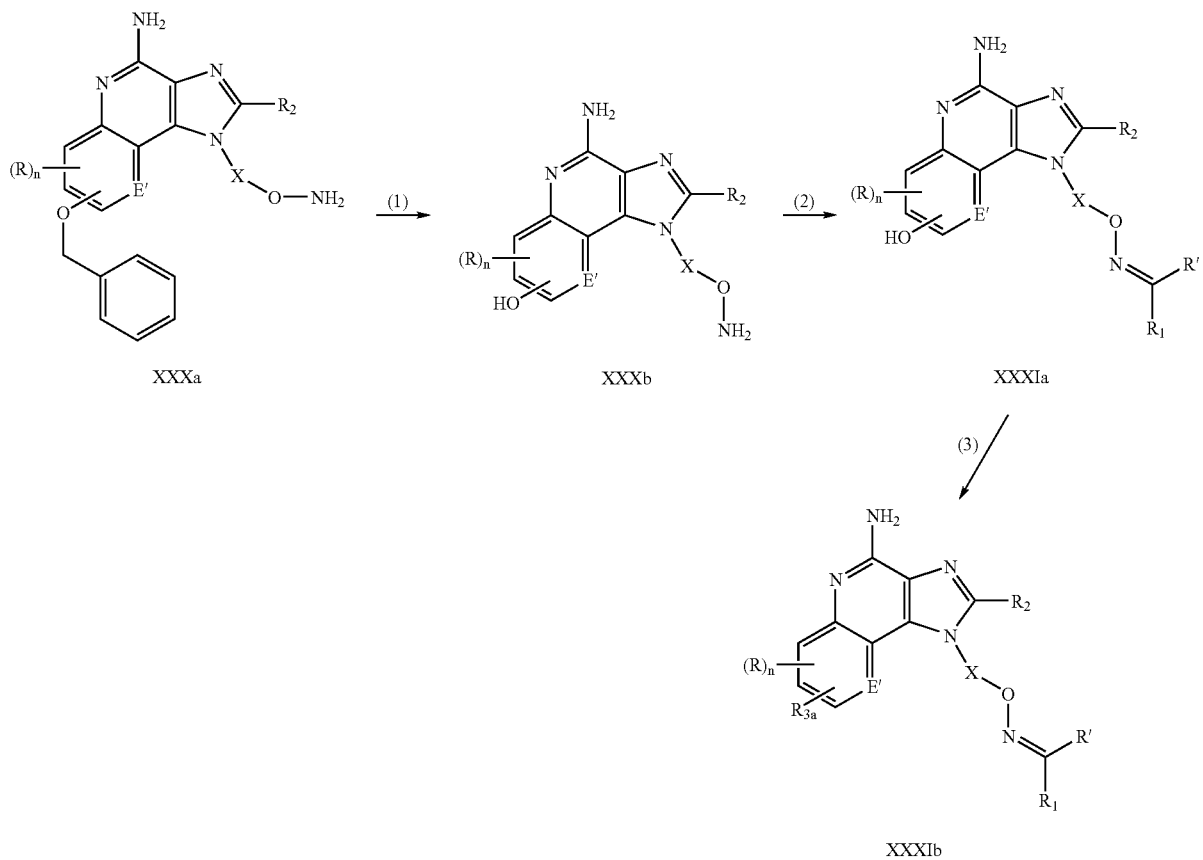

Compounds of the invention can also be prepared according to Reaction Scheme III, wherein R, R', $R_1$, $R_2$, E', and X are as defined above; Hal is —Br or —I; n is 0 or 1; and $R_{3b}$ and $R_{3c}$ are as defined below. Formula XXXc is a subset of Formula XXX, defined in Reaction Scheme I, wherein D is —Br or —I. Step (1) of Reaction Scheme III can be carried out using known palladium-catalyzed coupling reactions such as the Suzuki coupling and the Heck reaction. For example, a halogen substituted 1H-imidazo[4,5-c][1,5]naphthyridin-4-amine or 1H-imidazo[4,5-c]quinolin-4-amine of Formula XXXc undergoes Suzuki coupling with a boronic acid of Formula $R_{3b}$—B(OH)$_2$, an anhydride thereof, or a boronic acid ester of Formula $R_{3b}$—B(O-alkyl)$_2$ to provide a compound of Formula XXXd; wherein $R_{3b}$ is —$R_{4a}$, —X'$_a$—$R_4$, —X'$_b$—Y—$R_5$, or —X'$_b$—$R_5$; where X'$_a$ is alkenylene; X'$_b$ is arylene, heteroarylene, or alkenylene interrupted or terminated by arylene or heteroarylene; and $R_4$, $R_{4a}$, $R_5$, and Y are as defined above. The coupling is carried out by combining a compound of Formula XXXc with a boronic acid or an ester or anhydride thereof in the presence of palladium (II) acetate, triphenylphosphine, and a base such as sodium carbonate in a suitable solvent such as n-propanol. The reaction can be carried out at an elevated temperature, for example, at the reflux temperature. Numerous boronic acids of Formula $R_{3b}$—B(OH)$_2$, anhydrides thereof, and boronic acid esters of Formula $R_{3b}$—B(O—Slkyl)$_2$ are commercially available; others can be readily prepared using known synthetic methods. See, for example, Li, W. et al, *J. Org. Chem.*, 67, pp. 5394-5397 (2002). The product of Formula XXXd or a pharmaceutically acceptable salt thereof can be isolated by conventional methods.

The Heck reaction can also be used in step (1) of Reaction Scheme III to provide compounds of Formula XXXd, wherein $R_{3b}$ is —X'$_a$—$R_{4a}$ and —X'$_a$—Y—$R_4$. The Heck reaction is carried out by coupling a compound of Formula XXXc with a compound of the Formula H$_2$C=C(H)—$R_{4a}$ or H$_2$C=C(H)—Y—$R_4$. Several of these vinyl-substituted compounds are commercially available; others can be prepared by known methods. The reaction is conveniently carried out by combining the compound of Formula XXXc and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100-120° C. under an inert atmosphere. The product of Formula XXXd or pharmaceutically acceptable salt thereof can be isolated using conventional methods.

Compounds of Formula XXXd, wherein $R_{3b}$ is —X'$_c$—$R_4$, X'$_c$ is alkynylene, and $R_4$ is as defined above, can also be prepared by palladium catalyzed coupling reactions such as the Stille coupling or Sonogashira coupling. These reactions are carried out by coupling a compound of Formula XXXc with a compound of the Formula (alkyl)$_3$Sn—C≡C—$R_4$, (alkyl)$_3$Si—C≡C—$R_4$, or H—C≡C—$R_4$.

In step (2) of Reaction Scheme II, the hydroxylamine group in a 1H-imidazo[4,5-c][1,5]naphthyridinamine or 1H-imidazo[4,5-c]quinolin4-amine of Formula XXXd reacts with an aldehyde or ketone of Formula R$_1$C(O)R' to provide an oxime of Formula XXXIc, a subgenus of Formulas I and II. The reaction can be carried out as described above in step (11)

of Reaction Scheme I. The product or pharmaceutically acceptable salt thereof can be isolated using conventional methods.

Compounds of the invention, wherein $R_{3c}$ is —$X'_d$—$R_4$, —$X'_d$—Y—$R_4$, —$X'_e$—Y—$R_4$, or —$X'_e$—$R_5$, where $X'_d$ is alkylene; $X'_e$ is alkylene interrupted or terminated by arylene or heteroarylene; and $R_4$, $R_5$, and Y are as defined above, can be prepared as shown in steps (2a) and (2b) of Reaction Scheme ImI. In step (2a) of Reaction Scheme IIL a compound of Formula XXXd, wherein $R_{3b}$ is —$X'_a$—$R_4$, —$X'_a$—Y—$R_4$, —$X'_b$—Y—$R_4$, —$X'_b$—$R_5$, or —$X'_c$—$R_4$, where $X'_b$ is alkenylene interrupted or terminated by arylene or heteroarylene, and $X'_a$, $X'_c$, Y, $R_4$, and $R_5$ are as defined above, is reduced to provide a compound of Formula XXXe. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The product or pharmaceutically acceptable salt thereof can be isolated using conventional methods. Step (2b) of Reaction Scheme m can be carried out as described above in step (11) of Reaction Scheme I to provide a compound of the Formula XXXd, a subgenus of Formulas I and II.

Compounds of the Formula XXXIc and XXXId can be obtained using other routes. For example, the methods described in step (1) of Scheme DI can be carried out on a N-tert-butoxycarbonyl-protected hydroxylamine derivative of Formula XXXc, which can be synthesized from a compound of Formula XXXc using conventional chemistry. The reaction product can undergo deprotection of the tert-butoxycarbonyl group using a conventional method and the chemistry described in step (2) or steps (2a) and (2b) can be applied to afford a compound of Formula XXXIc or XXXId, respectively. In addition, several of the compounds shown in Reaction Scheme I such as compounds of the Formula XXVII, XXXVIII, XXXI, XXXII, and XXXIII, or appropriately protected derivatives thereof, wherein D is —Br or —I, could be used as substrates for the metal-mediated coupling chemistry described above in step (1) of Reaction Scheme III. The synthesis of compounds of Formula XXXIc or XXXId can be completed using the appropriate steps in Reaction Schemes I and III, with the addition of a deprotection step if necessary. For example, a compound of Formula XXXII wherein D is —Br or —I can be treated with di-tert-butyl dicarbonate to afford an N-tert-butoxycarbonyl-protected hydroxylamine compound of Formula XXXII that can undergo the metal-mediated coupling chemistry described in step (1) of Reaction Scheme III. The removal of the tert-butyloxycarbonyl group using conventional methods can be followed by the methods described in steps (9a), (10a), and (11a) of Reaction Scheme I to provide a compound of Formula XXXIc. Conveniently, a compound of Formula XXXI, wherein D is —Br or —I, can be subjected to the cross-coupling reaction conditions described in step (1) of Reaction Scheme III to provide a compound of Formula XXXIc, which may be reduced, when appropriate, according to the conditions described in step (2a) of Reaction Scheme In to provide a compound of Formula XXXId.

Reaction Scheme III

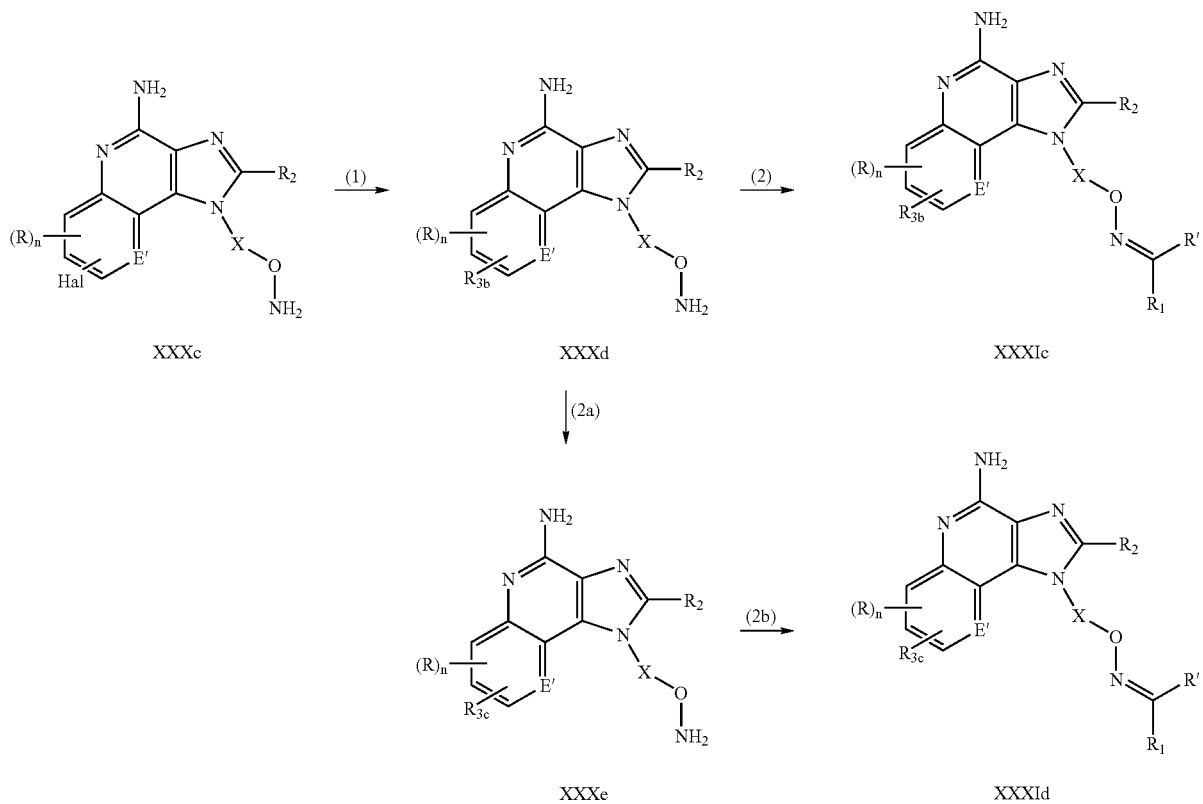

Tetrahydroquinolines and tetrahydronaphthyridines of the invention can be prepared according to Reaction Scheme IV, wherein E', X, R', and $R_1$ are as defined above; n is an integer from 0 to 4 (imidazoquinoline ring system) or 0 to 3 (imidazonaphthyridine ring system); $R_a$ is alkyl, alkoxy, or $-N(R_9)_2$; and $R_{2a}$ is a subset of $R_2$ as defined above that does not include those substituents that one skilled in the art would recognize as being susceptible to reduction under the acidic hydrogenation conditions of step (2). These susceptible groups include, for example, alkenyl, alkynyl, and aryl groups and groups bearing nitro substituents.

In step (1) of Reaction Scheme IV, a hydroxy-substituted compound of Formula XXVIIa is oxidized and amninated to provide a 1H-imidazo[4,5-c][1,5]naphthyridin-4-amine or 1H-imidazo[4,5-c]quinolin-amine of Formula XXXV. Compounds of Formula XXVIIa can be prepared as shown in Reaction Scheme I. The oxidation and amination can be carried out as described in steps (9) and (10) of Reaction Scheme I.

In step (2) of Reaction Scheme IV, a compound of Formula XXXV is reduced to a 6,7,8,9-tetrahydro compound of Formula XXXVI. The reaction is conveniently carried out under hetereogeneous hydrogenation conditions by adding platinum (IV) oxide to a solution of the compound of Formula XXXV in trifluoroacetic acid and placing the reaction under hydrogen pressure. The reaction can be carried out on a Parr apparatus at ambient temperature. The product or pharmaceutically acceptable salt thereof can be isolated by conventional methods.

In step (3) of Reaction Scheme V, a hydroxy-substituted compound of Formula XXXVI is converted to a hydroxylamine of Formula XXXVII. The reaction is carried out under the Mitsunobu reaction conditions as described for step (8) of Reaction Scheme I, and during the isolation of the reaction product, the N-phthalimide protecting group is removed by treatment with a strong base. Conveniently, an acidic aqueous solution of a N-phthalimide-protected hydroxylamine prepared from a compound of Formula XXXVI is treated with sodium hydroxide until the pH of the solution is basic. The hydroxylamine of Formula XXXVII can then be isolated using conventional methods. Alternatively, the Mitsunobu reaction can be carried out as described in step (8) of Reaction Scheme I to provide a N-phthalimide-protected hydroxylamine, which can be treated with hydrazine in a suitable solvent such as ethanol at ambient temperature to provide a hydroxylainine of Formula XXVII. The product or pharmaceutically acceptable salt thereof can be isolated by conventional methods.

In step (4) Reaction Scheme IV, the hydroxylamine group in a compound of Formula XXXVII reacts with an aldehyde or ketone of Formula $R_1C(O)R'$ to provide an oxime of Formula XXXVIII, a subgenus of Formulas I and II. The reaction can be carried out as described above in step (11) of Reaction Scheme I. The product or pharmaceutically acceptable salt thereof can be isolated by conventional methods.

Reaction Scheme IV

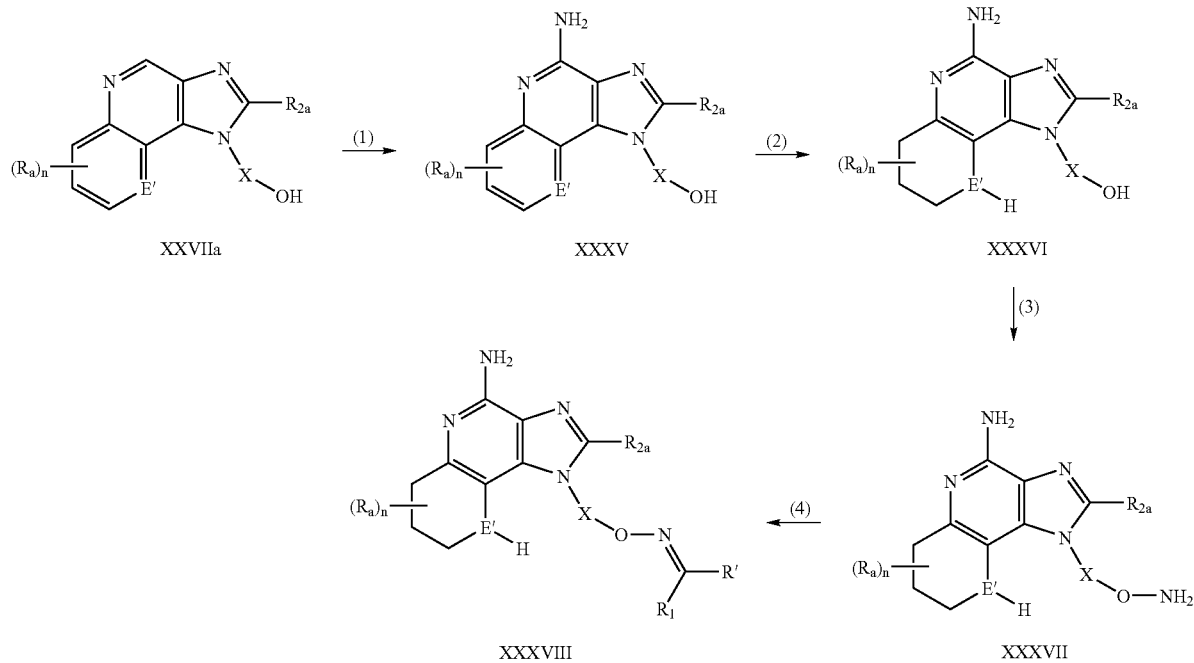

For some embodiments, compounds of the invention are prepared according to Reaction Scheme V, where Ph, R', $R_1$, $R_2$, $R_{A1}$, $R_{B1}$, and X are as defined above. In step (1) of Reaction Scheme V, a 2,4-dichloro-3-nitropyridine of Formula XXXIX is reacted with an amino alcohol of the Formula $H_2N-X-OH$ to form a 2-chloro-3-nitropyridine of Formula XL. The reaction is conveniently carried out by combining an amino alcohol of Formula $H_2N-X-OH$ and a 2,4-dichloro-3-nitropyridine of Formula XXXIX in the presence of a base such as triethylamine in an inert solvent such as DMF. The reaction can be carried out at ambient temperature, and the product can be isolated from the reaction mixture using conventional methods. Several amines of Formula $HO-X-NH_2$ are commercially available; others can be prepared by known synthetic methods. Many 2,4-dichloro-3-nitropyridines of the Formula XXXIX are known and can be readily prepared using known synthetic methods. (See, for example, Dellaria et al, U.S. Pat. No. 6,525,064 and the references cited therein.)

In step (2) of Reaction Scheme V, a 2-chloro-3-nitropyridine of Formula XL is reacted with an alkali metal azide to provide an 8-nitrotetrazolo[1,5-a]pyridin-7-amine of Formula XLI. The reaction can be carried out by combining the compound of Formula XL with an alkali metal azide, for example, sodium azide, in a suitable solvent such as acetonitrile/water, preferably 90/10 acetonitrile/water, in the presence of cerium(III) chloride, preferably cerium(III) chloride heptahydrate. Optionally, the reaction can be carried out with heating, for example, at the reflux temperature. Alternatively, the reaction can be carried out by combining the compound of Formula XL with an alkali metal azide, for example, sodium azide, in a suitable solvent such as DMF and heating, for example to about 50-60° C., optionally in the presence of ammonium chloride. The product can be isolated from the reaction mixture using conventional methods.

In step (3) of Reaction Scheme V, an 8-nitrotetrazolo[1,5-a]pyridin-7-amine of Formula XLI is reduced to provide a compound of Formula XLII. The reduction can be carried out as described in step (6) of Reaction Scheme I.

In step (4) of Reaction Scheme V, a tetrazolo[1,5-a]pyridine-7,8-diamine of Formula XLII is reacted with a carboxylic acid equivalent to provide a 7H-imidazo[4,5-c]tetrazolo[1,5-a]pyridine of Formula XLIII. The reaction can be carried out as described in step (7) of Reaction Scheme I.

A compound of Formula XLIII can also be prepared from a compound of Formula XLI, wherein the alcohol group in a compound of Formula XLI is first protected with an appropriate protecting group such as an acetyl group. The incorporation of the acetyl group, subsequent reduction and cyclization, and removal of the acetyl group is described in Reaction Scheme I.

In step (5) of Reaction Scheme V, a hydroxy-substituted compound of Formula XLIII is treated with N-hydroxyphthalimide under Mitsunobu reaction conditions to provide an N-phthalimide-protected hydroxylamine of Formula XVI. The reaction is carried out as described for step (8) of Route 1 of Reaction Scheme I.

In step (6) of Reaction Scheme V, the N-phthalimide-protected hydroxylamine of Formula XVI is treated with hydrazine in a suitable solvent such as ethanol to provide a hydroxylamine of Formula XVII. The reaction can be carried out at ambient temperature and the product can be isolated from the reaction mixture using conventional methods.

In step (7) Reaction Scheme V, the hydroxylamine group in a 7H-imidazo[4,5-c]tetrazolo[1,5-a]pyridine of Formula XVII reacts with an aldehyde or ketone of Formula $R_1C(O)R'$ to provide an oxime of Formula XVIII. The reaction can be carried out as described above in step (11) of Reaction Scheme I.

In step (8) of Reaction Scheme V, the tetrazolo ring can be removed from a 7H-imidazo[4,5-c]tetrazolo[1,5-a]pyridine of Formula XVHI by reaction with triphenylphosphine to form an N-triphenylphosphinyl intermediate of Formula XLIV. The reaction with triphenylphosphine can be run in a suitable solvent such as toluene or 1,2-dichlorobenzene under an atmosphere of nitrogen with heating, for example at the reflux temperature.

In step (9) of Reaction Scheme V, an N-triphenylphosphinyl intermediate of Formula XLIV is hydrolyzed to provide an oxime-substituted 1H-imidazo[4,5-c]pyridin-4-amine of Formula VI. The hydrolysis can be carried out by general methods well known to those skilled in the art, for example, by heating in a lower alkanol in the presence of an acid such as trifluoroacetic acid or hydrochloric acid. The product can be isolated from the reaction mixture using conventional methods as the compound of Formula VI or as a pharmaceutically acceptable salt thereof.

A compound of the Formula VI or a pharmaceutically acceptable salt thereof may also be obtained through an alternative route from a compound of Formula XVI. In step (6a) of Reaction Scheme V, a compound of Formula XVI is treated according to the reaction conditions described in steps (8) and (9) of Reaction Scheme V using hydrochloric acid as the acid in step (9). Under these reaction conditions, the N-phthalimide is removed to provide the hydroxylamine-substituted 1H-imidazo[4,5-c]pyridin-4-amine of Formula XLV. The product can be isolated and purified using conventional methods.

In step (7a) of Reaction Scheme V, a hydroxylamine-substituted 1H-imidazo[4,5-c]pyridin-4-amine of Formula XLV reacts with an aldehyde or ketone of Formula $R_1C(O)R'$ to provide an oxime of Formula VI. The reaction can be carried out as described above in step (11) of Reaction Scheme I. The product can be isolated from the reaction mixture using conventional methods as the compound of Formula VI or as a pharmaceutically acceptable salt thereof.

Reaction Scheme V

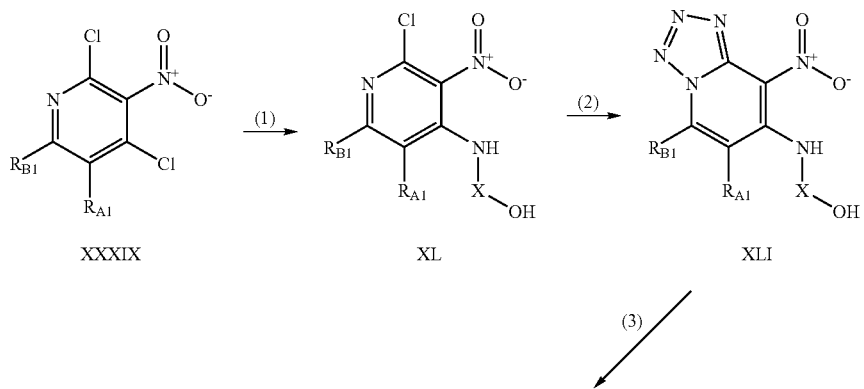

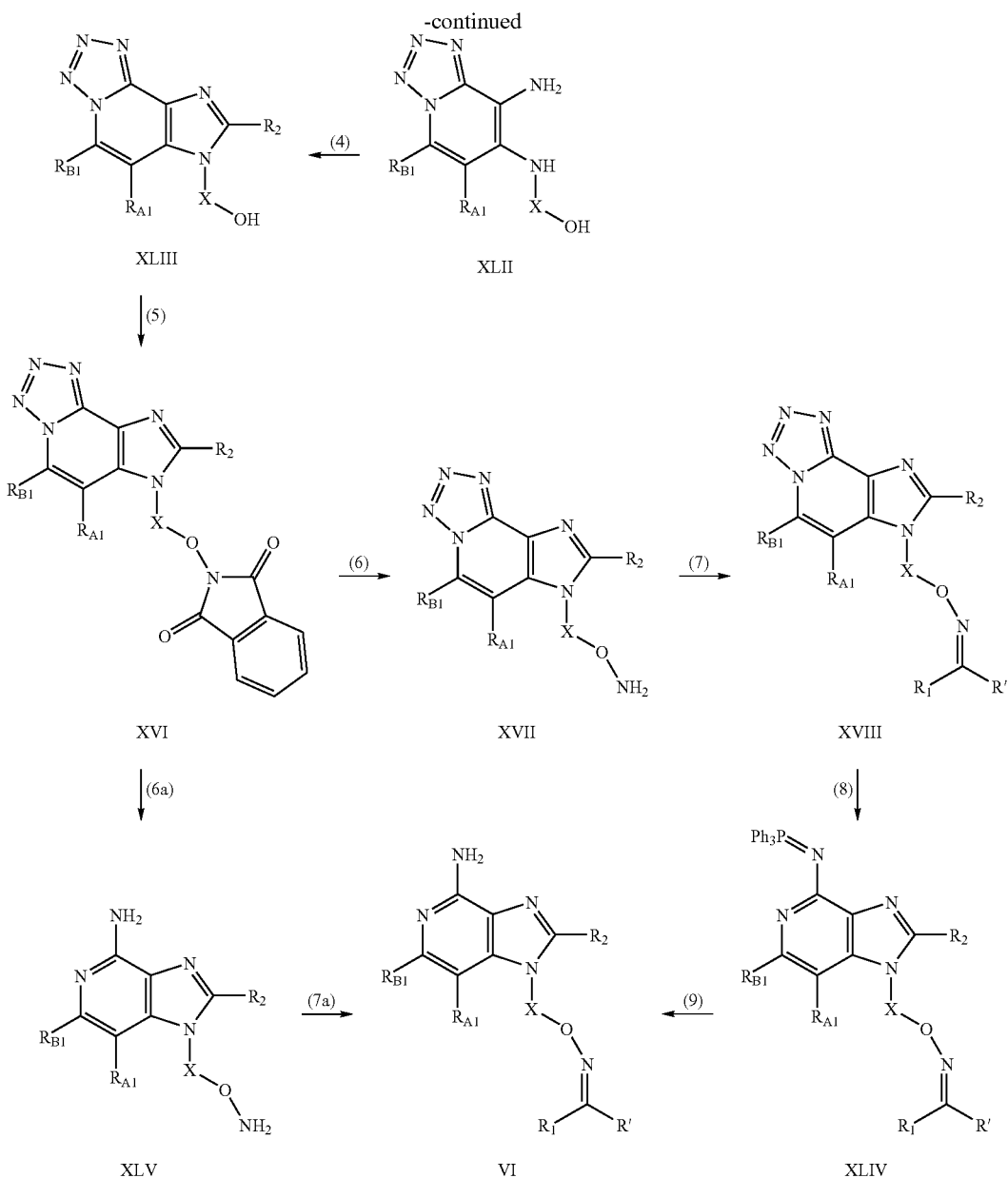

Pharmaceutical Compositions and Biological Activity

Pharmaceutical compositions of the invention contain a therapeutically effective amount of a compound of the invention as described above in combination with a pharmaceutically acceptable carrier.

The terms "a therapeutically effective amount" and "effective amount" mean an amount of the compound sufficient to induce a therapeutic or prophylactic effect, such as cytokine induction, immunomodulation, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound to the subject. A variety of dosage forms may be used, such as tablets, lozenges, capsules, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, antibodies, proteins, peptides, oligonucleotides, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and neoplastic diseases. Accordingly, the invention provides a method of inducing cytokine biosynthesis in an animal comprising administering an effective amount of a compound or composition of the invention to the animal. The animal to which the compound or composition is administered for induction of cytokine biosynthesis may have a disease as described infra, for example a viral disease or a neoplastic disease, and administration of the compound may provide therapeutic treatment. Alternatively, the compound may be administered to the animal prior to the animal acquiring the disease so that administration of the compound may provide a prophylactic treatment.

In addition to the ability to induce the production of cytokines, compounds of the invention can affect other aspects of the innate immune response. For example, natural killer cell activity may be stimulated, an effect that may be due to cytokine induction. The compounds may also activate macrophages, which in turn stimulate secretion of nitric oxide and the production of additional cytokines. Further, the compounds may cause proliferation and differentiation of B-lymphocytes.

Compounds of the invention can also have an effect on the acquired immune response. For example, the production of the T helper type 1 ($T_H1$) cytokine IFN-γ can be induced indirectly and the production of the T helper type 2 ($T_H2$) cytokines IL-4, IL-5 and IL-13 can be inhibited upon administration of the compounds.

Whether for prophylaxis or therapeutic treatment of a disease, and whether for effecting innate or acquired immunity, the compound or composition may be administered alone or in combination with one or more active components as in, for example, a vaccine adjuvant. When administered with other components, the compound and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, or Bordetella;

(c) other infectious diseases, such chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers; and (e) $T_H2$-mediated, atopic, and autoinmnune diseases, such as atopic dermatitis or eczema, eosinophilia, asthma, allergy, allergic rhinitis, systemic lupus erythematosus, essential thrombocythaemia, multiple sclerosis, Ommen's syndrome, discoid lupus, alopecia areata, inhibition of keloid formation and other types of scarring, and enhancing would healing, including chronic wounds.

IRMs identified herein also may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fingal, or bacterial immunogens, toxoids, toxins; self-antigens; polysaccharides; proteins; glycoproteins; peptides; cellular vaccines; DNA vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

IRMs may also be particularly helpful in individuals having compromised immune function. For example, IRM compounds may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

Objects and advantages of this invention are further illustrated by the following examples, but the particular materials and amounts thereof recited in these examples, as well as other conditions and details, should not be construed to unduly limit this invention.

EXAMPLES

Example 1

(1E)-Benzaldehyde O-[3-(4-amino-2-propyl-1H-imidazo[4,5-c]quinolin-1-yl)propyl]oxime

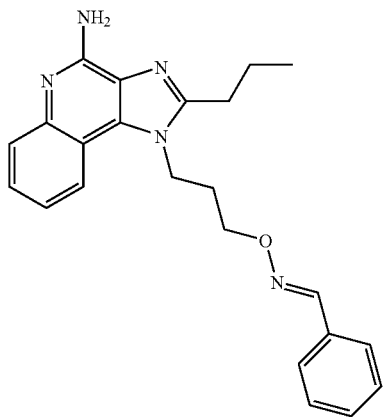 [SMILES: CCCc1nc2c(N)nc3ccccc3c2n1CCCO/N=C/c1ccccc1]

Part A

A solution of 3-(2-propyl-1H-imidazo[4,5-c]quinolin-1-yl)propan-1-ol (20.0 grams (g), 74.3 millimoles (mmol)) in tetrahydrofuran (300 milliliters (mL)) was cooled to approximately 0° C.; triphenylphosphine (23.4 g, 89.1 mmol) and N-hydroxyphthalimide (14.5 g, 89.1 mmol) were then added. After five minutes of stirring, diisopropyl azodicarboxylate (17.5 mL, 89.1 mmol) was added dropwise over a period of 15 minutes (min). The reaction was allowed to warm to room temperature and stirred overnight. The solvent was removed under reduced pressure, and the residue was dissolved in chloroform (300 mL). A solution of hydrochloric acid (150 mL of 6 molar (M) was then added, and approximately 50 mL of the solvent was removed under reduced pressure to provide a white precipitate, which was stirred for ten minutes and isolated by filtration. Additional salt eventually precipitated from the filtrate and was isolated by filtration. Chloroform (300 mL) and water (300 mL) were added to the salt, and solid sodium bicarbonate was added to the mixture to adjust to pH 8. The organic solution was then dried over magnesium sulfate, filtered, and concentrated under reduced pressure to provide 28.4 g of 2-[3-(2-propyl-1H-imidazo[4,5-c]quinolin-1-yl)propoxy]-1H-isoindole-1,3(2H)-dione as a white solid.

$^1$H NMR (300 MHz, CDCl$_3$) δ 9.3 (s, 1H), 8.3 (m, 2H), 7.9 (m, 2H), 7.8 (m, 2H), 7.6 (m, 2H), 5.0 (t, J=7.3 Hz, 2H), 4.4 (t, J=5.3 Hz, 2H), 3.1 (t, J=7.5 Hz, 2H), 2.4 (m, 2H), 2.1 (br s, m, 4H), 1.2 (t, J=7.3 Hz, 3H);

MS (APCI) m/z 415 (M+H)$^+$.

Part B

3-Chloroperoxybenzoic acid (14.9 g, 66.4 mmol) (mCPBA, available as an approximately 77% pure mixture) was added to a solution of 2-[3-(2-propyl-1H-imidazo[4,5-c]quinolin-1-yl)propoxy]-1H-isoindole-1,3(2H)-dione (25.0 g, 60.3 mmol) in chloroform (200 mL), and the reaction was stirred for seven hours at room temperature. An analysis by liquid chromatography/mass spectrometry (LC/MS) indicated that the reaction was incomplete, and additional mCPBA (4.96 g, 22.1 mmol) was added. The reaction was allowed to stir at room temperature overnight. The solution was then washed with brine (2×100 mL) and saturated aqueous sodium bicarbonate (2×100 nL), dried over magnesium sulfate, filtered, and concentrated under reduced pressure to provide a fluffy, light-brown solid. The solid was dried under high vacuum for one hour to provide 25.7 g of 2-[3-(5-oxido-2-propyl-1H-imidazo[4,5-c]quinolin-1-yl)propoxy]-1H-isoindole-1,3(2H)-dione as a white solid.

$^1$H NMR (300 MHz, CDCl$_3$) δ 9.1 (m, 2H), 8.3 (m, 1H), 7.9-7.7 (m, 6H), 5.0 (t, J=7.4 Hz, 2H), 4.4 (t, J=5.3 Hz, 2H), 3.1 (t, J=7.5 Hz, 2H), 2.4 (m, 2H), 2.1 (br s, m, 4H), 1.2 (t, J=7.3 Hz, 3H);

MS (APCI) m/z 431 (M+H)$^+$.

Part C

Ammonium hydroxide (75 mL) and p-toluenesulfonyl chloride (4.87 g, 25.6 mmol) were added to a solution of 2-[3-(5-oxido-2-propyl-1H-imidazo[4,5-c]quinolin-1-yl)propoxy]-1H-isoindole-1,3(2H1)-dione (10.0 g, 23.2 mmol) in chloroform (100 mL), and the resulting mixture was stirred vigorously for one hour. A white precipitate was removed by filtration, and the filtrate layers were separated. The organic solution was washed with brine (2×150 mL), dried over magnesium sulfate, filtered, and concentrated under reduced pressure to provide a yellow solid. The solid was purified by column chromatography on silica gel (eluting with dichloromethane:methanol:ammonium hydroxide ranging in ratios from 94:5:1 to 91:8:1) to provide 4.31 g of 1-[3-(aminooxy)propyl]-2-propyl-1H-imidazo[4,5-c]quinolin-4-amine as a beige powder, melting point (mp) 145-148° C.

$^1$H NMR (300 MHz, DMSO-d$_6$) δ 8.1 (d, J=7.5 Hz, 1H), 7.6 (d, J=8.3 Hz, 1H), 7.4 (t, J=8.1 Hz, 1H), 7.3 (t, J=8.1 Hz, 1H), 6.5 (br s, 2H), 6.1 (br s, 2H), 4.6 (t, J=7.2 Hz, 2H), 3.6 (t, J=5.6 Hz, 2H), 2.9 (t, J=7.4 Hz, 2H), 2.1 (m, 2H), 1.9 (m, 2H), 1.1 (t, J=7.3 Hz, 3H);

$^{13}$C NMR (75 MHz, DMSO-d$_6$) δ 153.4, 152.0, 145.0, 132.6, 126.8, 126.6, 121.5, 120.4, 115.1, 71.6, 42.5, 29.2, 28.5, 21.3, 14.2;

MS (APCI) m/z 300 (M+H)$^+$;

Anal. calcd for C$_{16}$H$_{21}$N$_5$O: C, 64.19; H, 7.07; N, 23.39. Found: C, 63.94; H, 7.20; N, 23.11.

Part D

Benzaldehyde (383 µL, 3.77 mmol) was added to a mixture of 1-[3-(aminooxy)propyl]-2-propyl-1H-imidazo[4,5-c]quinolin4-amine (0.800 g, 2.68 mmol) in methanol (15 mL), and the resulting red solution was stirred for two hours. The reaction was then concentrated under reduced pressure, and the residue was purified twice by column chromatography on silica gel (50-60 g, eluting sequentially with 98:2 dichloromethane:methanol and 95:5 dichloromethane:methanol) to provide 0.580 g of (1E)-benzaldehyde O-[3-(4-amino-2-propyl-1H-imidazo[4,5-c]quinolin-1-yl)propyl]oxime as a beige powder, mp 125-128° C.

$^1$H NMR (300 MHz, CDCl$_3$) 8.1 (s, 1H), 8.0 (d, J=7.5 Hz, 1H), 7.8 (d, J=8.3 Hz, 1H), 7.6 (m, 2H), 7.5 (m, 4H), 7.2 (m, 1H), 5.6 (br s, 2H), 4.6 (t, J=7.5 Hz, 2H), 4.3 (t, J=5.5 Hz, 2H), 2.9 (t, J=7.6 Hz, 2H), 2.4 (m, 2H), 1.9 (m, 2H), 1.1 (t, J=7.4 Hz, 3H);

$^{13}$C NMR (75 MHz, CDCl$_3$) δ 153.4, 151.2, 149.4, 144.6, 133.2, 131.9, 130.8, 130.2, 128.2, 127.1, 126.9, 122.2, 119.6, 115.4, 70.5, 42.7, 30.0, 29.2, 21.5, 14.0;

MS (APCI) n/z 388 (M+H)$^+$;

Anal. calcd for C$_{23}$H$_{25}$N$_5$O.0.37H$_2$O: C, 70.09; H, 6.58; N, 17.77. Found: C, 69.75; H, 6.60; N, 17.49.

Example 2

(1E)4-Fluorobenzaldehyde O-[3-(4-amino-2-propyl-1H-imidazo[4,5-c]quinolin-1-yl)propyl]oxime

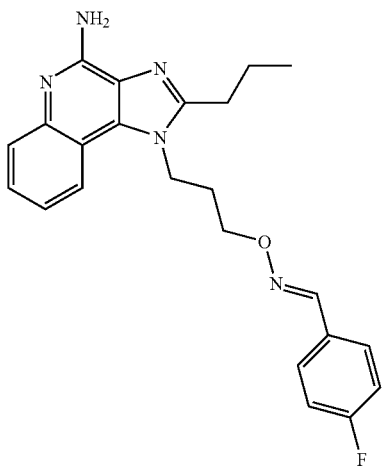 [SMILES: CCCc1nc2c(N)nc3ccccc3c2n1CCCO/N=C/c1ccc(F)cc1]

4-Fluorobenzaldehyde (307 μL, 2.86 mmol) was added to a mixture of 1-[3-(aminooxy)propyl]-2-propyl-1H-imidazo[4,5-c]quinolin-$^4$-amine (0.800 g, 2.68 mmol) in methanol (15 mL), and the resulting red solution was stirred for two hours. The reaction was then concentrated under reduced pressure, and the residue was purified twice by column chromatography on silica gel (50-60 g, eluting sequentially with 98:2 dichloromethane:methanol and 95:5 dichloromethane:methanol) to provide 600 milligrams (mg) of (1E)-4-fluorobenzaldehyde O-[3-(4-amino-2-propyl-1H-imidazo[4,5-c]quinolin-1-yl)propyl]oxime as a beige powder, mp 172-175° C.

$^1$H NMR (300 MHz, CDCl$_3$) δ 8.1 (s, 1H), 8.0 (d, J=8.2 Hz, 1H), 7.8 (d, J=7.8 Hz, 1H), 7.6 (m, 2H), 7.56 (m, 1H), 7.4 (m, 1H), 7.1 (m, 2H), 5.6 (br s, 2H), 4.6 (t, J=7.5 Hz, 2H), 4.3 (t, J=5.5 Hz, 2H), 2.9 (t, J=7.6 Hz, 2H), 2.4 (m, 2H), 1.9 (m, 2H), 1.1 (t, J=7.3 Hz, 3H);

$^{13}$C NMR (75 MHz, CDCl$_3$) δ 165.9, 162.6, 153.7, 151.6, 148.5, 145.7, 145.0, 133.6, 129.4, 129.3, 128.5, 127.5, 127.3, 122.6, 120.0, 116.5, 116.2, 115.8, 70.9, 43.1, 30.3, 29.6, 21.9, 14.4;

MS (APCI) m/z 406 (M+H)$^+$;

Anal. calcd for C$_{23}$H$_{24}$FN$_5$O: C, 68.13; H, 5.97; N, 17.27. Found: C, 67.82; H, 6.14; N, 16.94.

Example 3

Acetone O-[3-(4-amino-2-propyl-1H-imidazo[4,5-c]quinolin-1-yl)propyl]oxime

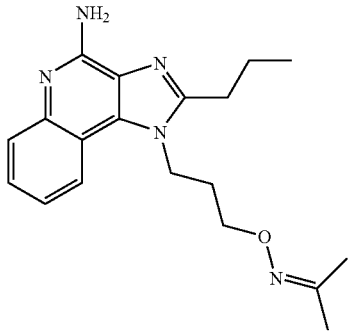 [SMILES: CCCc1nc2c(N)nc3ccccc3c2n1CCCON=C(C)C]

A mixture of 1-[3-(aminooxy)propyl]-2-propyl-1H-imidazo[4,5-c]quinolihn-4-amine (0.605 g, 2.02 mmol) in methanol was heated until the starting material dissolved. Acetone (3 mL, 40 mmol) was then added, and the resulting solution was stirred for two hours. The reaction was then concentrated under reduced pressure, and the residue (800 mg) was purified by column chromatography on silica gel (25 g, eluting sequentially with 98:2 dichloromethane:methanol and 95:5 dichloromethane:methanol) to provide 600 mg of acetone O-[3-(4-amino-2-propyl-1H-imidazo[4,5-c]quinolin-1-yl)propyl]oxime as a beige powder, mp 147-150° C.

$^1$H NMR (300 MHz, CDCl$_3$) δ 8.0 (d, J=8.2 Hz, 1H), 7.8 (d, J=8.4 Hz, 1H), 7.5 (t, J=7.1 Hz, 1H), 7.3 (t, J=8.4 Hz, 1H), 5.6 (br s, 2H), 4.6 (t, J=7.6 Hz, 2H), 4.2 (t, J=5.5 Hz, 2H), 2.9 (t, J=7.6 Hz, 2H), 2.3 (m, 2H), 2.0 (m, 8H), 1.1 (t, J=7.3 Hz, 3H);

$^{13}$C NMR (75 MHz, CDCl$_3$) δ 155.3, 153.3, 151.2, 144.7, 133.2, 127.1, 126.9, 122.1, 119.7, 115.5, 69.5, 42.9, 30.0, 29.2, 21.9, 21.6, 15.6, 14.1;

MS (APCI) m/z 340 (M+H)$^+$;

Anal. Calcd for C$_{19}$H$_{25}$N$_5$O.0.35H$_2$O: C, 66.00; H, 7.49; N, 20.26. Found: C, 66.34; H, 7.34; N, 19.88.

Example 4

Acetone O-[4-(4-amino-2-butyl-1H-imidazo[4,5-c]quinolin-1-yl)butyl]oxime

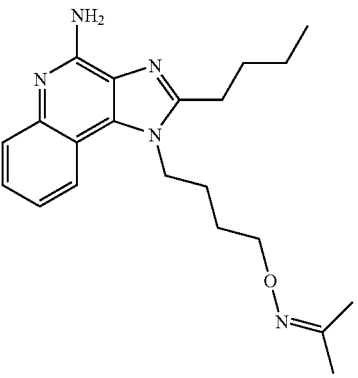 [SMILES: CCCCc1nc2c(N)nc3ccccc3c2n1CCCCON=C(C)C]

Part A

Triphenylphosphine (21.2 g, 80.7 mmol) and N-hydroxyphthalimide (13.2 g, 80.7 nmuol) were added to a solution of 4-(2-butyl-1H-imidazo[4,5-c]quinolin-1-yl)butan-1-ol (16.0 g, 53.8 mmol) in tetrahydrofuran (200 mL). The mixture was stirred for five minutes and then was cooled to approximately 0° C. Diisopropyl azodicarboxylate (19.6 g, 96.8 mmol) was added dropwise, and the reaction was allowed to warm to room temperature and stirred for three hours. An analysis by LC/MS indicated the presence of starting material, and the reaction was stirred at 60° C. overnight. An analysis by LC/MS indicated the presence of starting material, and additional triphenylphosphine, N-hydroxyphthalimide, and diisopropyl azodicarboxylate (26.9 mmol of each) were added to the reaction mixture. The reaction was stirred at room temperature for two hours and heated at reflux for three hours. The reaction was concentrated under reduced pressure, and the residue was dissolved in chloroform (200 mL). The resulting solution was washed with brine (3×150 mL), dried over magnesium sulfate, filtered through a layer of CELITE filter aid, and concentrated under reduced pressure. An analysis of the crude product mixture by LC/MS indicated that starting material was still present. The mixture was dissolved in tetrahydroiiran (200 mL) and treated with triphenylphosphine (21.2 g, 80.7 mmol), N-hydroxyphthalimide (13.2 g, 80.7 mmol), and diisopropyl azodicarboxylate (19.6 g, 96.8 mmol) as described above. The reaction was stirred overnight at room temperature. The product was present as a white precipitate, which was isolated by filtration and washed with tetrahydrofuran to provide 8.68 g of 2-[4-(2-butyl-1H-imidazo[4,5-c]quinolin-1-yl)butoxy]-1H-isoindole-1,3(2H)-dione as a white solid.

$^1$H NMR (300 MHz, CDCl$_3$) δ 9.3 (s, 1H), 8.3 (m, 2H), 7.9 (m, 2H), 7.8 (m, 2H), 7.7 (m, 2H), 4.7 (t, J=7.9 Hz, 2H), 4.3 (t, J=5.8 Hz, 2H), 3.1 (t, J=7.6 Hz, 2H), 2.3 (m, 2H), 2.0 (m, 4H), 1.6 (m, 2H), 1.1 (t, J=7.3 Hz, 3H);

MS (APCI) m/z 443 (M+H)$^+$.

Part B

A solution of 2-[4-(2-butyl-1H-imidazo[4,5-c]quinolin-1-yl)butoxy]-1H-isoindole-1,3(2H)-dione (7.65 g, 17.3 mmol) in dichloromethane (100 mL) was treated with mCPBA (4.65 g, 20.7 mmol), and the resulting orange solution was stirred for four hours at room temperature. The solution was then diluted with dichloromethane (100 ml), washed with brine (3×100 mL), dried over magnesium sulfate, filtered through a layer of CELITE filter aid, and concentrated under reduced pressure to provide 9.92 g of 2-[4-(2-butyl-5-oxido-1H-imidazo[4,5-c]quinolin-1-yl)butoxy]-1H-isoindole-1,3(2H)-dione as a red semi-solid.

Part C

A mixture of 2-[4-(2-butyl-5-oxido-1H-imidazo[4,5-c]quinolin-1-yl)butoxy]-1H-isoindole-1,3(2H)-dione (8.92 g, 19.5 mmol) in dichloroethane (100 mL) was shaken vigorously until it became homogeneous. With vigorous stirring, ammonium hydroxide (100 mL) andp-toluenesulfonyl chloride (4.45 g, 23.4 mmol) were added sequentially. The reaction was stirred overnight at room temperature. The product was present as a white precipitate, which was isolated by filtration to provide 1.97 g of 1-[4-(aminooxy)butyl]-2-butyl-1H-imidazo[4,5-c]quinolin-4-amine as a white solid.

$^1$H NMR (300 MHz, CDCl$_3$) δ 8.0 (d, J=8.2 Hz, 1H), 7.8 (d, J=8.3 Hz, 1H), 7.5 (t, J=7.1 Hz, 1H), 7.3 (t, J=7.1 Hz, 1H), 5.6 (br s, 2H), 5.2 (br s, 2H), 4.5 (t, J=7.8 Hz, 2H), 3.8 (t, J=6.2 Hz, 2H), 2.9 (t, J=7.6 Hz, 2H), 1.7-2.0 (m, 6H), 1.6 (m, 2H), 1.0 (t, J=7.3 Hz, 3H); MS (APCI) m/z 328 (M+H)$^+$.

The filtrate with diluted with chloroform, washed with brine (3×100 mL), dried over magnesium sulfate, filtered through a layer of CELITE filter aid, and concentrated under reduced pressure to provide 5.72 g additional product as a red semi-solid.

Part D

Acetone (444 mg, 7.65 mmol) was added to a solution of 1-[4-(aminooxy)butyl]-2-butyl-1H-imidazo[4,5-c]quinolin-4-amine (0.500 g, 1.53 mmol) in methanol (7 mL), and the reaction was stirred overnight at room temperature. The solvent was removed under reduced pressure and then firther dried under high vacuum to provide 358 mg of acetone O-[4-(4-amino-2-butyl-1H-imidazo[4,5-c]quinolin-1-yl)butyl]oxime as a white solid, mp 115-117° C.

$^1$H NMR (300 MHz, DMSO-d$_6$) δ 8.0 (d, J=7.8 Hz, 1H), 7.7 (d, J=8.3 Hz, 1H), 7.5 (t, J=8.0 Hz, 1H), 7.3 (t, J=8.1 Hz, 1H), 6.5 (br s, 2H), 4.5 (t, J=7.2 Hz, 2H), 4.0 (t, J=6.0 Hz, 2H), 2.9 (t, J=7.5 Hz, 2H), 1.9-1.6 (m, 12H), 1.5 (m, 2H), 1.1 (t, J=7.3 Hz, 3H);

$^{13}$C NMR (75 MHz, DMSO-d$_6$) δ 154.2, 153.4, 152.0, 144.8, 132.6, 128.4, 126.6, 126.4, 121.5, 120.3, 115.1, 71.9, 44.9, 30.0,26.8,26.5,25.9, 22.3, 21.6, 15.4, 14.1;

MS (APCI) m/z 368 (M+H)$^+$;

HRMS (ESI) Theoretical mass: 368.2469, measured mass: 368.2450.

For Examples 5, 6, and 7 the final compounds were purified by flash chromatography using a 10 g silica gel cartridge (RediSep, ISCO, 230-400 mesh) attached to a gradient pump system, 254 nanometers (nm) UV detector, and fraction collector (ISCO COMBIFLASH Sg100c system). The column was equilibrated with dichloromethane:methanol with or without approximately 1% ammonium hydroxide, and the reaction mixture was injected onto the column. The mixture was eluted with a gradient program using a solvent system consisting of dichloromethane:methanol with or without approximately 1% ammonium hydroxide. The gradient started with a lower percentage of methanol (approximately 1%) and the percentage of methanol was gradually increased (to up to approximately 10%) to elute the desired compound. Fractions were examined by thin layer chromatography and by LC/MS and those containing the desired compound were combined and concentrated.

Example 5

(1E)-Benzaldehyde O-{3-[4-amino-2-(ethoxymethyl)-1H-imidazo[4,5-c]quinolin-1-yl]propyl}oximne

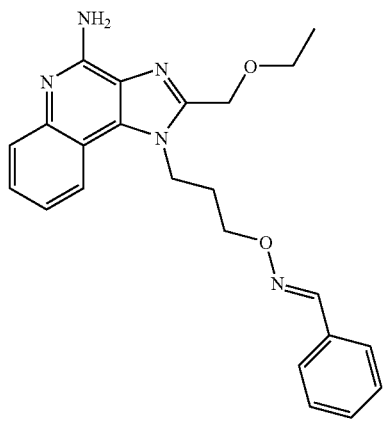 [SMILES: CCOCc1nc2c(N)nc3ccccc3c2n1CCCO/N=C/c1ccccc1]

Part A

Triphenylphosphine (8.71 g, 33.2 mmol) and N-hydroxyphthalimide (5.42 g, 33.2 mmol) were added to a solution of 3-[2-(ethoxymethyl)-1H-imidazo[4,5-c]quinolin-1-yl]propan-1-ol (6.31 g, 22.1 mmol) in tetrahydrofuran (150 mL). The reaction was stirred under nitrogen and cooled to approximately 0° C. Diisopropyl azodicarboxylate (17.5 mL, 89.1 mmol) was then added dropwise over a period of 15 minutes. The solvent was removed under reduced pressure, and the residue was dissolved in chloroform (200 naL). The solution was extracted with 6 normal (N) hydrochloric acid (3×200 mL), and sodium hydroxide pellets were added to the combined extracts until the solution was basic. The aqueous solution was then extracted with chloroform (4×), and the combined extracts were dried over magnesium sulfate, filtered through a layer of CELITE filter aid, and concentrated under reduced pressure to provide 4 g of 1-[3-(aniunooxy)propyl]-2-(ethoxymethyl)-1H-imidazo [4,5-c] quinoline.

Part B

Benzaldehyde (340 µL, 3.3 mmol) was added to a solution of 1-[3-(aminooxy)propyl]-2-(ethoxymethyl)-1H-imidazo[4,5-c]quinoline (1.00 g, 3.33 mmol) in methanol (4 mL), and the resulting solution was stirred overnight at room temperature. The methanol was removed under reduced pressure to provide 1.42 g of (1E)-benzaldehyde O-{3-[2-(ethoxymethyl)-1H-imidazo[4,5-c]quinolin-1-yl]propyl}oxime, which was used without purification.

Part C

The material from Part B was dissolved in dichloromethane (5 mL), and mCPBA (984 mg, 4.39 mmol) was added. The reaction was stirred for one hour and then diluted with dichloromethane. The solution was washed with saturated aqueous sodium bicarbonate (2×50 mL), dried over magnesium sulfate, filtered through a layer of CELITE filter aid, concentrated under reduced pressure, and further dried under high vacuum to provide 1.03 g of (1E)-benzaldehyde O-{3-[2-(ethoxymethyl)-5-oxido-1H-imidazo[4,5-c]quinolin-1-yl]propyl}oxine as a red, glassy solid.

Part D

Ammonium hydroxide (15 mL) was added with vigorous stirring to a solution of (1E)-benzaldehyde O-{3-[2-(ethoxymnethyl)-5-oxido-1H-imidazo[4,5-c]quinolin-1-yl]propyl}oxime (1.03 g, 2.55 mmol) in dichloroethane (15 mL). p-Toluenesulfonyl chloride (572 mg), 3.00 mmol) was added, and the reaction was stirred for two hours at room temperature. The reaction was diluted with dichloromethane, and the organic solution was washed with brine (2×50 mL), dried over magnesium sulfate, filtered through a layer of CELITE filter aid, concentrated under reduced pressure, and further dried under high vacuum to provide a brown and white solid. The solid was purified by flash chromatography using the method described above to provide 296 mg of (1E)-benzaldehyde O-{3-[4-amino-2-(ethoxymethyl)-1H-imidazo[4,5-c]quinolin-1-yl]propyl}oxime as a brown powder, mp 133-135° C.

$^1$H NMR (300 MHz, DMSO-$d_6$) δ 8.4 (s, 1H), 8.1 (d, J=7.9 Hz, 1H), 7.7 (m, 3H), 7.5 (m, 4H), 7.2 (t, J=7.1 Hz, 1H), 6.7 (br s, 2H), 4.8 (m, 4H), 4.4 (t, J=5.6 Hz, 2H), 3.7 (q, J=7.0 Hz, 2H), 2.3 (m, 2H), 1.2 (t, J=6.8 Hz, 3H);

MS (APCI) m/z 404 (M+H)$^+$;

Anal. calcd for $C_{23}H_{25}N_5O_2$: C, 68.47; H, 6.25; N, 17.36. Found: C, 68.18; H, 6.08; N, 17.07.

Example 6

(1E)4-Fluorobenzaldehyde O-{3-[4-amino-2-(ethoxymethyl)-1H-imidazo[4,5-c]quinolin-1-yl]propyl}oxime

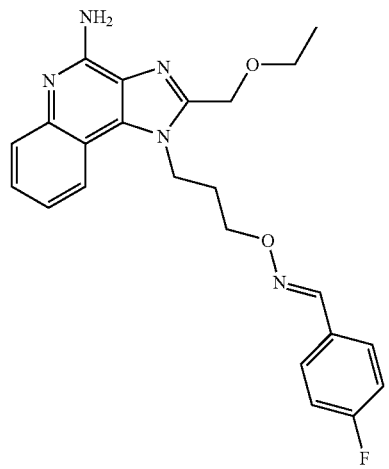 [SMILES: CCOCc1nc2c(N)nc3ccccc3c2n1CCCO/N=C/c1ccc(F)cc1]

Part A

4-Fluorobenzaldehyde (357 µL, 3.37 mmol) was added to a solution of 1-[3-(aminooxy)propyl]-2-(ethoxymethyl)-1H-imidazo[4,5-c]quinoline (1.00 g, 3.33 mmol), prepared in Part A of Example 5, in methanol (4 mL), and the resulting solution was stirred overnight at room temperature. The methanol was removed under reduced pressure to provide 1.29 g of (1E)-4-fluorobenzaldehyde O-{3-[2-(ethoxymethyl)-1H-imidazo[4,5-c]quinolin-1-yl]propyl}oxime, which was used without purification.

Part B

The general method described in Part C of Example 5 was used to oxidize (1E)-4-fluorobenzaldehyde O-{3-[2-(ethoxymethyl)-1H-imidazo[4,5-c]quinolin-1-yl]propyl}oxime (1.29 g, 3.18 mmol) with mCPBA (855 mg, 3.81 mmol) to provide 851 mg of (1E)-4-fluorobenzaldehyde O-{3-[2-(ethoxymethyl)-5-oxido-1H-imidazo[4,5-c]quinolin-1-yl]propyl}oxime as a red, tarry solid.

Part C

The general method described in Part D of Example 5 was used to aminate (1E)-4-fluorobenzaldehyde O-{3-[2-(ethoxymethyl)-5-oxido-1H-irnidazo[4,5-5 c]quinolin-1-yl]propyl}oxime (851 mg, 2.02 mmol). (1E)4-Fluorobenzaldehyde O-{3-[4-amino-2-(ethoxymethyl)-1H-imidazo[4,5-c]quinolin-1-yl]propyl}oxirne (346 mg) was obtained as a beige powder, mp 157-158° C.

$^1$H NMR (300 MHz, DMSO-$d_6$) δ 8.4 (s, 1H), 8.1 (d, J=7.5 Hz, 1H), 7.7 (m, 2H), 7.6 (d, J=8.4 Hz, 1H), 7.4 (t, J=7.1 Hz, 1H), 7.3 (m, 2H), 7.1 (t, J=8.2 Hz, 1H), 6.7 (br s, 2H), 4.8 (m, 4H), 4.3 (t, J=5.6 Hz, 2H), 3.6 (q, J=7.0 Hz, 2H), 2.3 (m, 2H), 1.2 (t, J=7.0 Hz, 3H);

MS (APCI) m/z 422 (M+H)$^+$;

Anal. calcd for $C_{23}H_{24}FN_5O_2$: C, 65.54; H, 5.74; N, 16.62. Found: C, 65.32; H, 5.81; N, 16.46.

Example 7

Acetone O-{3-[4-amino-2-(ethoxymethyl)-1H-imidazo[4,5-c]quinolin-1-yl]propyl}oxime

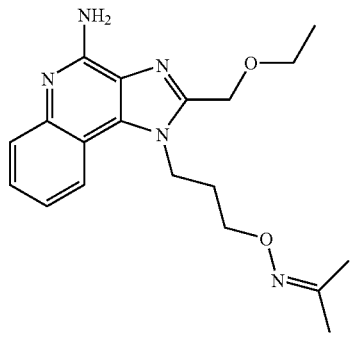 [SMILES: CCOCc1nc2c(N)nc3ccccc3c2n1CCCON=C(C)C]

Part A

Acetone (193 mg, 3.33 mmol) was added to a solution of 1-[3-(aminooxy)propyl]-2-(ethoxymethyl)-1H-imidazo[4,5-c]quinoline (1.00 g, 3.33 mmol), prepared in Part A of Example 5, in methanol (4 mL), and the resulting solution was stirred overnight at room temperature. The methanol was removed under reduced pressure to provide 1.06 g of acetone O-{3-[2-(ethoxymethyl)-1H-imidazo[4,5-c]quinolin-1-yl]propyl}oxime, which was used without purification.

Part B

The general method described in Part C of Example 5 was used to oxidize acetone O-{3-[2-(ethoxymethyl)-1H-imidazo[4,5-c]quinolin-1-yl]propyl}oxime (1.06 g, 3.12 mmol) with mCPBA (838 mg, 3.74 mmol) to provide 729 mg of acetone O-{3-[2-(ethoxymethyl)-5-oxido-1H-imidazo[4,5-c]quinolin-1-yl]propyl}oxime as a red solid.

Part C

The general method described in Part D of Example 5 was used to aminate acetone O-{3-[2-(ethoxymethyl)-5-oxido-1H-imidazo[4,5-c]quinolin-1-yl]propyl}oxime (726 mg, 2.04 mmol). Acetone O-{3-[4-amino-2-(ethoxymethyl)-1H-imidazo[4,5-c]quinolin-1-yl]propyl}oxime (136 mg) was obtained as an off-white crystalline solid, mp 109-111° C.

$^1$H NMR (300 MHz, CDCl$_3$) δ 8.1 (d, J=8.2 Hz, 1H), 7.8 (d, J=8.4 Hz, 1H), 7.5 (t, J=7.1 Hz, 1H), 7.3 (t, J=7.1 Hz, 1H), 5.6 (br s, 2H), 4.8 (s, 2H), 4.75 (t, J=6.1 Hz, 2H), 4.2 (t, J=5.5 Hz, 2H), 3.6 (q, J=7.0 Hz, 2H), 2.4 (m, 2H1), 2.0 (s, 3H), 1.9 (s, 3H), 1.3 (t, J=7.0 Hz, 3H); $^{13}$C NMR (75 MHz, CDCl$_3$) δ 155.6, 151.8, 149.5, 145.4, 134.5, 127.7, 127.5, 127.1, 122.7, 120.5, 115.8, 70.3, 66.6, 65.5, 44.1, 30.4, 22.3, 16.0, 15.5;

MS (APCI) m/z 356 (M+H)$^+$;

Anal. calcd for $C_{19}H_{25}N_5O_2$: C, 64.20; H, 7.09; N, 19.70. Found: C, 63.98; H, 7.22; N, 19.40.

Examples 8-83

An aldehyde or ketone from the table below (1.1 equivalents, 0.071 mmol) was added to a test tube containing a solution of 1-[3-(aminooxy)propyl]-2-propyl-1H-imidazo[4,5-c]quinolin-4-amine (20 mg, 0.066 mmol) in methanol (1 mL). The test tube was capped and placed on a shaker at ambient temperature overnight (approximately 18 hours). The solvent was removed by vacuum centrifugation. The compounds were purified by preparative high performance liquid chromatography (prep HPLC) using a Waters Fraction Lynx automated purification system. The prep HPLC fractions were analyzed using a Micromass LC-TOFMS, and the appropriate fractions were centrifuge evaporated to provide the trifluoroacetate salt of the desired compound. Column: Phenomenex LUNA C18(2), 21.2×50 millimeters (mm), 10 micron particle size, 100 Angstroms (Å) pore; flow rate: 25 mL/min: non-linear gradient elution from 5-95% B in 9 min, then hold at 95% B for 2 min, where A is 0.05% trirluoroacetic acid/water and B is 0.05% tifluoroacetic acid/acetonitrile; fraction collection by mass-selective triggering. The table below shows the ketone or aldehyde used for each example, the structure of the resulting compound, and the observed accurate mass for the isolated trifluoroacetate salt.

Examples 8-83

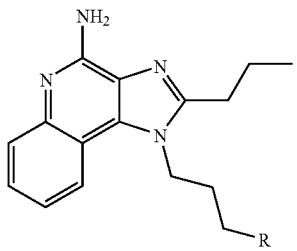

| Ex. | Aldehyde or Ketone | R | Measured Mass (M + H) |
|---|---|---|---|
| 8 | Cyclopropane-carboxaldehyde | ![structure] | 352.2163 |

-continued
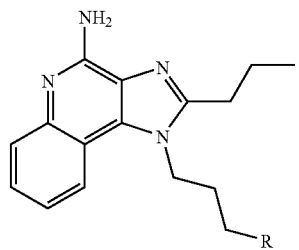
| Ex. | Aldehyde or Ketone | R | Measured Mass (M + H) |
|---|---|---|---|
| 9 | Butyraldehyde | propyl-CH=N-O- | 354.2321 |
| 10 | Cyclopentanone | cyclopentylidene=N-O- | 366.2313 |
| 11 | Isovaleraldehyde | isobutyl-CH=N-O- | 368.2447 |
| 12 | Trimethylacetaldehyde | t-butyl-CH=N-O- | 368.2451 |
| 13 | 3-Furaldehyde | 3-furyl-CH=N-O- | 378.1914 |
| 14 | Furfural | 2-furyl-CH=N-O- | 378.1929 |
| 15 | Cyclohexanone | cyclohexylidene=N-O- | 380.2452 |

-continued
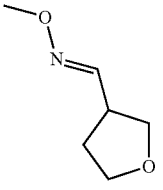
| Ex. | Aldehyde or Ketone | R | Measured Mass (M + H) |
|---|---|---|---|
| 16 | Tetrahydrofuran-3-carboxaldehyde (50% in water) |  | 382.2266 |
| 17 | 3-(Methylthio)propionaldehyde | 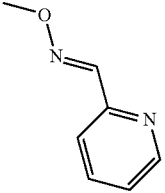 | 386.2041 |
| 18 | 2-Pyridinecarboxaldehyde | 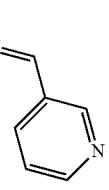 | 389.2112 |
| 19 | 3-Pyridinecarboxaldehyde | 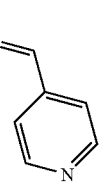 | 389.2113 |
| 20 | 4-Pyridinecarboxaldehyde |  | 389.2090 |
| 21 | 1-Methylpyrrole-2-carboxaldehyde | 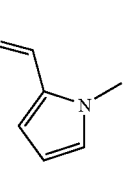 | 391.2253 |

-continued
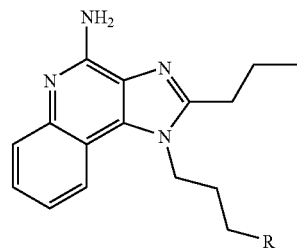
| Ex. | Aldehyde or Ketone | R | Measured Mass (M + H) |
|---|---|---|---|
| 22 | 5-Methylfurfural | | 392.2091 |
| 23 | 1-Methyl-2-imidazolecarboxaldehyde | | 392.2209 |
| 24 | 3-Thiophenecarboxaldehyde | | 394.1690 |
| 25 | 4-Methylcyclohexanone | | 394.2638 |
| 26 | Cycloheptanone | | 394.2619 |
| 27 | Cyclohexanecarboxaldehyde | | 394.2636 |
| 28 | 1-Methyl-4-piperidone | | 395.2582 |

-continued
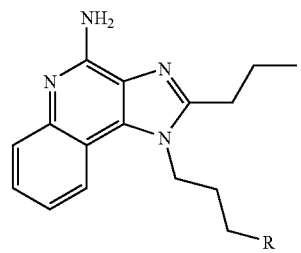
| Ex. | Aldehyde or Ketone | R | Measured Mass (M + H) |
|---|---|---|---|
| 29 | m-Tolualdehyde | 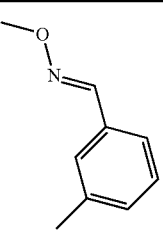 | 402.2304 |
| 30 | p-Tolualdehyde | 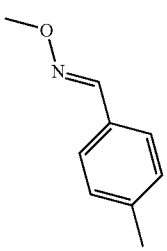 | 402.2317 |
| 31 | Phenylacetaldehyde | 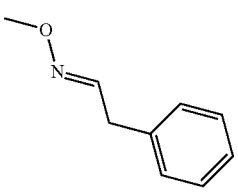 | 402.2297 |
| 32 | 5-Norbornene-2-carboxaldehyde | 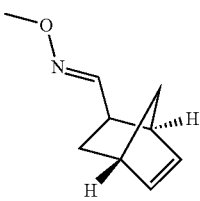 | 404.2444 |
| 33 | 2-Fluorobenzaldehyde | 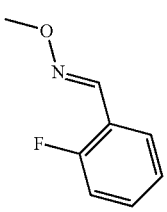 | 406.2079 |

-continued
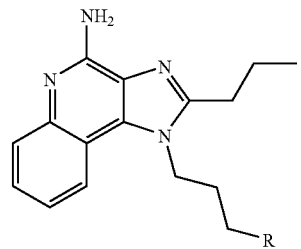
| Ex. | Aldehyde or Ketone | R | Measured Mass (M + H) |
|---|---|---|---|
| 34 | 3-Fluorobenzaldehyde | 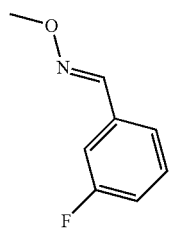 | 406.2060 |
| 35 | Octanal | 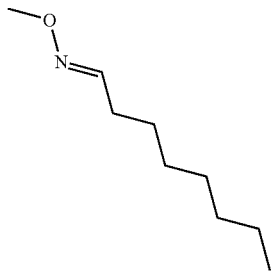 | 410.2934 |
| 36 | 3-Cyanobenzaldehyde | 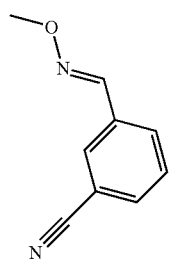 | 413.2113 |
| 37 | 2-Indanone | 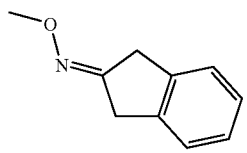 | 414.2309 |
| 38 | 2-Phenylpropionaldehyde | 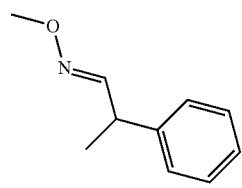 | 416.2444 |

-continued
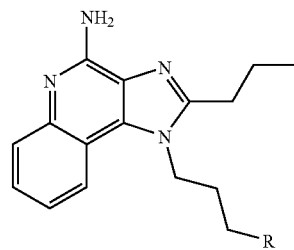
| Ex. | Aldehyde or Ketone | R | Measured Mass (M + H) |
|---|---|---|---|
| 39 | 3,4-Dimethylbenzaldehyde | | 416.2476 |
| 40 | 3,5-Dimethylbenzaldehyde | | 416.2473 |
| 41 | 3-Phenylpropionaldehyde | | 416.2482 |
| 42 | 2-Methoxybenzaldehyde | | 418.2265 |
| 43 | p-Anisaldehyde | | 418.2257 |

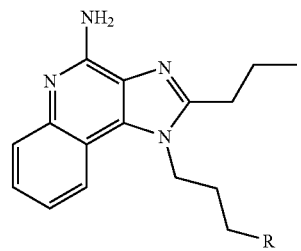
| Ex. | Aldehyde or Ketone | R | Measured Mass (M + H) |
|---|---|---|---|
| 44 | 2-Chlorobenzaldehyde | | 422.1773 |
| 45 | 3-Chlorobenzaldehyde | | 422.1741 |
| 46 | 1-Acetyl-4-piperidone | | 423.2539 |
| 47 | 1-Propyl-4-piperidone | | 423.2877 |
| 48 | 2,3-Difluorobenzaldehyde | | 424.1971 |
| 49 | 2,4-Difluorobenzaldehyde | | 424.1985 |

-continued
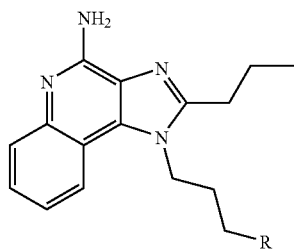
| Ex. | Aldehyde or Ketone | R | Measured Mass (M + H) |
|---|---|---|---|
| 50 | 2,5-Difluorobenzaldehyde | 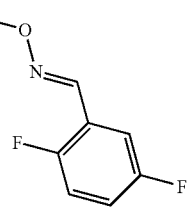 | 424.1946 |
| 51 | 2,6-Difluorobenzaldehyde | 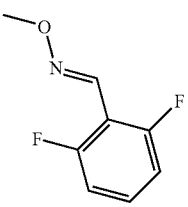 | 424.1976 |
| 52 | 3,4-Difluorobenzaldehyde | 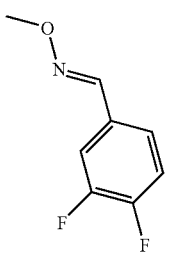 | 424.1960 |
| 53 | 3,5-Difluorobenzaldehyde | 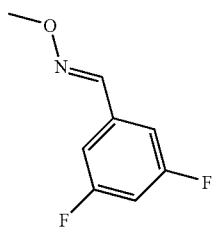 | 424.1975 |
| 54 | 3-Phenylbutyraldehyde | 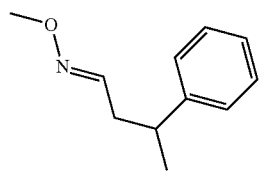 | 430.2623 |

-continued
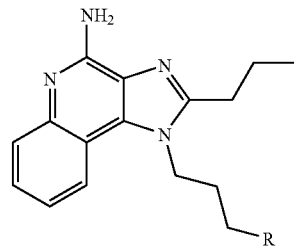
| Ex. | Aldehyde or Ketone | R | Measured Mass (M + H) |
|---|---|---|---|
| 55 | Cuminaldehyde | 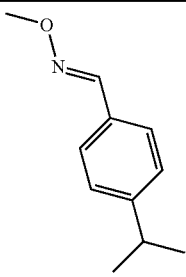 | 430.2630 |
| 56 | 3-Hydroxy-4-Methoxybenzaldehyde | 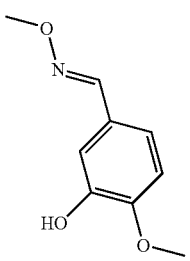 | 434.2180 |
| 57 | 2-(Methylthio)benzaldehyde | 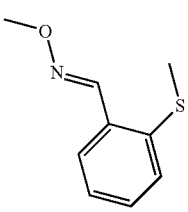 | 434.2025 |
| 58 | 4-tert-Butylcyclohexanone | 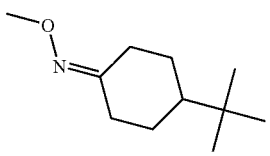 | 436.3089 |
| 59 | 2,2,6,6-Tetramethyl-4-piperidone | 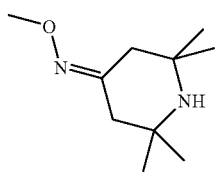 | 437.3042 |
| 60 | 1-Naphthaldehyde | 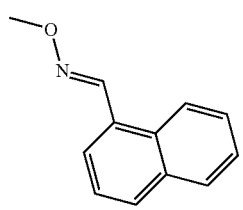 | 438.2296 |

-continued
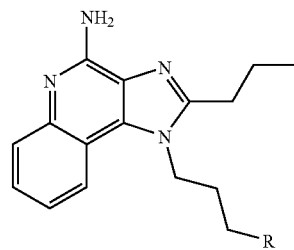
| Ex. | Aldehyde or Ketone | R | Measured Mass (M + H) |
|---|---|---|---|
| 61 | 2-Naphthaldehyde | 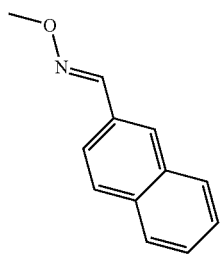 | 438.2321 |
| 62 | 4-Quinolinecarboxaldehyde | 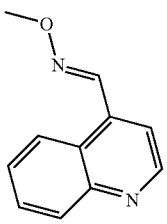 | 439.2276 |
| 63 | 2-Chloro-6-fluorobenzaldehyde |  | 440.1650 |
| 64 | 3-Chloro-4-fluorobenzaldehyde | 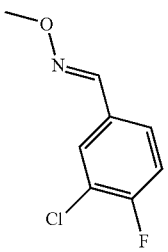 | 440.1657 |
| 65 | 1-Methylindole-3-carboxaldehyde | 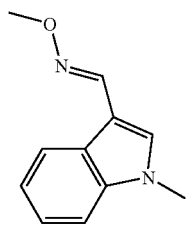 | 441.2405 |

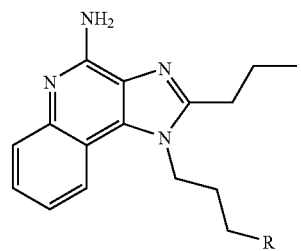
| Ex. | Aldehyde or Ketone | R | Measured Mass (M + H) |
|---|---|---|---|
| 66 | Thianaphthene-3-carboxaldehyde | 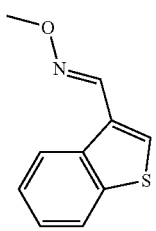 | 444.1878 |
| 67 | 4-tert-Butylbenzaldehyde | 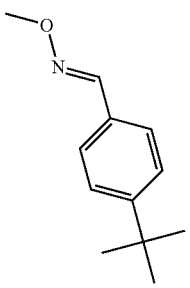 | 444.2747 |
| 68 | 4-Acetamidobenzaldehyde | 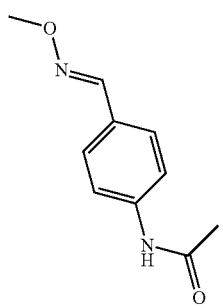 | 445.2375 |
| 69 | Methyl 4-formylbenzoate | 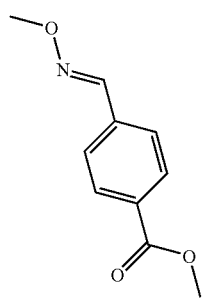 | 446.2195 |

-continued
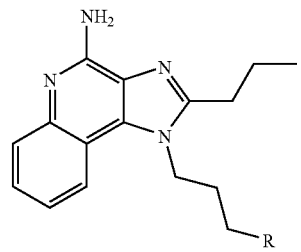
| Ex. | Aldehyde or Ketone | R | Measured Mass (M + H) |
|---|---|---|---|
| 70 | 2,4-Dimethoxybenzaldehyde | 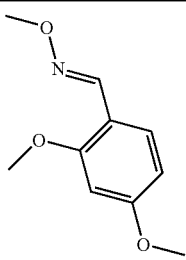 | 448.2351 |
| 71 | 3,4-Dimethoxybenzaldehyde | 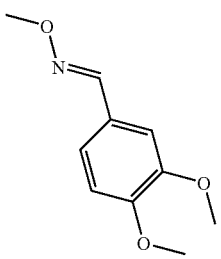 | 448.2359 |
| 72 | 4-(1H-Imidazol-1-yl)benzaldehyde | 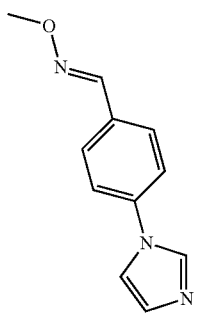 | 454.2388 |
| 73 | 4-Phenylcyclohexanone | 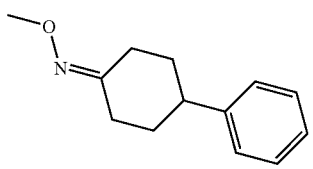 | 456.2742 |
| 74 | 2,3-Dichlorobenzaldehyde | 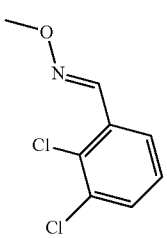 | 456.1371 |

-continued
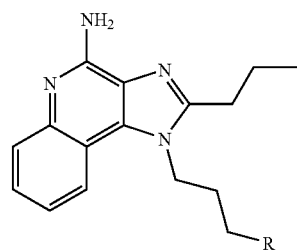
| Ex. | Aldehyde or Ketone | R | Measured Mass (M + H) |
|---|---|---|---|
| 75 | 2,4-Dichlorobenzaldehyde | 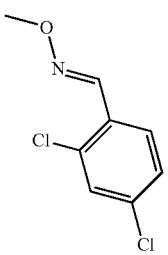 | 456.1389 |
| 76 | 2,6-Dichlorobenzaldehyde | 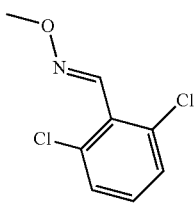 | 456.1345 |
| 77 | 4-Biphenylcarboxaldehyde | 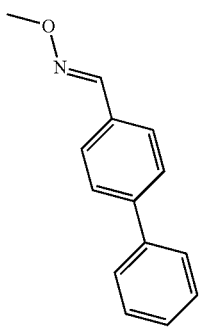 | 464.2472 |
| 78 | 4-(2-Pyridyl)benzaldehyde | 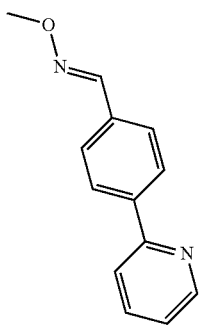 | 465.2433 |

-continued
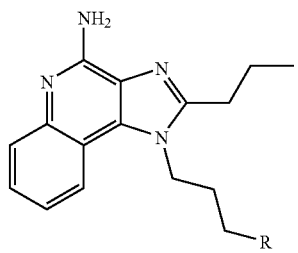
| Ex. | Aldehyde or Ketone | R | Measured Mass (M + H) |
|---|---|---|---|
| 79 | 1-Benzyl-4-piperidone | 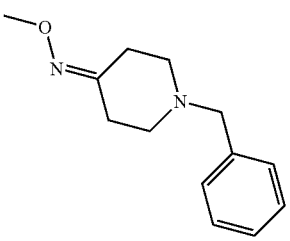 | 471.2900 |
| 80 | 3-Phenoxybenzaldehyde | 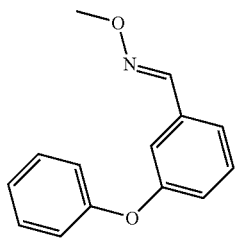 | 480.2427 |
| 81 | 4-Phenoxybenzaldehyde | 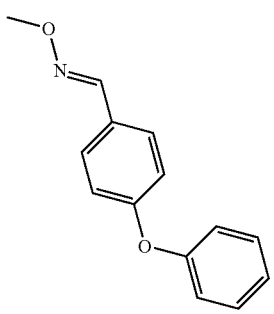 | 480.2393 |
| 82 | 3-Benzyloxybenzaldehyde | 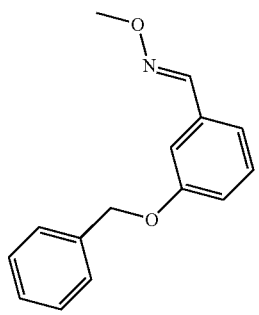 | 494.2564 |

-continued

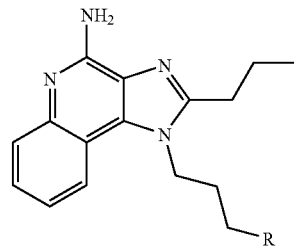

| Ex. | Aldehyde or Ketone | R | Measured Mass (M + H) |
|---|---|---|---|
| 83 | 4-Benzyloxybenzaldehyde | 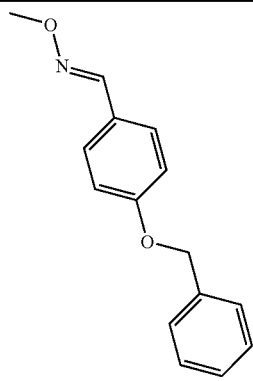 | 494.2585 |

Examples 84-126

An aldehyde or ketone from the table below (1.1 equivalents, 0.11 mmol) was added to a test tube containing a solution of 1-[4-(aminooxy)butyl]-2-butyl-1H-imidazo[4,5-c]quinolin-4-amine (32 mg, 0.098 mmol) in methanol (1 mL). The test tube was capped and placed on a shaker at ambient temperature overnight (~18 hours). The solvent was removed by vacuum centrifuigation. The compounds were purified as described for Examples 8-83. The table below shows the ketone or aldehyde used for each example, the structure of the resulting compound, and the observed accurate mass for the isolated trifluoroacetate salt.

Examples 84-126

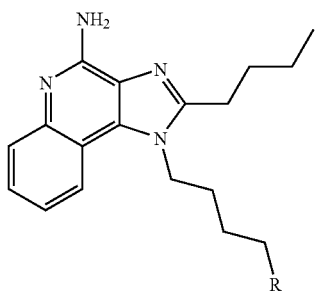

| Ex. | Aldehyde or Ketone | R | Measured Mass (M + H) |
|---|---|---|---|
| 84 | Isovaleraldehyde | 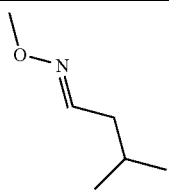 | 396.2747 |

-continued
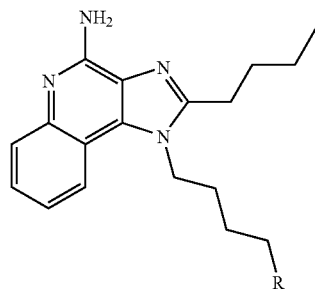
| Ex. | Aldehyde or Ketone | R | Measured Mass (M + H) |
|---|---|---|---|
| 85 | Trimethylacetaldehyde | | 396.2743 |
| 86 | 3-Furaldehyde | | 406.2266 |
| 87 | Furfural | | 406.2257 |
| 88 | Cyclohexanone | | 408.2744 |
| 89 | Benzaldehyde | | 416.2440 |
| 90 | 2-Pyridinecarboxaldehyde | | 417.2394 |
| 91 | 3-Pyridinecarboxaldehyde | | 417.2365 |

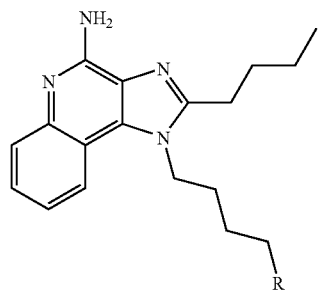
| Ex. | Aldehyde or Ketone | R | Measured Mass (M + H) |
|---|---|---|---|
| 92 | 4-Pyridinecarboxaldehyde | 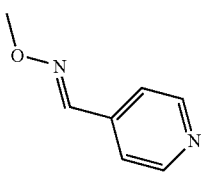 | 417.2430 |
| 93 | 1-Methylpyrrole-2-carboxaldehyde | 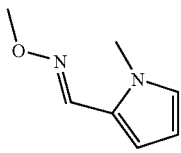 | 419.2578 |
| 94 | 1-Methyl-2-imidazolecarboxaldehyde | 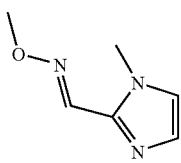 | 420.2485 |
| 95 | 2-Thiophenecarboxaldehyde | 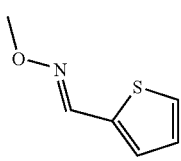 | 422.2002 |
| 96 | 3-Thiophenecarboxaldehyde | 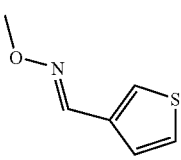 | 422.2031 |
| 97 | 1-Methyl-4-piperidone | 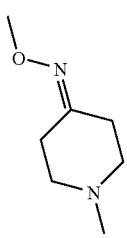 | 423.2871 |

-continued
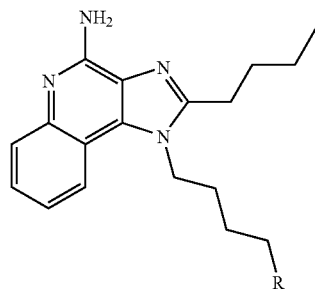
| Ex. | Aldehyde or Ketone | R | Measured Mass (M + H) |
|---|---|---|---|
| 98 | m-Tolualdehyde | 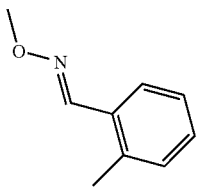 | 430.2621 |
| 99 | o-Tolualdehyde | 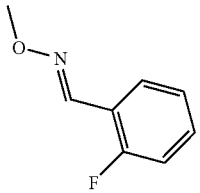 | 430.2603 |
| 100 | 2-Fluorobenzaldehyde | 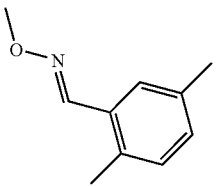 | 434.2378 |
| 101 | 2,5-Dimethylbenzaldehyde | 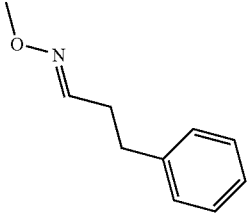 | 444.2778 |
| 102 | 3-Phenylpropionaldehyde | | 444.2782 |
| 103 | 2-Methoxybenzaldehyde | 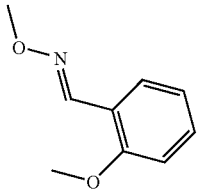 | 446.2560 |

-continued
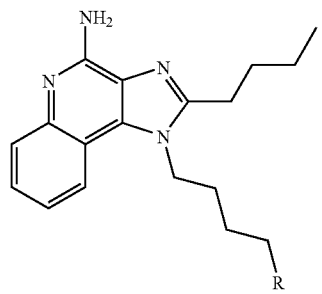
| Ex. | Aldehyde or Ketone | R | Measured Mass (M + H) |
|---|---|---|---|
| 104 | 3-Methoxybenzaldehyde | 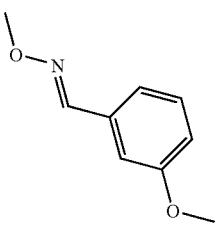 | 446.2574 |
| 105 | p-Anisaldehyde | 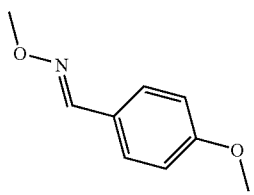 | 446.2578 |
| 106 | 2-Chlorobenzaldehyde | 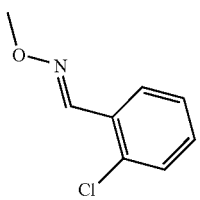 | 450.2086 |
| 107 | 3-Chlorobenzaldehyde | 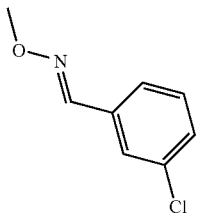 | 450.2083 |
| 108 | 1-Acetyl-4-piperidone | 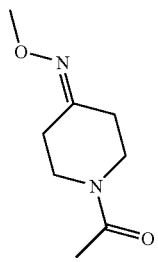 | 451.2798 |

-continued
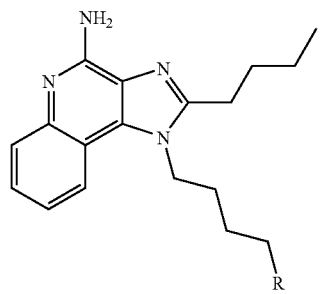
| Ex. | Aldehyde or Ketone | R | Measured Mass (M + H) |
|---|---|---|---|
| 109 | 2,3-Difluorobenzaldehyde | 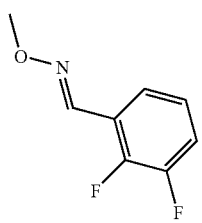 | 452.2256 |
| 110 | 2,4-Difluorobenzaldehyde | 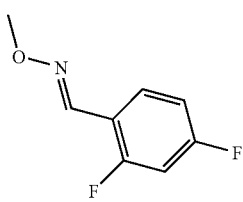 | 452.2295 |
| 111 | 2,5-Difluorobenzaldehyde | 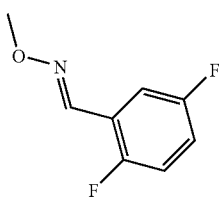 | 452.2298 |
| 112 | 2,6-Difluorobenzaldehyde | 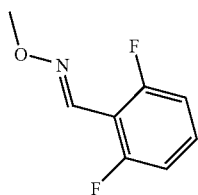 | 452.2282 |
| 113 | 3,5-Difluorobenzaldehyde | 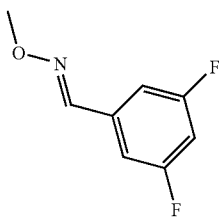 | 452.2297 |

-continued
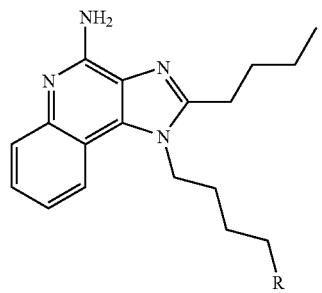
| Ex. | Aldehyde or Ketone | R | Measured Mass (M + H) |
|---|---|---|---|
| 114 | 3-Phenylbutyraldehyde | | 458.2908 |
| 115 | 2-Naphthaldehyde | | 466.2631 |
| 116 | 2-Quinolinecarboxaldehyde | | 467.2558 |
| 117 | 4-Acetamidobenzaldehyde | | 473.2665 |
| 118 | 2,4-Dimethoxybenzaldehyde | | 476.2665 |
| 119 | 2,5-Dimethoxybenzaldehyde | | 476.2667 |

-continued
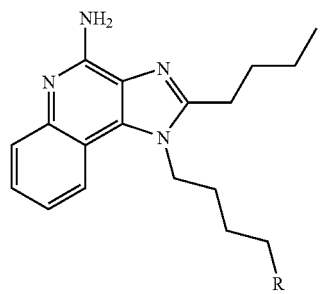
| Ex. | Aldehyde or Ketone | R | Measured Mass (M + H) |
|---|---|---|---|
| 120 | 3,5-Dimethoxybenzaldehyde | 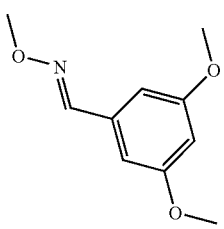 | 476.2677 |
| 121 | 4-(1H-Imidazol-1-yl)benzaldehyde | 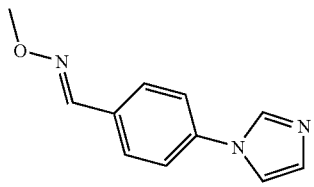 | 482.2682 |
| 122 | 2,4-Dichlorobenzaldehyde | 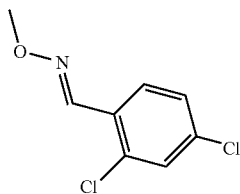 | 484.1685 |
| 123 | 2,6-Dichlorobenzaldehyde | 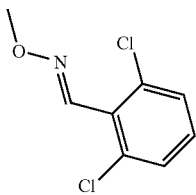 | 484.1673 |
| 124 | 3,4-Dichlorobenzaldehyde | 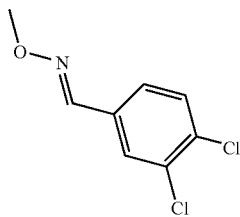 | 484.1673 |

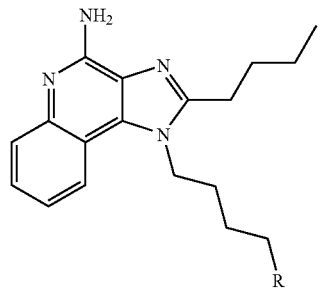

| Ex. | Aldehyde or Ketone | R | Measured Mass (M + H) |
|---|---|---|---|
| 125 | 3,5-Dichlorobenzaldehyde | O-N=CH-(3,5-dichlorophenyl) | 484.1679 |
| 126 | 4-Biphenylcarboxaldehyde | O-N=CH-(4-biphenyl) | 492.2738 |

Examples 127-135

Part A

To a solution of 4-chloro-3-nitro[1,5]naphthyridine (18.0 g, 85.9 mmol) in dichloromethane (220 mL) at room temperature was added triethylamine (15.6 mL, 112 mmol) and 3-amino-1-propanol (7.20 ML, 94.5 mmol). The solution was stirred for 4 hours, then was concentrated under reduced pressure to yield an orange solid. The solid was slurried in water (250 mL) for 30 minutes, isolated by filtration, washed with water (3×30 mL), and dried at 70° C. in a vacuum oven to afford 20.9 g of 3-[(3-nitro[1,5]naphthyridin-4-yl)amino] propan-1-ol as a yellow solid.

Part B

Acetic anhydride (7.30 mL, 77.3 mmol) was added slowly to a 0° C. solution of 3-[(3-nitro[1 ,5]naphthyridin-4-yl) amino]propan-1-ol (16.0 g, 64.5 numol), 4-dimethylaminopyridine (0.39 g, 3.2 mmol), and triethylamine (12.6 mL, 90.2 mmol) in dichloromethane (250 mL). The solution was stirred at 0° C. for 45 minutes, then was diluted with dichloromethane (50 mL) and washed with saturated aqueous sodium bicarbonate (150 mL). The aqueous layer was extracted with dichloromethane (2×40 mL). The organic layers were combined, dried over magnesium sulfate, filtered, and concentrated under reduced pressure to afford 19.74 g of 3-[(3-nitro[1,5]naphthyridin-4-yl]aminopropyl acetate as a yellow solid, which contained a trace amount of triethylamine and acetic acid and was used without purification.

Part C

A mixture of the 3-[(3-nitro[1,5]naphthyridinyl]aminopropyl acetate (12.00 g, 41.3 mmol) and 5% platinum on carbon (1.2 g) in ethyl acetate (125 mL) was hydrogenated at 30 psi ($2.1 \times 10^5$ Pa) on a Parr apparatus for 3 hours. The mixture was filtered through CELITE filter agent, which was rinsed with ethyl acetate (100 mL). The filtrate was concentrated under reduced pressure to 12.7 g of 3-[(3-amino[1,5]naphthyridin-4-yl)amino]propyl acetate as a golden oil.

Part D

Butyryl chloride (4.7 mL, 45.4 rumol) was added dropwise to a solution of material from Part C in dichloromethane (160 mL) at 0° C. The solution was allowed to warm to room temperature and stir for 1 hour, then was concentrated under reduced pressure to provide 3-{[3-(butyrylamino)[1,5]naphthyridin-4-yl]amino}propyl acetate hydrochloride as a dark orange foam that was used directly in the next step.

Part E

To the material from.Part D was added ethanol (165 mL) and 2 M sodium hydroxide (62.0 mL, 124 mmol). The resulting solution was heated at 60° C. for 7 hours, then was stirred at room temperature overnight. The solution was concentrated under reduced pressure and the resulting residue was dissolved in dichloromethane (250 mL) and washed with water (125 mL). The aqueous layer was extracted with dichioromethane (75 mL). The combined organic layers were washed with brine (100 mL), dried over magnesium sulfate, filtered, and concentrated under reduced pressure to provide 9.24 g of 3-(2-propyl-1H-imidazo[4,5-c][1,5]naphthyridin-1-yl)propan-1-ol as a brown oil.

Part F

Diisopropyl azodicarboxylate (8.10 mL, 48.4 inmol) was added dropwise over ten minutes to a stirred solution of 3-(2-propyl-1H-imidazo[4,5-c][1,5]naphthyridin-1-yl)propan-1-ol (10.9 g, 40.3 mmol), triphenylphosphine (12.7 g, 48.4 mmol), and N-hydroxyphthalimide (7.89 g, 48.4 mmol) in tetrahydrofuran (160 mL) at 0° C. The reaction was allowed to warm to room temperature and was stirred overnight. The solvent was removed under reduced pressure to afford an oil that was dissolved in ethyl acetate (200 mL) and extracted with 2 M HCl (3×100 mL). The aqueous layers were combined, and the pH was adjusted to 7 with the addition of solid sodium bicarbonate. A precipitate formed, was isolated by filtration, and was dissolved in dichloromethane (300 mL). The solution was dried over magnesium sulfate, filtered, and concentrated under reduced pressure to afford 17.38 g of 2-[3-(2-propyl-1H-imidazo[4,5-c][1,5]naphthyridin-1-yl)propoxy]-1H-isoindole-1,3(2H)-dione as a tan solid.

Part G

To a solution of 2-[3-(2-propyl-1H-imidazo[4,5-c][1,5]naphthyridin-1-yl)propoxy]-1H-isoindole-1,3(2H)-dione (6.00 g, 14.4 mmol) in chloroform (70 mL) at room temperature was added mCPBA (3.37 g, 19.5 mmol). The reaction was stirred for 5 hours and then concentrated ammonium hydroxide (40 mL) was added followed by portionwise addition of p-toluenesulfonyl chloride (3.03 g, 15.9 mmol). The mixture was stirred overnight and then was filtered to afford 3.99 g of crude product. The filtrate was diluted with brine (50 mL) and extracted with dichloromethane (2×20 mL). The organic layers were combined, dried over magnesium sulfate, filtered, and concentrated under reduced pressure to afford an orange solid, which was triturated with methanol and isolated by filtration to provide an additional 0.450 g of product. The product was combined and purified by chromatography on a HORIZON HPFC system (an automated, modular high-performance flash purification product available from Biotage, Inc, Charlottesville, Va., USA) (silica gel, gradient elution with 0-35% CMA in chloroform where. CMA is 80:18:2 chloroform/methanol/concentrated ammonium hydroxide) to afford 2.23 g of 1-[3-(aminooxy)propyl]-2-propyl-1H-imidazo[4,5-c][1,5]naphthyridin4-amine as a pale yellow solid.

Part H

For the synthesis of Examples 127-135, the following procedure was used: to a 0.2 M suspension of 1-[3-(aminooxy)propyl]-2-propyl-1H-imidazo[4,5-c][1,5]naphthyridin-4-amine (typically 0.9-3 mmol) in methanol at room temperature was added a ketone or an aldehyde from the table below. The equivalents of ketone or aldehyde used relative to the amount of 1-[3-(aminooxy)propyl]-2-propyl-1H-imidazo[4,5-c][1,5]naphthyridin-4-amine are shown in the table. The reaction mixture was stirred at room temperature for the length of time indicated in the table. In all cases except Example 127, a solution formed that was concentrated under reduced pressure. The resulting residue was purified by chromatography on a HORIZON HPFC system (silica gel, gradient elution with CMA in chloroform). The solid obtained after chromatography was concentrated from acetonitrile (Examples 128, 129, and 131), or triturated with acetonitrile (Example 130), or recrystallized from ethyl acetate/hexanes (example 132) or from dichloromethane/hexanes (example 133). In Example 127, the reaction mixture was filtered directly to yield crude product, which was subsequently purified by trituration with methanol and then concentrated from ethyl acetate. In all cases, the final material was dried at elevated temperature under vacuum to yield the Examples listed in Table 1. Example 128 was isolated as a 70:30 mixture of E:Z isomers.

TABLE 1

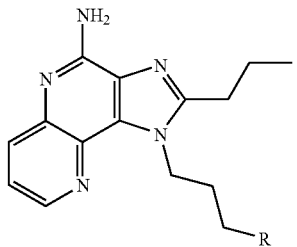

| Example | Ketone or Aldehyde | R | Equivalents | Reaction Time |
|---|---|---|---|---|
| 127 | Acetone | ![structure] | 13.6 | 3 days |
| 128 | Acetaldehyde | ![structure] | 5.0 | 2 hours |

TABLE 1-continued

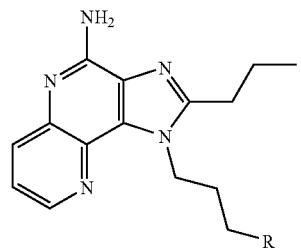

| Example | Ketone or Aldehyde | R | Equivalents | Reaction Time |
|---|---|---|---|---|
| 129 | Benzaldehyde | methoxyimino-phenyl | 1.3 | 4 hours |
| 130 | 3-Pyridinecarboxaldehyde | methoxyimino-(3-pyridyl) | 1.2 | 18 hours |
| 131 | Cyclohexanone | methoxyimino-cyclohexyl | 1.2 | 1 hour |
| 132 | N-Acetyl-4-piperidone | methoxyimino-(N-acetylpiperidin-4-yl) | 1.2 | 2.5 hours |
| 133 | Cyclohexanecarboxaldehyde | methoxyimino-methylcyclohexyl | 1.2 | 18 hours |
| 134 | N-Methyl-4-piperidone | methoxyimino-(N-methylpiperidin-4-yl) | 1.1 | 18 hours |

TABLE 1-continued

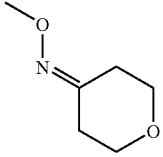

| Example | Ketone or Aldehyde | R | Equivalents | Reaction Time |
|---|---|---|---|---|
| 135 | Tetrahydro-4H-pyran-4-one | | 1.05 | 18 hours |

The characterization data for Examples 127-135 are shown in the table below.

| Example | Name | Form, Mp (°C.) | Elemental Analysis |
|---|---|---|---|
| 127 | Acetone O-[3-(4-amino-2-propyl-1H-imidazo[4,5-c]-1,5-naphthyridin-1-yl)propyl]oxime | off-white crystals, 160-162 | Anal. calcd for $C_{18}H_{24}N_6O$: C, 63.51; H, 7.11; N, 24.69. Found: C, 63.26; H, 7.40; N, 24.61 |
| 128 | (1E)-Ethanal O-[3-(4-amino-2-propyl-1H-imidazo[4,5-c]-1,5-naphthyridin-1-yl)propyl]oxime | off-white needles, 140-143 | Anal. calcd for $C_{17}H_{22}N_6O$: C, 62.56; H, 6.79; N, 25.75. Found: C, 62.28; H, 6.93; N, 25.86 |
| 129 | (1E)-Benzaldehyde O-[3-(4-amino-2-propyl-1H-imidazo[4,5-c]-1,5-naphthyridin-1-yl)propyl]oxime | beige needles, 112-114 | Anal. calcd for $C_{22}H_{24}N_6O$: C, 68.02; H, 6.23; N, 21.63. Found: C, 67.76; H, 6.29; N, 21.78 |
| 130 | (1E)-Nicotinaldehyde O-[3-(4-amino-2-propyl-1H-imidazo[4,5-c]-1,5-naphthyridin-1-yl)propyl]oxime | off-white needles, 152-154 | Anal. calcd for $C_{21}H_{23}N_7O$: C, 64.76; H, 5.95; N, 25.18. Found: C, 64.43; H, 6.11; N, 25.46 |
| 131 | Cyclohexanone O-[3-(4-amino-2-propyl-1H-imidazo[4,5-c]-1,5-naphthyridin-1-yl)propyl]oxime | off-white needles, 138-140 | Anal. calcd for $C_{21}H_{28}N_6O$: C, 66.29; H, 7.42; N, 22.09. Found: C, 66.00; H, 7.68; N, 22.19 |
| 132 | 1-Acetylpiperidin-4-one O-[3-(4-amino-2-propyl-1H-imidazo[4,5-c]-1,5-naphthyridin-1-yl)propyl]oxime | beige needles, 164-165 | Anal. calcd for $C_{22}H_{29}N_7O_2$: C, 62.39; H, 6.90; N, 23.15. Found: C, 62.09; H, 7.09; N, 23.26 |
| 133 | (1E)-Cyclohexanecarbaldehyde O-[3-(4-amino-2-propyl-1H-imidazo[4,5-c]-1,5-naphthyridin-1-yl)propyl]oxime | beige needles, 123-124 | Anal. calcd for $C_{22}H_{30}N_6O$: C, 66.98; H, 7.66; N, 21.30. Found: C, 66.87; H, 7.85; N, 21.36 |
| 134 | 1-Methylpiperidin-4-one O-[3-(4-amino-2-propyl-1H-imidazo[4,5-c]-1,5-naphthyridin-1-yl)propyl]oxime | yellow needles, 126-127 | Anal. calcd for $C_{21}H_{29}N_7O$: C, 63.77; H, 7.39; N, 24.79. Found: C, 63.50; H, 7.39; N, 24.76 |
| 135 | Tetrahydro-4H-pyran-4-one O-[3-(4-amino-2-propyl-1H-imidazo[4,5-c]-1,5-naphthyridin-1-yl)propyl]oxime | beige needles, 166-167 | Anal. calcd for $C_{20}H_{26}N_6O_2$: C, 62.81; H, 6.85; N, 21.97. Found: C, 62.61; H, 7.04; N, 21.94 |

Example 136

Acetone O-[3-(4-amino-1H-imidazo[4,5-c][1,5] naphthyridin-1-yl)propyl]oxime

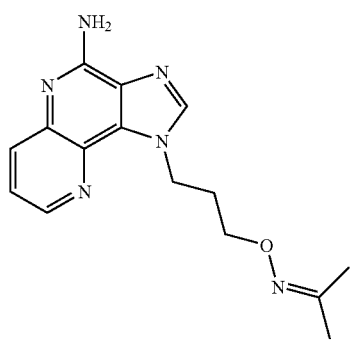 [SMILES: CC(C)=NOCCCn1cnc2c(N)nc3cccnc3c21]

Part A

Triethyl orthoformate (1.86 mL, 17.0 mmol) and pyridine hydrochloride (0.164 g, 1.42 mrnmol) were added to a stirred suspension of 3-[(3-amino[1,5]naphthyridin-4-yl)amino] propyl acetate (prepared as described in Part C of Examples 127-135, 3.70 g, 14.2 mmol) in toluene (70 mL). The mixture was heated at reflux with a Dean-Stark trap. After 2.5 hours, additional triethyl orthoformate (1 mL) was added and heating was continued for another 2 hours. The mixture was allowed to cool to room temperature and was concentrated under reduced pressure to afford a dark oil that was dissolved in dichloromethane (100 mL). The solution was washed with saturated aqueous sodium bicarbonate (50 mL), dried over magnesium sulfate, filtered, and concentrated under reduced pressure to afford 3.50 g of 3-(1H-imidazo[4,5-c][1,5]naphthyridin-1-yl)propyl acetate as an orange oil that was used without further purification in the next step.

Part B

Solid potassium carbonate (2.68 g, 19.4 mmol) was added to a solution of 3-(1H-imidazo[4,5-c][1,5]naphthyridin-1-yl)propyl acetate (3.50 g, 12.9 mmol) in methanol (65 mL) at room temperature. The mixture was stirred for 3 hours, then the solvent was removed under reduced pressure. The residue was partitioned between dichloromethane (150 mL) and water (75 mL). The organic layer was washed with brine (75 mL), dried over magnesium sulfate, filtered, and concentrated under reduced pressure to yield a brown semi-solid that was triturated with dichloromethane and isolated by filtration to afford 0.48 g of 3-(1H-imidazo[4,5-c][1,5]naphthyridin-1-yl)propan-1-ol. The filtrate was concentrated under reduced pressure, and the residue was purified by chromatography on a HORIZON HPFC system (silica gel, gradient elution with 0-50% CMA in chloroform) to provide an additional 0.67 g of 3-(1H-imidazo[4,5-c][1,5]naphthyridin-1-yl)propan-1-ol.

Part C

Diisopropyl azodicarboxylate (1.01 mL, 6.05 mmol) was added dropwise to a stirred solution of 3-(1H-imidazo[4,5-c][1,5]naphthyridin-1-yl)propan-1-ol (1.15 g, 5.04 mmol), triphenylphosphine (1.59 g, 6.05 mmol), and N-hydroxyphthalimide (0.986 g, 6.05 mmol) in tetrahydrofuran (25 mL) at 0° C. The reaction was allowed to warrn to room temperature and was stirred overnight. The product was isolated by filtration and washed with a minimal amount of tetrahydrofuran to afford 1.47 g of 2-[3-(1H-imidazo[4,5-c][1,5]naphthyridin-1-yl)propoxy]-1H-isoindole-1,3(2H)-dione as a pale yellow solid.

Part D

A modification of the procedure described in Part G of Examples 127-135 was used to convert 2-[3-(1H-imidazo[4,5-c][1,5]naphthyridin-1-yl)propoxy]-1H-isoindole-1,3(2H)-dione (1.47 g, 3.94 imnol) into 0.237 g of 1-[3-(aminooxy)propyl]-1H-imidazo[4,5-c][1,5]naphthyridin-4-amine. In this case, the solid isolated from the crude reaction mixture was not the desired product. The filtrate was diluted with saturated aqueous sodium bicarbonate (50 mL) and extracted with chloroform (2×40 mL). The combined organic layers were dried over magnesium sulfate, filtered, and concentrated under reduced pressure to an oil that was purified by chromatography on a HORIZON HPFC system (0-50% CMA in chloroform) to afford 0.237 g of 1-[3-(aminooxy)propyl]-1H-imidazo[4,5-c][1,5]naphthyridin-4-amine.

Part E

Acetone (1 mL) was added to a suspension of 1-[3-(aminooxy)propyl]-1H-imidazo[4,5-c][1,5]naphthyridin-4-amine (0.237 g, 0.92 mmol) in methanol (6 mL) at room temperature. The mixture was stirred and eventually a solution formed. After 6 hours, the volatiles were removed and the crude product was purified by chromatography on a HORIZON HPFC system (silica gel, gradient elution with 0-25% CMA in chloroform) to give a white powder that was crystallized from acetonitrile to yield 0.110 g of acetone O-[3-(4-amino-1H-imidazo[4,5-c][1,5]naphthyridin-1-yl)propyl]oxime as white needles, mp 120-121° C.

MS (APCI) m/z 299 (M+H)$^+$;

Anal. calcd for $C_{15}H_{18}N_6O$: C, 60.39; H, 6.08; N, 28.17. Found: C, 60.34; H, 6.21; N, 28.37.

Example 137

Acetone O-{2-[2-(4-amino-2-propyl-1H-imidazo[4,5-c][1,5]naphthyridin-1-yl)ethoxy]ethyl}oxime

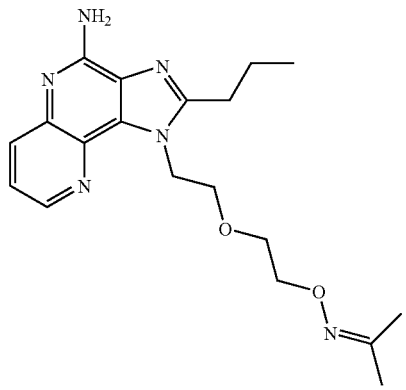 [SMILES: CCCc1nc2c(N)nc3cccnc3c2n1CCOCCON=C(C)C]

Part A

Following the general procedures described in Parts A-D of Examples 127-135, 4-chloro-3-nitro[1,5]naphthyridine (5.29 g, 25.2 mmol) was converted into 2-(2-{[3-(butyrylamino)[1,5]naphthyridin-4-yl]amino}ethoxy)ethyl acetate hydrochloride (approximately 24.5 mmol) using 2-(2-aminoethoxy)ethanol (2.8 mL, 27.8 mmol) in lieu of 3-amino-1-butanol in Part A of Examples 127-135.

Part B

Modifying the procedure described in Part E of Examples 127-135, 2-(2-{[3-(butyrylamino)[1,5]naphthyridin-4-yl]amino}ethoxy)ethyl acetate hydrochloride (approximately 24.5 mmol) was treated with 2 M NaOH (37 mL, 73.5 mmol) in ethanol. After the solution was heated at 60° C. overnight, more 2 M NaOH was added (1 equivalent) and the mixture was heated at 70° C. for 8 hours. After the work-up described in Part E of Examples 127-135, 6.55 g of 2-[2-(2-propyl-1H-imidazo[4,5-c][1,5]naphthyridin-1-yl)ethoxy]ethanol was isolated as an orange solid.

Part C

Following the general procedure described in Part F of Examples 127-135, 2-[2-(2-propyl-1H-imidazo[4,5-c][1,5]naphthyridin-1-yl)ethoxy]ethanol (6.50 g, 21.6 mmol) was converted into 2-{2-[2-(2-propyl-1H-imidazo[4,5-c][1,5]naphthyridin-1-yl)ethoxy]ethoxy}-1H-isoindole-1,3(2H)-dione. After the work-up described in Part F of Examples 127-135, the resulting oil was triturated with acetonitrile (60 mL) and a solid was isolated by filtration and dried to provide 7.76 g of 2-{2-[2-(2-propyl-1H-imidazo[4,5-c][1,5]naphthyridin-1-yl)ethoxy]ethoxy}-1H-isoindole-1,3(2H)-dione as a pale yellow solid.

Part D

Following the general procedure described in Part D of Example 136, 2-{2-[2-2-propyl-1H-imidazo[4,5-c] [1,5]naphthyridin-1-yl)ethoxy]ethoxy}-1H-isoindole-1,3(2H)-dione (7.76 g, 18.7 mmol) was converted into 1-{2-[2-(aminooxy)ethoxy]ethyl}-2-propyl-1H-imidazo[4,5-c][1,5]naphthyridin-4-amine. In this case, purification by chromatography was unnecessary and the crude product was triturated with acetonitrile to afford 2.71 g of 1-{2-[2-(aminooxy)ethoxy]ethyl}-2-propyl-1H-imidazo[4,5-c][1,5]naphthyridin4amine.

Part E

Following the general procedure described in Part E of Example 136, 1-{2-[2-(aminooxy)ethoxy]ethyl}-2-propyl-1H-imidazo[4,5-c][1,5]naphthyridin-4-amine (0.510 g, 1.54 mmol) was converted into acetone O-{2-[2-(4-amino-2-propyl-1H-imidazo[4,5-c] [1,5]naphthyridin-1-yl)ethoxy]ethyl}oxirne. After purification of the crude product by chromatography on a HORIZON HPFC system, the resulting white solid was triturated with acetonitrile and dried under vacuum to provide 0.229 g of acetone O-{2-[2-(4-amino-2-propyl-1H-imidazo [4,5-c] [1,5]naphthyridin-1-yl)ethoxy]ethyl}oxime as white needles, mp 127-128° C.

MS (APC) m/z 371 (M+H)+;

Anal. calcd for $C_{19}H_{26}N_6O_2$: C, 61.60; H, 7.07; N, 22.69. Found: C, 61.60; H, 7.25; N, 22.77.

Example 138

Acetone O-{3-[4-amino-2-(ethoxymethyl)-1H-imidazo[4,5-c][1,5]naphthyridin-1-yl]propyl}oxime

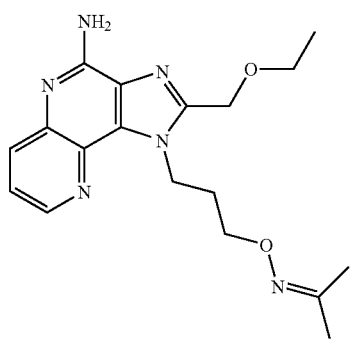 [SMILES: CCOCc1nc2c(N)nc3cccnc3c2n1CCCON=C(C)C]

Part A

Following the general procedures described in Parts D and E of Examples 127-135, 3-[(3-amino[1,5]naphthyridin-4-yl)amino]propyl acetate (prepared as described in Parts A-C of Examples 127-135, approximately 14.6 mmol) was converted into 3.18 g of 3-[2-(ethoxymethyl)-1H-imidazo[4,5-c][1,5]naphthyridin-1-yl]propan-1-ol using ethoxyacetyl chloride in lieu of butyryl chloride in Part D of Examples 127-135.

Part B

Following the general procedure described in Part F of Examples 127-135, 3-[2-(ethoxymethyl)-1H-imidazo[4,5-c][1,5]naphthyridin-1-yl]propan-1-ol (3.18 g, 11.1 mmol) was converted into 2-{3-[2-(ethoxymethyl)-1H-imidazo[4,5-c][1,5]naphthyridin-1-yl]propoxy}-1H-isoindole-1,3(2H)-dione. During the extraction with 2 N HCl, a solid formed which was isolated, washed with water, and dried. The solid was dissolved in dichloromethane (150 mL) and washed with saturated aqueous sodium bicarbonate (100 mL). The aqueous layer was back-extracted with dichloromethane (30 mL). The organic layers were combined, dried over magnesium sulfate, filtered, and concentrated under reduced pressure to afford 2.80 g of 2-{3-[2-(ethoxymethyl)-1H-imidazo[4,5-c][1,5]naphthyridin-1-yl]propoxy}-1H-isoindole-1,3(2H)-dione as a yellow solid.

Part C

Following the general procedure described in Part G of Examples 127-135, 2-{3-[2-(ethoxymethyl)-1H-imidazo[4, 5-c] [1,5]naphthyridin-1-yl]propoxy}-1H-isoindole-1,3 (2H)-dione (2.80 g, 6.49 mmol) was converted into 1.16 g of 1-[3-(aminooxy)propyl]-2-(ethoxymethyl)-1H-imidazo[4,5-c][1,5]naphthyridinamine.

Part D

Following the general procedure described in Part E of Example 136, 1-[3-(aminooxy)propyl]-2-(ethoxymethyl)-1H-imidazo[4,5-c] [1,5]naphthyridin-4-amine (0.315 g, 1.0 nunol) was converted into 0.234 g of acetone O-{3-[4-amino-2-(ethoxymethyl)-1H-imidazo[4,5-c][1,5]naphthyridin-1-yl]propyl}oxime, which was obtained as beige needles, mp 96-97° C.

MS (APCI) m/z 357 (M+H)+;

Anal. calcd for $C_{18}H_{24}N_6O_2$: C, 60.66; H, 6.79; N, 23.58. Found: C, 60.65; H, 6.86; N, 23.96.

Example 139

1-Acetylpiperidin-4-one O-{3-[4-amino-2-(ethoxymethyl)-1H-imidazo[4,5-c] [1,5]naphthyridin-1-yl]propyl}oximne

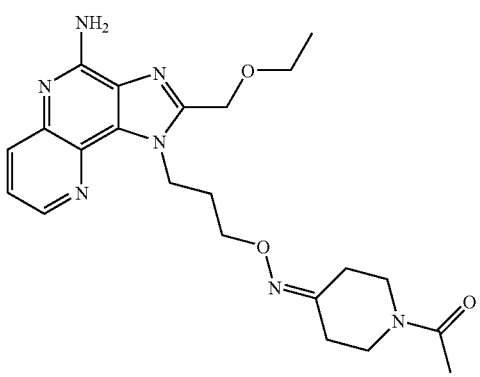 [SMILES: CCOCc1nc2c(N)nc3cccnc3c2n1CCCON=C1CCN(C(C)=O)CC1]

To a solution of 1-[3-(aminooxy)propyl]-2-(ethoxymethyl)-1H-imidazo[4,5-c][1,5]naphthyridin-4-amine (prepared as described in Parts A-C of Example 138, 0.395 g, 1.25 mmol) in methanol (8 mL) was added 4-acetyl piperidone (0.160 mL, 1.31 mmol). The solution was stirred at room temperature overnight. The solvent was removed under reduced pressure and the residue was purified by chromatography on a HORIZON HPFC system (silica gel, gradient elution using 0-25% CMA in chloroform). The purified material was triturated twice with acetonitrile and dried at elevated temperature under vacuum to provide 0.312 g of 1-acetylpiperidin4-one O-{3-[4-amino-2-(ethoxymethyl)-1H-imidazo [4,5-c][1,5]naphthyridin-1-yl]propyl}oxime as beige needles, mp 162-163° C.

MS (APCI) m/z 440 (M+H)+;

Anal. calcd for $C_{22}H_{29}N_7O_3$: C, 60.12; H, 6.65; N, 22.31. Found: C, 59.89; H, 6.88; N, 22.33.

Example 140

1-Methylpiperidin-4-one O-{3-[4-amino-2-(ethoxymethyl)-1H-imidazo[4,5-c][1,5]naphthyridin-1-yl]propyl}oxime

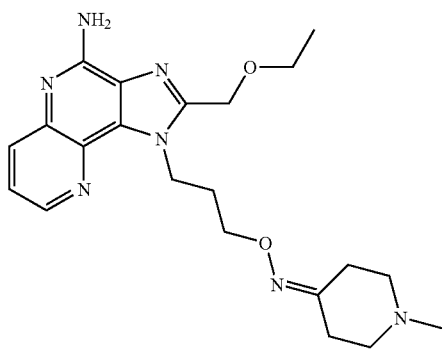 [SMILES: CCOCc1nc2c(N)nc3cccnc3c2n1CCCON=C1CCN(C)CC1]

To a solution of 1-[3-(aminooxy)propyl]-2-ethoxymethyl)-1H-imidazo[4,5-c][1,5]naphthyridin-4-amine (prepared as described in Parts A-C of Example 138, 0.378 g, 1.19 mmol) in methanol (8 mL) was added N-methylffpiperidone (0.160 mL, 1.31 mmol). The solution was stirred at room temperature overnight. The solvent was removed under reduced pressure and the residue was purified by chromatography on a HORIZON HPFC system (silica gel, gradient elution using 0-30% CMA in chloroform). The purified material was crystallized from acetonitrile and dried at elevated temperature under vacuum to provide 93 mg of 1-methylpiperidin-4-one O-{3-[4-amino-2-(ethoxymethyl)-1H-imidazo[4,5-c][1,5]naphthyridin-1-yl]propyl}oxime as white needles, mp 111-112° C.

MS (APCI) m/z 412 (M+H)$^+$;

Anal. calcd for $C_{21}H_{29}N_7O_2$: C, 61.29; H, 7.10; N, 23.83. Found. C, 61.05; H, 6.95; N, 23.80.

Example 141

Acetone O-{5-[4-amino-2-(ethoxymethyl)-1H-imidazo[4,5-c][1,5]naphthyridin-1-yl]pentyl}oxime

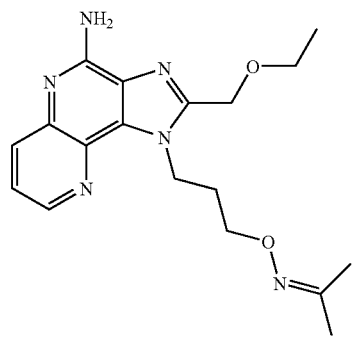 [SMILES: CCOCc1nc2c(N)nc3cccnc3c2n1CCCON=C(C)C]

Part A

Following the general procedures described in Parts A-D of Examples 127-135, 4-chloro-3-nitro[1,5]naphthyridine (10.0 g, 47.7 mmol) was converted into 5-({3-[(2-ethoxyacetyl)amino][1,5]naphthyridin-4-yl}amino)pentyl acetate hydrochloride (approximately 23.3 mmol) using 5-amino-1-pentanol in lieu of 3-amino-1-butanol in Part A and ethoxyacetyl chloride in lieu of butyryl chloride in Part D of Examples 127-135.

Part B

To a solution of the material from Part A in 3:1 ethanol/water was added 6 M $K_2CO_3$ (11.7 ML, 69.9 mmol). The reaction was stirred at room temperature for 7 days. The reaction was concentrated under reduced pressure and partitioned between dichloromethane (150 mL) and water (75 mL). The aqueous layer was extracted with dichloromethane (50 mL), and the combined organic layers were washed with brine (75 mL), dried over magnesium sulfate, filtered, and concentrated under reduced pressure to afford a brown oil. The oil was dissolved in methanol (100 mL) and solid potassium carbonate (3 g) was added. The mixture was stirred at room temperature for 1 hour, filtered, and concentrated to an oily residue that was partitioned between dichloromethane (100 mL) and water (50 mL). The aqueous layer was extracted with dichloromethane (30 mL). The combined organic layers were dried over magnesium sulfate, filtered, and concentrated under reduced pressure to yield an oil. The oil was dissolved in a minimal amount of ethyl acetate. Hexanes were added until the solution become cloudy and mixture was sonicated. A solid formed that was isolated by filtration. The filtrate was concentrated to yield a residue that was triturated with acetonitrile to produce a solid that was isolated by filtration. This last procedure was repeated twice to provide three crops of solid. The solids were combined to afford 4.52 g of 5-[2-(ethoxymethyl)-1H-imidazo[4,5-c][1,5]naphthyridin-1-yl]pentan-1-ol as a pale tan solid.

Part C

Following the general procedure described in Part B of Example 138, 5-[2-(ethoxymethyl)-1H-imidazo[4,5-c][1,5]naphthyridin-1-yl]pentan-1-ol (4.52 g, 14.4 mmol) was converted into 4.65 g of 2-({5-[2-(ethoxymethyl)-1H-imidazo[4,5-c][1 ,5]naphthyridin-1-yl]pentyl}oxy)-1H-isoindole-1,3 (2H)-dione.

Part D

Following the general procedure described in Part G of Examples 127-135, 2-({5-[2-(ethoxymethyl)-1H-imidazo[4,5-c][1 ,5]naphthyridin-1-yl]pentyl}oxy)-1H-isoindole-1,3 (2H)-dione (4.65 g, 10.1 mmol) was converted into 1-[5-(aminooxy)pentyl]-2-(ethoxymethyl)-1H-imidazo[4,5-c][1,5]naphthyridin-4-amine. In the workup after the reaction mixture was filtered, the filtrate was diluted with brine (30 mL) and chloroform (60 mL). The aqueous layer was extracted with chloroform (2×40 mL). The combined organic layers were dried over magnesium sulfate, filtered, and concentrated to afford a red solid that was triturated twice with acetonitrile and isolated by filtration to afford 1.35 g of a yellow solid. The filtrates were combined, concentrated under reduced pressure, and purified by chromatography on a HORIZON HPFC system (silica gel, gradient elution with 0-25% CMA in chloroform) to afford additional yellow solid. The solids were combined and dissolved in dichloromethane (150 mL). The solution was washed with saturated aqueous sodium bicarbonate (2×75 mL). The combined aqueous layers were back-extracted with dichloromethane (30 mL). The organic layers were combined, dried over magnesium sulfate, filtered, and concentrated under reduced pressure to afford 2.17 g of 1-[5-(aminooxy)pentyl]-2-(ethoxymethyl)-1H-imidazo[4,5-c][1,5]naphthyridin-4-amine as a pale yellow solid.

Part E

Using the general procedure described in Part E of Example 136, 1-[5-(aminooxy)pentyl]-2-(ethoxymethyl)-1H-imidazo[4,5-c][1,5]naphthyridin-4-amine (0.60 g, 1.74 mmol) was converted into acetone O-{5-[4-amino-2-(ethoxymethyl)-1H-imidazo[4,5-c][1,5]naphthyridin-1-yl]pentyl}oxime. The crude product was purified by chromatography on a HORIZON HPFC system (silica gel, gradient elution using 0-25% CMA in chloroform) to yield an oil that formed a solid upon standing at room temperature. The solid was dried at elevated temperature under vacuum to yield 0.244 g of acetone O-{5-[4-amino-2-(ethoxymethyl)-1H-imidazo[4,5-c][1,5]naphthyridin-1-yl]pentyl}oxime as beige needles, mp 91-92° C.

MS (APCI) m/z 385 (M+H)+;

Anal. calcd for $C_{20}H_{28}N_6O_2$: C, 62.48; H, 7.34; N, 21.86. Found: C, 62.41; H, 7.64; N, 21.88.

Examples 142-168

An aldehyde or ketone (0.11 mmol, 1.1 equivalents) from the table below was added to a test tube containing a 1-[3-(aminooxy)propyl]-2-propyl-1H-imidazo[4,5-c][1,5]naphthyridin-4-amine (prepared as described in Parts A-G of Examples 127-135, 29 mg, 0.10 mmol) in methanol (1 mL). The test tubes were capped and shaken overnight at ambient temperature. The solvent was removed by vacuum centrifugation. The compounds were purified by prep HPLC using a Waters FractiomLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

EXAMPLES 142-168

| Example | Reagent | R | Measured Mass (M + H) |
|---|---|---|---|
| 142 | Cyclopropanecarboxaldehyde | | 353.2096 |
| 143 | Butyraldehyde | | 355.2273 |
| 144 | 3-Furaldehyde | | 379.1894 |
| 145 | Furfural | | 379.1919 |

EXAMPLES 142-168-continued
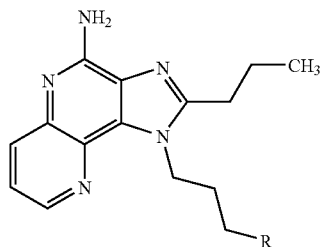
| Example | Reagent | R | Measured Mass (M + H) |
|---|---|---|---|
| 146 | Tetrahydrofuran-3-Carboxaldehyde | | 383.2163 |
| 147 | 3-(Methylthio)propionaldehyde | | 387.1989 |
| 148 | Benzaldehyde | | 389.2115 |
| 149 | 4-Pyridinecarboxaldehyde | | 390.2054 |
| 150 | 3-Pyridinecarboxaldehyde | | 390.2058 |
| 151 | 2-Pyridinecarboxaldehyde | | 390.2045 |

EXAMPLES 142-168-continued
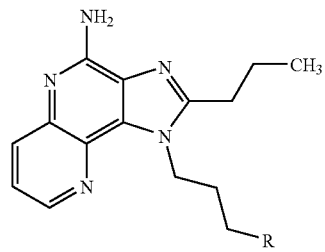
| Example | Reagent | R | Measured Mass (M + H) |
|---|---|---|---|
| 152 | 1-Methyl-2-imidazolecarboxaldehyde | —O—N=CH—(1-methylimidazol-2-yl) | 393.2142 |
| 153 | 2-Thiophenecarboxaldehyde | —O—N=CH—(2-thienyl) | 395.1666 |
| 154 | 2-Heptanone | —O—N=C(CH₃)—(CH₂)₄CH₃ | 397.2704 |
| 155 | m-Tolualdehyde | —O—N=CH—(3-methylphenyl) | 403.2257 |
| 156 | o-Tolualdehyde | —O—N=CH—(2-methylphenyl) | 403.2234 |
| 157 | Phenylacetaldehyde | —O—N=CH—CH₂—phenyl | 403.2243 |

EXAMPLES 142-168-continued
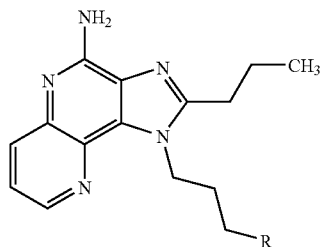
| Example | Reagent | R | Measured Mass (M + H) |
|---|---|---|---|
| 158 | p-Tolualdehyde | 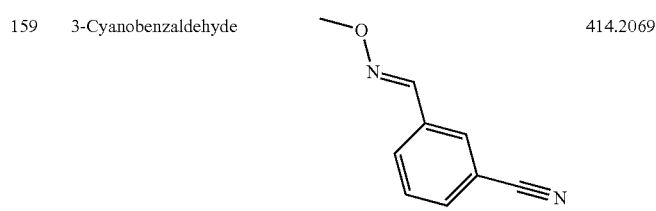 | 403.2263 |
| 159 | 3-Cyanobenzaldehyde | 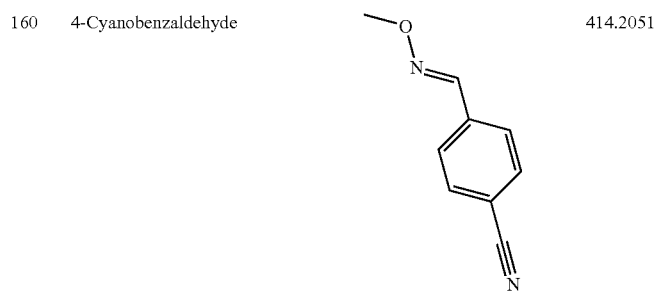 | 414.2069 |
| 160 | 4-Cyanobenzaldehyde | 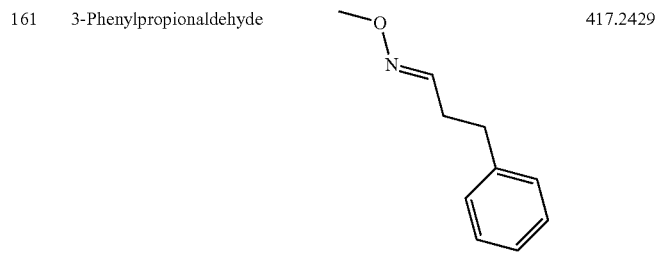 | 414.2051 |
| 161 | 3-Phenylpropionaldehyde | 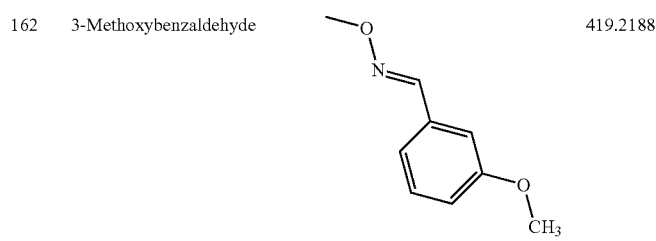 | 417.2429 |
| 162 | 3-Methoxybenzaldehyde | | 419.2188 |

EXAMPLES 142-168-continued
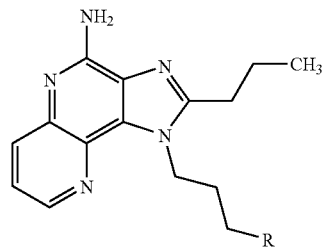
| Example | Reagent | R | Measured Mass (M + H) |
|---|---|---|---|
| 163 | o-Anisaldehyde | | 419.2211 |
| 164 | p-Anisaldehyde | | 419.2189 |
| 165 | 2-Naphthaldehyde | | 439.2252 |
| 166 | 2-Quinolinecarboxaldehyde | | 440.2214 |

EXAMPLES 142-168-continued

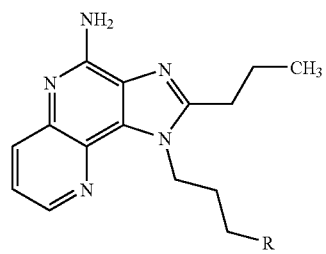

| Example | Reagent | R | Measured Mass (M + H) |
|---|---|---|---|
| 167 | 4-Biphenylcarboxaldehyde | | 465.2410 |
| 168 | 4-(2-Pyridyl)benzaldehyde | | 466.2325 |

Example 169

Acetone O-[3-(4-aniino-6,7-dimethyl-2-propyl-1H-imidazo[4,5-c]pyridin-1-yl)propyl]oxime

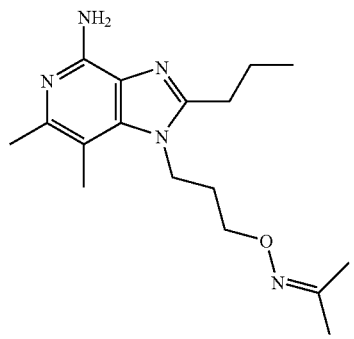 [SMILES: CCCc1nc2c(N)nc(C)c(C)c2n1CCCON=C(C)C]

Part A

3-Amino-1-propanol (6.92 mL, 90.5 mmol) was added dropwise to a stirred solution of 2,4-dichloro-5,6-dimethyl-3-nitropyridine (20.0 g, 90.5 mmol) and triethylatnine (18.9 mL, 136 nmuol) in DMF (300 mL) at room temperature. After 16 hours, the solvent was removed under reduced pressure and the resulting oil was partitioned between ethyl acetate (450 mL) and water (50 mL). The layers were separated and the organic layer was washed with water (3×50 mL). The combined aqueous layers were back-extracted with ethyl acetate (2×30 mL). The combined organic layers were dried over magnesium sulfate, filtered, and concentrated under reduced pressure. The resulting orange solid was triturated with hexanes/ethyl acetate (2: 1) and was isolated by filtration to yield 12.43 g of 3-[(2-chloro-5,6-dimethyl-3-nitropyridin-4-yl)amino]propan-1-ol as a yellow solid.

Part B

A mixture of 3-[(2-chloro-5,6-dimethyl-3-nitropyridin-4-yl)amino]propan-1-ol (12.4 g, 47.8 mmol), sodium azide (6.20 g, 95.5 nmnol), and cerium (III) chloride heptahydrate (8.90 g, 23.9 inmol) in 9:1 acetonitrile/water (160 mL) was heated at reflux for 16 hours, then was allowed to cool to room temperature. DMF was added and the mixture was filtered. The filter cake was washed with DMF. The filtrate was concentrated under reduced pressure to give an orange solid that was triturated with ethyl acetate to yield 9.60 g of 3-[(5,6-dimethyl-8-nitrotetraazolo[1,5-a]pyridin-7-yl)amino]propan-1-ol as a yellow solid.

Part C

A mixture of 3-[(5,6-dimethyl-8-nitrotetraazolo[1,5-a]pyridin-7-yl)amino]propan-1-ol (4.00 g, 15.0 mmol) and 10% palladium on carbon (0.40 g) in acetonitrile (75 mL) was hydrogenated at 50 psi (3.5×10⁵ Pa) on a Parr apparatus for 16 hours. The mixture was filtered through CELITE filter agent, which was rinsed with methanol. The filtrate was concentrated under reduced pressure to yield 3.48 g of 3-[(8-amino-5,6-dimethyltetraazolo[1,5-a]pyridin-7-yl)amnino]propan-1-ol.

Part D

A mixture of 3-[(8-amino-5,6dirnethyltetraazolo[1,5-a]pyridin-7-yl)amino]propan-1-ol (3.45 g, 14.6 mmol), pyridine hydrochloride (0.64 g, 5.5 mmol) and trimethyl orthobutyrate (2.60 mL, 16.1 mmol) in toluene (100 mL) was heated to reflux. Additional trimethyl orthobutyrate was added (1.1 equivalents). The mixture was heated at reflux for 16 hours. The mixture was allowed to cool to room temperature and 3.21 g of the product, 3-(5,6-dinethyl-8-propyl-7H-imidazo[4,5-c]tetraazolo[1,5-a]pyridin-7-yl)propan-1-ol, was isolated by filtration.

Part E

Diisopropyl azodicarboxylate (372 μL, 1.89 mmol) was added to a stirred solution of 3-(5,6-dimethyl-8-propyl-7H-imidazo[4,5-c]tetraazolo[1,5-a]pyridin-7-yl)propan-1-ol (500 mg, 1.72 mmol), triphenylphosphine (496 mg, 1.89 mmol), and N-hydroxyphthalimide (308 mg, 1.89 mmol) in DMF (17 mL) at room temperature. After 4 hours, the solvent was removed under reduced pressure to afford an oil that was triturated with ethyl acetate to generate a pink solid. The solid was isolated by filtration and washed with ethyl acetate to yield 630 mg of 2-[3-(5,6-dimethyl-8-propyl-7H-imidazo[4,5-c]tetraazolo[1,5-a]pyridin-7-yl)propoxy]-1H-isoindole-1,3(2H)-dione as a pink powder.

Part F

Anhydrous hydrazine (108 μL, 3.45 mmol) was added to a stirred suspension of 2-[3-(5,6-dimethyl-8-propyl-7H-imidazo[4,5-c]tetraazolo[1,5-a]pyridin-7-yl)propoxy]-1H-isoindole-1,3(2H)-dione (500 mg, 1.15 mmol) in ethanol (8 mL) at room temperature. After 30 minutes, dichloromethane (2.5 mL) was added to help dissolve the starting material. The solution was stirred for 4 hours, then was concentrated under reduced pressure to yield crude 7-[3-(aminooxy)propyl]-5,6-dimethyl-8-propyl-7H-imidazo[4,5-c]tetraazolo[1,5-a]pyridine. Acetone (6 mL) and methanol (6 mL) were added to crude 7-[3-(aminooxy)propyl]-5,6-dimethyl-8-propyl-7H-imidazo[4,5-c]tetraazolo[1,5-a]pyridine and the resulting solution was stirred at room temperature for 16 hours. The solvent was removed under reduced pressure. The residue was treated with 1 M NaOH and the mixture was sonicated for 1 minute to provide a white solid that was isolated by filtration and washed with water. The solid was dried under vacuum with heating at 70° C. to provide 300 mg of the product, acetone O-[3-(5,6-dimethyl-8-propyl-7H-imidazo[4,5-c]tetraazolo[1,5-a]pyridin-7-yl)propyl]oxime, as a white solid.

Part G

A solution of acetone O-[3-(5,6-dimethyl-8-propyl-7H-imidazo[4,5-c]tetraazolo[1,5-a]pyridin-7-yl)propyl]oxime (290 mg, 0.84 mmol) and triphenylphosphine (443 mg, 1.69 mmol) in 1,2-dichlorobenzene (8.5 mL) was heated at 120° C. for 3 days. The solution was allowed to cool to room temperature and methanol (1 mL) and trifluoroacetic acid (2 mL) were added. After the stirred solution was heated at 60° C. for 2 hours, the solution was allowed to cool to room temperature for 16 hours, and then was heated again at 60° C. for 6 hours. The solvent was removed under reduced pressure and the residue was partitioned between dichloromethane (50 mL) and saturated aqueous sodium carbonate (10 mL). The aqueous layer was extracted with dichloromethane (2×5 mL). The combined organic layers were washed with saturated aqueous sodium carbonate (3×10 mL), dried over sodium sulfate, filtered, and concentrated. The crude product was purified by chromatography on a HORIZON HPFC system (silica gel, gradient elution with 15-40% CMA in chloroform) to yield a solid that was recrystallized fiom acetonitrile to provide 191 mg of the product, acetone O-[3-(4amino-6,7-dimethyl-2-propyl-1H-imidazo[4,5-c]pyridin-1-yl)propyl]oxime as a white powder, mp 105.0-106.0° C.

Anal. Calcd for $C_{17}H_{27}N_5O$: C, 64.32; H, 8.57; N, 22.06. Found: C, 64.07; H, 8.43; N, 21.87.

Example 170

(1E)-1-Phenylethanone O-[3-(4-amino-6,7-dimethyl-2-propyl-1H-imidazo[4,5-c]pyridin-1-yl)propyl] oxime

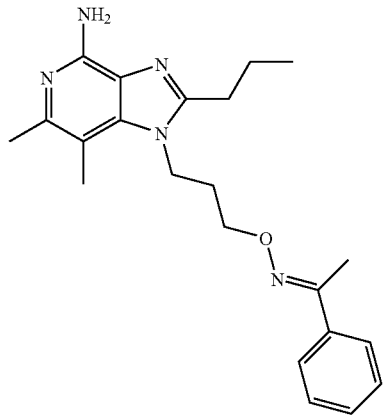 [SMILES: CCCc1nc2c(N)nc(C)c(C)c2n1CCCO/N=C(\C)c1ccccc1]

Part A

A solution of 2-[3-(5,6-dimethyl-8-propyl-7H-irnidazo[4,5-c]tetraazolo[1,5-a]pyridin-7-yl)propoxy]-1H-isoindole-1,3(2B)-dione (prepared as described in Parts A-E of Example 169, 8.50 g, 19.6 mmol) and triphenylphosphine (10.3 g, 39.2 mmol) in 1,2-dichlorobenzene (200 mL) was heated at 125° C. for 2 days, then was allowed to stand at room temperature for 3 days. The solvent was removed under reduced pressure. To the resulting residue was added methanol (40 mL) and 1 M HCl (20 mL). The solution was heated at 50° C. for 5 h, was allowed to cool to room temperature, and was concentrated under reduced pressure. Water (20 mL) was added and the mixture was extracted with chloroform (3×10 mL). The aqueous layer was adjusted to pH 11 with the addition of 1 M NaOH. The aqueous layer was extracted with chloroform (4×30 mL). The combined organic layers were dried over sodium sulfate, filtered, and concentrated under reduced pressure. The crude product was purified by chromatography on a HORIZON HPFC system (silica gel, gradient elution with CMA in chloroform) to yield 1.00 g of 1-[3-(aminooxy)propyl]-6,7-dimethyl-2-propyl-1H-imidazo[4,5-c]pyridin-4-amine.

Part B

A solution of 1-[3-(aminooxy)propyl]-6,7Aimethyl-2-propyl-1H-imidazo[4,5-c]pyridin-4-amine (0.64 g, 2.3 mmol) and acetophenone (325 μL, 2.76 mmol) in methanol (23 mL) was stirred overnight at room temperature, then heated at 50° C. for 4 hours. Pyridine hydrochloride (100 mg)

was added to the solution and stirring was continued at 50° C. overnight. Additional pyridine hydrochloride was added and the solution was heated at reflux for 5 hours. The solvent was removed under reduced pressure and the resulting off-white solid was partitioned between chloroform (100 mL) and saturated aqueous sodium carbonate (30 mL). The aqueous layer was extracted with chloroform (3×30 mL). The combined organic layers were washed with saturated aqueous sodium carbonate (2×20 mL), dried over sodium sulfate, filtered, and concentrated under reduced pressure. The crude product was purified by chromatography on a HORIZON HPFC system (silica gel, gradient elution with 5-30% CMA in chloroform) to yield a solid that was triturated with acetonitrile and dried under vacuum at 70° C. overnight to provide 105 mg of (1E)-1-phenylethanone O-[3-(4-amino-6,7-dimethyl-2-propyl-1H-imidazo[4,5-c]pyridin-1-yl)propyl]oxime as a white powder, mp 125.0-127.0° C.

Anal. Calcd for $C_{22}H_{29}N_5O$: C, 69.63; H, 7.70; N, 18.45. Found: C, 69.41; H, 7.73; N, 18.36.

The product was obtained as a 90:10 mixture of E:Z isomers.

Example 171

Ethanal O-[3-(4amino-6,7-dimethyl-2-propyl-1H-imidazo[4,5-c]pyridin-1-yl)propyl]oxime

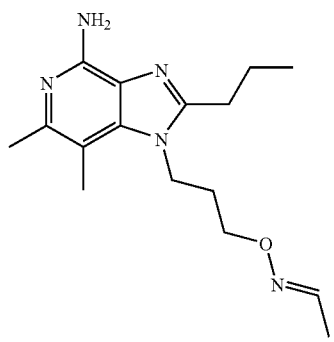 [SMILES: C/C=N/OCCCn1c(CCC)nc2c(N)nc(C)c(C)c21]

Part A

2-[3-(5,6-Dimethyl-8-propyl-7H-imidazo[4,5-c]tetraazolo[1,5-a]pyridin-7-yl)propoxy]-1H-isoindole-1,3(2H)-dione (prepared as described in Parts A-E of Example 169, 5.94 g, 13.7 mmol) was converted into 3.88 g of ethanal O-[3-(5, 6-dimethyl-8-propyl-7H-imidazo[4,5-c]tetraazolo[1 ,5-a] pyridin-7-yl)propyl]oxime using acetaldehyde in lieu of acetone in the procedure described in Part F of Example 169. The product was obtained as a 55:45 mixture of E:Z isomers.

Part B

Using the method described in Part G of Example 169, ethanal O-[3-(5,6-dimethyl-8-propyl-7H-imidazo[4,5-c]tetraazolo[1,5-a]pyridin-7-yl)propyl]oxime (3.86 g, 11.7 mmol) was converted into 1.2 g of ethanal O-[3-(4-amino-6, 7-dimethyl-2-propyl-1H-imidazo[4,5-c]pyridin-1-yl)propyl]oxime, which was isolated as a white powder, mp 117.0-119.0° C. Anal. Calcd for $C_{16}H_{25}N_5O$: C, 63.34; H, 8.31; N, 23.08. Found: C, 63.27; H, 8.55; N, 23.08.

The product was obtained as a 55:45 mixture of E:Z isomers.

Example 172

Acetone O-{3-[4-amino-2-(ethoxymethyl)-6,7diethyl-1H-imidazo[4,5-c]pyridin-1-yl]propyl}oxime

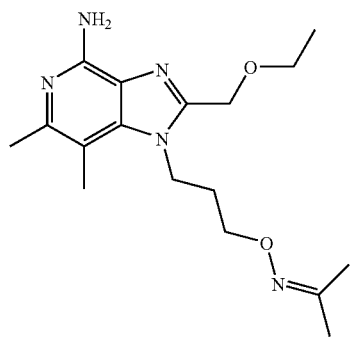 [SMILES: CCOCc1nc2c(N)nc(C)c(C)c2n1CCCON=C(C)C]

Part A

To a stirred suspension of 3-[(5,6-direthyl-8-nitrotetraazolo[1,5-a]pyridin-7-yl)amino]propan-1-ol (prepared as described in Parts A-B of Example 169, 1.00 g, 3.76 nrnol) in dichloromethane (38 mL) at 0° C. were added triethylamine (0.68 mL, 4.9 mmol) and acetic anhydride (0.39 mL, 4.1 mmol). The reaction was allowed to warm to room temperature and was stirred overnight. The suspension was filtered and the filter cake was washed with dichloromethane. The filtrate was transferred to a separatory funnel and was extracted with saturated aqueous sodium bicarbonate (20 mL). The aqueous layer was back extracted with dichoromethane (3×20 mL). The combined organic layers were washed with saturated aqueous sodium bicarbonate (3×20 mL), dried over magnesium sulfate, filtered, and concentrated under reduced pressure to give 0.48 g of 3-[(5,6-dimethyl-8-nitrotetraazolo[1,5-a]pyridin-7-yl)amino]propyl acetate as yellow oil that crystallized upon standing at room temperature for 1 hour.

Part B

A mixture of 3-[(5,6-dimethyl-8-nitrotetraazolo[1,5-a]pyridin-7-yl)amino]propyl acetate (0.43 g, 1.4 mmol) and 10% platinum on carbon (43 mg) in acetonitrile (14 iL) was hydrogenated at 50 psi ($3.5\times10^5$ Pa) on a Parr apparatus for 3 hours. The mixture was filtered through CELITE filter agent, which was rinsed with chloroform. The filtrate was concentrated under reduced pressure to yield 0.36 g of 3-[(8-amino-5,6-dimethyltetraazolo[1,5-a]pyridin-7-yl)amino]propyl acetate as a white solid.

Part C

Ethoxyacetyl chloride (175 mg, 1.43 mmol) and triethylamine (236 μL, 1.69 mmol) were sequentially added to a solution of 3-[(8-amino-5,6-dimethyltetraazolo[1,5-a]pyridin-7-yl)amino]propyl acetate (0.36 g, 1.3 mmol) in dichloromethane (13 mL) at 0° C. The solution was allowed to warm to room temperature and was stirred for 2.5 hours. Additional ethoxyacetyl chloride (20 mg) was added. After another hour, the solvent was removed under reduced pressure and the crude 3-({8-[(ethoxyacetyl)amino]-5,6-dimethyltetraazolo [1,5-a]pyridin-7-yl}amino)propyl acetate was carried on to the next step.

Part D

A solution of 6 M potassium carbonate (0.9 mL, 5.2 mmmol) was added to a solution of crude 3-({8-[(ethoxyacetyl)amino]-5,6-dimethyltetraazolo[1,5-a]pyridin-7-yl}amino)propyl acetate from Part C in 3:1 ethanol/water (12 mL) at room temperature. The solution was stirred for 3 days, then was heated to 80° C. More 6 M potassium carbonate (3 mL) was added after 1 day. After another day, 6 M potassium carbonate (5 mL) was added again. The temperature was increased to 85° C. and stirring was continued one more day. The solvent was removed under reduced pressure and the residue was partitioned between chloroform (100 mL) and saturated aqueous sodium bicarbonate (30 mL). The layers were separated and the aqueous layer was extracted with chloroform (3×20 mL). The combined organic layers were washed with saturated aqueous sodium bicarbonate (2>20 mL), dried over magnesium sulfate, filtered, and concentrated under reduced pressure to yield 0.35 g of 3-[8-(ethoxyrnethyl)-5,6-dimethyl-7H-imidazo[4,5-c]tetraazolo[1,5-a]pyridin-7-yl]propan-1-ol as a white solid.

Part E

Following the general method described in Part E of Example 169, 3-[8-(ethoxymethyl)-5,6-dirnethyl-7H-iridazo[4,5-c]tetraazolo[1,5-a]pyridin-7-yl]propan-1-ol (0.90 g, 3.0 mmol) was converted into 2-{3-[8-(ethoxymethyl)-5,6-dimethyl-7H-imidazo[4,5-c]tetraazolo[1,5-a]pyridin-7-yl]propoxy}-1H-isoindole-1,3(2H)-ione. The product was isolated by filtering the reaction directly, washing the filter cake with ethyl acetate, and drying the solid under vacuum to provide 0.90 g of 2-{3-[8-(ethoxymethyl)-5,6-dimethyl-7H-inidazo[4,5-c]tetraazolo[1,5-a]pyridin-7-yl]propoxy}-1H-isoindole-1,3(2H)-dione as a pink powder.

Part F

Anhydrous hydrazine (190 lIL, 6.0 mmol) was added to a stirred suspension of 2-{3-[8-(eth6xymethyl)-5,6-dimethyl-7H-imidazo[4,5-c]tetraazolo[1 ,5-a]pyridin-7-yl]propoxy}-1H-isoindole-1,3(2H)-dione (0.90 g, 2.0 mmol) in ethanol (15 mL) at room temperature. After approximately 16 hours, acetone (6 mL) was added and the reaction was stirred for 1 day. The solvent was removed under reduced pressure. The residue was treated with 1 M NaOH and the mixture was sonicated for 1 minute to provide a white solid that was isolated by filtration and washed with water. The solid was dried under vacuum with heating to provide 0.54 g of the product, acetone O-{3-[8-(ethoxymethyl)-5,6-dimethyl-7H-imidazo[4,5-c]tetraazolo[1,5-a]pyridin-7-yl]propyl}oxime.

Part G

Following the general method described in Part G of Example 169, acetone O-{3-[8-(ethoxymethyl)-5,6-dimethyl-7H-imidazo[4,5-c]tetraazolo[1,5-a]pyridin-7-yl]propyl}oxime (0.54 g, 1.5 mmol) was converted into 0.18 g of acetone O-{3-[4-amino-2-(ethoxymethyl)-6,7-dimethyl-1H-imidazo[4,5-c]pyridin-1-yl]propyl}oxime. The solvent system used during the chromatographic purification was 5-30% CMA in chloroform (gradient elution) to afford the product as a white solid, which was triturated with acetonitrile and isolated by filtration to provide acetone O-{3-[4-amino-2-(ethoxymethyl)-6,7-dimethyl-1H-imidazo[4,5-c]pyridin-1-yl]propyl}oxime as a white powder, mp 123.0-125.0° C.

Anal. Calcd for $C_{17}H_{27}N_5O_2$: C, 61.24; H, 8.16; N. 21.00. Found: C, 61.15; H, 8.31; N, 21.27.

Examples 173-199

An aldehyde or ketone (0.12 mmol, 1.2 equivalents) from the table below was added to a test tube containing 1-[3-(aminooxy)propyl]-6,7-dimethyl-2-propyl-1H-imidazo[4,5-c]pyridin-4-amine (27 mg, 0.10 mmol) in methanol (1 mL). The test tubes were capped and shaken overnight at ambient temperature. The solvent was removed by vacuum centrifugation. The compounds were purified as described for Examples 142-168. The table below shows the reagent used for each example, the structure of the resulting compound, and the observed accurate mass for the isolated trifluoroacetate salt.

Examples 173-199

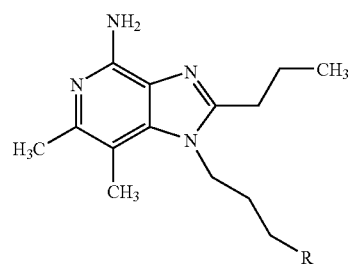

| Example | Reagent | R | Measured Mass (M + H) |
|---|---|---|---|
| | Starting Material Only - No Reagent Added | —O—NH₂ (—O—N(H)H) | 278.1955 |
| 173 | Cyclopropanecarboxaldehyde | —O—N=CH—cyclopropyl | 330.2270 |
| 174 | Butryaldehyde | —O—N=CH—CH₂CH₂CH₃ | 332.2452 |
| 175 | Cyclopentanone | —O—N=cyclopentyl | 344.2455 |
| 176 | 3-Furaldehyde | —O—N=CH—(3-furyl) | 356.2081 |

-continued

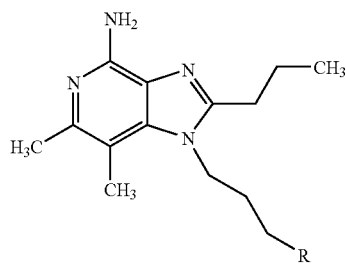

| Example | Reagent | R | Measured Mass (M + H) |
|---|---|---|---|
| 177 | Furfural |  | 356.2097 |
| 178 | Tetrahydrofuran-3-carboxayaldehyde | 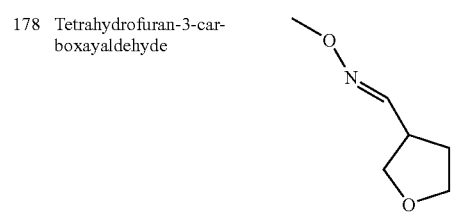 | 360.2401 |
| 179 | 3-(Methylthio)propionaldehyde | 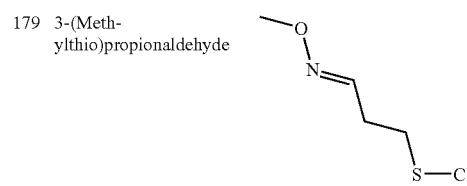 | 364.2198 |
| 180 | Benzaldehyde | 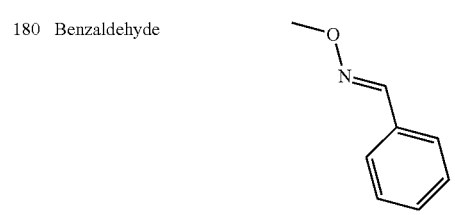 | 366.2307 |
| 181 | 4-Pyridinecarboxaldehyde | 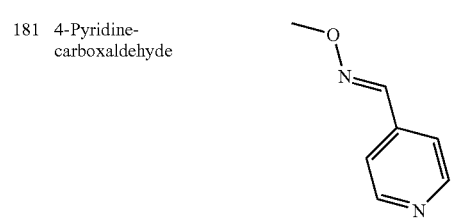 | 367.2243 |
| 182 | 3-Pyridinecarboxaldehyde | 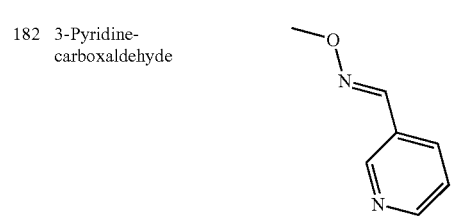 | 367.2252 |

-continued

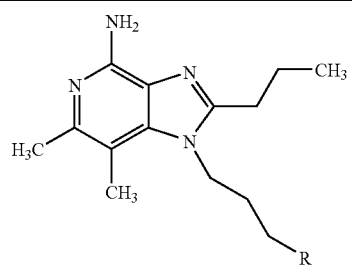

| Example | Reagent | R | Measured Mass (M + H) |
|---|---|---|---|
| 183 | 2-Pyridinecarboxaldehyde | 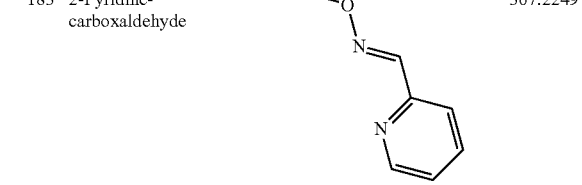 | 367.2249 |
| 184 | 1-Methyl-2-imidazolecarboxaldehyde | 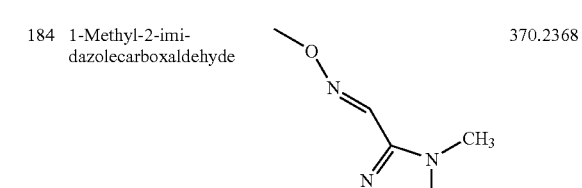 | 370.2368 |
| 185 | 2-Thiophenecarboxaldehyde | 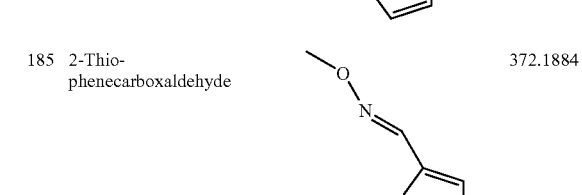 | 372.1884 |
| 186 | 3-Thiophenecarboxaldehyde | 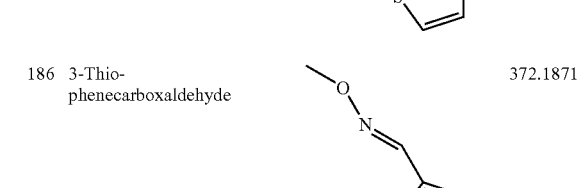 | 372.1871 |
| 187 | m-Tolualdehyde | 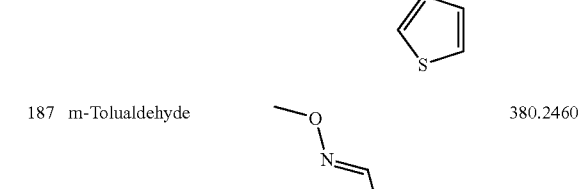 | 380.2460 |
| 188 | Phenylacetaldehyde | 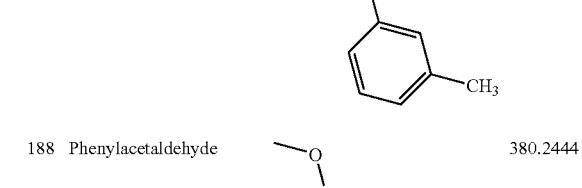 | 380.2444 |

165
-continued
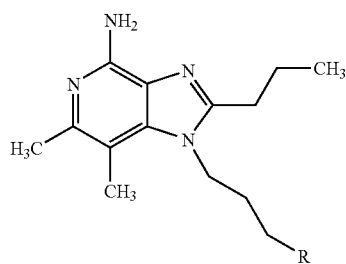
| Example | Reagent | R | Measured Mass (M + H) |
|---|---|---|---|
| 189 | p-Tolualdehyde | | 380.2445 |
| 190 | 5-Norbornene-2-carboxyaldehyde | | 382.2620 |
| 191 | 3-Cyanobenzaldehyde | | 391.2263 |
| 192 | 4-Cyanobenzaldehyde | | 391.2276 |
| 193 | 2-Phenylpropionaldehyde | | 394.2601 |
166
-continued
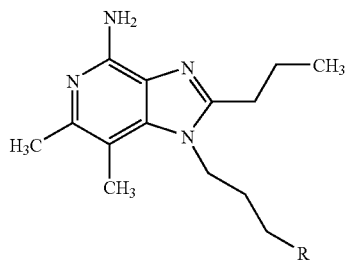
| Example | Reagent | R | Measured Mass (M + H) |
|---|---|---|---|
| 194 | 3-Phenylpropionaldehyde | | 394.2617 |
| 195 | 3-Methoxybenzaldehyde | | 396.2401 |
| 196 | o-Anisaldehyde | | 396.2407 |
| 197 | 2-Naphthaldehyde | | 416.2451 |
| 198 | 2-Quinolinecarboxaldehyde | | 417.2426 |

-continued

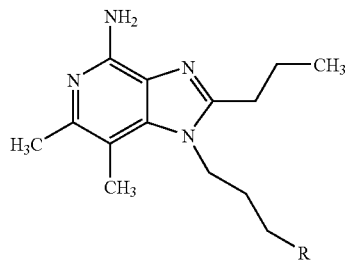

| Example | Reagent | R | Measured Mass (M + H) |
|---|---|---|---|
| 199 | 4-Biphenylcarboxaldehyde | (structure shown) | 442.2584 |

Examples 200-202

Part A

A solution of 2-(2-aminoethoxy)ethanol (30.3 g, 288 mmol) in a minimal amount of dichloromethane was added dropwise to a stirred mixture of 4chloro-3-nitroquinoline (50.0 g, 240 nimol), potassium carbonate (33.1 g, 240 mmol), and triethylamine (36.4 g mL, 360 mmol) in DMF (200 mL) at 0° C. A yellow precipitate formed and more dichloromethane (several mL) was added. The mixture was allowed to warm to room temperature and stir overnight. A yellow solid was isolated by filtration, washed with water and dichloromethane, and dried. The filtrate was washed twice with brine, dried over magnesium sulfate, and filtered. Additional orange solid was isolated from the filtrate. The solids dried in a vacuum oven to afford 2-{2-[(3-nitroquinolin-4-yl)amino]ethoxy}ethanol.

Part B

A mixture of 2-{2-[(3-nitroquinolin-4-yl)amino]ethoxy}ethanol (66.2 g, 239 mmol) and 5% platinum on carbon (7.5 g) in ethanol (250 mL) was hydrogenated at approximately 30 psi (2.1×10$^5$ Pa) on a Parr apparatus overnight. Magnesium sulfate was added to the mixture, which was then filtered through CELITE filter agent. The filtrate was concentrated to provide 43.0 g of crude 2-{2-[(3-aminoquinolinyl)amino]ethoxy}ethanol as a yellow solid.

Part C

A mixture of 2-{2-[(3-aminoquinolin4-yl)amino]ethoxy}ethanol (43.0 g, 155 mmol) and pyridine hydrochloride (1.79 g, 15.5 mmol) in toluene (200 mL) and dichloroethane (100 mL) was heated at reflux until a solution formed. The solution was allowed to cool to room temperature, then was cooled to 0° C. Triethyl orthopropionate (30.1 g, 171 minol) was added and the mixture was heated at reflux for 3 hours. The solution was allowed to cool to room temperature and was concentrated under reduced pressure. The residue was diluted with chloroform and 4 M NaOH was added to adjust the pH to 9. The mixture was filtered and the isolated solid dissolved when it was washed with water and chloroform. The filtrate was transferred to a separatory fimnel and washed twice with brine. The combined aqueous layers were back-extracted with dichloromethane. The combined organic layers were dried over magnesium sulfate, filtered, and concentrated to provide 40.0 g of 2-[2-(2-ethyl-1H-imidazo[4,5-c]quinolin-1-yl)ethoxy]ethanol as a tan solid.

Part D

The general procedure described in Part A of Example 1 was used to convert 2-[2-(2-ethyl-1H-imidazo[4,5-c]quinolin-1-yl)ethoxy]ethanol (35.6 g, 125 mmol) into 2-{2-[2-(2-ethyl-1H-imidazo[4,5-c]quinolin-1-yl)ethoxy]ethoxy}-1H-isoindole-1,3(2B)-dione. For the work-up, the solvent was removed and the residue was dissolved in chloroform (300 mL). To the solution was added 6 M HCl. Some of the solvent was removed from the mixture under reduced pressure, but the product did not precipitate so the mixture was transferred to a separatory funnel. The organic layer was removed. To the aqueous layer was added 6 M NaOH (240 mL), causing a precipitate to form. The mixture was extracted with chloroform three times. The later organic layers were combined, dried over magnesium sulfate, filtered, and concentrated under reduced pressure. The crude product was purified by flash chromatography (silica gel, gradient elution with 0-5% methanol in dichloromethane) to provide 11.0 g of 2-{2-[2-(2-ethyl-1H-imidazo[4,5-c]quinolin-1-yl)ethoxy]ethoxy}-1H-isoindole-1,3(2H)-dione.

Part E

To a solution of 2-{2-[2-(2-ethyl-1H-imidazo[4,5-c]quinolin-1-yl)ethoxy]ethoxy}-1H-isoindole-1,3(2H)-dione (11.0 g, 25.5 mmol) in chloroform (150 mL) was added mCPBA (11.4 g, 51.1 mmol). The solution was stirred at room temperature for 2 hours. Concentrated ammonium hydroxide (100 mL) was added, followed by p-toluenesulfonyl chloride (5.40 g, 28.1 mmol). The mixture was stirred overnight at room temperature. The mixture was transferred to a separatory fimnel and was washed twice with 5% aqueous ammonium chloride and once with aqueous sodium carbonate solution, dried over magnesium sulfate, filtered, and concentrated. The crude product was purified by flash chromatography (silica gel, gradient elution with 0-5% methanol in dichloromethane) to provide 6 g of 1-{2-[2-(aminooxy)ethoxy]ethyl}-2-ethyl-1H-imidazo[4,5-c]quinolin-4-amine.

Part F

The method described in Part D of Example 1 can be used to treat 1-{2-[2-(aminooxy)ethoxy]ethyl}-2-ethyl-1H-imidazo[4,5-c]quinolin4farmnie with an aldehyde or ketone shown in the table below to provide a compound with a structure shown in the table below.

Examples 200-202

| Example | Ketone or Aldehyde | R |
|---|---|---|
| 200 | acetone | |
| 201 | 2-pentanone | |
| 202 | benzaldehyde | |

Example 203

Acetone O-[3-(4-amino-7-bromo-2-propyl-1H-imidazo[4,5-c]quinolin-1-yl)propyl]oxime

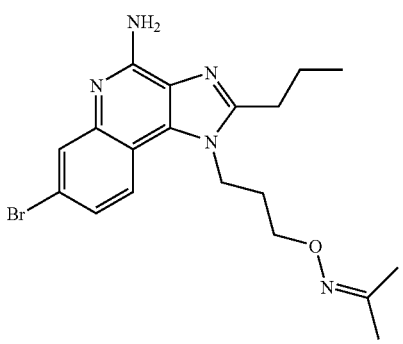 [SMILES: CCCc1nc2c(N)nc3cc(Br)ccc3c2n1CCCON=C(C)C]

Part A

A mixture of triethyl orthoformate (154 g, 1.04 mol) and Meldrum's acid (142 g, 0.983 mol) was heated to 55° C. for 4 hours. After cooling to 50° C., a solution of 3-bromoaniline (162.6 g, 0.945 mol) in ethanol (300 mL) was added such that the temperature of the reaction was maintained between 50-55° C. After half of the 3-bromoaniline had been added, stirring became difficult due to the formation of solids, so more ethanol (1 L) was added to facilitate stirring. Upon complete addition, the reaction was cooled to room temperature, and the solids were collected by filtration. The filter cake was washed with ice cold ethanol until the washings were nearly colorless, and the product was dried at 65° C. under vacuum to afford 287 g of 5-[(3-bromophenylimino)methyl]-2,2-dimethyl-1,3-dioxane4,6-dione as an off-white solid.

$^1$H NMR (300 MHz, CDCl$_3$) δ 11.19 (brd, J=12.8 Hz, 1H), 8.60 (d, J=14.0 Hz, 1H), 7.44-7.38 (m, 2H), 7.30 (t, J=8.0 Hz, 1H), 7.18 (ddd, J=8.0, 2.2, 0.9 Hz, 1H), 1.75 (s, 6H).

Part B

7-Bromoquinolin-4-ol was prepared in accordance with the literature procedure (D. Dibyendu et al., *J. Med. Chem.,* 41, 4918-4926 (1998)) or by thermolysis of 5-[(3-bromophenyliuino)methyl]-2,2-dimethyl-1,3-dioxane-4,6-dione in DOWTHERM A heat transfer fluid and had the following spectral properties:

$^1$H NMR (300 MHz, d$_6$-DMSO) δ 11.70 (brs, 1H), 8.00 (d, J=8.7 Hz, 1H), 7.92 (d, J=7.5 Hz, 1H), 7.74 (d, J=1.9 Hz, 1H), 7.44 (dd, J=8.7, 1.9 Hz, 1H), 6.05 (d, J=7.5 Hz, 1H).

Part C

A stirred suspension of 7-bromoquinolin-4-ol (162 g, 0.723 mol) in propionic acid (1500 mL) was brought to 110° C. Nitric acid (85 g of 70%) was added dropwise over 1 h such that the temperature was maintained between 110-115° C. After half of the nitric acid had been added, stirring became difficult due to the formation of solids and an additional 200 mL of propionic acid was added. Upon complete addition, the reaction was stirred for 1 hour at 110° C., cooled to room temperature, and the solid was collected by filtration. The filter cake was washed with ice cold ethanol until the washings were nearly colorless (800 mL), and the product was dried at 60° C. under vacuum to afford 152 g of 7-bromo-3-nitro-quinolin-4-ol as a pale yellow solid.

$^1$H NMR (300 MHz, d$_6$-DMSO) δ 13.0 (brs, 1H), 9.22 (s, 1H), 8.15 (d, J=8.4 Hz, 1H), 7.90 (d, J=1.6 Hz, 1H), 7.66 (dd, J=8.7, 1.9 Hz, 1H).

Part D

7-Bromo-3-nitroquinolin-4-ol (42 g, 156 nmmol) was suspended in POCl$_3$ (130 mL) and brought to 102° C. under an atmosphere of N$_2$. After 45 min, all of the solids had dissolved, so the reaction was cooled to room temperature. The resulting solids were collected by filtration, washed with H$_2$O, and then partitioned with CH$_2$Cl$_2$ (3 L) and 2M Na$_2$CO$_3$ (500 mL). The organic layer was separated, washed with H$_2$O (1×), dried over Na$_2$SO$_4$, filtered, and concentrated to afford 33.7 g of 7-bromo-4-chloro-3-nitroquinoline as a beige solid.

$^1$H NMR (300 MHz, CDCl$_3$) δ 9.26 (s, 1H), 8.41 (d, J=1.8 Hz, 1H), 8.30 (d, J=9.0 Hz, 1H), 7.90 (dd, J=8.9, 2.1 Hz, 1H).

Part E

To a solution of 7-bromochloro-3-nitroquinoline (10.00 g, 34.78 mmol) in dichloromethane (140 mL) was added triethylanine (10.2 mL, 73.1 mmol). The solution was cooled to 0° C., and 3-amino-1-butanol (2.80 mL, 36.5 mmol) was added. The solution was stirred overnight at ambient temperature and then filtered to collect a precipitate. The precipitate was washed with dichloromethane and water. The filtrate was washed with saturated aqueous sodium bicarbonate and then added to the precipitate. The mixture was concentrated under reduced pressure. Methanol and toluene were added several times and removed under reduced pressure. The resulting solid was dried under high vacuum to provide 11.34 g of 3-[(7-bromo-3-nitroquinolin-4-yl)amino]propan-1-ol as a yellow solid.

Part F

A solution of sodium dithionate (27.5 g, 158 mmol) in water (60 mL) was added to a solution of 3-[(7-bromo-3-nitroquinolin-4-yl)ariino]propan-1-ol (10.3 g, 31.6 mmol) in ethanol (175 mL), and the mixture was stirred vigorously for four hours at ambient temperature. The solvent was removed under reduced pressure, and the residue was partitioned between dichloromethane/chloroform/methanol (500 mL) and saturated aqueous sodium bicarbonate (200 mL). The aqueous layer was separated and extracted with chloroform (5×200 mL), and the combined organic fractions were dried over sodium sulfate, filtered, and concentrated under reduced pressure to provide 7.27 g of 3-[(3-amino-7-bromoquinolin-4-yl)amino]propan-1-ol.

Part G

A mixture of 3-[(3-amino-7-bromoquinolin-4-yl)amino]propan-1-ol (7.2 g, 24 mmol), pyridine hydrochloride (1.05 g, 9.09 mmol) and trimethyl orthobutyrate (4.05 mL, 25.5 mmol) in toluene (240 mL) was heated at reflux for two hours under an atmosphere of nitrogen. The solvent was removed under reduced pressure, and the residue was dissolved in methanol (100 mL). Aqueous sodium hydroxide (15 mL of 6 M) was added to the solution, and the resulting mixture was stirred for two hours at ambient temperature. A portion of the solvent was removed under reduced pressure, and the resulting mixture was adjusted to pH 7 with the addition of 6 N hydrochloric acid. The mixture was then extracted with chloroform (4>150 mL), and the combined extracts were washed sequentially with saturated aqueous sodium bicarbonate (40 mL) and brine (30 mL), dried over magnesium sulfate, filtered, and concentrated under reduced pressure. An analysis by nuclear magnetic resonance spectroscopy indicated the presence of starting material, and the procedure was repeated using 1 mL trimethyl orthobutyrate and heating at reflux for one hour. Following the work-up procedure, the resulting solid was triturated with ethyl acetate and isolated by filtration to provide 7.30 g of 3-(7-bromo-2-propyl-1H-imidazo[4,5-c]quinolin-1-yl)propan-1-ol.

Part H

A modification of the method described in Part A of Example 1 was followed using 3-(7-bromo-2-propyl-1H-imidazo[4,5-c]quinolin-1-yl)propan-1-ol (4.60 g, 13.2 mmol), triphenylphosphine (4.17 g, 15.9 mmol), diisopropyl azodicarboxylate (3.13 mL, 15.9 mmol), and N-hydroxyphthalimide (2.59 g, 15.9 mmol). After the solvent was removed under reduced pressure, the residue was dissolved in chloroform (200 mL), washed sequentially with saturated aqueous sodium bicarbonate (2×30 mL) and brine (20 mL), dried over magnesium sulfate, filtered, and concentrated under reduced pressure. The crude product was triturated twice with ethyl acetate to provide 4.68 g of 2-[3-(7-bromo-2-propyl-1H-imidazo[4,5-c]quinolin-1-yl)propoxy]-1H-isoindole-1,3(2H)-dione.

Part I

To a solution of 2-[3-(7-bromo-2-propyl-1H-imidazo[4,5-c]quinolin-1-yl)propoxy]-1H-isoindole-1,3(2H)-dione (1.00 g, 2.03 mmol) in chloroform (20 mL) at room temperature and under an atmosphere of nitrogen was added mCPBA (1.00 g, 4.06 mmol). The reaction was stirred for 1.5 hours and cooled to 0° C. Concentrated ammonium hydroxide (4 mL) was added followed by p-toluenesulfonyl chloride (425 mg, 2.23 mmol) in portions. The mixture was stirred for one hour at 0° C., and then acetone (20 mL) was added. The reaction was stirred vigorously for one hour and then concentrated under reduced pressure. The residue was partitioned between chloroform (200 mL) and saturated aqueous sodium bicarbonate (40 mL). The organic layer was separated and washed sequentially with saturated aqueous sodium bicarbonate (50 mL) and brine (20 mL), dried over sodium sulfate, filtered, and concentrated under reduced pressure. The crude product was purified twice by chromatography on a HORIZON HPFC system (silica gel, gradient elution with 0-35% CMA in chloroform), then was recrystallized twice from acetonitrile, triturated with ethyl acetate, and recrystallized from acetonitrile to afford 41 mg of acetone O-[3-(4-amino-7-bromo-2-propyl-1H-imidazo[4,5-c]quinolin-1-yl)propyl]oxime as a white powder, mp 182.0-183.0° C.

Anal. Calcd for $C_{19}H_{24}BrN_5O$: C, 54.55; H, 5.78; N, 16.74. Found: C, 54.65; H, 5.75; N, 16.64.

Example 204

Acetone O-[3-(4-amino-7-phenyl-2-propyl-1H-imidazo[4,5-c]quinolin-1-yl)propyl]oxime

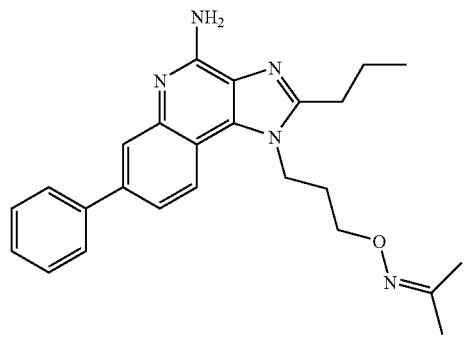 [SMILES: CCCc1nc2c(N)nc3cc(-c4ccccc4)ccc3c2n1CCCON=C(C)C]

In a pressure vessel under a nitrogen atmosphere, acetone O-[3-(4-amino-7-bromo-2-propyl-1H-imidazo[4,5-c]quinolin-1-yl)propyl]oxime (500 mg, 1.20 mmol), phenylboronic acid (219 mg, 1.80 mmol), a solution of palladium (II) acetate (2.7 mg, 0.012 mmol) in hot toluene (0.5 mL), triphenylphosphine (9.5 mg, 0.036 mmol), and 2 M aqueous sodium carbonate (0.72 mL, 1.44 mmol) were combined in 5:1 n-propanol:water (2.4 mL). The solution was placed under vacuum and back-filled with nitrogen three times. The pressure vessel was sealed and heated at 100° C. overnight, then was allowed to cool to ambient temperature. Chloroform (60 mL) was added and the mixture was washed with water (2×10 mL) and brine (10 mL), dried over sodium sulfate, filtered, and concentrated under reduced pressure. The product was purified by chromatography on a HORIZON HPFC system (silica gel, gradient elution with 0-35% CMA in chloroform) to yield a solid that was triturated twice with acetonitrile and isolated to yield 278 mg of acetone O-[3-(4-amino-7-phenyl-2-propyl-1H-imidazo[4,5-c]quinolin-1-yl)propyl]oxime as a white powder, mp 164.0-165.0° C.

Anal. Calcd for C$_{25}$H$_{29}$N$_5$O·0.75H$_2$O: C, 69.99; H, 7.17; N, 16.32. Found: C, 70.20; H, 7.36; N, 16.39.

Example 205

Acetone O-{3-[4-amino-7-bromo-2-(ethoxymethyl)-1H-imidazo[4,5-c][1,5]naphthyridin-1-yl]propyl}oxime

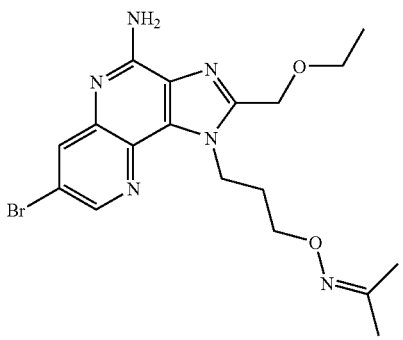 [SMILES: CCOCc1nc2c(N)nc3cc(Br)cnc3c2n1CCCON=C(C)C]

Part A

A mixture of triethyl orthoformate (10 mL, 60.1 mmol) and 2,2dimethyl-1,3-dioxane-4,6-dione (40.9 g, 0.23 mol) (Meldrum's acid) was heated at 92° C. for 90 minutes and then cooled to 70° C. over one hour. 3-Amino-5-bromopyridine (40.9 g, 0.20 mol) was slowly added over 10 minutes with an ethanol rinse while maintaining the reaction temperature between 60 and 70° C. The reaction was then heated for an additional 20 minutes and allowed to cool to room temperature. The reaction mixture was filtered and washed with ethanol (150 mL) yielding a tan solid. The solid was dried under vacuum for 2 hours to yield 59.14 g of 5-{[(5-bromopyridin-3-yl)imino]methyl}-2,2-dimethyl-1,3-dioxane-4,6-dione as a light yellow crystalline solid, mp 200-202° C.

$^1$H NMR (300 MHz, CDCl$_3$) δ 11.26 (d, J=14.3 Hz, 1H), 8.80 (d, J=2.3 Hz, 1H), 8.62 (d, J=14.3 Hz, 1H), 8.56 (d, J=1.9 Hz, 1H), 8.44-8.40 (m, 1H), 1.68 (s, 6H).

Part B

5-{[(5-Bromopyridin-3-yl)imino]methyl}-2,2-dimethyl-1,3-dioxane-4,6-dione (59 g, 0.18 mol) was slowly added to DOWTHERM A heat transfer fluid (2000 mL) over a period of 5 minutes at 235-238° C. Following addition, the reaction was maintained for an additional 5 minutes and then allowed to cool to 40° C. A brown precipitate formed, which was filtered and washed with hexanes (150 mL). The brown solid was suspended in an ethanol/water mixture (90:10, 1500 mL), heated to a boil for 30 minutes, isolated by filtration, and washed with ethanol (200 mL) to yield 30.8 g of 7-bromo[1,5]naphthyridin-4-ol as a dark brown powder.

$^1$H NMR (300 MHz, CDCl$_3$) δ 11.81 (br s, 1H), 8.69 (d, J=1.9 Hz, 1H), 8.21 (d, J=1.9 Hz, 1H), 7.95 (d, J=7.7 Hz, 1H), 6.22 (d, J=7.5 Hz, 1H).

Part C

A mixture of 7-bromo[1,5]naphthyridin-4-ol (33 g, 0.147 mol) and fuming nitric acid (350 mL) was heated at reflux (90° C. internal reaction vessel temperature) for 3 hours. The reaction mixture was cooled to 50° C., poured over 1 L of ice and adjusted to pH 2-3 with the addition of 50% aqueous NaOH. The resulting precipitate was filtered, washed with water, and dried over vacuum for 3 days to yield 25.1 g of 7-bromo-3-nitro[1,5]naphthyridin-4-ol as a yellow crystalline solid.

$^1$H NMR (300 MHz, CDCl$_3$) δ 13.06 (br s, 1H), 9.26 (s, 1H), 8.88 (d, J=2.0 Hz, 1H), 8.37 (d, J=2.0 Hz, 1H).

Part D

Phosphorous oxychloride (16.76 g, 10.19 mL, 109.3 mmol) was added slowly dropwise to a suspension of 7-bromo-3-nitro[1,5]naphthyridin-4-ol (21.09 g, 78.1 mmol) in DMF (250 mL) at ambient temperature and stirred for 3 hours. The reaction mixture was then added to ice water (400 mL) with stirring. A solid precipitate formed, which was isolated by vacuum filtration and washed with water. The material was dried under high vacuum at ambient temperature to yield 7-bromo-4-chloro-3-nitro[1,5]naphthyridine as a tan solid.

$^1$H NMR (300 MHz, CDCl$_3$) δ 9.51 (s, 1H), 9.36 (d, J=2.2 Hz, 1H), 9.02 (d, J=2.1 Hz, 1H).

Part E

To a solution of 7-bromo-4-chloro-3-nitro[1,5]naphthyridine (22.53 g, 78.10 g) in dichloromethane (260 mL) at room temperature was added triethylamine (14.2 mL, 102 mmol). The solution was cooled to 0° C. and 3-amino-1-propanol (6.57 mL, 85.9 mmol) was added. The solution was stirred for 20 minutes at room temperature and then was concentrated under reduced pressure to yield a yellow solid. Water (250 mL) was added to the solid, and the mixture was sonicated for 10 minutes. The solid was isolated by filtration, washed with water, and dried at 70° C. under vacuum to afford 22.60 g of 3-[(7-bromo-3-nitro[1,5]naphthyridin-4-yl)amino]propan-1-ol as a yellow powder.

Part F

3-[(7-Bromo-3-nitro[1,5]naphthyridin-4-yl)amino]propan-1-ol (22.60 g, 69.08 mmol) was converted into 25.30 g of 3-[(7-bromo-3-nitro[1,5]naphthyridin-4-yl)amino]propyl acetate, which contained a trace amount of 4-dimethylaminopyridine, using the method described in Part B of Examples 127-135.

Part G

3-[(7-Bromo-3-nitro[1,5]naphthyridin-4-yl)amino]propyl acetate (25.3 g, 68.5 mmol) was converted into 3-[(3-amino-7-bromo[1,5]naphthyridin4-yl)amino]propyl acetate using the method described in Part C of Examples 127-135.

Part H

The general procedures described in Parts D and E of Examples 127-135 were used to convert the material from Part G (approximately 68.5 nimol) into 22.2 g of 3-[7-bromo-2-(ethoxymethyl)-1H-imidazo[4,5-c][1,5]naphthyridin-1-yl]propan-1-ol using ethoxyacetyl chloride in lieu of butyryl chloride in Part D of Examples 127-135. Extra dichloromethane (250 mL) was used in the acylation reaction, and the reaction time was lengthened to overnight. In the cyclization reaction, the reaction was heated for 45 minutes instead of 7 hours.

Part I

Diisopropyl azodicarboxylate (6.47 mL, 32.9 mmol) was added dropwise over ten minutes to a stirred solution of 3-[7-bromo-2-(ethoxymethyl)-1H-imidazo[4,5-c][1,5]naphthyridin-1-yl]propan-1-ol (10.0 g, 27.4 mmol), triphenylphosphine (8.62 g, 32.9 mmol), and N-hydroxyphthalimide (5.36 g, 32.9 mmol) in DMF (110 mL) at 0° C. The reaction was allowed to warm to room temperature and was stirred overnight. The solvent was removed under reduced pressure to afford a solid that was slurried in ethyl acetate, isolated by filtration, washed with ethyl acetate, and dried under vacuum to yield 11.45 g of 2-{3-[7-bromo-2-(ethoxymethyl)-1H-imidazo[4,5-c][1,5]naphthyridin-1-yl]propoxy}-1H-isoindole-1,3(2H)Aione as a pink solid.

Part J mCPBA (11.06 g, 44.88 mmol) was added to a stirred solution of 2-{3-[7-bromo-2-(ethoxymethyl)-1H-imidazo[4,5-c][1,5]naphthyridin-1-yl]propoxy}-1H-isoindole-1,3(2H)-dione (11.40 g, 22.44 inmol) in chloroform (225 mL) at room temperature. After 1 hour, additional mCPBA (1.5 g) was added and stirring was continued for another 30 minutes. The solution was cooled to 0° C. and concentrated anmmonium hydroxide (45 mL) was added followed by p-toluenesulfonyl chloride (added in portions, 4.71 g, 24.7 mmol). After 1 hour, additional p-toluenesulfonyl chloride (1.0 g) was added and stirring was continued at 0° C. After another 2 hours, more p-toluenesulfonyl chloride (0.4 g) was added, then the reaction was stirred at room temperature for 1 hour. Acetone (225 mL) was added and the reaction was stirred overnight at room temperature. The mixture was filtered and the filtrate was concentrated under reduced pressure. The residue was dissolved in chloroform (700 nmL) and the solution was washed with saturated aqueous sodium bicarbonate (2×100 mL) and brine (70 mL), dried over sodium sulfate, filtered, and concentrated under reduced pressure. The crude material, which contained about 50% of the unreacted N-oxide intermediate, was dissolved in chloroform (220 mL). The solution was cooled to 0° C. and concentrated ammonium hydroxide (20 mL) was added, followed by portionwise addition ofp-toluenesulfonyl chloride (4 g). The reaction was allowed to warm to room temperature and was stirred overnight. The mixture was filtered again and the filtrate was treated to the workup described above. The crude product was purified by chromatography on a HORIZON HPFC system (silica gel, gradient elution with 0-25% CMA in chloroform), recrystallized from ethyl acetate/hexanes, and dried under vacuum to provide 2.8 g of acetone O-{3-[4-amino-7-bromo-2-(ethoxymethyl)-1H-imidazo[4,5-c][1,5]naphthyridin-1-yl]propyl}oxime as a beige powder, mp 128.0-130.0° C.

$^1$H NMR (300 MHz, DMSO-$d_6$) δ 8.55 (d, J=2.2 Hz, 1H), 8.11 (d, J=2.2 Hz, 1H), 7.13 (s, 2H), 4.84 (t, J=7.1 Hz, 2H), 4.77 (s, 2H), 4.03 (t, J=6.0 Hz, 2H), 3.56 (q, J=7.0 Hz, 2H), 2.28-2.15 (m, 2H), 1.75 (s, 3H), 1.73 (s, 3H), 1.16 (t, J=7.0 Hz, 3H);

HRMS (EI) calcd for $C_{18}H_{23}BrN_6O_2$ (N+H)$^+$: 435.1144. Found: 435.1142.

Example 206

Acetone O-{3-[4-amino-2-(ethoxymethyl)-7-phenyl-1H-imidazo[4,5-c][1,5]naphthyridin-1-yl]propyl}oxime

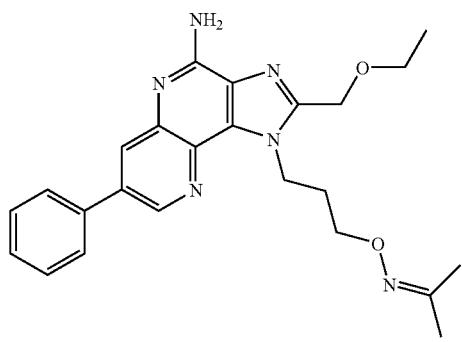 [SMILES: CCOCc1nc2c(N)nc3cc(-c4ccccc4)cnc3c2n1CCCON=C(C)C]

In a pressure vessel under a nitrogen atmosphere, acetone O-{3-[4-amino-7-bromo-2-(ethoxymethyl)-1H-imidazo[4,5-c][1,5]naphthyridin-1-yl]propyl}oxime (2.50 g, 5.74 mmol), phenylboronic acid (1.05 g, 8.61 nmmol), palladium (II) acetate (13 mg, 0.057 rmmol), triphenylphosphine (45 mg, 0.17 mmol), and 2 M aqueous sodium carbonate (3.45 mL, 6.89 mmol) were combined in 5:1 n-propanol:water (12 mL). The solution was placed under vacuum and back-filled with nitrogen three times. The pressure vessel was sealed and heated at 100° C. for 2 days, then was allowed to cool to ambient temperature. Chloroform (200 mL) was added and the mixture was washed with water (40 mL) and brine (40 mL), dried over sodium sulfate, filtered, and concentrated under reduced pressure. The product was purified by chromatography on a HORIZON HPFC system (silica gel, gradient elution with 0-25% CMA in chloroform) to yield 2.4 g of acetone O-{3-[4-amino-2-(ethoxymethyl)-7-phenyl-1H-imidazo[4,5-c][1,5]naphthyridin-1-yl]propyl}oxime as a yellow powder, mp 134.0-136.0° C.

$^1$H NMR (300 Mz, DMSO-$d_6$) δ 8.85 (d, J=2.2 Hz, 1H), 8.13 (d, J=2.2 Hz, 1H), 7.92-7.80 (m, 2H), 7.57-7.39 (m, 3H), 6.94 (s, 2H), 4.91 (dd, J=7.6, 6.6 Hz, 2H), 4.79 (s, 2H), 4.06 (t, J=6.0 Hz, 2H), 3.57 (q, J=7.0 Hz, 2H), 2.35-2.21 (m, 2H), 1.77 (s, 3H), 1.76 (s, 3H), 1.18 (t, J=7.0 Hz, 3H);

HRMS (EI) calcd for $C_{24}H_{28}N_6O_2$ (M+H)$^+$: 433.2352. Found: 433.2342.

Example 207

Acetone O-[4-(4-amino-6,7,8,9-tetrahydro-1H-imidazo[4,5-c]quinolin-1-yl)butyl]oximne

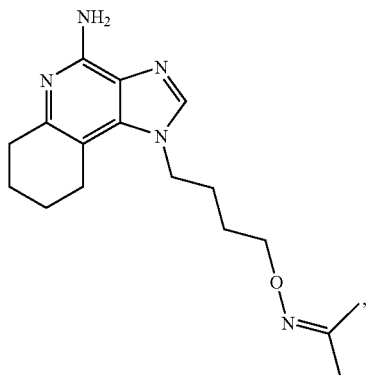 [SMILES: CC(C)=NOCCCCn1cnc2c(N)nc3c(c21)CCCC3]

Part A

Platinum (IV) oxide (3.5 g) was added to a solution of 4-(4-amino-1H-imidazo[4,5-c]quinolin-1-yl)butan-1-ol (prepared as described in Example 9 of U.S. Pat. No. 6,664,264, 4.00 g, 15.6 mmol) in trifluoroacetic acid (200 mL), and the mixture was shaken under hydrogen pressure for 2 days on a Parr apparatus. The reaction mixture was concentrated under reduced pressure, carefully diluted with methanol, and filtered through a layer of CELITE filter agent. The filtrate was concentrated under reduced pressure. The resulting residue was diluted with a solution of 4 M hydrogen chloride in 1,4-ioxane (100 mL) and stirred at ambient temperature for 1 hour; then 4 M aqueous sodium hydroxide was added to adjust the mixture to pH 13. The mixture was transferred to a separatory funnel, and dichloromethane was added. The mixture was shaken and allowed to stand overnight at ambient temperature. The organic layer was separated and the aqueous layer was extracted with dichloromethane. The organic layers were combined, dried over magnesium sulfate, filtered, and concentrated under reduced pressure to provide 1.0 g of 4-(4-aniino-6,7,8,9-tetrahydro-1H-imidazo[4,5-c]quinolin-1-yl)butan-1-ol as a white solid.

Part B

A cloudy solution of 4-(4-amino-6,7,8,9-tetrahydro-1H-imidazo[4,5-c]quinolin-1-yl)butan-1-ol (1.0 g, 3.8 mmol), triphenylphosphine (1.49 g, 5.7 mmol) and N-hydroxyphthalimide (0.93 g, 5.7 mmol) in tetrahydrofuran (50 mL) was cooled to approximately 0° C.; then diisopropyl azodicarboxylate (1.33 mL, 6.8 mmol) was added dropwise. The reaction was allowed to warm to ambient temperature and was stirred for 5 hours. The solvent was removed under reduced pressure, and the resulting solid was purified by chromatography on silica gel (gradient elution with 0-10% methanol in dichloromethane with a small amount of concentrated ammonium hydroxide added) to provide 600 mg of 2-[4-(4amino-6,7,8,9-tetrahydro-1H-imidazo[4,5-c]quinolin-1-yl)butoxy]-1H-isoindole-1,3(2H)-dione as a yellow solid.

Part C

Anhydrous hydrazine (94 mg, 2.96 mmol) was added to 2-[4-(4-amino-6,7,8,9-tetrahydro-1H-imidazo[4,5-c]quinolin-1-yl)butoxy]-1H-isoindole-1,3(2H)-dione (600 mg, 1.48 mmol) in ethanol (25 mL) at ambient temperature. The reaction was stirred overnight, and additional hydrazine (2 equivalents) was added. After sting for 2 hours at ambient temperature, the reaction was concentrated under reduced pressure. The residue was diluted with dichloromethane and concentrated under reduced pressure three times to remove the hydrazine and then dried under vacuum to provide 550 mg of impure 1-[4-(aminooxy)butyl]-6,7,8,9-tetrahydro-1H-imidazo[4,5-c]quinolin4-amine as an orange solid.

Part D

Acetone (59 µL, 0.80 mmol) was added to a solution of the material from Part C (200 mg, 0.73 mmol) in methanol (25 mL). The solution was stirred for 30 minutes, and then more acetone (1 equivalent) was added. After 1 hour, the cloudy white solution was concentrated under reduced pressure. The crude product was purified by chromatography (silica gel, gradient elution with 0-10% methanol in dichloromethane with a small amount of concentrated ammonium hydroxide added). The appropriate fractions were combined and concentrated to yield 100 mg of acetone O-[4-(4-amino-6,7,8,9-tetrahydro-1H-imidazo[4,5-c]quinolin-1-yl)butyl]oxime as an off-white solid, mp 151.0-153.0° C.

$^1$H NMR (300 MHz, DMSO-d$_6$) δ 7.93 (s, 1H), 5.90 (br s, 2H), 4.28 (t, J=7.1 Hz, 2H), 3.94 (t, J=6.3 Hz, 2H), 2.93 (m, 2H), 2.67 (ni, 2H), 1.81-1.72 (m, 12H), 1.56 (m, 2H); $^{13}$C NMHR (300 MHz, DMSO-d$_6$) δ 154.1, 150.0, 146.6, 142.8, 137.3, 126.6, 105.6, 71.9, 45.9, 32.4, 28.8, 26.1, 23.6, 23.0, 21.6, 15.5;

MS (ESI) m/z 316 (M+H)$^+$;

HRMS (EI) calcd for $C_{17}H_{25}N_5O$ (M+H)$^+$: 316.2137. Found: 316.2142.

Example 208

Acetone O-{4-[4-amino-2-(ethoxymethyl)-6,7,8,9-tetrahydro-1H-imidazo[4,5-c]quinolin-1-yl]butyl}oxime

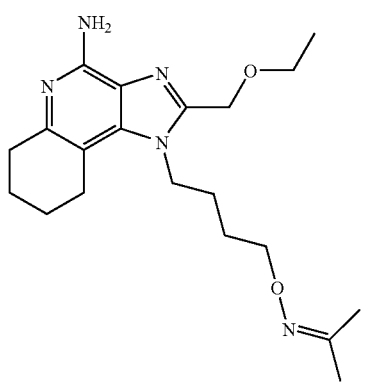 [SMILES: CCOCc1nc2c(N)nc3c(c2n1CCCCON=C(C)C)CCCC3]

Part A

The methods described in Parts B and C of Example 1 can be used to treat 4-[2-(ethoxymethyl)-1H-imidazo[4,5-c]quinolin-1-yl)butan-1-ol with mCPBA and ammonium hydroxide to provide 4-[4-amino-2-(ethoxymethyl)-1H-imidazo[4,5-c]quinolin-1-yl)butan-1-ol.

Part B

The method described in Part A of Example 207 can be used to reduce 4-[4-amino-2-(ethoxymethyl)-1H-imidazo[4,5-c]quinolin-1-yl)butan-1-ol to 4-[4-amino-2-(ethoxymethyl)-6,7,8,9-tetrahydro-1H-imidazo[4,5-c]quinolin-1-yl)butan-1-ol.

Part C

The method described in Part A of Example 1 can be used to convert 4-[4-amino-2-(ethoxymethyl)-6,7,8,9-tetrahydro-1H-imidazo[4,5-c]quinolin-1-yl)butan-1-ol to 2-{4-[4-amino-2-(ethoxymethyl)-6,7,8,9-tetrahydro-1H-imidazo[4,5-c]quinolin-1-yl)butoxy]-1H-isoindole-1,3(2H)-dione.

Part D

The method described in Part F of Example 169 can be used to treat 2-{4-[4-amino-2-(ethoxymethyl)-6,7,8,9-tetrahydro-1H-imidazo[4,5-c]quinolin-1-yl)butoxy]-1H-isoindole-1,3(2H)-dione with anhydrous hydrazine to provide 1-[4-(aminooxy)butyl]-2-(ethoxymethyl)-6,7,8,9-tetrahydro-1H-imidazo[4,5-c]quinolin-4-amine.

Part E

The method described in Example 3 can be used to treat 1-[4-(aminooxy)butyl]-2-(ethoxymethyl)-6,7,8,9-tetrahydro-1H-imidazo[4,5-c]quinolin-4-amine with acetone to provide acetone O-{4-[4-amino-2-(ethoxymethyl)-6,7,8,9-tetrahydro-1H-imidazo[4,5-c]quinolin-1-yl]butyl}oxime.

Example 209

Acetone O-{2-[2-(4-amino-2-butyl-1H-imidazo[4,5-c]quinolin-1-yl)ethoxy]ethyl}oxinme

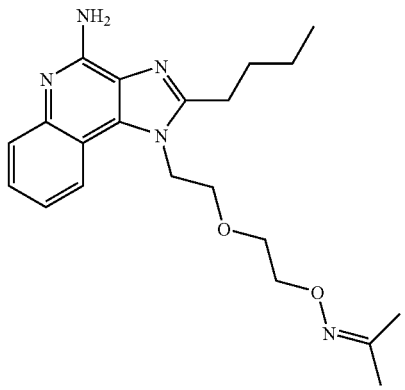 [SMILES: CCCCc1nc2c(N)nc3ccccc3c2n1CCOCCON=C(C)C]

Part A

Phosphorous oxychloride (84.3 g, 0.55 mol) was added to a stirred suspension of 3-nitroquinolin-4-ol (95.0 g, 0.50 mol) in DMF (500 mL), and an exotherm was observed. After the addition was complete, the solution was heated on a steam bath for 15 minutes. The solution was poured over ice to precipitate 4-chloro-3-nitroquinoline. The 4-chloro-3-nitroquinoline was isolated by filtration, washed with water, and pressed dry. The 4-chloro-3-nitroquinoline was dissolved in dichloromethane (1 L) and the solution was dried over magnesium sulfate and filtered. 2-(2-Aminoethoxy)ethanol (60.7 g, 0.6 mol) and triethylamine (104 mL, 0.75 mol) were added to the filtrate. The resulting solution was heated at reflux for 30 minutes. The mixture was concentrated under reduced pressure. The residue was dissolved in dilute aqueous hydrochloric acid and filtered. Ammonium hydroxide was added to the filtrate and a yellow solid formed. The solid was isolated by filtration, washed with water, and dried to provide 104.5 g of 2-{2-[(3-nitroquinolin-4-yl)aniino]ethoxy}ethanol as a yellow solid.

Part B

A mixture of 2-{2-[(3-nitroquinolin4-yl)ammo]ethoxy}ethanol (55.5 g, 0.2 mol), acetic anhydride (37.6 mL, 0.4 mol), and pyridine (250 mL) was heated at reflux for 30 minutes. The solution was allowed to cool to ambient temperature and was concentrated under reduced pressure to remove about 50-75% of the pyridine. The residual solution was poured into water to precipitate the product as an oil which solidified upon stirring. The solid was isolated by filtration, washed with water, and dried. The crude product was recrystallized from 2-propanol (200 mL) to provide 55.6 g of 2-{2-[(3-nitroquinolin-4-yl)amino]ethoxy}ethyl acetate as a bright yellow solid.

Part C

A mixture of 2-{2-[(3-nitroquinolin-4-yl)amino]ethoxy}ethyl acetate (104.7 g), magnesium sulfate (30 g) and 5% platinum on carbon (5 g) in ethyl acetate was hydrogenated at 30 psi (2.1×10$^5$ Pa) overnight on a Parr apparatus. The mixture was filtered through CELITE filter agent. The filtrate was concentrated under reduced pressure to provide an oil that was used in the next step.

Part D

Valeryl chloride (39 mL, 0.33 mol) was added to a solution of the material from Part C in acetonitrile (1 L) at room temperature. After 3 hours, a solid precipitated from the solution. The mixture was allowed to stand overnight and the solid was isolated by filtration, washed with acetonitrile, and used in the next step.

Part E

The crude material from Part D was divided into four high pressure reaction vessels and 5% ammonia in methanol was added. The reaction vessels were heated at 150° C. for 6 hours. The vessels were allowed to cool to room temperature, and then their contents were combined and concentrated under reduced pressure. Dichloromethane and water were added to the resulting oil, and a precipitate formed that was isolated by filtration. The tan solid was dried to provide 85 g of 2-[2-(2-butyl-1H-imidazo[4,5-c]quinolin-1-yl)ethoxy]ethanol.

Part F

A cloudy solution of 2-[2-(2-butyl-1H-imlidazo[4,5-c]quinolin-1-yl)ethoxy]ethanol (10.0 g, 31.9 mmol), triphenylphosphine (14.2 g, 70.2 mmol) and N-hydroxyphthalimide (8.85 g, 70.2 mmol) in tetrahydrofuran (250 mL) was cooled to approximately 0° C.; then diisopropyl azodicarboxylate (10.7 mL, 70.2 mmol) was added dropwise. The reaction was allowed to warm to ambient temperature and was stirred overnight. Additional tetrahydrofuran (100 mL) followed by DMF (25 mL) was added to the mixture, and the mixture was stirred overnight at room temperature. Over a 1 day period, more diisopropyl azodicarboxylate, triphenylphosphine, and N-hydroxyphthalimide (1 equivalent of each) and DMF (50 mL) were added to the mixture. Chloroform (200 mL) was added and the solution was washed with saturated aqueous sodium bicarbonate (5×500 mL), dried over sodium sulfate, filtered, and concentrated under reduced pressure. The crude product was subjected to flash chromatography (silica gel, eluted with 1.5% methanol in chloroform) to yield 12.46 g of 2-{2-[2-(2-butyl-1H-imidazo[4,5-c]quinolin-1-yl)ethoxy]ethoxy}-1H-isoindole-1,3(2H)-dione.

Part G mCPBA (12.6 g, 36.5 mmol) was added to a stirred solution of 2-{2-[2-(2-butyl-1H-imidazo[4,5-c]quinolin-1-yl)ethoxy]ethoxy}-1H-isoindole-1,3(2H1)-dione (12.89 g, 28.1 mmol) in dichloromethane (130 mL) at room temperature. After 1.3 hours, additional mCPBA (1.8 g) was added, and stirring was continued for another 30 minutes. Concentrated ammonium hydroxide (65 mL) was added followed by p-toluenesulfonyl chloride (12.57 g, 36.5 mmol), which was added slowly. The reaction was stirred at room temperature overnight. The organic phase was isolated, dried over sodium sulfate, and concentrated under reduced pressure. A small portion of the crude product was purified by chromatography on a HORIZON HPFC system (silica gel, gradient elution with 0-40% CMA in chloroform) to yield 1-{2-[2-(aminooxy)ethoxy]ethyl}-2-butyl-1H-imidazo[4,5-c]quinoline in approximately 80% purity. This material was used without further purification in the next step.

Part H

Acetone (2 mL) was added to a solution of the material from Part G (0.78 g, 2.3 irnol) in methanol (13 mL). The solution was stirred overnight at room temperature. The solution was concentrated under reduced pressure to yield an oil that was purified by flash chromatography (silica gel, elution with 0.5% methanol in chloroform). Analysis by $^1$H NMR indicated that the N-oxide was still present. The material was treated with ammonium hydroxide and p-toluenesulfonyl chloride as described in Part G. The organic phase was isolated, diluted with chloroform, washed with 1% aqueous sodium carbonate, dried over sodium sulfate, filtered, and concentrated under reduced pressure. The crude product was triturated with hexanes at room temperature overnight and then was isolated by filtration and dried under vacuum at 70° C. to provide 0.06 g of acetone O-{2-[2-(4-amino-2-butyl-1H-imidazo[4,5-c]quinolin-1-yl)ethoxy]ethyl}oxime as a yellow solid, mp 116.5-117.5° C.

$^1$H NMR (300 MHz, DMSO-$d_6$) δ 8.02 (d, J=7.8 Hz, 1H), 7.62 (d, J=8.3 Hz, 1H), 7.40 (t, J=8.2 Hz, 1H), 7.21 (t, J=8.2 Hz, 1H), 6.43 (s, 2H), 4.70 (t, J=5.2 Hz, 2H), 3.92 (m, J=5.9 Hz, 4H), 3.51 (t, J=4.7, 2H), 2.94 (t, J=7.9, 2H), 1.84 (pentet, J=7.4, 2H), 1.71 (s, 3H), 1.64 (s, 3H), 1.45 (sextet, J=7.4 Hz, 2H), 0.95 (t, J=7.4 Hz, 3H);

MS (APCI) m/z 384 CM+H)$^+$;

Anal. calcd for $C_{21}H_{29}N_5O_2$: C, 65.77; H, 7.62; N, 18.26. Found: C, 65.49; H, 7.89; N, 18.37.

Exemplary Compounds

Certain exemplary compounds, including some of those described above in the Examples, have the following Formulas (IIIa and VIIIa) and the following R', $R_1$, X, $R_2$ and $R_3$ substituents, wherein each line of the table is matched with Formula IIIa or VIIIa to represent a specific embodiment of the invention.

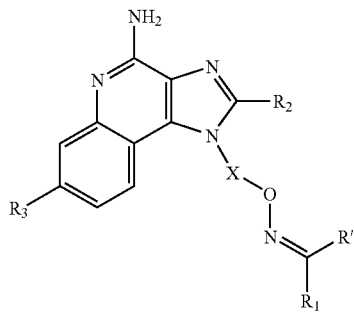

IIIa

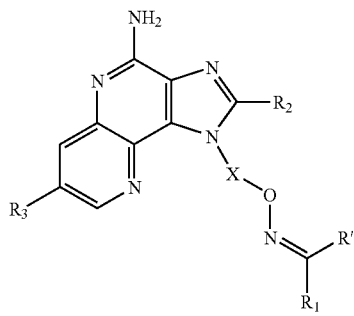

VIIIa

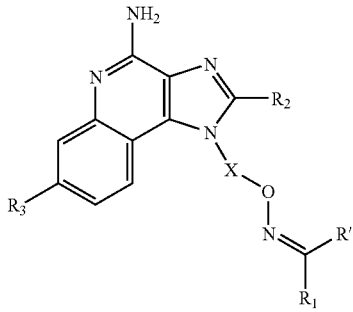

IIIa

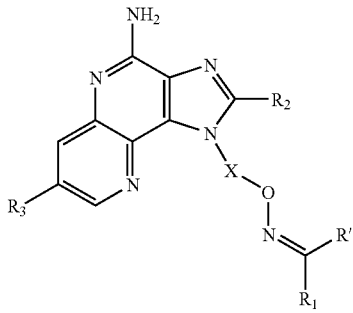

VIIIa

| $R_1$ | $R^1$ | X | $R_2$ | $R_3$ |
|---|---|---|---|---|
| hydrogen | hydrogen | —(CH$_2$)$_3$— | hydrogen | 3-pyridyl |
| hydrogen | hydrogen | —(CH$_2$)$_3$— | hydrogen | phenyl |
| hydrogen | hydrogen | —(CH$_2$)$_3$— | ethyl | 3-pyridyl |
| hydrogen | hydrogen | —(CH$_2$)$_3$— | ethyl | phenyl |
| hydrogen | hydrogen | —(CH$_2$)$_3$— | propyl | 3-pyridyl |
| hydrogen | hydrogen | —(CH$_2$)$_3$— | propyl | phenyl |
| hydrogen | hydrogen | —(CH$_2$)$_3$— | ethoxymethyl | 3-pyridyl |
| hydrogen | hydrogen | —(CH$_2$)$_3$— | ethoxymethyl | phenyl |
| hydrogen | hydrogen | —(CH$_2$)$_3$— | butyl | 3-pyridyl |
| hydrogen | hydrogen | —(CH$_2$)$_3$— | butyl | phenyl |
| hydrogen | hydrogen | —(CH$_2$)$_4$— | hydrogen | 3-pyridyl |
| hydrogen | hydrogen | —(CH$_2$)$_4$— | hydrogen | phenyl |
| hydrogen | hydrogen | —(CH$_2$)$_4$— | ethyl | 3-pyridyl |
| hydrogen | hydrogen | —(CH$_2$)$_4$— | ethyl | phenyl |
| hydrogen | hydrogen | —(CH$_2$)$_4$— | propyl | 3-pyridyl |
| hydrogen | hydrogen | —C(H$_2$)$_4$— | propyl | phenyl |
| hydrogen | hydrogen | —(CH$_2$)$_4$— | ethoxymethyl | 3-pyridyl |
| hydrogen | hydrogen | —(CH$_2$)$_4$— | ethoxymethyl | phenyl |
| hydrogen | hydrogen | —(CH$_2$)$_4$— | butyl | 3-pyridyl |
| hydrogen | hydrogen | —(CH$_2$)$_4$— | butyl | phenyl |
| hydrogen | hydrogen | —CH$_2$C(CH$_3$)$_2$CH$_2$— | hydrogen | 3-pyridyl |
| hydrogen | hydrogen | —CH$_2$C(CH$_3$)$_2$CH$_2$— | hydrogen | phenyl |
| hydrogen | hydrogen | —CH$_2$C(CH$_3$)$_2$CH$_2$— | ethyl | 3-pyridyl |
| hydrogen | hydrogen | —CH$_2$C(CH$_3$)$_2$CH$_2$— | ethyl | phenyl |
| hydrogen | hydrogen | —CH$_2$C(CH$_3$)$_2$CH$_2$— | propyl | 3-pyridyl |
| hydrogen | hydrogen | —CH$_2$C(CH$_3$)$_2$CH$_2$— | propyl | phenyl |
| hydrogen | hydrogen | —CH$_2$C(CH$_3$)$_2$CH$_2$— | ethoxymethyl | 3-pyridyl |
| hydrogen | hydrogen | —CH$_2$C(CH$_3$)$_2$CH$_2$— | ethoxymethyl | phenyl |

183
-continued

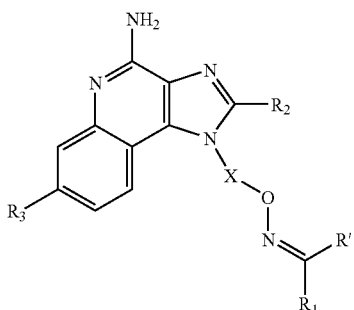

IIIa

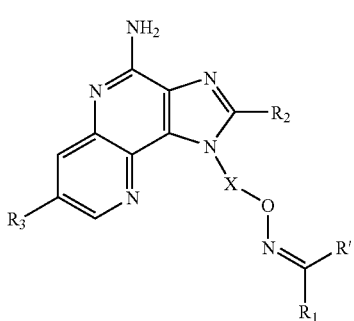

VIIIa

| R₁ | R¹ | X | R₂ | R₃ |
|---|---|---|---|---|
| hydrogen | hydrogen | —CH₂C(CH₃)₂CH₂— | butyl | 3-pyridyl |
| hydrogen | hydrogen | —CH₂C(CH₃)₂CH₂— | butyl | phenyl |
| hydrogen | hydrogen | —(CH₂)₂O(CH₂)₂— | hydrogen | 3-pyridyl |
| hydrogen | hydrogen | —(CH₂)₂O(CH₂)₂— | hydrogen | phenyl |
| hydrogen | hydrogen | —(CH₂)₂O(CH₂)₂— | ethyl | 3-pyridyl |
| hydrogen | hydrogen | —(CH₂)₂O(CH₂)₂— | ethyl | phenyl |
| hydrogen | hydrogen | —(CH₂)₂O(CH₂)₂— | propyl | 3-pyridyl |
| hydrogen | hydrogen | —(CH₂)₂O(CH₂)₂— | propyl | phenyl |
| hydrogen | hydrogen | —(CH₂)₂O(CH₂)₂— | ethoxymethyl | 3-pyridyl |
| hydrogen | hydrogen | —(CH₂)₂O(CH₂)₂— | ethoxymethyl | phenyl |
| hydrogen | hydrogen | —(CH₂)₂O(CH₂)₂— | butyl | 3-pyridyl |
| hydrogen | hydrogen | —(CH₂)₂O(CH₂)₂— | butyl | phenyl |
| hydrogen | methyl | —(CH₂)₃— | hydrogen | 3-pyridyl |
| hydrogen | methyl | —(CH₂)₃— | hydrogen | phenyl |
| hydrogen | methyl | —(CH₂)₃— | ethyl | 3-pyridyl |
| hydrogen | methyl | —(CH₂)₃— | ethyl | phenyl |
| hydrogen | methyl | —(CH₂)₃— | propyl | 3-pyridyl |
| hydrogen | methyl | —(CH₂)₃— | propyl | phenyl |
| hydrogen | methyl | —(CH₂)₃— | ethoxymethyl | 3-pyridyl |
| hydrogen | methyl | —(CH₂)₃— | ethoxymethyl | phenyl |
| hydrogen | methyl | —(CH₂)₃— | butyl | 3-pyridyl |
| hydrogen | methyl | —(CH₂)₃— | butyl | phenyl |

184
-continued

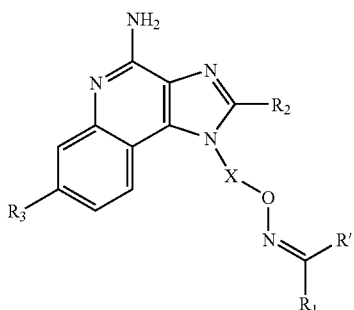

IIIa

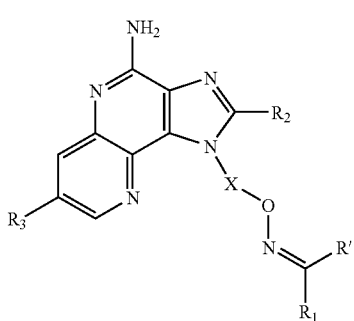

VIIIa

| R₁ | R¹ | X | R₂ | R₃ |
|---|---|---|---|---|
| hydrogen | methyl | —(CH₂)₄— | hydrogen | 3-pyridyl |
| hydrogen | methyl | —(CH₂)₄— | hydrogen | phenyl |
| hydrogen | methyl | —(CH₂)₄— | ethyl | 3-pyridyl |
| hydrogen | methyl | —(CH₂)₄— | ethyl | phenyl |
| hydrogen | methyl | —(CH₂)₄— | propyl | 3-pyridyl |
| hydrogen | methyl | —(CH₂)₄— | propyl | phenyl |
| hydrogen | methyl | —(CH₂)₄— | ethoxymethyl | 3-pyridyl |
| hydrogen | methyl | —(CH₂)₄— | ethoxymethyl | phenyl |
| hydrogen | methyl | —(CH₂)₄— | butyl | 3-pyridyl |
| hydrogen | methyl | —(CH₂)₄— | butyl | phenyl |
| hydrogen | methyl | —CH₂C(CH₃)₂CH₂— | hydrogen | 3-pyridyl |
| hydrogen | methyl | —CH₂C(CH₃)₂CH₂— | hydrogen | phenyl |
| hydrogen | methyl | —CH₂C(CH₃)₂CH₂— | ethyl | 3-pyridyl |
| hydrogen | methyl | —CH₂C(CH₃)₂CH₂— | ethyl | phenyl |
| hydrogen | methyl | —CH₂C(CH₃)₂CH₂— | propyl | 3-pyridyl |
| hydrogen | methyl | —CH₂C(CH₃)₂CH₂— | propyl | phenyl |
| hydrogen | methyl | —CH₂C(CH₃)₂CH₂— | ethoxymethyl | 3-pyridyl |
| hydrogen | methyl | —CH₂C(CH₃)₂CH₂— | ethoxymethyl | phenyl |
| hydrogen | methyl | —CH₂C(CH₃)₂CH₂— | butyl | 3-pyridyl |
| hydrogen | methy | —CH₂C(CH₃)₂CH₂— | butyl | phenyl |
| hydrogen | methyl | —(CH₂)₂O(CH₂)₂— | hydrogen | 3-pyridyl |
| hydrogen | methyl | —(CH₂)₂O(CH₂)₂— | hydrogen | phenyl |

185
-continued

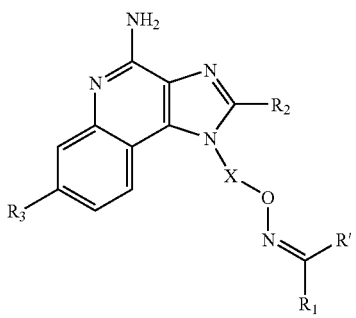

IIIa

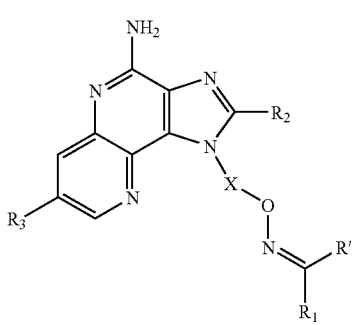

VIIIa

| R₁ | R¹ | X | R₂ | R₃ |
|---|---|---|---|---|
| hydrogen | methyl | —(CH₂)₂O(CH₂)₂— | ethyl | 3-pyridyl |
| hydrogen | methyl | —(CH₂)₂O(CH₂)₂— | ethyl | phenyl |
| hydrogen | methyl | —(CH₂)₂O(CH₂)₂— | propyl | 3-pyridyl |
| hydrogen | methyl | —(CH₂)₂O(CH₂)₂— | propyl | phenyl |
| hydrogen | methyl | —(CH₂)₂O(CH₂)₂— | ethoxymethyl | 3-pyridyl |
| hydrogen | methyl | —(CH₂)₂O(CH₂)₂— | ethoxymethyl | phenyl |
| hydrogen | methyl | —(CH₂)₂O(CH₂)₂— | butyl | 3-pyridyl |
| hydrogen | methyl | —(CH₂)₂O(CH₂)₂— | butyl | phenyl |
| hydrogen | 3-pyridyl | —(CH₂)₃— | hydrogen | 3-pyridyl |
| hydrogen | 3-pyridyl | —(CH₂)₃— | hydrogen | phenyl |
| hydrogen | 3-pyridyl | —(CH₂)₃— | ethyl | 3-pyridyl |
| hydrogen | 3-pyridyl | —(CH₂)₃— | ethyl | phenyl |
| hydrogen | 3-pyridyl | —(CH₂)₃— | propyl | 3-pyridyl |
| hydrogen | 3-pyridyl | —(CH₂)₃— | propyl | phenyl |
| hydrogen | 3-pyridyl | —(CH₂)₃— | ethoxymethyl | 3-pyridyl |
| hydrogen | 3-pyridyl | —(CH₂)₃— | ethoxymethyl | phenyl |
| hydrogen | 3-pyridyl | —(CH₂)₃— | butyl | 3-pyridyl |
| hydrogen | 3-pyridyl | —(CH₂)₃— | butyl | phenyl |
| hydrogen | 3-pyridyl | —(CH₂)₄— | hydrogen | 3-pyridyl |
| hydrogen | 3-pyridyl | —(CH₂)₄— | hydrogen | phenyl |
| hydrogen | 3-pyridyl | —(CH₂)₄— | ethyl | 3-pyridyl |
| hydrogen | 3-pyridyl | —(CH₂)₄— | ethyl | phenyl |

186
-continued

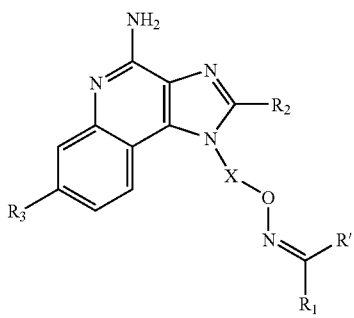

IIIa

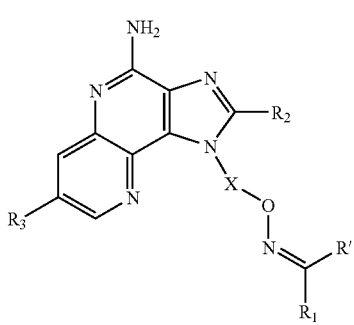

VIIIa

| R₁ | R¹ | X | R₂ | R₃ |
|---|---|---|---|---|
| hydrogen | 3-pyridyl | —(CH₂)₄— | propyl | 3-pyridyl |
| hydrogen | 3-pyridyl | —(CH₂)₄— | propyl | phenyl |
| hydrogen | 3-pyridyl | —(CH₂)₄— | ethoxymethyl | 3-pyridyl |
| hydrogen | 3-pyridyl | —(CH₂)₄— | ethoxymethyl | phenyl |
| hydrogen | 3-pyridyl | —(CH₂)₄— | butyl | 3-pyridyl |
| hydrogen | 3-pyridyl | —(CH₂)₄— | butyl | phenyl |
| hydrogen | 3-pyridyl | —CH₂C(CH₃)₂CH₂— | hydrogen | 3-pyridyl |
| hydrogen | 3-pyridyl | —CH₂C(CH₃)₂CH₂— | hydrogen | phenyl |
| hydrogen | 3-pyridyl | —CH₂C(CH₃)₂CH₂— | ethyl | 3-pyridyl |
| hydrogen | 3-pyridyl | —CH₂C(CH₃)₂CH₂— | ethyl | phenyl |
| hydrogen | 3-pyridyl | —CH₂C(CH₃)₂CH₂— | propyl | 3-pyridyl |
| hydrogen | 3-pyridyl | —CH₂C(CH₃)₂CH₂— | propyl | phenyl |
| hydrogen | 3-pyridyl | —CH₂C(CH₃)₂CH₂— | ethoxymethyl | 3-pyridyl |
| hydrogen | 3-pyridyl | —CH₂C(CH₃)₂CH₂— | ethoxymethyl | phenyl |
| hydrogen | 3-pyridyl | —CH₂C(CH₃)₂CH₂— | butyl | 3-pyridyl |
| hydrogen | 3-pyridyl | —CH₂C(CH₃)₂CH₂— | butyl | phenyl |
| hydrogen | 3-pyridyl | —(CH₂)₂O(CH₂)₂— | hydrogen | 3-pyridyl |
| hydrogen | 3-pyridyl | —(CH₂)₂O(CH₂)₂— | hydrogen | phenyl |
| hydrogen | 3-pyridyl | —(CH₂)₂O(CH₂)₂— | ethyl | 3-pyridyl |
| hydrogen | 3-pyridyl | —(CH₂)₂O(CH₂)₂— | ethyl | phenyl |
| hydrogen | 3-pyridyl | —(CH₂)₂O(CH₂)₂— | propyl | 3-pyridyl |
| hydrogen | 3-pyridyl | —(CH₂)₂O(CH₂)₂— | propyl | phenyl |

-continued

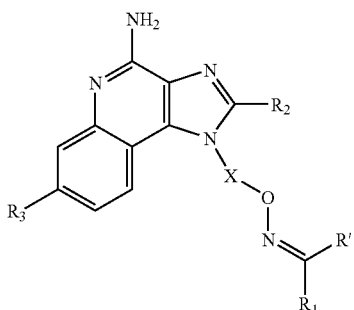
IIIa

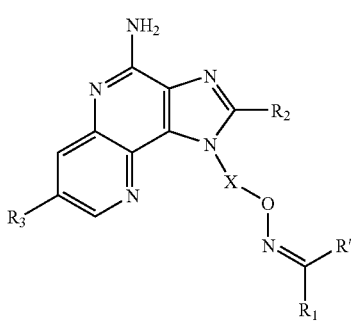
VIIIa

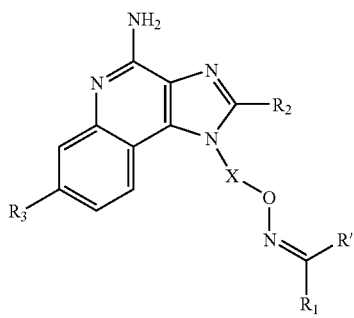
IIIa

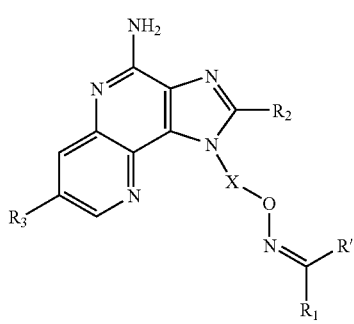
VIIIa

| $R_1$ | $R^1$ | X | $R_2$ | $R_3$ |
|---|---|---|---|---|
| hydrogen | 3-pyridyl | —(CH$_2$)$_2$O(CH$_2$)$_2$— | ethoxymethyl | 3-pyridyl |
| hydrogen | 3-pyridyl | —(CH$_2$)$_2$O(CH$_2$)$_2$— | ethoxymethyl | phenyl |
| hydrogen | 3-pyridyl | —(CH$_2$)$_2$O(CH$_2$)$_2$— | butyl | 3-pyridyl |
| hydrogen | 3-pyridyl | —(CH$_2$)$_2$O(CH$_2$)$_2$— | butyl | phenyl |
| methyl | methyl | —(CH$_2$)$_3$— | hydrogen | 3-pyridyl |
| methyl | methyl | —(CH$_2$)$_3$— | hydrogen | phenyl |
| methyl | methyl | —(CH$_2$)$_3$— | ethyl | 3-pyridyl |
| methyl | methyl | —(CH$_2$)$_3$— | ethyl | phenyl |
| methyl | methyl | —(CH$_2$)$_3$— | propyl | 3-pyridyl |
| methyl | methyl | —(CH$_2$)$_3$— | propyl | phenyl |
| methyl | methyl | —(CH$_2$)$_3$— | ethoxymethyl | 3-pyridyl |
| methyl | methyl | —(CH$_2$)$_3$— | ethoxymethyl | phenyl |
| methyl | methyl | —(CH$_2$)$_3$— | butyl | 3-pyridyl |
| methyl | methyl | —(CH$_2$)$_3$— | butyl | phenyl |
| methyl | methyl | —(CH$_2$)$_4$— | hydrogen | 3-pyridyl |
| methyl | methyl | —(CH$_2$)$_4$— | hydrogen | phenyl |
| methyl | methyl | —(CH$_2$)$_4$— | ethyl | 3-pyridyl |
| methyl | methyl | —(CH$_2$)$_4$— | ethyl | phenyl |
| methyl | methyl | —(CH$_2$)$_4$— | propyl | 3-pyridyl |
| methyl | methyl | —(CH$_2$)$_4$— | propyl | phenyl |
| methyl | methyl | —(CH$_2$)$_4$— | ethoxymethyl | 3-pyridyl |
| methyl | methyl | —(CH$_2$)$_4$— | ethoxymethyl | phenyl |
| methyl | methyl | —(CH$_2$)$_4$— | butyl | 3-pyridyl |
| methyl | methyl | —(CH$_2$)$_4$— | butyl | phenyl |
| methyl | methyl | —CH$_2$C(CH$_3$)$_2$CH$_2$— | hydrogen | 3-pyridyl |
| methyl | methyl | —CH$_2$C(CH$_3$)$_2$CH$_2$— | hydrogen | phenyl |
| methyl | methyl | —CH$_2$C(CH$_3$)$_2$CH$_2$— | ethyl | 3-pyridyl |
| methyl | methyl | —CH$_2$C(CH$_3$)$_2$CH$_2$— | ethyl | phenyl |
| methyl | methyl | —CH$_2$C(CH$_3$)$_2$CH$_2$— | propyl | 3-pyridyl |
| methyl | methyl | —CH$_2$C(CH$_3$)$_2$CH$_2$— | propyl | phenyl |
| methyl | methyl | —CH$_2$C(CH$_3$)$_2$CH$_2$— | ethoxymethyl | 3-pyridyl |
| methyl | methyl | —CH$_2$C(CH$_3$)$_2$CH$_2$— | ethoxymethyl | phenyl |
| methyl | methyl | —CH$_2$C(CH$_3$)$_2$CH$_2$— | butyl | 3-pyridyl |
| methyl | methyl | —CH$_2$C(CH$_3$)$_2$CH$_2$— | butyl | phenyl |
| methyl | methyl | —(CH$_2$)$_2$O(CH$_2$)$_2$— | hydrogen | 3-pyridyl |
| methyl | methyl | —(CH$_2$)$_2$O(CH$_2$)$_2$— | hydrogen | phenyl |
| methyl | methyl | —(CH$_2$)$_2$O(CH$_2$)$_2$— | ethyl | 3-pyridyl |
| methyl | methyl | —(CH$_2$)$_2$O(CH$_2$)$_2$— | ethyl | phenyl |
| methyl | methyl | —(CH$_2$)$_2$O(CH$_2$)$_2$— | propyl | 3-pyridyl |
| methyl | methyl | —(CH$_2$)$_2$O(CH$_2$)$_2$— | propyl | phenyl |
| methyl | methyl | —(CH$_2$)$_2$O(CH$_2$)$_2$— | ethoxymethyl | 3-pyridyl |
| methyl | methyl | —(CH$_2$)$_2$O(CH$_2$)$_2$— | ethoxymethyl | phenyl |
| methyl | methyl | —(CH$_2$)$_2$O(CH$_2$)$_2$— | butyl | 3-pyridyl |
| methyl | methyl | —(CH$_2$)$_2$O(CH$_2$)$_2$— | butyl | phenyl |
| methyl | 3-pyridyl | —(CH$_2$)$_3$— | hydrogen | 3-pyridyl |
| methyl | 3-pyridyl | —(CH$_2$)$_3$— | hydrogen | phenyl |
| methyl | 3-pyridyl | —(CH$_2$)$_3$— | ethyl | 3-pyridyl |
| methyl | 3-pyridyl | —(CH$_2$)$_3$— | ethyl | phenyl |
| methyl | 3-pyridyl | —(CH$_2$)$_3$— | propyl | 3-pyridyl |
| methyl | 3-pyridyl | —(CH$_2$)$_3$— | propyl | phenyl |
| methyl | 3-pyridyl | —(CH$_2$)$_3$— | ethoxymethyl | 3-pyridyl |
| methyl | 3-pyridyl | —(CH$_2$)$_3$— | ethoxymethyl | phenyl |
| methyl | 3-pyridyl | —(CH$_2$)$_3$— | butyl | 3-pyridyl |
| methyl | 3-pyridyl | —(CH$_2$)$_3$— | butyl | phenyl |
| methyl | 3-pyridyl | —(CH$_2$)$_4$— | hydrogen | 3-pyridyl |
| methyl | 3-pyridyl | —(CH$_2$)$_4$— | hydrogen | phenyl |
| methyl | 3-pyridyl | —(CH$_2$)$_4$— | ethyl | 3-pyridyl |
| methyl | 3-pyridyl | —(CH$_2$)$_4$— | ethyl | phenyl |
| methyl | 3-pyridyl | —(CH$_2$)$_4$— | propyl | 3-pyridyl |
| methyl | 3-pyridyl | —(CH$_2$)$_4$— | propyl | phenyl |
| methyl | 3-pyridyl | —(CH$_2$)$_4$— | ethoxymethyl | 3-pyridyl |
| methyl | 3-pyridyl | —(CH$_2$)$_4$— | ethoxymethyl | phenyl |
| methyl | 3-pyridyl | —(CH$_2$)$_4$— | butyl | 3-pyridyl |
| methyl | 3-pyridyl | —(CH$_2$)$_4$— | butyl | phenyl |
| methyl | 3-pyridyl | —CH$_2$C(CH$_3$)$_2$CH$_2$— | hydrogen | 3-pyridyl |
| methyl | 3-pyridyl | —CH$_2$C(CH$_3$)$_2$CH$_2$— | hydrogen | phenyl |
| methyl | 3-pyridyl | —CH$_2$C(CH$_3$)$_2$CH$_2$— | ethyl | 3-pyridyl |
| methyl | 3-pyridyl | —CH$_2$C(CH$_3$)$_2$CH$_2$— | ethyl | phenyl |
| methyl | 3-pyridyl | —CH$_2$C(CH$_3$)$_2$CH$_2$— | propyl | 3-pyridyl |
| methyl | 3-pyridyl | —CH$_2$C(CH$_3$)$_2$CH$_2$— | propyl | phenyl |
| methyl | 3-pyridyl | —CH$_2$C(CH$_3$)$_2$CH$_2$— | ethoxymethyl | 3-pyridyl |
| methyl | 3-pyridyl | —CH$_2$C(CH$_3$)$_2$CH$_2$— | ethoxymethyl | phenyl |
| methyl | 3-pyridyl | —CH$_2$C(CH$_3$)$_2$CH$_2$— | butyl | 3-pyridyl |
| methyl | 3-pyridyl | —CH$_2$C(CH$_3$)$_2$CH$_2$— | butyl | phenyl |
| methyl | 3-pyridyl | —(CH$_2$)$_2$O(CH$_2$)$_2$— | hydrogen | 3-pyridyl |
| methyl | 3-pyridyl | —(CH$_2$)$_2$O(CH$_2$)$_2$— | hydrogen | phenyl |
| methyl | 3-pyridyl | —(CH$_2$)$_2$O(CH$_2$)$_2$— | ethyl | 3-pyridyl |
| methyl | 3-pyridyl | —(CH$_2$)$_2$O(CH$_2$)$_2$— | ethyl | phenyl |
| methyl | 3-pyridyl | —(CH$_2$)$_2$O(CH$_2$)$_2$— | propyl | 3-pyridyl |
| methyl | 3-pyridyl | —(CH$_2$)$_2$O(CH$_2$)$_2$— | propyl | phenyl |
| methyl | 3-pyridyl | —(CH$_2$)$_2$O(CH$_2$)$_2$— | ethoxymethyl | 3-pyridyl |
| methyl | 3-pyridyl | —(CH$_2$)$_2$O(CH$_2$)$_2$— | ethoxymethyl | phenyl |
| methyl | 3-pyridyl | —(CH$_2$)$_2$O(CH$_2$)$_2$— | butyl | 3-pyridyl |
| methyl | 3-pyridyl | —(CH$_2$)$_2$O(CH$_2$)$_2$— | butyl | phenyl |

-continued

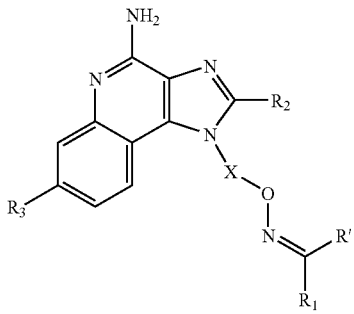

IIIa

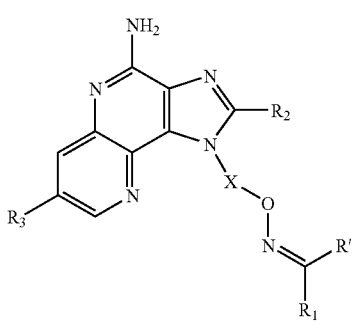

VIIIa

-continued

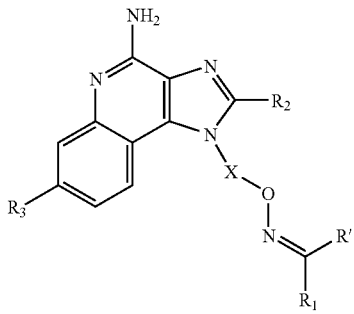

IIIa

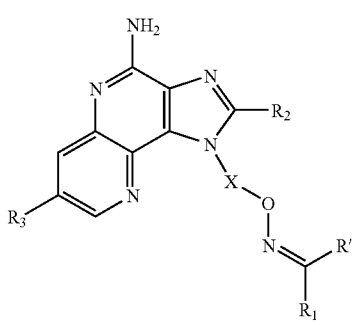

VIIIa

| R₁ | R¹ | X | R₂ | R₃ | R₁ | R¹ | X | R₂ | R₃ |
|---|---|---|---|---|---|---|---|---|---|
| methyl | hydrogen | —(CH₂)₃— | hydrogen | 3-pyridyl | 3-pyridyl | hydrogen | —(CH₂)₃— | ethyl | 3-pyridyl |
| methyl | hydrogen | —(CH₂)₃— | hydrogen | phenyl | 3-pyridyl | hydrogen | —(CH₂)₃— | ethyl | phenyl |
| methyl | hydrogen | —(CH₂)₃— | ethyl | 3-pyridyl | 3-pyridyl | hydrogen | —(CH₂)₃— | propyl | 3-pyridyl |
| methyl | hydrogen | —(CH₂)₃— | ethyl | phenyl | 3-pyridyl | hydrogen | —(CH₂)₃— | propyl | phenyl |
| methyl | hydrogen | —(CH₂)₃— | propyl | 3-pyridyl | 3-pyridyl | hydrogen | —(CH₂)₃— | ethoxymethyl | 3-pyridyl |
| methyl | hydrogen | —(CH₂)₃— | propyl | phenyl | 3-pyridyl | hydrogen | —(CH₂)₃— | ethoxymethyl | phenyl |
| methyl | hydrogen | —(CH₂)₃— | ethoxymethyl | 3-pyridyl | 3-pyridyl | hydrogen | —(CH₂)₃— | butyl | 3-pyridyl |
| methyl | hydrogen | —(CH₂)₃— | ethoxymethyl | phenyl | 3-pyridyl | hydrogen | —(CH₂)₃— | butyl | phenyl |
| methyl | hydrogen | —(CH₂)₃— | butyl | 3-pyridyl | 3-pyridyl | hydrogen | —(CH₂)₄— | hydrogen | 3-pyridyl |
| methyl | hydrogen | —(CH₂)₃— | butyl | phenyl | 3-pyridyl | hydrogen | —(CH₂)₄— | hydrogen | phenyl |
| methyl | hydrogen | —(CH₂)₄— | hydrogen | 3-pyridyl | 3-pyridyl | hydrogen | —(CH₂)₄— | ethyl | 3-pyridyl |
| methyl | hydrogen | —(CH₂)₄— | hydrogen | phenyl | 3-pyridyl | hydrogen | —(CH₂)₄— | ethyl | phenyl |
| methyl | hydrogen | —(CH₂)₄— | ethyl | 3-pyridyl | 3-pyridyl | hydrogen | —(CH₂)₄— | propyl | 3-pyridyl |
| methyl | hydrogen | —(CH₂)₄— | ethyl | phenyl | 3-pyridyl | hydrogen | —(CH₂)₄— | propyl | phenyl |
| methyl | hydrogen | —(CH₂)₄— | propyl | 3-pyridyl | 3-pyridyl | hydrogen | —(CH₂)₄— | ethoxymethyl | 3-pyridyl |
| methyl | hydrogen | —(CH₂)₄— | propyl | phenyl | 3-pyridyl | hydrogen | —(CH₂)₄— | ethoxymethyl | phenyl |
| methyl | hydrogen | —(CH₂)₄— | ethoxymethyl | 3-pyridyl | 3-pyridyl | hydrogen | —(CH₂)₄— | butyl | 3-pyridyl |
| methyl | hydrogen | —(CH₂)₄— | ethoxymethyl | phenyl | 3-pyridyl | hydrogen | —(CH₂)₄— | butyl | phenyl |
| methyl | hydrogen | —(CH₂)₄— | butyl | 3-pyridyl | 3-pyridyl | hydrogen | —CH₂C(CH₃)₂CH₂— | hydrogen | 3-pyridyl |
| methyl | hydrogen | —(CH₂)₄— | butyl | phenyl | 3-pyridyl | hydrogen | —CH₂C(CH₃)₂CH₂— | hydrogen | phenyl |
| methyl | hydrogen | —CH₂C(CH₃)₂CH₂— | hydrogen | 3-pyridyl | 3-pyridyl | hydrogen | —CH₂C(CH₃)₂CH₂— | ethyl | 3-pyridyl |
| methyl | hydrogen | —CH₂C(CH₃)₂CH₂— | hydrogen | phenyl | 3-pyridyl | hydrogen | —CH₂C(CH₃)₂CH₂— | ethyl | phenyl |
| methyl | hydrogen | —CH₂C(CH₃)₂CH₂— | ethyl | 3-pyridyl | | | | | |
| methyl | hydrogen | —CH₂C(CH₃)₂CH₂— | ethyl | phenyl | | | | | |
| methyl | hydrogen | —CH₂C(CH₃)₂CH₂— | propyl | 3-pyridyl | | | | | |
| methyl | hydrogen | —CH₂C(CH₃)₂CH₂— | propyl | phenyl | | | | | |
| methyl | hydrogen | —CH₂C(CH₃)₂CH₂— | ethoxymethyl | 3-pyridyl | | | | | |
| methyl | hydrogen | —CH₂C(CH₃)₂CH₂— | ethoxymethyl | phenyl | | | | | |
| methyl | hydrogen | —CH₂C(CH₃)₂CH₂— | butyl | 3-pyridyl | | | | | |
| methyl | hydrogen | —CH₂C(CH₃)₂CH₂— | butyl | phenyl | | | | | |
| methyl | hydrogen | —(CH₂)₂O(CH₂)₂— | hydrogen | 3-pyridyl | | | | | |
| methyl | hydrogen | —(CH₂)₂O(CH₂)₂— | hydrogen | phenyl | | | | | |
| methyl | hydrogen | —(CH₂)₂O(CH₂)₂— | ethyl | 3-pyridyl | | | | | |
| methyl | hydrogen | —(CH₂)₂O(CH₂)₂— | ethyl | phenyl | | | | | |
| methyl | hydrogen | —(CH₂)₂O(CH₂)₂— | propyl | 3-pyridyl | | | | | |
| methyl | hydrogen | —(CH₂)₂O(CH₂)₂— | propyl | phenyl | | | | | |
| methyl | hydrogen | —(CH₂)₂O(CH₂)₂— | ethoxymethyl | 3-pyridyl | | | | | |
| methyl | hydrogen | —(CH₂)₂O(CH₂)₂— | ethoxymethyl | phenyl | | | | | |
| methyl | hydrogen | —(CH₂)₂O(CH₂)₂— | butyl | 3-pyridyl | | | | | |
| methyl | hydrogen | —(CH₂)₂O(CH₂)₂— | butyl | phenyl | | | | | |
| 3-pyridyl | hydrogen | —(CH₂)₃— | hydrogen | 3-pyridyl | | | | | |
| 3-pyridyl | hydrogen | —(CH₂)₃— | hydrogen | phenyl | | | | | |

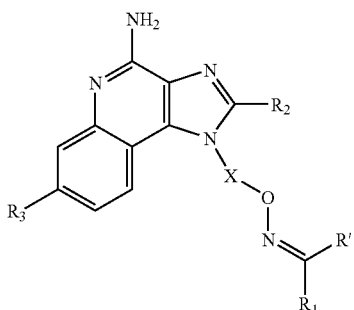

IIIa

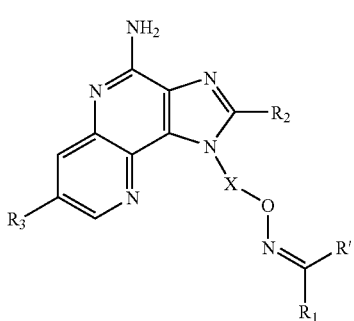

VIIIa

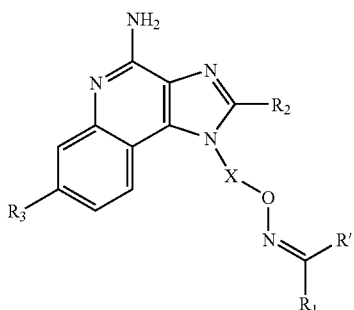

IIIa

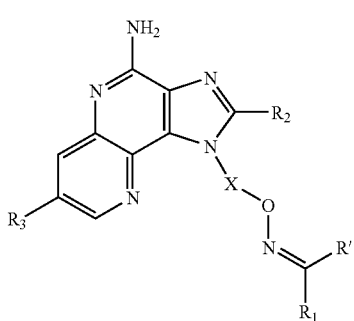

VIIIa

| R₁ | R¹ | X | R₂ | R₃ | R₁ | R¹ | X | R₂ | R₃ |
|---|---|---|---|---|---|---|---|---|---|
| 3-pyridyl | hydrogen | —CH₂C(CH₃)₂CH₂— | propyl | 3-pyridyl | 3-pyridyl | methyl | —(CH₂)₃— | ethoxymethyl | 3-pyridyl |
| 3-pyridyl | hydrogen | —CH₂C(CH₃)₂CH₂— | propyl | phenyl | 3-pyridyl | methyl | —(CH₂)₃— | ethoxymethyl | phenyl |
| 3-pyridyl | hydrogen | —CH₂C(CH₃)₂CH₂— | ethoxymethyl | 3-pyridyl | 3-pyridyl | methyl | —(CH₂)₃— | butyl | 3-pyridyl |
| 3-pyridyl | hydrogen | —CH₂C(CH₃)₂CH₂— | ethoxymethyl | phenyl | 3-pyridyl | methyl | —(CH₂)₃— | butyl | phenyl |
| 3-pyridyl | hydrogen | —CH₂C(CH₃)₂CH₂— | butyl | 3-pyridyl | 3-pyridyl | methyl | —(CH₂)₄— | hydrogen | 3-pyridyl |
| 3-pyridyl | hydrogen | —CH₂C(CH₃)₂CH₂— | butyl | phenyl | 3-pyridyl | methyl | —(CH₂)₄— | hydrogen | phenyl |
| 3-pyridyl | hydrogen | —(CH₂)₂O(CH₂)₂— | hydrogen | 3-pyridyl | 3-pyridyl | methyl | —(CH₂)₄— | ethyl | 3-pyridyl |
| 3-pyridyl | hydrogen | —(CH₂)₂O(CH₂)₂— | hydrogen | phenyl | 3-pyridyl | methyl | —(CH₂)₄— | ethyl | phenyl |
| 3-pyridyl | hydrogen | —(CH₂)₂O(CH₂)₂— | ethyl | 3-pyridyl | 3-pyridyl | methyl | —(CH₂)₄— | propyl | 3-pyridyl |
| 3-pyridyl | hydrogen | —(CH₂)₂O(CH₂)₂— | ethyl | phenyl | 3-pyridyl | methyl | —(CH₂)₄— | propyl | phenyl |
| 3-pyridyl | hydrogen | —(CH₂)₂O(CH₂)₂— | propyl | 3-pyridyl | 3-pyridyl | methyl | —(CH₂)₄— | ethoxymethyl | 3-pyridyl |
| 3-pyridyl | hydrogen | —(CH₂)₂O(CH₂)₂— | propyl | phenyl | 3-pyridyl | methyl | —(CH₂)₄— | ethoxymethyl | phenyl |
| 3-pyridyl | hydrogen | —(CH₂)₂O(CH₂)₂— | ethoxymethyl | 3-pyridyl | 3-pyridyl | methyl | —(CH₂)₄— | butyl | 3-pyridyl |
| 3-pyridyl | hydrogen | —(CH₂)₂O(CH₂)₂— | ethoxymethyl | phenyl | 3-pyridyl | methyl | —(CH₂)₄— | butyl | phenyl |
| 3-pyridyl | hydrogen | —(CH₂)₂O(CH₂)₂— | butyl | 3-pyridyl | 3-pyridyl | methyl | —CH₂C(CH₃)₂CH₂— | hydrogen | 3-pyridyl |
| 3-pyridyl | hydrogen | —(CH₂)₂O(CH₂)₂— | butyl | phenyl | 3-pyridyl | methyl | —CH₂C(CH₃)₂CH₂— | hydrogen | phenyl |
| 3-pyridyl | methyl | —(CH₂)₃— | hydrogen | 3-pyridyl | 3-pyridyl | methyl | —CH₂C(CH₃)₂CH₂— | ethyl | 3-pyridyl |
| 3-pyridyl | methyl | —(CH₂)₃— | hydrogen | phenyl | 3-pyridyl | methyl | —CH₂C(CH₃)₂CH₂— | ethyl | phenyl |
| 3-pyridyl | methyl | —(CH₂)₃— | ethyl | 3-pyridyl | 3-pyridyl | methyl | —CH₂C(CH₃)₂CH₂— | propyl | 3-pyridyl |
| 3-pyridyl | methyl | —(CH₂)₃— | ethyl | phenyl | 3-pyridyl | methyl | —CH₂C(CH₃)₂CH₂— | propyl | phenyl |
| 3-pyridyl | methyl | —(CH₂)₃— | propyl | 3-pyridyl | 3-pyridyl | methyl | —CH₂C(CH₃)₂CH₂— | ethoxymethyl | 3-pyridyl |
| 3-pyridyl | methyl | —(CH₂)₃— | propyl | phenyl | 3-pyridyl | methyl | —CH₂C(CH₃)₂CH₂— | ethoxymethyl | phenyl |

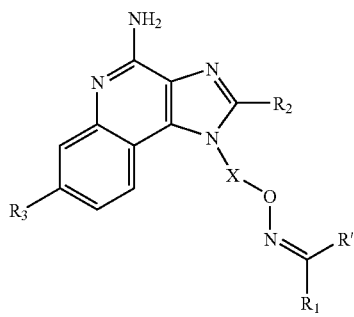

IIIa

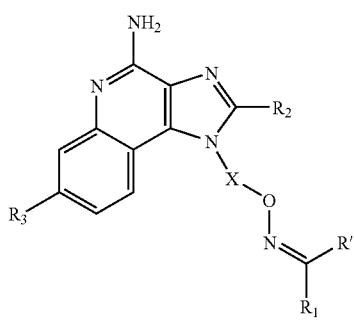

IIIa

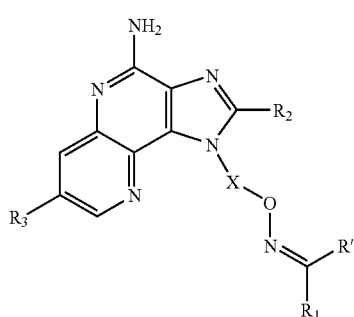

VIIIa

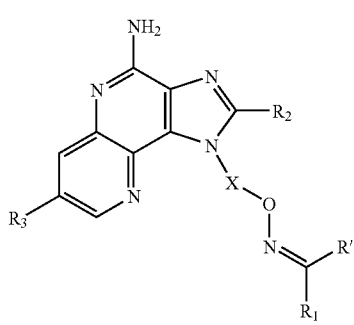

VIIIa

| $R_1$ | $R'$ | X | $R_2$ | $R_3$ |
|---|---|---|---|---|
| 3-pyridyl | methyl | —CH$_2$C(CH$_3$)$_2$CH$_2$— | butyl | 3-pyridyl |
| 3-pyridyl | methyl | —CH$_2$C(CH$_3$)$_2$CH$_2$— | butyl | phenyl |
| 3-pyridyl | methyl | —(CH$_2$)$_2$O(CH$_2$)$_2$— | hydrogen | 3-pyridyl |
| 3-pyridyl | methyl | —(CH$_2$)$_2$O(CH$_2$)$_2$— | hydrogen | phenyl |
| 3-pyridyl | methyl | —(CH$_2$)$_2$O(CH$_2$)$_2$— | ethyl | 3-pyridyl |
| 3-pyridyl | methyl | —(CH$_2$)$_2$O(CH$_2$)$_2$— | ethyl | phenyl |
| 3-pyridyl | methyl | —(CH$_2$)$_2$O(CH$_2$)$_2$— | propyl | 3-pyridyl |
| 3-pyridyl | methyl | —(CH$_2$)$_2$O(CH$_2$)$_2$— | propyl | phenyl |
| 3-pyridyl | methyl | —(CH$_2$)$_2$O(CH$_2$)$_2$— | ethoxymethyl | 3-pyridyl |
| 3-pyridyl | methyl | —(CH$_2$)$_2$O(CH$_2$)$_2$— | ethoxymethyl | phenyl |
| 3-pyridyl | methyl | —(CH$_2$)$_2$O(CH$_2$)$_2$— | butyl | 3-pyridyl |
| 3-pyridyl | methyl | —(CH$_2$)$_2$O(CH$_2$)$_2$— | butyl | phenyl |

Certain exemplary compounds, including some of those described above in the Examples, have the following Formulas (IIIa and VIIIa) and the following R', $R_1$, X, $R_2$ and $R_3$ substituents, wherein R' and $R_1$ join to form a ring, and each line of the table is matched with Formula IIIa or VIIIa to represent a specific embodiment of the invention.

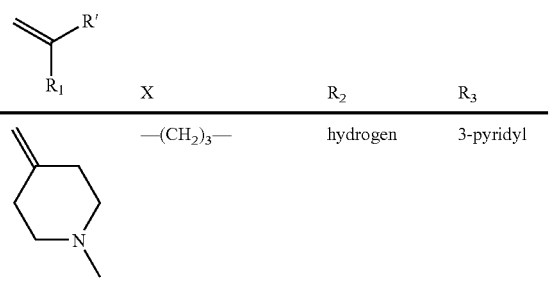

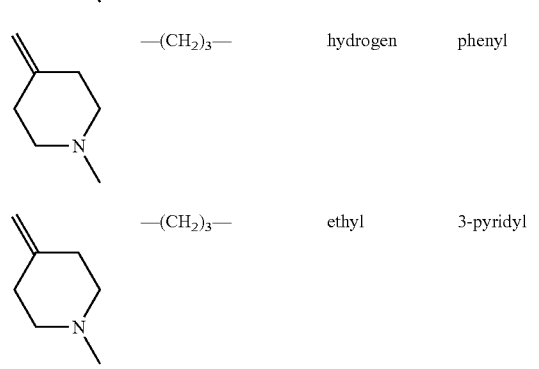

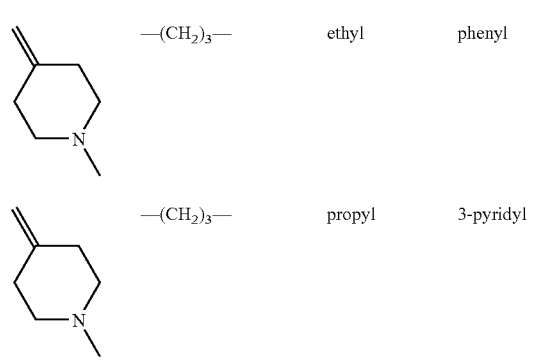

| $R_1$ | X | $R_2$ | $R_3$ |
|---|---|---|---|
| (N-methylpiperidin-4-ylidene) | —(CH$_2$)$_3$— | hydrogen | 3-pyridyl |
| (N-methylpiperidin-4-ylidene) | —(CH$_2$)$_3$— | hydrogen | phenyl |
| (N-methylpiperidin-4-ylidene) | —(CH$_2$)$_3$— | ethyl | 3-pyridyl |
| (N-methylpiperidin-4-ylidene) | —(CH$_2$)$_3$— | ethyl | phenyl |
| (N-methylpiperidin-4-ylidene) | —(CH$_2$)$_3$— | propyl | 3-pyridyl |

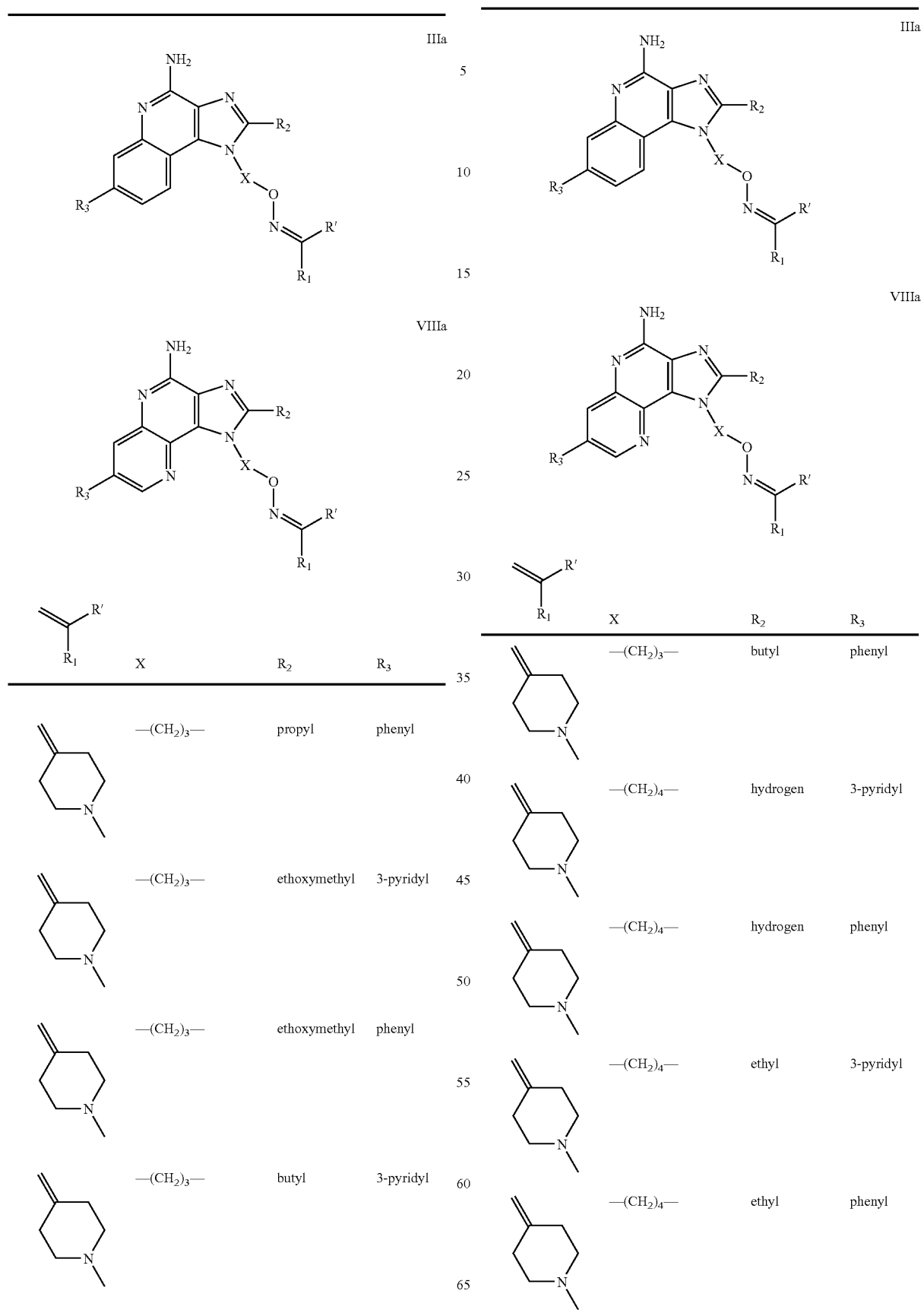

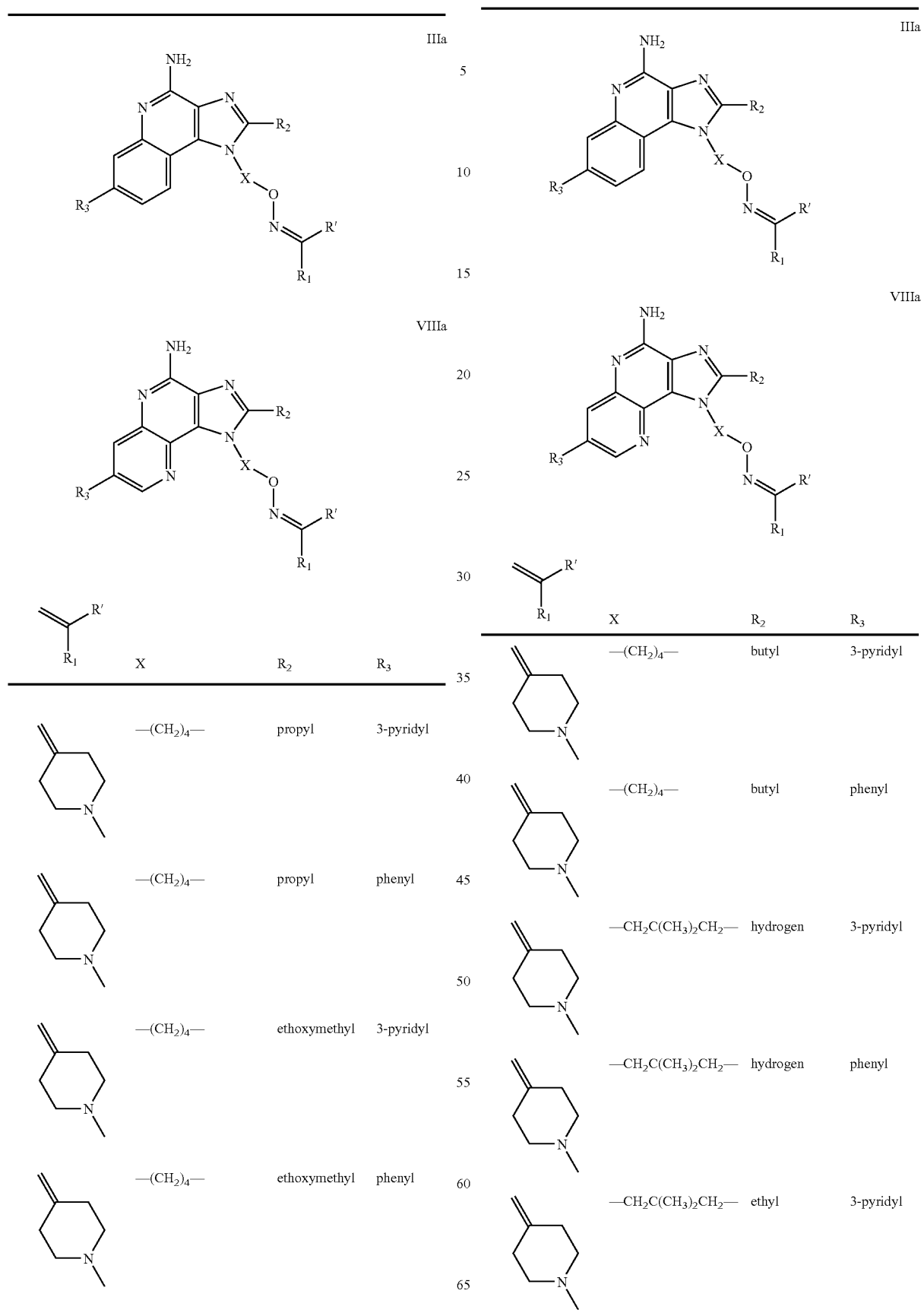

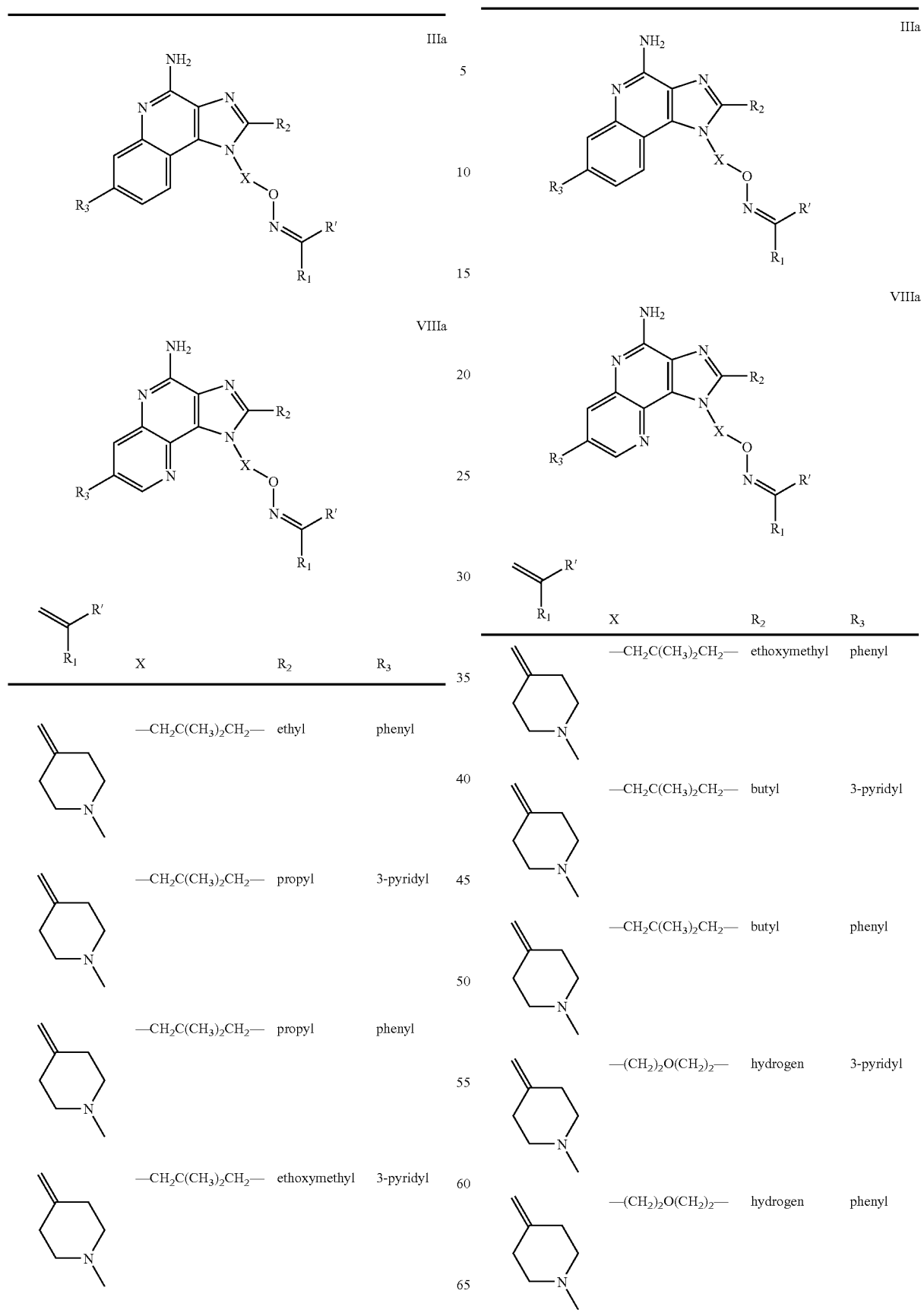

-continued

IIIa (col. 201)

| R₁ (=CR'R₁) | X | R₂ | R₃ |
|---|---|---|---|
| 1-methylpiperidin-4-ylidene | —(CH₂)₂O(CH₂)₂— | ethyl | 3-pyridyl |
| 1-methylpiperidin-4-ylidene | —(CH₂)₂O(CH₂)₂— | ethyl | phenyl |
| 1-methylpiperidin-4-ylidene | —(CH₂)₂O(CH₂)₂— | propyl | 3-pyridyl |
| 1-methylpiperidin-4-ylidene | —(CH₂)₂O(CH₂)₂— | propyl | phenyl |

IIIa (col. 202)

| R₁ (=CR'R₁) | X | R₂ | R₃ |
|---|---|---|---|
| 1-methylpiperidin-4-ylidene | —(CH₂)₂O(CH₂)₂— | ethoxymethyl | 3-pyridyl |
| 1-methylpiperidin-4-ylidene | —(CH₂)₂O(CH₂)₂— | ethoxymethyl | phenyl |
| 1-methylpiperidin-4-ylidene | —(CH₂)₂O(CH₂)₂— | butyl | 3-pyridyl |
| 1-methylpiperidin-4-ylidene | —(CH₂)₂O(CH₂)₂— | butyl | phenyl |

VIIIa structures shown for both columns.

| | 203 -continued | | | | 204 -continued | | |
|---|---|---|---|---|---|---|---|
| | 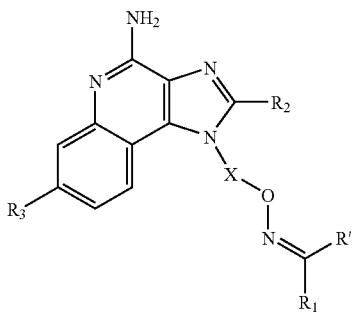 IIIa | | | | 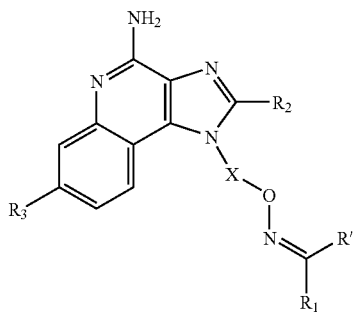 IIIa | | |
| | 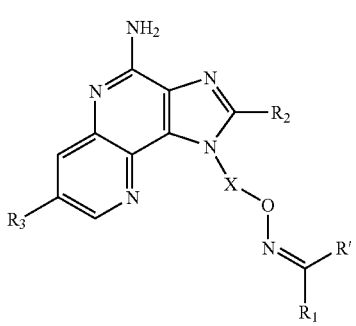 VIIIa | | | | 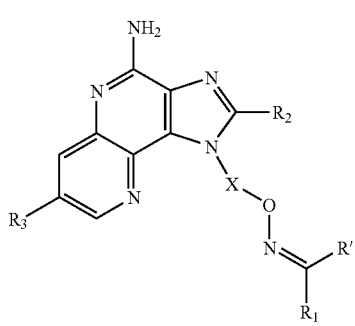 VIIIa | | |
|  | X | R₂ | R₃ | | 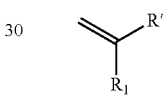 X | R₂ | R₃ |
| 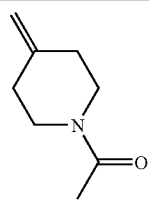 | —(CH₂)₃— | hydrogen | 3-pyridyl | | —(CH₂)₃— | propyl | 3-pyridyl |
| 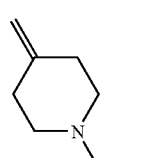 | —(CH₂)₃— | hydrogen | phenyl | | —(CH₂)₃— | propyl | phenyl |
| 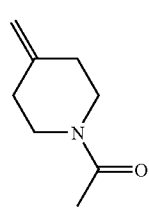 | —(CH₂)₃— | ethyl | 3-pyridyl | | —(CH₂)₃— | ethoxymethyl | 3-pyridyl |
| 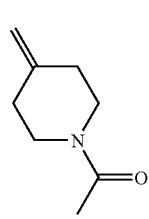 | —(CH₂)₃— | ethyl | phenyl | | —(CH₂)₃— | ethoxymethyl | phenyl |

| | 205 -continued | | | | 206 -continued | | |
|---|---|---|---|---|---|---|---|
| | IIIa 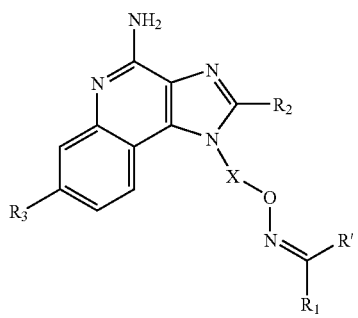 | | | | IIIa 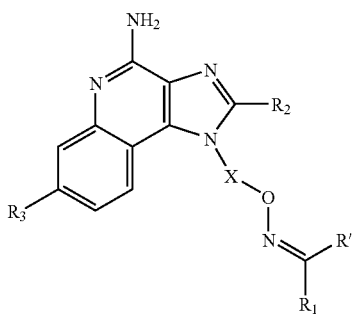 | | |
| | VIIIa 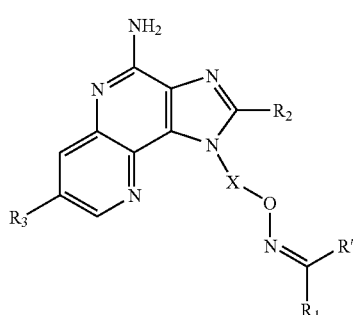 | | | | VIIIa 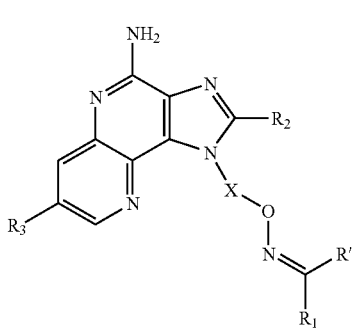 | | |
|  | X | R₂ | R₃ | |  | R₂ | R₃ |
| 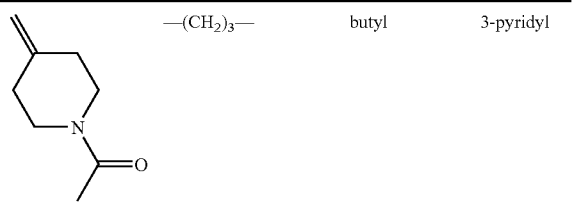 | —(CH₂)₃— | butyl | 3-pyridyl | 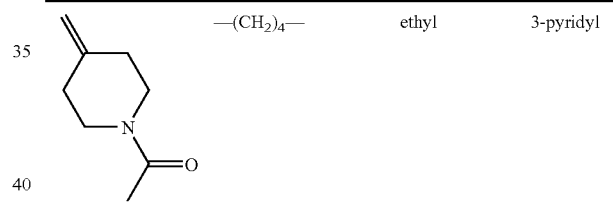 | —(CH₂)₄— | ethyl | 3-pyridyl |
| 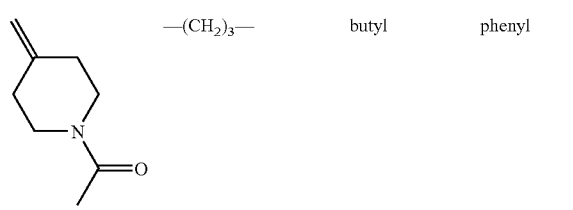 | —(CH₂)₃— | butyl | phenyl | 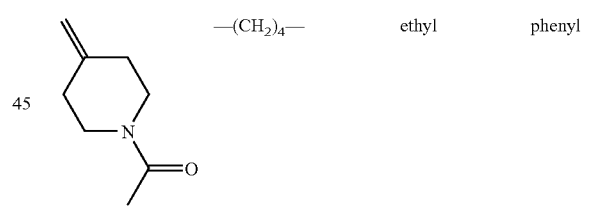 | —(CH₂)₄— | ethyl | phenyl |
| 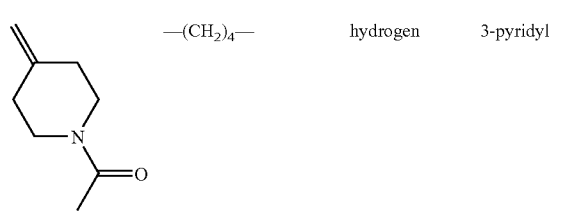 | —(CH₂)₄— | hydrogen | 3-pyridyl | 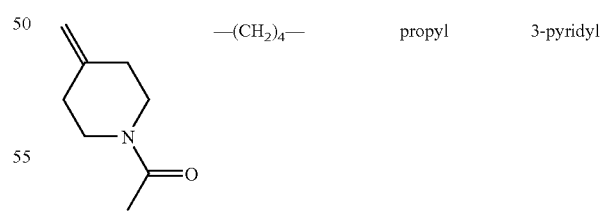 | —(CH₂)₄— | propyl | 3-pyridyl |
| 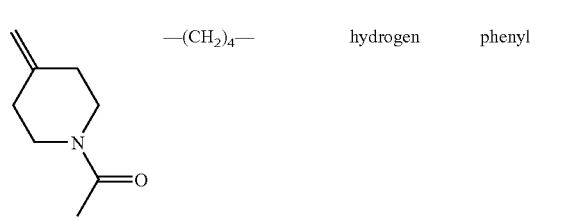 | —(CH₂)₄— | hydrogen | phenyl | 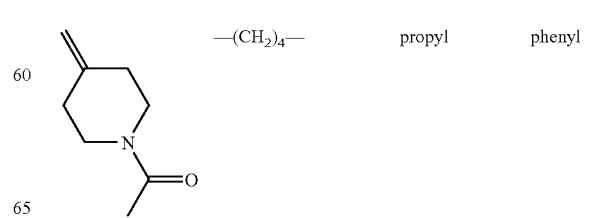 | —(CH₂)₄— | propyl | phenyl |

| | 207-continued | | | | 208-continued | | |
|---|---|---|---|---|---|---|---|
| | 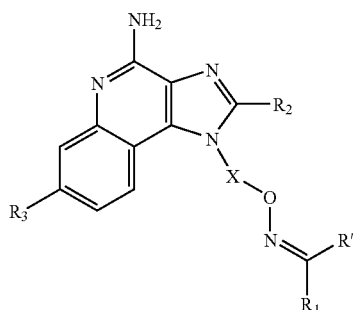 IIIa | | | | 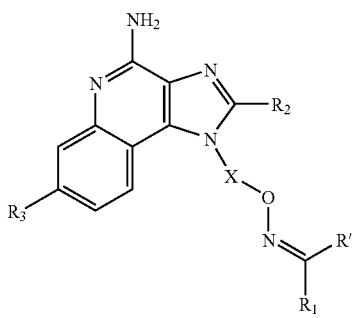 IIIa | | |
| | 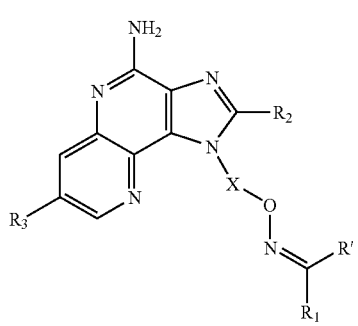 VIIIa | | | | 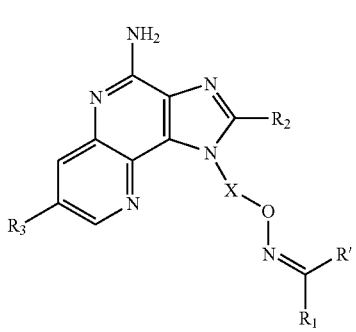 VIIIa | | |
| $\begin{array}{c}R'\\ \diagup\\ R_1\end{array}$ | X | $R_2$ | $R_3$ | | X | $R_2$ | $R_3$ |
|  | —(CH$_2$)$_4$— | ethoxymethyl | 3-pyridyl | | —CH$_2$C(CH$_3$)$_2$CH$_2$— | hydrogen | 3-pyridyl |
| 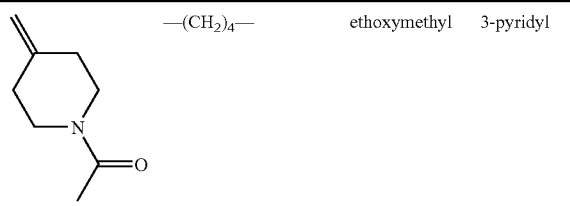 | —(CH$_2$)$_4$— | ethoxymethyl | phenyl | | —CH$_2$C(CH$_3$)$_2$CH$_2$— | hydrogen | phenyl |
| 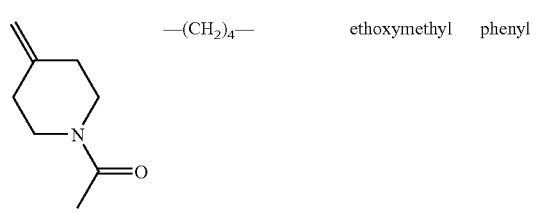 | —(CH$_2$)$_4$— | butyl | 3-pyridyl | | —CH$_2$C(CH$_3$)$_2$CH$_2$— | ethyl | 3-pyridyl |
| 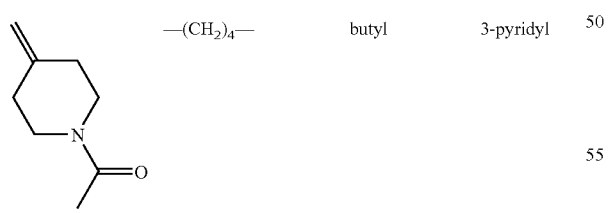 | —(CH$_2$)$_4$— | butyl | phenyl | | —CH$_2$C(CH$_3$)$_2$CH$_2$— | ethyl | phenyl |

| | 209 -continued | | | | 210 -continued | | |
|---|---|---|---|---|---|---|---|
| | 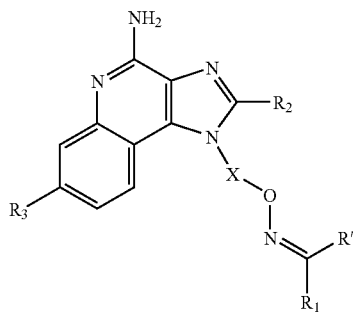 | | IIIa | | 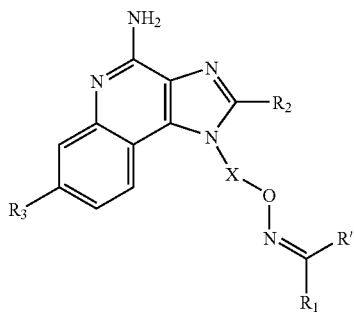 | | IIIa |
| | 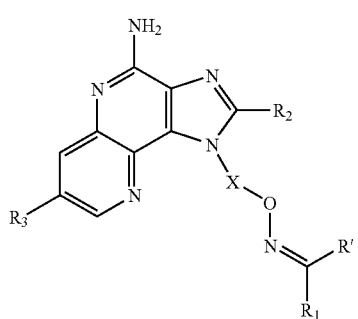 | | VIIIa | | 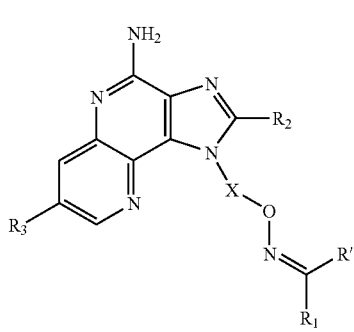 | | VIIIa |
|  | X | R₂ | R₃ |  | X | R₂ | R₃ |
| 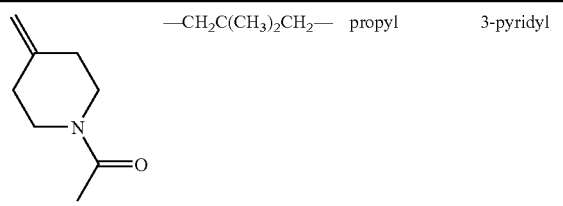 | —CH₂C(CH₃)₂CH₂— | propyl | 3-pyridyl | 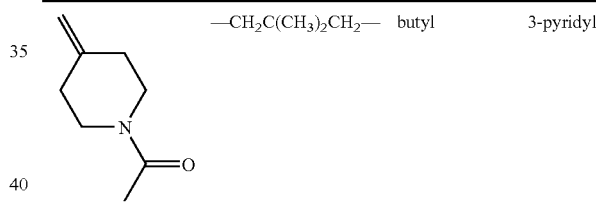 | —CH₂C(CH₃)₂CH₂— | butyl | 3-pyridyl |
| 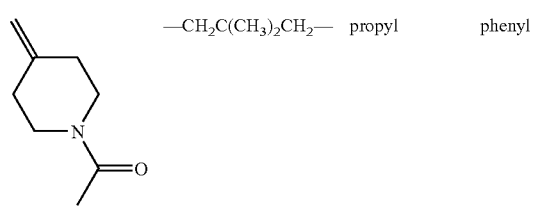 | —CH₂C(CH₃)₂CH₂— | propyl | phenyl | 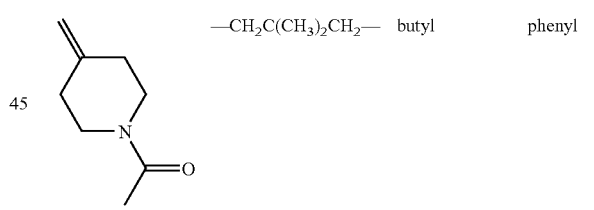 | —CH₂C(CH₃)₂CH₂— | butyl | phenyl |
| 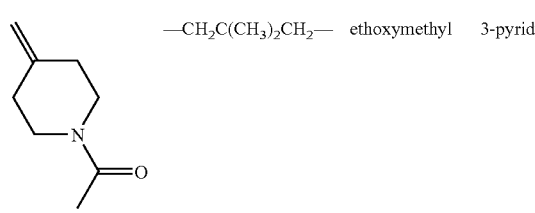 | —CH₂C(CH₃)₂CH₂— | ethoxymethyl | 3-pyridyl | 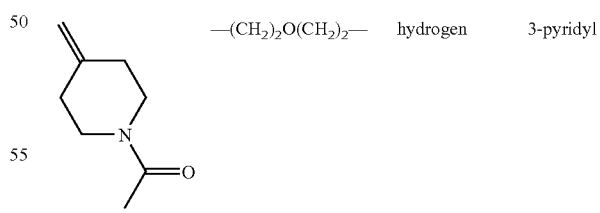 | —(CH₂)₂O(CH₂)₂— | hydrogen | 3-pyridyl |
| 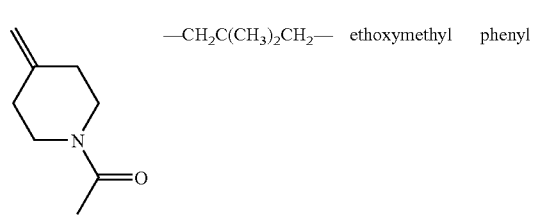 | —CH₂C(CH₃)₂CH₂— | ethoxymethyl | phenyl | 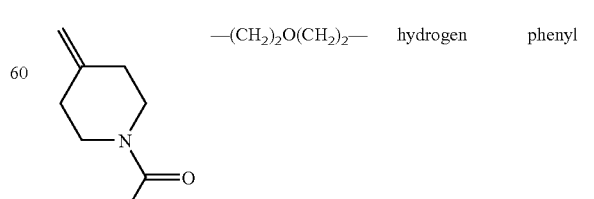 | —(CH₂)₂O(CH₂)₂— | hydrogen | phenyl |

211
-continued

IIIa

VIIIa

| ⟨R'/R₁⟩ | X | R₂ | R₃ |
|---|---|---|---|
| 4-(1-acetylpiperidinyl)methylene | —(CH₂)₂O(CH₂)₂— | ethyl | 3-pyridyl |
| 4-(1-acetylpiperidinyl)methylene | —(CH₂)₂O(CH₂)₂— | ethyl | phenyl |
| 4-(1-acetylpiperidinyl)methylene | —(CH₂)₂O(CH₂)₂— | propyl | 3-pyridyl |
| 4-(1-acetylpiperidinyl)methylene | —(CH₂)₂O(CH₂)₂— | propyl | phenyl |

212
-continued

IIIa

VIIIa

| ⟨R'/R₁⟩ | X | R₂ | R₃ |
|---|---|---|---|
| 4-(1-acetylpiperidinyl)methylene | —(CH₂)₂O(CH₂)₂— | ethoxymethyl | 3-pyridyl |
| 4-(1-acetylpiperidinyl)methylene | —(CH₂)₂O(CH₂)₂— | ethoxymethyl | phenyl |
| 4-(1-acetylpiperidinyl)methylene | —(CH₂)₂O(CH₂)₂— | butyl | 3-pyridyl |
| 4-(1-acetylpiperidinyl)methylene | —(CH₂)₂O(CH₂)₂— | butyl | phenyl |

213
-continued

IIIa

Structure IIIa: 4-amino imidazoquinoline with R3 at position 7, R2 on imidazole, N-X-O-N=C(R1)(R') substituent

VIIIa

Structure VIIIa: 4-amino imidazo-naphthyridine with R3, R2, and N-X-O-N=C(R1)(R') substituent

| R1/R' (=CH-cyclopentyl) | X | R2 | R3 |
|---|---|---|---|
| methylenecyclopentane | —(CH₂)₃— | hydrogen | 3-pyridyl |
| methylenecyclopentane | —(CH₂)₃— | hydrogen | phenyl |
| methylenecyclopentane | —(CH₂)₃— | ethyl | 3-pyridyl |
| methylenecyclopentane | —(CH₂)₃— | ethyl | phenyl |
| methylenecyclopentane | —(CH₂)₃— | propyl | 3-pyridyl |
| methylenecyclopentane | —(CH₂)₃— | propyl | phenyl |
| methylenecyclopentane | —(CH₂)₃— | ethoxymethyl | 3-pyridyl |
| methylenecyclopentane | —(CH₂)₃— | ethoxymethyl | phenyl |
| methylenecyclopentane | —(CH₂)₃— | butyl | 3-pyridyl |

214
-continued

IIIa

Structure IIIa

VIIIa

Structure VIIIa

| R1/R' | X | R2 | R3 |
|---|---|---|---|
| methylenecyclopentane | —(CH₂)₃— | butyl | phenyl |
| methylenecyclopentane | —(CH₂)₄— | hydrogen | 3-pyridyl |
| methylenecyclopentane | —(CH₂)₄— | hydrogen | phenyl |
| methylenecyclopentane | —(CH₂)₄— | ethyl | 3-pyridyl |
| methylenecyclopentane | —(CH₂)₄— | ethyl | phenyl |
| methylenecyclopentane | —(CH₂)₄— | propyl | 3-pyridyl |
| methylenecyclopentane | —(CH₂)₄— | propyl | phenyl |
| methylenecyclopentane | —(CH₂)₄— | ethoxymethyl | 3-pyridyl |
| methylenecyclopentane | —(CH₂)₄— | ethoxymethyl | phenyl |

215
-continued

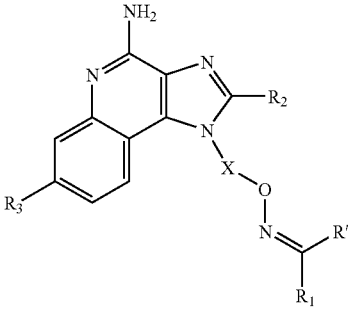
IIIa

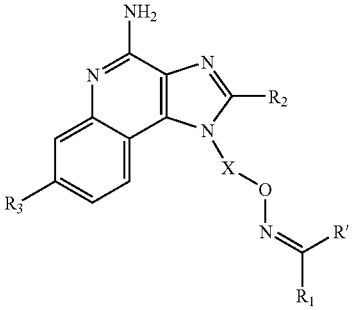
VIIIa

| R'/R₁ | X | R₂ | R₃ |
|---|---|---|---|
| 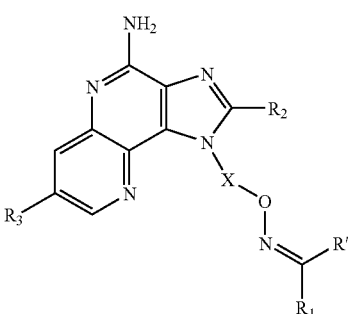 | —(CH₂)₄— | butyl | 3-pyridyl |
|  | —(CH₂)₄— | butyl | phenyl |
| 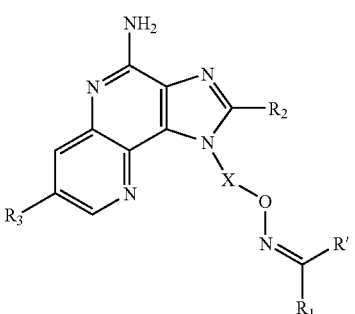 | —CH₂C(CH₃)₂CH₂— | hydrogen | 3-pyridyl |
| 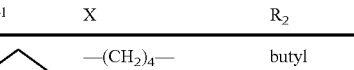 | —CH₂C(CH₃)₂CH₂— | hydrogen | phenyl |
|  | —CH₂C(CH₃)₂CH₂— | ethyl | 3-pyridyl |
|  | —CH₂C(CH₃)₂CH₂— | ethyl | phenyl |
|  | —CH₂C(CH₃)₂CH₂— | propyl | 3-pyridyl |
|  | —CH₂C(CH₃)₂CH₂— | propyl | phenyl |
|  | —CH₂C(CH₃)₂CH₂— | ethoxymethyl | 3-pyridyl |

216
-continued

IIIa

VIIIa

| R'/R₁ | X | R₂ | R₃ |
|---|---|---|---|
|  | —CH₂C(CH₃)₂CH₂— | ethoxymethyl | phenyl |
|  | —CH₂C(CH₃)₂CH₂— | butyl | 3-pyridyl |
|  | —CH₂C(CH₃)₂CH₂— | butyl | phenyl |
|  | —(CH₂)₂O(CH₂)₂— | hydrogen | 3-pyridyl |
|  | —(CH₂)₂O(CH₂)₂— | hydrogen | phenyl |
|  | —(CH₂)₂O(CH₂)₂— | ethyl | 3-pyridyl |
|  | —(CH₂)₂O(CH₂)₂— | ethyl | phenyl |
|  | —(CH₂)₂O(CH₂)₂— | propyl | 3-pyridyl |
|  | —(CH₂)₂O(CH₂)₂— | propyl | phenyl |

217
-continued

IIIa

(Structure IIIa: 4-amino imidazoquinoline with R₃ substituent and N-X-O-N=C(R₁)(R') side chain)

VIIIa

(Structure VIIIa: 4-amino imidazo-naphthyridine with R₃ substituent and N-X-O-N=C(R₁)(R') side chain)

| $\overset{R'}{\underset{R_1}{\diagdown}}$ | X | R₂ | R₃ |
|---|---|---|---|
| methylenecyclopentyl | —(CH₂)₂O(CH₂)₂— | ethoxymethyl | 3-pyridyl |
| methylenecyclopentyl | —(CH₂)₂O(CH₂)₂— | ethoxymethyl | phenyl |
| methylenecyclopentyl | —(CH₂)₂O(CH₂)₂— | butyl | 3-pyridyl |
| methylenecyclopentyl | —(CH₂)₂O(CH₂)₂— | butyl | phenyl |
| methylenecyclohexyl | —(CH₂)₃— | hydrogen | 3-pyridyl |
| methylenecyclohexyl | —(CH₂)₃— | hydrogen | phenyl |
| methylenecyclohexyl | —(CH₂)₃— | ethyl | 3-pyridyl |

218
-continued

IIIa

(Structure IIIa: 4-amino imidazoquinoline with R₃ substituent and N-X-O-N=C(R₁)(R') side chain)

VIIIa

(Structure VIIIa: 4-amino imidazo-naphthyridine with R₃ substituent and N-X-O-N=C(R₁)(R') side chain)

| $\overset{R'}{\underset{R_1}{\diagdown}}$ | X | R₂ | R₃ |
|---|---|---|---|
| methylenecyclohexyl | —(CH₂)₃— | ethyl | phenyl |
| methylenecyclohexyl | —(CH₂)₃— | propyl | 3-pyridyl |
| methylenecyclohexyl | —(CH₂)₃— | propyl | phenyl |
| methylenecyclohexyl | —(CH₂)₃— | ethoxymethyl | 3-pyridyl |
| methylenecyclohexyl | —(CH₂)₃— | ethoxymethyl | phenyl |
| methylenecyclohexyl | —(CH₂)₃— | butyl | 3-pyridyl |

219
-continued

IIIa, VIIIa structures with substituents X, R₂, R₃, R₁, R′

| R₁/R′ | X | R₂ | R₃ |
|---|---|---|---|
| methylenecyclohexane | —(CH₂)₃— | butyl | phenyl |
| methylenecyclohexane | —(CH₂)₄— | hydrogen | 3-pyridyl |
| methylenecyclohexane | —(CH₂)₄— | hydrogen | phenyl |
| methylenecyclohexane | —(CH₂)₄— | ethyl | 3-pyridyl |
| methylenecyclohexane | —(CH₂)₄— | ethyl | phenyl |
| methylenecyclohexane | —(CH₂)₄— | propyl | 3-pyridyl |

220
-continued

IIIa, VIIIa structures with substituents X, R₂, R₃, R₁, R′

| R₁/R′ | X | R₂ | R₃ |
|---|---|---|---|
| methylenecyclohexane | —(CH₂)₄— | propyl | phenyl |
| methylenecyclohexane | —(CH₂)₄— | ethoxymethyl | 3-pyridyl |
| methylenecyclohexane | —(CH₂)₄— | ethoxymethyl | phenyl |
| methylenecyclohexane | —(CH₂)₄— | butyl | 3-pyridyl |
| methylenecyclohexane | —(CH₂)₄— | butyl | phenyl |
| methylenecyclohexane | —CH₂C(CH₃)₂CH₂— | hydrogen | 3-pyridyl |

221
-continued

IIIa

VIIIa

| R'/R₁ (=CH-cyclohexyl) | X | R₂ | R₃ |
|---|---|---|---|
| methylenecyclohexane | —CH₂C(CH₃)₂CH₂— | hydrogen | phenyl |
| methylenecyclohexane | —CH₂C(CH₃)₂CH₂— | ethyl | 3-pyridyl |
| methylenecyclohexane | —CH₂C(CH₃)₂CH₂— | ethyl | phenyl |
| methylenecyclohexane | —CH₂C(CH₃)₂CH₂— | propyl | 3-pyridyl |
| methylenecyclohexane | —CH₂C(CH₃)₂CH₂— | propyl | phenyl |
| methylenecyclohexane | —CH₂C(CH₃)₂CH₂— | ethoxymethyl | 3-pyridyl |

222
-continued

IIIa

VIIIa

| R'/R₁ (=CH-cyclohexyl) | X | R₂ | R₃ |
|---|---|---|---|
| methylenecyclohexane | —CH₂C(CH₃)₂CH₂— | ethoxymethyl | phenyl |
| methylenecyclohexane | —CH₂C(CH₃)₂CH₂— | butyl | 3-pyridyl |
| methylenecyclohexane | —CH₂C(CH₃)₂CH₂— | butyl | phenyl |
| methylenecyclohexane | —(CH₂)₂O(CH₂)₂— | hydrogen | 3-pyridyl |
| methylenecyclohexane | —(CH₂)₂O(CH₂)₂— | hydrogen | phenyl |
| methylenecyclohexane | —(CH₂)₂O(CH₂)₂— | ethyl | 3-pyridyl |

223
-continued

IIIa

[Structure IIIa: 4-amino imidazoquinoline with R2, R3, and N-X-O-N=C(R1)R' substituent]

VIIIa

[Structure VIIIa: 4-amino imidazo-naphthyridine with R2, R3, and N-X-O-N=C(R1)R' substituent]

| $\underset{R_1}{\overset{R'}{\diagup}}$ | X | R₂ | R₃ |
|---|---|---|---|
| cyclohexylidene | —(CH₂)₂O(CH₂)₂— | ethyl | phenyl |
| cyclohexylidene | —(CH₂)₂O(CH₂)₂— | propyl | 3-pyridyl |
| cyclohexylidene | —(CH₂)₂O(CH₂)₂— | propyl | phenyl |
| cyclohexylidene | —(CH₂)₂O(CH₂)₂— | ethoxymethyl | 3-pyridyl |
| cyclohexylidene | —(CH₂)₂O(CH₂)₂— | ethoxymethyl | phenyl |
| cyclohexylidene | —(CH₂)₂O(CH₂)₂— | butyl | 3-pyridyl |

224
-continued

IIIa

[Structure IIIa]

VIIIa

[Structure VIIIa]

| $\underset{R_1}{\overset{R'}{\diagup}}$ | X | R₂ | R₃ |
|---|---|---|---|
| cyclohexylidene | —(CH₂)₂O(CH₂)₂— | butyl | phenyl |

Certain exemplary compounds, including some of those described above in the Examples, have the following Formulas (Va, VIIa, VIIIb, and VIa) and the following R', R₁, X, and R₂ substituents, wherein each line of the table is matched with Formula Va, VIIa, VIIIb, or VIa to represent a specific embodiment of the invention.

Va

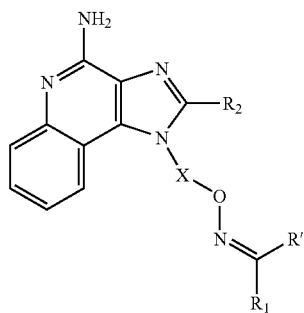

VIIa

225 -continued

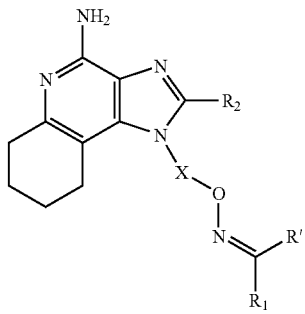 VIIIb

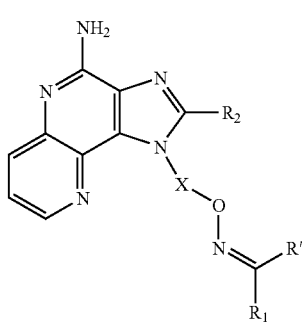 VIa

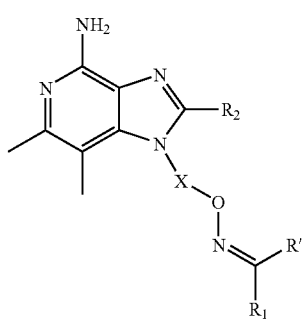

| R₁ | R' | X | R₂ |
|---|---|---|---|
| hydrogen | hydrogen | —(CH₂)₃— | hydrogen |
| hydrogen | hydrogen | —(CH₂)₃— | ethyl |
| hydrogen | hydrogen | —(CH₂)₃— | propyl |
| hydrogen | hydrogen | —(CH₂)₃— | butyl |
| hydrogen | hydrogen | —(CH₂)₃— | ethoxymethyl |
| hydrogen | hydrogen | —(CH₂)₄— | hydrogen |
| hydrogen | hydrogen | —(CH₂)₄— | ethyl |
| hydrogen | hydrogen | —(CH₂)₄— | propyl |
| hydrogen | hydrogen | —(CH₂)₄— | butyl |
| hydrogen | hydrogen | —(CH₂)₄— | ethoxymethyl |
| hydrogen | hydrogen | —CH₂C(CH₃)₂CH₂— | hydrogen |
| hydrogen | hydrogen | —CH₂C(CH₃)₂CH₂— | ethyl |
| hydrogen | hydrogen | —CH₂C(CH₃)₂CH₂— | propyl |
| hydrogen | hydrogen | —CH₂C(CH₃)₂CH₂— | butyl |
| hydrogen | hydrogen | —CH₂C(CH₃)₂CH₂— | ethoxymethyl |
| hydrogen | hydrogen | —(CH₂)₂O(CH₂)₂— | hydrogen |
| hydrogen | hydrogen | —(CH₂)₂O(CH₂)₂— | ethyl |
| hydrogen | hydrogen | —(CH₂)₂O(CH₂)₂— | propyl |
| hydrogen | hydrogen | —(CH₂)₂O(CH₂)₂— | butyl |
| hydrogen | hydrogen | —(CH₂)₂O(CH₂)₂— | ethoxymethyl |
| hydrogen | methyl | —(CH₂)₃— | hydrogen |
| hydrogen | methyl | —(CH₂)₃— | ethyl |
| hydrogen | methyl | —(CH₂)₃— | propyl |
| hydrogen | methyl | —(CH₂)₃— | butyl |
| hydrogen | methyl | —(CH₂)₃— | ethoxymethyl |
| hydrogen | methyl | —(CH₂)₄— | hydrogen |
| hydrogen | methyl | —(CH₂)₄— | ethyl |
| hydrogen | methyl | —(CH₂)₄— | propyl |
| hydrogen | methyl | —(CH₂)₄— | butyl |

226 -continued

| R₁ | R' | X | R₂ |
|---|---|---|---|
| hydrogen | methyl | —(CH₂)₄— | ethoxymethyl |
| hydrogen | methyl | —CH₂C(CH₃)₂CH₂— | hydrogen |
| hydrogen | methyl | —CH₂C(CH₃)₂CH₂— | ethyl |
| hydrogen | methyl | —CH₂C(CH₃)₂CH₂— | propyl |
| hydrogen | methyl | —CH₂C(CH₃)₂CH₂— | butyl |
| hydrogen | methyl | —CH₂C(CH₃)₂CH₂— | ethoxymethyl |
| hydrogen | methyl | —(CH₂)₂O(CH₂)₂— | hydrogen |
| hydrogen | methyl | —(CH₂)₂O(CH₂)₂— | ethyl |
| hydrogen | methyl | —(CH₂)₂O(CH₂)₂— | propyl |
| hydrogen | methyl | —(CH₂)₂O(CH₂)₂— | butyl |
| hydrogen | methyl | —(CH₂)₂O(CH₂)₂— | ethoxymethyl |
| hydrogen | 3-pyridyl | —(CH₂)₃— | hydrogen |
| hydrogen | 3-pyridyl | —(CH₂)₃— | ethyl |
| hydrogen | 3-pyridyl | —(CH₂)₃— | propyl |
| hydrogen | 3-pyridyl | —(CH₂)₃— | butyl |
| hydrogen | 3-pyridyl | —(CH₂)₃— | ethoxymethyl |
| hydrogen | 3-pyridyl | —(CH₂)₄— | hydrogen |
| hydrogen | 3-pyridyl | —(CH₂)₄— | ethyl |
| hydrogen | 3-pyridyl | —(CH₂)₄— | propyl |
| hydrogen | 3-pyridyl | —(CH₂)₄— | butyl |
| hydrogen | 3-pyridyl | —(CH₂)₄— | ethoxymethyl |
| hydrogen | 3-pyridyl | —CH₂C(CH₃)₂CH₂— | hydrogen |
| hydrogen | 3-pyridyl | —CH₂C(CH₃)₂CH₂— | ethyl |
| hydrogen | 3-pyridyl | —CH₂C(CH₃)₂CH₂— | propyl |
| hydrogen | 3-pyridyl | —CH₂C(CH₃)₂CH₂— | butyl |
| hydrogen | 3-pyridyl | —CH₂C(CH₃)₂CH₂— | ethoxymethyl |
| hydrogen | 3-pyridyl | —(CH₂)₂O(CH₂)₂— | hydrogen |
| hydrogen | 3-pyridyl | —(CH₂)₂O(CH₂)₂— | ethyl |
| hydrogen | 3-pyridyl | —(CH₂)₂O(CH₂)₂— | propyl |
| hydrogen | 3-pyridyl | —(CH₂)₂O(CH₂)₂— | butyl |
| hydrogen | 3-pyridyl | —(CH₂)₂O(CH₂)₂— | ethoxymethyl |
| methyl | methyl | —(CH₂)₃— | hydrogen |
| methyl | methyl | —(CH₂)₃— | ethyl |
| methyl | methyl | —(CH₂)₃— | propyl |
| methyl | methyl | —(CH₂)₃— | butyl |
| methyl | methyl | —(CH₂)₃— | ethoxymethyl |
| methyl | methyl | —(CH₂)₄— | hydrogen |
| methyl | methyl | —(CH₂)₄— | ethyl |
| methyl | methyl | —(CH₂)₄— | propyl |
| methyl | methyl | —(CH₂)₄— | butyl |
| methyl | methyl | —(CH₂)₄— | ethoxymethyl |
| methyl | methyl | —CH₂C(CH₃)₂CH₂— | hydrogen |
| methyl | methyl | —CH₂C(CH₃)₂CH₂— | ethyl |
| methyl | methyl | —CH₂C(CH₃)₂CH₂— | propyl |
| methyl | methyl | —CH₂C(CH₃)₂CH₂— | butyl |
| methyl | methyl | —CH₂C(CH₃)₂CH₂— | ethoxymethyl |
| methyl | methyl | —(CH₂)₂O(CH₂)₂— | hydrogen |
| methyl | methyl | —(CH₂)₂O(CH₂)₂— | ethyl |
| methyl | methyl | —(CH₂)₂O(CH₂)₂— | propyl |
| methyl | methyl | —(CH₂)₂O(CH₂)₂— | butyl |
| methyl | methyl | —(CH₂)₂O(CH₂)₂— | ethoxymethyl |
| methyl | 3-pyridyl | —(CH₂)₃— | hydrogen |
| methyl | 3-pyridyl | —(CH₂)₃— | ethyl |
| methyl | 3-pyridyl | —(CH₂)₃— | propyl |
| methyl | 3-pyridyl | —(CH₂)₃— | butyl |
| methyl | 3-pyridyl | —(CH₂)₃— | ethoxymethyl |
| methyl | 3-pyridyl | —(CH₂)₄— | hydrogen |
| methyl | 3-pyridyl | —(CH₂)₄— | ethyl |
| methyl | 3-pyridyl | —(CH₂)₄— | propyl |
| methyl | 3-pyridyl | —(CH₂)₄— | butyl |
| methyl | 3-pyridyl | —(CH₂)₄— | ethoxymethyl |
| methyl | 3-pyridyl | —CH₂C(CH₃)₂CH₂— | hydrogen |
| methyl | 3-pyridyl | —CH₂C(CH₃)₂CH₂— | ethyl |
| methyl | 3-pyridyl | —CH₂C(CH₃)₂CH₂— | propyl |
| methyl | 3-pyridyl | —CH₂C(CH₃)₂CH₂— | butyl |
| methyl | 3-pyridyl | —CH₂C(CH₃)₂CH₂— | ethoxymethyl |
| methyl | 3-pyridyl | —(CH₂)₂O(CH₂)₂— | hydrogen |
| methyl | 3-pyridyl | —(CH₂)₂O(CH₂)₂— | ethyl |
| methyl | 3-pyridyl | —(CH₂)₂O(CH₂)₂— | propyl |
| methyl | 3-pyridyl | —(CH₂)₂O(CH₂)₂— | butyl |
| methyl | 3-pyridyl | —(CH₂)₂O(CH₂)₂— | ethoxymethyl |
| 3-pyridyl | methyl | —(CH₂)₃— | hydrogen |
| 3-pyridyl | methyl | —(CH₂)₃— | ethyl |
| 3-pyridyl | methyl | —(CH₂)₃— | propyl |
| 3-pyridyl | methyl | —(CH₂)₃— | butyl |
| 3-pyridyl | methyl | —(CH₂)₃— | ethoxymethyl |
| 3-pyridyl | methyl | —(CH₂)₄— | hydrogen |
| 3-pyridyl | methyl | —(CH₂)₄— | ethyl |
| 3-pyridyl | methyl | —(CH₂)₄— | propyl |
| 3-pyridyl | methyl | —(CH₂)₄— | butyl |

| | | | |
|---|---|---|---|
| 3-pyridyl | methyl | —(CH₂)₄— | ethoxymethyl |
| 3-pyridyl | methyl | —CH₂C(CH₃)₂CH₂— | hydrogen |
| 3-pyridyl | methyl | —CH₂C(CH₃)₂CH₂— | ethyl |
| 3-pyridyl | methyl | —CH₂C(CH₃)₂CH₂— | propyl |
| 3-pyridyl | methyl | —CH₂C(CH₃)₂CH₂— | butyl |
| 3-pyridyl | methyl | —CH₂C(CH₃)₂CH₂— | ethoxymethyl |
| 3-pyridyl | methyl | —(CH₂)₂O(CH₂)₂— | hydrogen |
| 3-pyridyl | methyl | —(CH₂)₂O(CH₂)₂— | ethyl |
| 3-pyridyl | methyl | —(CH₂)₂O(CH₂)₂— | propyl |
| 3-pyridyl | methyl | —(CH₂)₂O(CH₂)₂— | butyl |
| 3-pyridyl | methyl | —(CH₂)₂O(CH₂)₂— | ethoxymethyl |
| 3-pyridyl | hydrogen | —(CH₂)₃— | hydrogen |
| 3-pyridyl | hydrogen | —(CH₂)₃— | ethyl |
| 3-pyridyl | hydrogen | —(CH₂)₃— | propyl |
| 3-pyridyl | hydrogen | —(CH₂)₃— | butyl |
| 3-pyridyl | hydrogen | —(CH₂)₃— | ethoxymethyl |
| 3-pyridyl | hydrogen | —(CH₂)₄— | hydrogen |
| 3-pyridyl | hydrogen | —(CH₂)₄— | ethyl |
| 3-pyridyl | hydrogen | —(CH₂)₄— | propyl |
| 3-pyridyl | hydrogen | —(CH₂)₄— | butyl |
| 3-pyridyl | hydrogen | —(CH₂)₄— | ethoxymethyl |
| 3-pyridyl | hydrogen | —CH₂C(CH₃)₂CH₂— | hydrogen |
| 3-pyridyl | hydrogen | —CH₂C(CH₃)₂CH₂— | ethyl |
| 3-pyridyl | hydrogen | —CH₂C(CH₃)₂CH₂— | propyl |
| 3-pyridyl | hydrogen | —CH₂C(CH₃)₂CH₂— | butyl |
| 3-pyridyl | hydrogen | —CH₂C(CH₃)₂CH₂— | ethoxymethyl |
| 3-pyridyl | hydrogen | —(CH₂)₂O(CH₂)₂— | hydrogen |
| 3-pyridyl | hydrogen | —(CH₂)₂O(CH₂)₂— | ethyl |
| 3-pyridyl | hydrogen | —(CH₂)₂O(CH₂)₂— | propyl |
| 3-pyridyl | hydrogen | —(CH₂)₂O(CH₂)₂— | butyl |
| 3-pyridyl | hydrogen | —(CH₂)₂O(CH₂)₂— | ethoxymethyl |
| methyl | hydrogen | —(CH₂)₃— | hydrogen |
| methyl | hydrogen | —(CH₂)₃— | ethyl |
| methyl | hydrogen | —(CH₂)₃— | propyl |
| methyl | hydrogen | —(CH₂)₃— | butyl |
| methyl | hydrogen | —(CH₂)₃— | ethoxymethyl |
| methyl | hydrogen | —(CH₂)₄— | hydrogen |
| methyl | hydrogen | —(CH₂)₄— | ethyl |
| methyl | hydrogen | —(CH₂)₄— | propyl |
| methyl | hydrogen | —(CH₂)₄— | butyl |
| methyl | hydrogen | —(CH₂)₄— | ethoxymethyl |
| methyl | hydrogen | —CH₂C(CH₃)₂CH₂— | hydrogen |
| methyl | hydrogen | —CH₂C(CH₃)₂CH₂— | ethyl |
| methyl | hydrogen | —CH₂C(CH₃)₂CH₂— | propyl |
| methyl | hydrogen | —CH₂C(CH₃)₂CH₂— | butyl |
| methyl | hydrogen | —CH₂C(CH₃)₂CH₂— | ethoxymethyl |
| methyl | hydrogen | —(CH₂)₂O(CH₂)₂— | hydrogen |
| methyl | hydrogen | —(CH₂)₂O(CH₂)₂— | ethyl |
| methyl | hydrogen | —(CH₂)₂O(CH₂)₂— | propyl |
| methyl | hydrogen | —(CH₂)₂O(CH₂)₂— | butyl |
| methyl | hydrogen | —(CH₂)₂O(CH₂)₂— | ethoxymethyl |

Certain exemplary compounds, including some of those described above in the Examples, have the following Formulas (Va, VIIa, VIIIb, and VIa) and the following R', R₁, X, and R₂ substituents, wherein R' and R₁ join to form a ring, and each line of the table is matched with Formula Va, VIIa, VIIIb, or VIa to represent a specific embodiment of the invention.

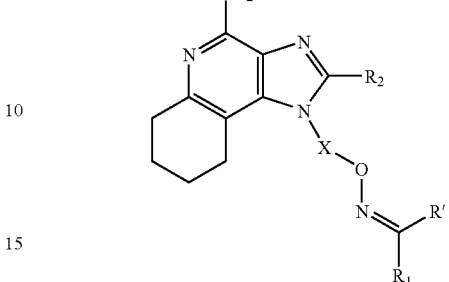

VIIa

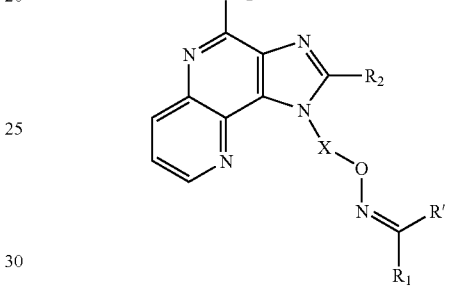

VIIIb

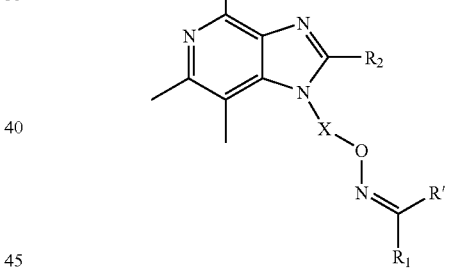

VIa

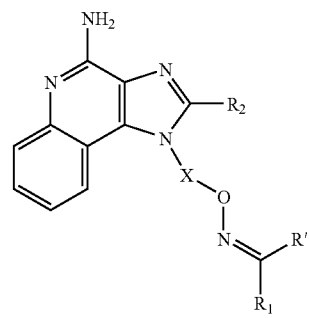

Va

| R' R₁ | X | R₂ |
|---|---|---|
| 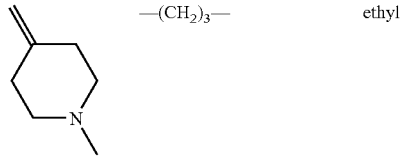 | —(CH₂)₃— | hydrogen |
| 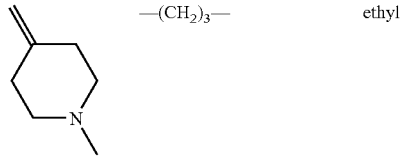 | —(CH₂)₃— | ethyl |

| 229 -continued | | |
|---|---|---|
| 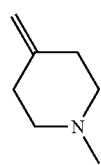 | —(CH$_2$)$_3$— | propyl |
| 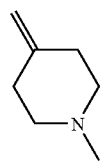 | —(CH$_2$)$_3$— | butyl |
| 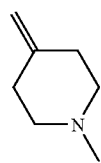 | —(CH$_2$)$_3$— | ethoxymethyl |
| 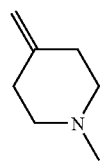 | —(CH$_2$)$_4$— | hydrogen |
| 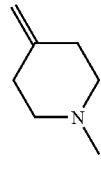 | —(CH$_2$)$_4$— | ethyl |
| 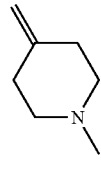 | —(CH$_2$)$_4$— | propyl |
| 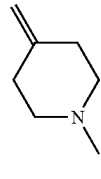 | —(CH$_2$)$_4$— | butyl |
| 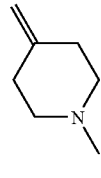 | —(CH$_2$)$_4$— | ethoxymethyl |
| 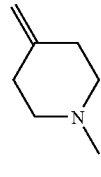 | —CH$_2$C(CH$_3$)$_2$CH$_2$— | hydrogen |

| 230 -continued | | |
|---|---|---|
| 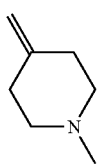 | —CH$_2$C(CH$_3$)$_2$CH$_2$— | ethyl |
| 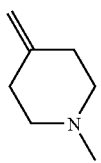 | —CH$_2$C(CH$_3$)$_2$CH$_2$— | propyl |
| 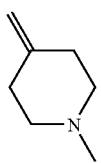 | —CH$_2$C(CH$_3$)$_2$CH$_2$— | butyl |
| 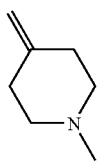 | —CH$_2$C(CH$_3$)$_2$CH$_2$— | ethoxymethyl |
| 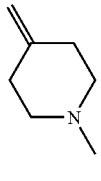 | —(CH$_2$)$_2$O(CH$_2$)$_2$— | hydrogen |
| 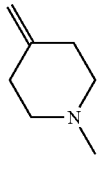 | —(CH$_2$)$_2$O(CH$_2$)$_2$— | ethyl |
| 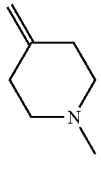 | —(CH$_2$)$_2$O(CH$_2$)$_2$— | propyl |
| 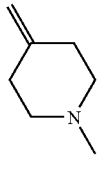 | —(CH$_2$)$_2$O(CH$_2$)$_2$— | butyl |
| 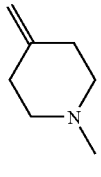 | —(CH$_2$)$_2$O(CH$_2$)$_2$— | ethoxymethyl |

| | | |
|---|---|---|
| 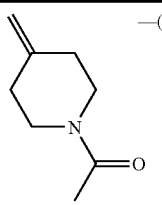 | —(CH₂)₃— | hydrogen |
| 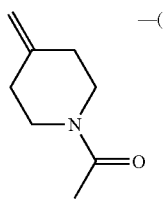 | —(CH₂)₃— | ethyl |
| 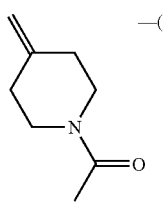 | —(CH₂)₃— | propyl |
| 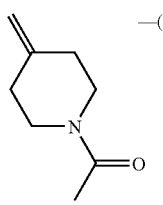 | —(CH₂)₃— | butyl |
| 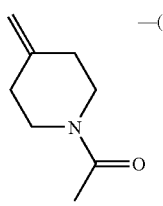 | —(CH₂)₃— | ethoxymethyl |
| 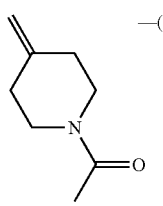 | —(CH₂)₄— | hydrogen |
| 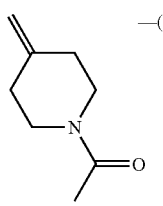 | —(CH₂)₄— | ethyl |
| 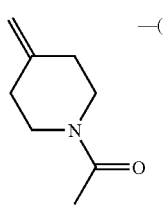 | —(CH₂)₄— | propyl |
| | | |
|---|---|---|
| 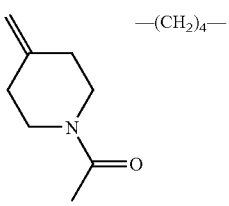 | —(CH₂)₄— | butyl |
| 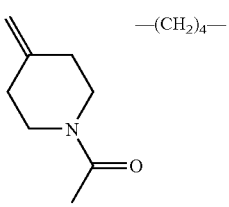 | —(CH₂)₄— | ethoxymethyl |
| 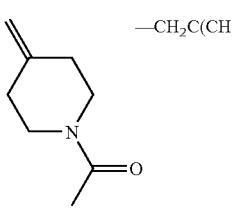 | —CH₂C(CH₃)₂CH₂— | hydrogen |
| 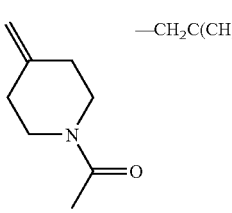 | —CH₂C(CH₃)₂CH₂— | ethyl |
| 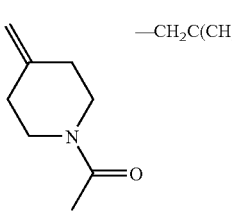 | —CH₂C(CH₃)₂CH₂— | propyl |
| 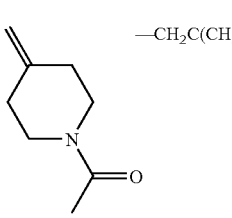 | —CH₂C(CH₃)₂CH₂— | butyl |
| 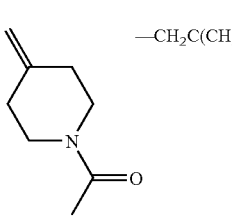 | —CH₂C(CH₃)₂CH₂— | ethoxymethyl |

| 233 -continued | | |
|---|---|---|
| 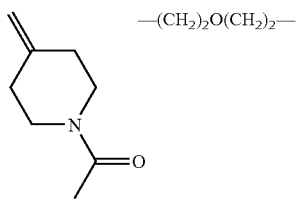 | —(CH$_2$)$_2$O(CH$_2$)$_2$— | hydrogen |
| 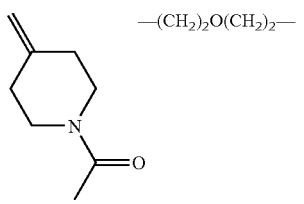 | —(CH$_2$)$_2$O(CH$_2$)$_2$— | ethyl |
| 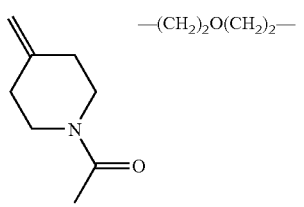 | —(CH$_2$)$_2$O(CH$_2$)$_2$— | propyl |
| 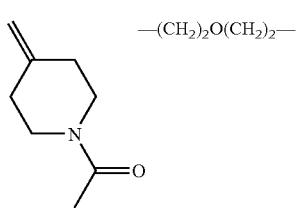 | —(CH$_2$)$_2$O(CH$_2$)$_2$— | butyl |
| 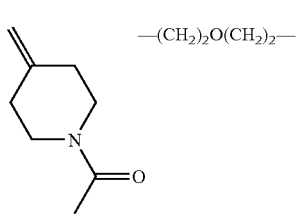 | —(CH$_2$)$_2$O(CH$_2$)$_2$— | ethoxymethyl |
| 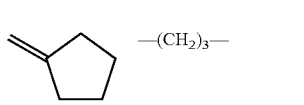 | —(CH$_2$)$_3$— | hydrogen |
| 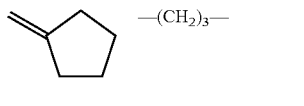 | —(CH$_2$)$_3$— | ethyl |
| 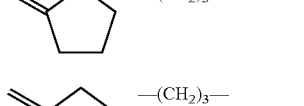 | —(CH$_2$)$_3$— | propyl |
| 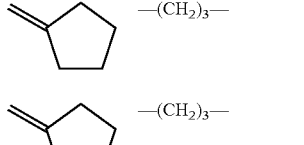 | —(CH$_2$)$_3$— | butyl |
| 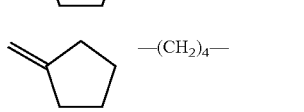 | —(CH$_2$)$_3$— | ethoxymethyl |
|  | —(CH$_2$)$_4$— | hydrogen |

| 234 -continued | | |
|---|---|---|
| 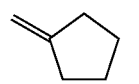 | —(CH$_2$)$_4$— | ethyl |
| 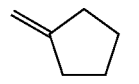 | —(CH$_2$)$_4$— | propyl |
| 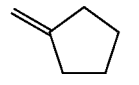 | —(CH$_2$)$_4$— | butyl |
| 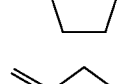 | —(CH$_2$)$_4$— | ethoxymethyl |
| 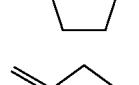 | —CH$_2$C(CH$_3$)$_2$CH$_2$— | hydrogen |
| 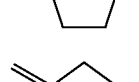 | —CH$_2$C(CH$_3$)$_2$CH$_2$— | ethyl |
| 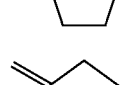 | —CH$_2$C(CH$_3$)$_2$CH$_2$— | propyl |
| 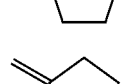 | —CH$_2$C(CH$_3$)$_2$CH$_2$— | butyl |
| 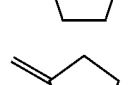 | —CH$_2$C(CH$_3$)$_2$CH$_2$— | ethoxymethyl |
| 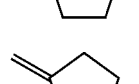 | —(CH$_2$)$_2$O(CH$_2$)$_2$— | hydrogen |
| 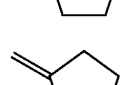 | —(CH$_2$)$_2$O(CH$_2$)$_2$— | ethyl |
| 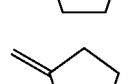 | —(CH$_2$)$_2$O(CH$_2$)$_2$— | propyl |
| 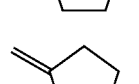 | —(CH$_2$)$_2$O(CH$_2$)$_2$— | butyl |
| 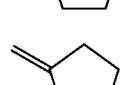 | —(CH$_2$)$_2$O(CH$_2$)$_2$— | ethoxymethyl |
| 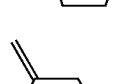 | —(CH$_2$)$_3$— | hydrogen |
| 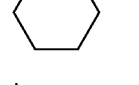 | —(CH$_2$)$_3$— | ethyl |

| | | |
|---|---|---|
| 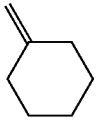 | —(CH$_2$)$_3$— | propyl |
| 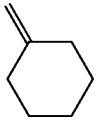 | —(CH$_2$)$_3$— | butyl |
| 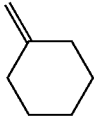 | —(CH$_2$)$_3$— | ethoxymethyl |
| 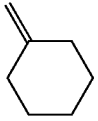 | —(CH$_2$)$_4$— | hydrogen |
| 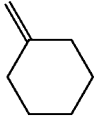 | —(CH$_2$)$_4$— | ethyl |
| 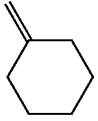 | —(CH$_2$)$_4$— | propyl |
| 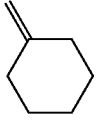 | —(CH$_2$)$_4$— | butyl |
| 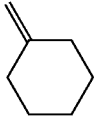 | —(CH$_2$)$_4$— | ethoxymethyl |
| 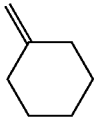 | —CH$_2$C(CH$_3$)$_2$CH$_2$— | hydrogen |
| 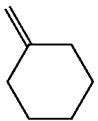 | —CH$_2$C(CH$_3$)$_2$CH$_2$— | ethyl |
| 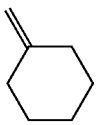 | —CH$_2$C(CH$_3$)$_2$CH$_2$— | propyl |
| 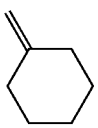 | —CH$_2$C(CH$_3$)$_2$CH$_2$— | butyl |
| 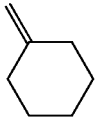 | —CH$_2$C(CH$_3$)$_2$CH$_2$— | ethoxymethyl |
| 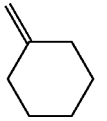 | —(CH$_2$)$_2$O(CH$_2$)$_2$— | hydrogen |
| 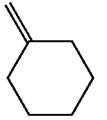 | —(CH$_2$)$_2$O(CH$_2$)$_2$— | ethyl |
| 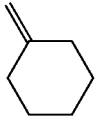 | —(CH$_2$)$_2$O(CH$_2$)$_2$— | propyl |
| 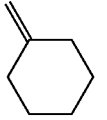 | —(CH$_2$)$_2$O(CH$_2$)$_2$— | butyl |
| 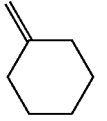 | —(CH$_2$)$_2$O(CH$_2$)$_2$— | ethoxymethyl |

Cytokine Induction in Human Cells

Compounds of the invention have been found to induce cytokine biosynthesis when tested using the method described below.

An in vitro human blood cell system is used to assess cytokine induction. Activity is based on the measurement of interferon ($\alpha$) and tumor necrosis factor ($\alpha$) (IFN and TNF, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at 4×10$^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 micromolar (µM).

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30-0.014 μM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30° C. to −70° C. until analysis. The samples are analyzed for interferon (a) by ELISA and for tumor necrosis factor (a) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series hImunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the formula (II):

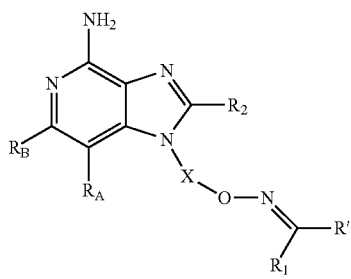

II wherein:
X is —CH($R_{9a}$)-alkylene-, wherein the alkylene is optionally interrupted by one or more —O— groups;
$R_1$ and R' are independently selected from the group consisting of:
hydrogen,
alkyl,
aryl,
arylalkylenyl,
heteroaryl,
heterocyclyl, and
alkyl, aryl, arylalkylenyl, heteroaryl, or heterocyclyl, substituted by one or more substituents selected from the group consisting of:
hydroxyl,
alkyl,
alkoxy,
—S(O)$_{0-2}$-alkyl,
halogen,
nitrile,
aryl,
heteroaryl,
aryloxy,
arylalkyleneoxy,
—C(O)—O-alkyl, and
—N($R_8$)—C(O)-alkyl;
or $R_1$ and R' can join together to form a ring system selected from the group consisting of:

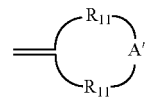

wherein the total number of atoms in the ring is 4 to 9, and

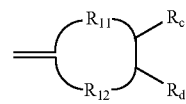

wherein the total number of atoms in the ring is 4 to 9;
$R_A$ and $R_B$ are taken together to form a 6-membered fused aryl ring, wherein the aryl ring is unsubstituted or substituted by one or more R groups, or substituted by one $R_3$ group, or substituted by one $R_3$ group and one R group;
R is halogen;
$R_2$ is selected from the group consisting of:
-hydrogen,
-alkyl, and
-alkoxyalkyl;
$R_3$ is phenyl or pyridinyl;
each $R_4$ is independently selected from the group consisting of hydrogen, alkyl, aryl, and arylalkylenyl, wherein the alkyl, aryl, and arylalkylenyl groups can be unsubstituted or substituted by one or more substituents independently selected from the group consisting of alkyl, alkoxy, haloalkyl, and halogen;
each $R_6$ is independently selected from the group consisting of =O and =S;
each $R_8$ is independently selected from the group consisting of hydrogen and $C_{1-10}$ alkyl;
$R_{9a}$ is selected from the group consisting of hydrogen and alkyl which is optionally interrupted by one or more —O— groups;
$R_c$ and $R_d$ are independently selected from the group consisting of hydrogen, halogen, alkyl, aryl, and haloalkyl;
each $R_{11}$ is independently $C_{1-6}$ alkylene;
$R_{12}$ is selected from the group consisting of a bond and $C_{1-5}$ alkylene;

A' is selected from the group consisting of —O—, —N(-Q-R$_4$)—, and —CH$_2$—; and each Q is independently selected from the group consisting of a bond and —C(R$_6$);

or a pharmaceutically acceptable salt thereof.

2. The compound or salt of claim 1 wherein X is —C$_{3-5}$ alkylene- or —CH$_2$CH$_2$OCH$_2$CH$_2$—.

3. The compound or salt of claim 1 wherein at least one of R' or R$_1$ is hydrogen.

4. The compound or salt of claim 1 wherein at least one of R' or R$_1$ is selected from the group consisting of aryl, heteroaryl, and alkyl, wherein the aryl, heteroaryl, and alkyl are optionally substituted.

5. The compound or salt of claim 1 wherein R' and R$_1$ join together to form a ring system of the formula:

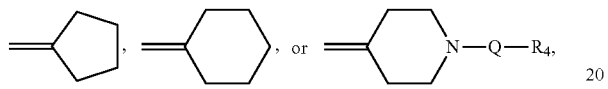

wherein Q is a bond or —C(O)—, and R$_4$ is alkyl.

6. The compound or salt of claim 1 wherein R$_1$ and R' are each methyl.

7. The compound or salt of claim 1 wherein R$_2$ is selected from the group consisting of hydrogen, methyl, ethyl, propyl, butyl, ethoxymethyl, methoxyethyl, and methoxymethyl.

8. The compound or salt of claim 1 wherein R$_A$ and R$_B$ form a fused aryl ring, wherein the aryl ring is unsubstituted.

9. A compound of the formula (III):

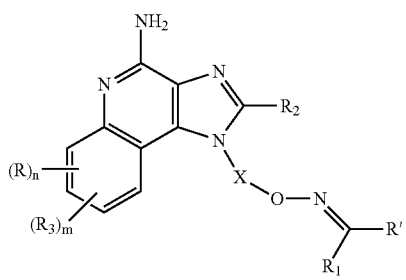

wherein:
X is —CH(R$_{9a}$)-alkylene-, wherein the alkylene is optionally interrupted by one or more —O— groups;
each R is halogen
R$_1$ and R' are independently selected from the group consisting of:
  hydrogen,
  alkyl,
  aryl,
  arylalkylenyl,
  heteroaryl,
  heterocyclyl, and
  alkyl, aryl, arylalkylenyl, heteroaryl, or heterocyclyl, substituted by one or more substituents selected from the group consisting of:
    hydroxyl,
    alkoxy,
    —S(O)$_{0-2}$-alkyl,
    halogen,
    nitrile,
    aryl,
    heteroaryl,
    aryloxy,
    arylalkyleneoxy,
    —C(O)—O-alkyl, and
    —N(R$_8$)—C(O)-alkyl;
or R$_1$ and R' can join together to form a ring system selected from the group consisting of:

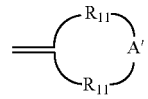

wherein the total number of atoms in the ring is 4 to 9, and

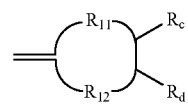

wherein the total number of atoms in the ring is 4 to 9;
R$_2$ is selected from the group consisting of:
  -hydrogen,
  -alkyl, and
  -alkoxyalkyl;
each R$_4$ is independently selected from the group consisting of hydrogen, alkyl, aryl, and arylalkylenyl, wherein the alkyl, aryl, and arylalkylenyl, groups can be unsubstituted or substituted by one or more substituents independently selected from the group consisting of alkyl, alkoxy, haloalkyl, and halogen;
each R$_6$ is independently selected from the group consisting of ═O and ═S;
each R$_8$ is independently selected from the group consisting of hydrogen and C$_{1-10}$ alkyl;
R$_{9a}$ is selected from the group consisting of hydrogen and alkyl which is optionally interrupted by one or more —O— groups;
R$_c$ and R$_d$ are independently selected from the group consisting of hydrogen, halogen, alkyl, aryl, and haloalkyl;
each R$_{11}$ is independently C$_{1-6}$ alkylene;
R$_{12}$ is selected from the group consisting of a bond and C$_{1-5}$ alkylene;
A' is selected from the group consisting of —O—, —N(-Q-R$_4$)—, and —CH$_2$—; and
each Q is independently selected from the group consisting of a bond and —C(R$_6$)—;
n is an integer from 0 to 4;
and m is 0;
or a pharmaceutically acceptable salt thereof.

10. The compound or salt of claim 9 wherein X is —C$_{3-5}$ alkylene- or —CH$_2$CH$_2$OCH$_2$CH$_2$—.

11. The compound or salt of claim 9 wherein at least one of R' or R$_1$ is hydrogen.

12. The compound or salt of claim 9 wherein at least one of R' or R$_1$ is selected from the group consisting of aryl, heteroaryl, and alkyl, wherein the aryl, heteroayl, and alkyl are optionally substituted.

13. The compound or salt of claim 9 wherein R' and $R_1$ join together to form a ring system of the formula:

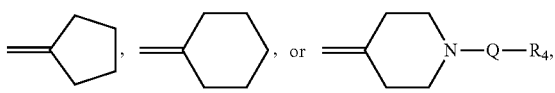

wherein Q is a bond or —C(O)—, and $R_4$ is alkyl.

14. The compound or salt of claim 9 wherein $R_1$ and R' are each methyl.

15. The compound or salt of claim 9 wherein $R_2$ is selected from the group consisting of hydrogen, methyl, ethyl, propyl, butyl, ethoxymethyl, 2-methoxyethyl, and methoxymethyl.

16. The compound of salt of claim 9 wherein m and n are each 0.

17. A compound of the formula (V):

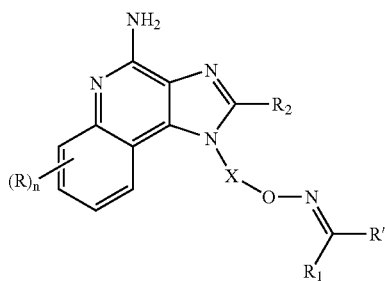

wherein:
X is —CH($R_{9a}$)-alkylene-;
$R_1$ and R' are independently selected from the group consisting of:
hydrogen,
alkyl,
aryl,
alkylene-aryl,
heteroaryl,
heterocyclyl, and
alkyl, aryl, arylalkylenyl, heteroaryl or heterocyclyl substituted by one or more substituents selected from the group consisting of:
hydroxyl,
alkyl,
—O-alkyl,
—S-alkyl,
halogen,
nitrile,
aryl,
heteroaryl,
—O-aryl,
—O-alkylene-aryl,
—C(O)—O-alkyl, and
—N($R_{8a}$)—C(O)-alkyl;
or $R_1$ and R' can join together to form a ring system containing one or two saturated or unsaturated rings optionally including one or more heteroatoms;
n is an integer from 0 to 4;
each R is halogen;
$R_2$ is selected from the group consisting of:
hydrogen,
alkyl, and
alkoxyalkyl;
$R_{9a}$ is selected from the group consisting of hydrogen and alkyl which may be optionally interrupted by one or more —O— groups; and
each $R_{8a}$ is independently selected from the group consisting of hydrogen and $C_{1-10}$ alkyl; or a pharmaceutically acceptable salt thereof.

18. A pharmaceutical composition comprising a therapeutically effective amount of a compound or salt of claim 1 in combination with a pharmaceutically acceptable carrier.

19. A pharmaceutical composition comprising a therapeutically effective amount of a compound or salt of claim 9 in combination with a pharmaceutically acceptable carrier.

* * * * *

UNITED STATES PATENT AND TRADEMARK OFFICE
CERTIFICATE OF CORRECTION

PATENT NO.       : 8,673,932 B2
APPLICATION NO.  : 10/595065
DATED            : March 18, 2014
INVENTOR(S)      : Tushar Kshirsagar Page 1 of 13

It is certified that error appears in the above-identified patent and that said Letters Patent is hereby corrected as shown below:

Title page, References Cited

Page 6, Column 1 (Other Publications)
Line 57, Delete "burgdorferiouter" and insert -- burgdorferi outer --, therefor.
Line 61, Delete "lmmunostimulation," and insert -- Immunostimulation, --, therefor.
Line 68, Delete "Chmica" and insert -- Chimica --, therefor.

Page 7, Column 1 (Other Publications)
Line 22, Delete "et W.," and insert -- et al., --, therefor.
Line 25, Delete "IFN-αProducing" and insert -- IFN-α Producing --, therefor.
Line 41, Delete "Hydocarbons" and insert -- Hydrocarbons --, therefor.
Line 46, Delete "Clinidal" and insert -- Clinical --, therefor.

Page 7, Column 2 (Other Publications)
Line 12, Delete "Napthyridines Hydroxynaphthyridies," and
insert -- Naphthyridines Hydroxynaphthyridines, --, therefor.
Line 28, Delete "Gessellschaft" and insert -- Gesellschaft --, therefor.

Page 8, Column 2 (Other Publications)
Line 19, Delete "Omithine." and insert -- Ornithine. --, therefor.
Line 71, Delete "Dermatologi;" and insert -- Dermatology; --, therefor.

Page 9, Column 1 (Other Publications)
Line 24, Delete "Structure-Activtiy" and insert -- Structure-Activity --, therefor.

Page 9, Column 2 (Other Publications)
Line 11, Delete "Hely" and insert -- Helv --, therefor.
Line 27, Delete "ansidines," and insert -- anisidines, --, therefor.

Signed and Sealed this
Twenty-seventh Day of January, 2015

Michelle K. Lee
*Deputy Director of the United States Patent and Trademark Office*

CERTIFICATE OF CORRECTION (continued)
U.S. Pat. No. 8,673,932 B2

Page 9, Column 2 (Other Publications)
Line 50, Delete "imizazo" and insert -- imidazo --, therefor.

Page 10, Column 1 (Other Publications)
Line 14, Delete "Bacteroids" and insert -- Bacteroides --, therefor.
Line 29, Delete "80/1933." and insert -- 80-1933. --, therefor.
Line 31, Delete "lodoarenes," and insert -- Iodoarenes, --, therefor.

Page 10, Column 2 (Other Publications)
Line 58, Delete "Kerhof," and insert -- Kerkhof, --, therefor.

Page 11, Column 1 (Other Publications)
Line 5, Delete "Imiguimod." and insert -- Imiquimod. --, therefor.

Page 11, Column 2 (Other Publications)
Line 38, Delete "Heterocylic" and insert -- Heterocyclic --, therefor.

In the Specification

Column 1
Line 7, Delete "The is" and insert -- This --, therefor.
Line 23, Delete "lH-imidazo" and insert -- 1H-imidazo --, therefor.

Column 3
Line 16, Delete "mn," and insert -- m, --, therefor.
Line 47, Delete "Examnples" and insert -- Examples --, therefor.

Column 4
Line 25, Delete "finther" and insert -- further --, therefor.

Column 8
Line 38, Delete "alkyiene-" and insert -- alkylene- --, therefor.
Line 38, Delete "allylene" and insert -- alkylene --, therefor.

Column 9
Line 58, Delete "$(O)_{0.2}$—," and insert -- $(O)_{0-2}$—, --, therefor.

Column 10
Line 15, Delete "(diaLlylamino)" and insert -- (dialkylamino) --, therefor.

Column 12
Line 29, Delete "allynylene" and insert -- alkynylene --, therefor.

Column 17
Line 11, Delete "—$(O)_2$—;" and insert -- —$S(O)_2$—; --, therefor.

CERTIFICATE OF CORRECTION (continued)
U.S. Pat. No. 8,673,932 B2

Column 18
Line 12, Delete "alky," and insert -- alkyl, --, therefor.

Column 19
Line 50, Delete "alenylene-," and insert -- alkenylene-, --, therefor.
Line 56, Delete "alkyl" and insert -- alkyl, --, therefor.

Column 21
Line 49, Delete "haloaOlyl," and insert -- haloalkyl, --, therefor.

Column 22
Line 1, Delete "each R" and insert -- each $R_6$ --, therefor.
Line 67, Delete "alkylyl," and insert -- alkyl, --, therefor.

Column 23
Line 15, Delete "heteroarylakylenyl," and insert -- heteroarylalkylenyl, --, therefor.
Line 22, Below "hydroxyl," insert -- alkyl, --.

Column 24
Line 34, Delete "allynyl," and insert -- alkynyl, --, therefor.

Column 25
Line 2, Delete "interruptedby" and insert -- interrupted by --, therefor.
Line 10, Delete "alylene" and insert -- alkylene --, therefor.

Column 27
Line 66, Delete "(dialkylanmino)" and insert -- (dialkylamino) --, therefor.

Column 32
Line 43, Below "consisting of:" insert -- —Z—$R_4$, --.

Column 33
Line 47, Delete "aalkenyl," and insert -- alkenyl, --, therefor.

Column 35
Line 47-48, Delete "heteroarylalkyienyl," and insert -- heteroarylalkylenyl, --, therefor.

Column 36
Line 32, Below "—$R_4$," insert -- —X'—$R_4$, --.

Column 37
Line 13, Delete "aRyl," and insert -- alkyl, --, therefor.

Column 39
Line 15, Delete "subsfituents" and insert -- substituents --, therefor.

Column 42
Line 11, Delete "alllylene;" and insert -- alkylene; --, therefor.
Line 16, Delete "heteroatorns;" and insert -- heteroatoms; --, therefor.
Line 17, Delete "$C_{2-4}$" and insert -- $C_{2-6}$ --, therefor.
Line 36, Delete "—(O)$_2$—;" and insert -- —S(O)$_2$—; --, therefor.

Column 43
Line 49, Delete "—N(R$_{8a}$)$_2$." and insert -- —N(R$_{8a}$)$_2$, --, therefor.

Column 45
Line 57, Delete "—S(O)$_2$—N(R$_6$)—," and insert -- —S(O)$_2$—N(R$_8$)—, --, therefor.

Column 47
Line 6, Delete "the.group" and insert -- the group --, therefor.
Line 41, Delete "—S(O)$_2$—N(R$_6$)—," and insert -- —S(O)$_2$—N(R$_8$)—, --, therefor.

Column 48
Line 7, Delete "of." and insert -- of: --, therefor.

Column 50
Line 51, Delete "slill" and insert -- skill --, therefor.

Column 51
Line 1, Delete "arylallylenyl," and insert -- arylalkylenyl, --, therefor.
Line 14, Delete "not imiting" and insert -- not limiting --, therefor.
Line 22, Delete "heteratoms" and insert -- heteroatoms --, therefor.

Column 52
Line 60, Delete "—Z—X—R$_4$," and insert -- —Z—X'—R$_4$, --, therefor.
Line 62, Delete "pyridin4-yl," and insert -- pyridin-4-yl, --, therefor.
Line 63, Delete "(morpholine4" and insert -- (morpholine-4 --, therefor.

Column 53
Line 30, Delete "each R" and insert -- each R$_6$ --, therefor.

Column 55
Line 64, Delete "norbomenyl." and insert -- norbornenyl. --, therefor.

Column 56
Line 48, Delete "flilrher" and insert -- further --, therefor.

Column 57
Line 3, Delete "dioxane4,6" and insert -- dioxane-4,6 --, therefor.
Line 3, Delete "(Meldrun's" and insert -- (Meldrum's --, therefor.
Line 6, Delete "amunopyridine" and insert -- aminopyridine --, therefor.

CERTIFICATE OF CORRECTION (continued)

Column 57
Line 6, Delete "rnixture" and insert -- mixture --, therefor.
Line 18, Delete "DOWTBERM A" and insert -- DOWTHERM A --, therefor.
Line 32, Delete "XXV." and insert -- XXIV. --, therefor.
Line 34, Delete "NN-" and insert -- N,N- --, therefor.
Line 41, Delete "arnine" and insert -- amine --, therefor.

Column 59
Line 22, Delete "XXVM" and insert -- XXVIII --, therefor.
Line 24, Delete "irnidazo" and insert -- imidazo --, therefor.
Line 36, Delete "naphthyridinamine" and insert -- naphthyridin-4-amine --, therefor.
Line 43, Delete "orp-toluenesulfonyl" and insert -- or p-toluenesulfonyl --, therefor.
Line 49, Delete "XXX" and insert -- XXIX --, therefor.
Line 54-55, Delete "naphthyridin4-amine" and insert -- naphthyridin-4-amine --, therefor.

Column 60
Line 37, Delete "XXIII," and insert -- XXXIII, --, therefor.
Line 57, Delete "furter" and insert -- further --, therefor.

Column 61-62
Line 10,

After " 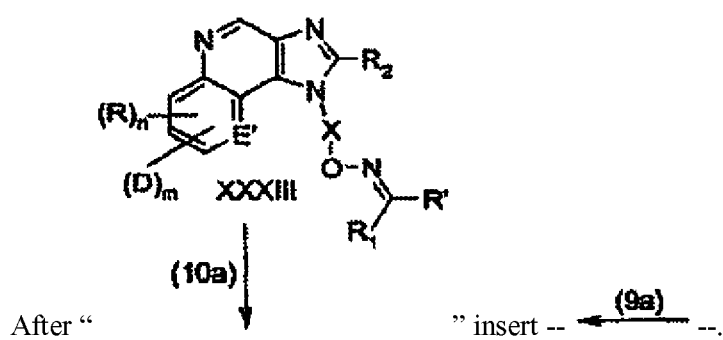 " insert -- ←(9a)── --.

Column 63
Line 53, Delete "annine" and insert -- amine --, therefor.

Column 64
Line 63, Delete "XXII," and insert -- XXXII, --, therefor.
Line 63, Delete "abenzyloxy" and insert -- a benzyloxy --, therefor.

Column 65
Line 51, Delete "—X'$_b$—Y—R$_5$," and insert -- —X'$_b$—Y—R$_4$, --, therefor.
Line 62, Delete "Slkyl)$_2$" and insert -- alkyl)$_2$ --, therefor.

Column 66
Line 62, Delete "II," and insert -- III, --, therefor.
Line 63, Delete "naphthyridinamine" and insert -- naphthyridine-4-amine --, therefor.

Column 66
Line 64, Delete "quinolin4-amine" and insert -- quinolin-4-amine --, therefor.

Column 67
Line 22, Delete "Scheme m" and insert -- Scheme III --, therefor.
Line 24, Delete "XXXd," and insert -- XXXId, --, therefor.
Line 28, Delete "Scheme DI" and insert -- Scheme III --, therefor.

Column 68
Line 6, Delete "XXXVIII," and insert -- XXVIII, --, therefor.
Line 28, Delete "Scheme In" and insert -- Scheme III --, therefor.
Line 67, Delete "defmed" and insert -- defined --, therefor.

Column 69
Line 10, Delete "amninated" and insert -- aminated --, therefor.
Line 51, Delete "hetereogeneous" and insert -- heterogeneous --, therefor.

Column 70
Line 8, Delete "hydroxylainine" and insert -- hydroxylamine --, therefor.
Line 8, Delete "XXVII." and insert -- XXXVII. --, therefor.

Column 72
Line 10, Delete "XVHI" and insert -- XVIII --, therefor.

Column 73
Line 53, Delete "descnbed" and insert -- described --, therefor.

Column 75
Line 53, Delete "picomavirus" and insert -- picornavirus --, therefor.
Line 57, Delete "papovavinus" and insert -- papovavirus --, therefor.

Column 76
Line 7, Delete "carnii" and insert -- carinii --, therefor.
Line 14, Delete "myelogeous" and insert -- myelogenous --, therefor.
Line 18, Delete "autoinmnune" and insert -- autoimmune --, therefor.
Line 21, Delete "Ommen's" and insert -- Omenn's --, therefor.
Line 30, Delete "fingal," and insert -- fungal, --, therefor.
Line 37, Delete "hemophilus" and insert -- haemophilus --, therefor.

Column 77
Line 53, Delete "stinring," and insert -- stirring, --, therefor

Column 78
Line 20, Delete "nL)," and insert -- mL), --, therefor.
Line 32, Delete "andp-toluenesulfonyl" and insert -- and p-toluenesulfonyl --, therefor.

Column 78
Line 35, Delete "1,3(2H1)" and insert -- 1,3(2H) --, therefor.
Line 61, Delete "quinolin4-amine" and insert -- quinolin-4-amine --, therefor.

Column 79
Line 12, Delete "n/z" and insert -- m/z --, therefor.
Line 46, Delete "quinolin-$^4$-amine" and insert -- quinolin-4-amine --, therefor.

Column 80
Line 25, Delete "quinolihn-4-amine" and insert -- quinolin-4-amine --, therefor.

Column 81
Line 3, Delete "nmuol)" and insert -- mmol) --, therefor.
Line 23-24, Delete "tetrahydroiiran" and insert -- tetrahydrofuran --, therefor.
Line 55, Delete "andp-toluenesulfonyl" and insert -- and p-toluenesulfonyl --, therefor.

Column 82
Line 9, Delete "firther" and insert -- further --, therefor.
Line 46, Delete "oximne" and insert -- oxime --, therefor.

Column 83
Line 11, Delete "naL)." and insert -- mL). --, therefor.
Line 20, Delete "(aniunooxy)" and insert -- (aminooxy) --, therefor.
Line 43, Delete "oxine" and insert -- oxime --, therefor.

Column 84
Line 56, Delete "irnidazo[4,5-5 c]" and insert -- imidazo[4,5-c] --, therefor.
Line 59, Delete "oxirne" and insert -- oxime --, therefor.

Column 85
Line 1, Delete "caled" and insert -- calcd --, therefor.
Line 32, Delete "oxine," and insert -- oxime, --, therefor.

Column 86
Line 35, Delete "mL/min:" and insert -- mL/min; --, therefor.
Line 36-37, Delete "trirluoroacetic" and insert -- trifluoroacetic --, therefor.

Column 116
Line 33, Delete "centrifuigation." and insert -- centrifugation. --, therefor.

Column 131
Line 43, Delete "ML," and insert -- mL, --, therefor.
Line 52, Delete "[1 ,5]" and insert -- [1,5] --, therefor.
Line 53, Delete "numol)," and insert -- mmol), --, therefor.
Line 62, Delete "aminopropyl" and insert -- amino]propyl --, therefor.

Column 131
Line 66-67, Delete "naphthyridinyl]aminopropyl" and insert -- naphthyridin-4-yl)amino]propyl --, therefor.

Column 132
Line 44, Delete "rumol)" and insert -- mmol) --, therefor.
Line 46, Delete "warrn" and insert -- warm --, therefor.
Line 52, Delete "from.Part" and insert -- from Part --, therefor.
Line 59, Delete "dichioromethane" and insert -- dichloromethane --, therefor.
Line 65, Delete "inmol)" and insert -- mmol) --, therefor.

Column 133
Line 23, Delete "ofp-toluenesulfonyl" and insert -- of p-toluenesulfonyl --, therefor.

Column 134
Line 6, Delete "[4,5-c] [1,5]naphthyridin4-amine" and insert
-- [4,5-c][1,5]naphthyridine-4-amine --, therefor.
Line 9, Delete "l-[3-" and insert -- 1-[3- --, therefor.
Line 25, Delete "(example" and insert -- (Example --, therefor.
Line 25, Delete "(example" and insert -- (Example --, therefor.

Column 138
Line 57, Delete "mrnmol)" and insert -- mmol) --, therefor.

Column 139
Line 30, Delete "warrn" and insert -- warm --, therefor.
Line 41, Delete "imnol)" and insert -- mmol) --, therefor.
Line 51, Delete "[1 ,5]" and insert -- [1,5] --, therefor.

Column 140
Line 4, Delete "[1 ,5]" and insert -- [1,5] --, therefor.
Line 47, Delete "[1 ,5]" and insert -- [1,5] --, therefor.
Line 59, Delete "[2-2-propyl" and insert -- [2-(2-propyl --, therefor.
Line 59, Delete "[4,5-c] [1,5]" and insert -- [4,5-c][1,5] --, therefor.
Line 65, Delete "I-{2-[2" and insert -- 1-{2-[2 --, therefor.
Line 67, Delete "naphthyridin4amine." and insert -- naphthyridin-4-amine. --, therefor.

Column 141
Line 6, Delete "[4,5-c] [1,5]" and insert -- [4,5-c][1,5] --, therefor.
Line 7, Delete "oxirne." and insert -- oxime. --, therefor.
Line 11, Delete "[4,5-c] [1,5]" and insert -- [4,5-c][1,5] --, therefor.
Line 13, Delete "(APC)" and insert -- (APCI) --, therefor.
Line 66-67, Delete "[4,5-c] [1,5]" and insert -- [4,5-c][1,5] --, therefor.

Column 142
Line 3, Delete "naphthyridinamine." and insert -- naphthyridin-4-amine. --, therefor.
Line 8, Delete "[4,5-c] [1,5]" and insert -- [4,5-c][1,5] --, therefor.
Line 9, Delete "nunol)" and insert -- mmol) --, therefor.
Line 22, Delete "[4,5-c] [1,5]" and insert -- [4,5-c][1,5] --, therefor.
Line 23, Delete "oximne" and insert -- oxime --, therefor.
Line 60-61, Delete "acetylpiperidin4-one" and insert -- acetylpiperidin-4-one --, therefor.

Column 143
Line 25, Delete "4arnine" and insert -- 4-amine --, therefor.
Line 27, Delete "N-methylffpiperidone" and insert -- N-methyl-4-piperidone --, therefor.
Line 45, Delete "[1 ,5]" and insert -- [1,5] --, therefor.

Column 143
Line 47-61,

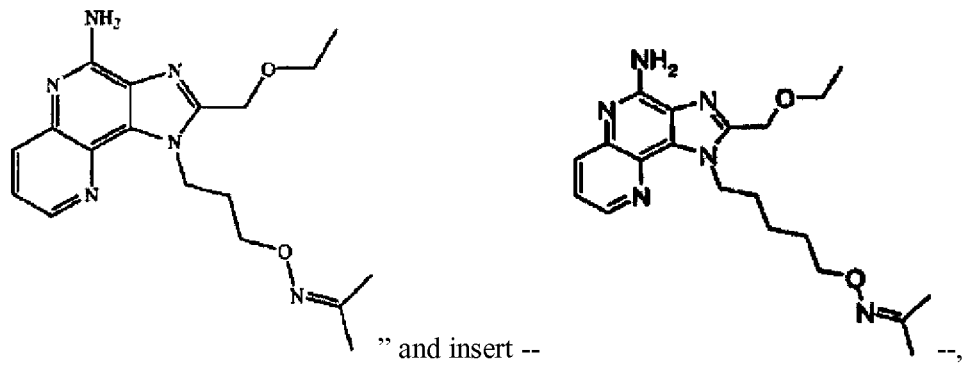

Delete "                    " and insert --                    --, therefor.

Column 144
Line 7, Delete "ML," and insert -- mL, --, therefor.
Line 37, Delete "[1 ,5]" and insert -- [1,5] --, therefor.
Line 42, Delete "5-c][1 ,5]" and insert -- 5-c][1,5] --, therefor.

Column 145
Line 8-9, Delete "imnidazo" and insert -- imidazo --, therefor.

Column 146
Line 7, Delete "FractiomLynx" and insert -- FractionLynx --, therefor.

Column 155
Line 46, Delete "aniino" and insert -- amino --, therefor.

Column 156
Line 44, Delete "triethylatnine" and insert -- triethylamine --, therefor.
Line 45, Delete "nmuol)" and insert -- mmol) --, therefor.
Line 59, Delete "nmnol)," and insert -- mmol), --, therefor.
Line 60, Delete "inmol)" and insert -- mmol) --, therefor.

Column 157
Line 9, Delete "amnino]" and insert -- amino] --, therefor.
Line 12, Delete "5,6dirnethyltetraazolo" and insert -- 5,6-dimethyltetraazolo --, therefor.
Line 19, Delete "dinethyl" and insert -- dimethyl --, therefor.

Column 158
Line 8, Delete "fiom" and insert -- from --, therefor.
Line 9, Delete "(4amino" and insert -- (4-amino --, therefor.
Line 41, Delete "irnidazo" and insert -- imidazo --, therefor.
Line 43, Delete "3(2B)" and insert -- 3(2H) --, therefor.
Line 63, Delete "6,7Aimethyl" and insert -- 6,7-dimethyl --, therefor.

Column 159
Line 28, Delete "(4amino" and insert -- (4-amino --, therefor.
Line 54, Delete "[1 ,5-a]" and insert -- [1,5-a] --, therefor.

Column 160
Line 6-7, Delete "6,7diethyl" and insert -- 6,7-dimethyl --, therefor.
Line 26, Delete "direthyl" and insert -- dimethyl --, therefor.
Line 28, Delete "nrnol)" and insert -- mmol) --, therefor.
Line 38, Delete "dichoromethane" and insert -- dichloromethane --, therefor.
Line 48, Delete "(14 il)" and insert -- (14 mL) --, therefor.

Column 161
Line 3, Delete "mmmol)" and insert -- mmol) --, therefor.
Line 16, Delete "(2>20" and insert -- (2×20 --, therefor.
Line 18-19, Delete "(ethoxyrnethyl)" and insert -- (ethoxymethyl) --, therefor.
Line 23, Delete "dirnethyl" and insert -- dimethyl --, therefor.
Line 23, Delete "iridazo" and insert -- imidazo --, therefor.
Line 27, Delete "-ione." and insert -- -dione. --, therefor.
Line 30, Delete "inidazo" and insert -- imidazo --, therefor.
Line 34, Delete "(190 llL," and insert -- (190 µL, --, therefor.
Line 35, Delete "(eth6xymethyl)" and insert -- (ethoxymethyl) --, therefor.
Line 36, Delete "[1 ,5-a]" and insert -- [1,5-a] --, therefor.

Column 162
Line 44, Delete "Butryaldehyde" and insert -- Butyraldehyde --, therefor.

Column 163
Line 25-26, Delete "carboxayaldehyde" and insert -- carboxyaldehyde --, therefor.

Column 167
Line 37, Delete "4chloro" and insert -- 4-chloro --, therefor.

Column 167
Line 38, Delete "nimol)," and insert -- mmol), --, therefor.
Line 60-61, Delete "aminoquinolinyl)" and insert -- aminoquinolin-4-yl) --, therefor.
Line 63, Delete "aminoquinolin4-yl)" and insert -- aminoquinolin-4-yl) --, therefor.

Column 168
Line 3, Delete "minol)" and insert -- mmol) --, therefor.
Line 11, Delete "fimnel" and insert -- funnel --, therefor.
Line 25, Delete "(2B)" and insert -- (2H) --, therefor.
Line 55, Delete "fimnel" and insert -- funnel --, therefor.
Line 67, Delete "quinolin4farmnie" and insert -- quinolin-4-amine --, therefor.

Column 170
Line 13, Delete "dioxane4,6-dione" and insert -- dioxane-4,6-dione --, therefor.
Line 20-21, Delete "[(3-bromophenyliuino)" and insert -- [(3-bromophenylimino --, therefor.
Line 21, Delete "dinethyl" and insert -- dimethyl --, therefor.
Line 45, Delete "nmmol)" and insert -- mmol) --, therefor.
Line 57, Delete "7-bromochloro" and insert -- 7-bromo-4-chloro --, therefor.
Line 58-59, Delete "triethylanine" and insert -- triethylamine --, therefor.

Column 171
Line 7, Delete "ariino]" and insert -- amino] --, therefor.
Line 31, Delete "(4>150" and insert -- (4×150 --, therefor.

Column 173
Line 7, Delete "[1 ,5]" and insert -- [1,5] --, therefor.
Line 28, Delete "2,2dimethyl" and insert -- 2,2-dimethyl --, therefor.
Line 44, Delete "5-{ [(5-" and insert -- 5-{[(5- --, therefor.

Column 174
Line 18, Delete "[l,5]" and insert -- [1,5] --, therefor.
Line 31, Delete "[l,5]" and insert -- [1,5] --, therefor.
Line 39, Delete "[l,5]" and insert -- [1,5] --, therefor.
Line 41, Delete "naphthyridin4-yl)" and insert -- naphthyridin-4-yl) --, therefor.
Line 46, Delete "nimol)" and insert -- mmol) --, therefor.
Line 67, Delete "Aione" and insert -- -dione --, therefor.

Column 175
Line 4, Delete "[1 ,5]" and insert -- [1,5] --, therefor.
Line 5, Delete "inmol)" and insert -- mmol) --, therefor.
Line 8-9, Delete "anmmonium" and insert -- ammonium --, therefor.
Line 18, Delete "nmL)" and insert -- mL) --, therefor.
Line 26, Delete "ofp-toluenesulfonyl" and insert -- of p-toluenesulfonyl --, therefor.
Line 41, Delete "(N+H)$^{+}$:" and insert -- (M+H)$^{+}$: --, therefor.

Column 176
Line 2, Delete "nmmol)," and insert -- mmol), --, therefor.
Line 3, Delete "rmmol)," and insert -- mmol), --, therefor.
Line 18, Delete "Mz," and insert -- MHz, --, therefor.
Line 29, Delete "oximne" and insert -- oxime --, therefor.
Line 60, Delete "1,4-ioxane" and insert -- 1,4-dioxane --, therefor.

Column 177
Line 2, Delete "aniino" and insert -- amino --, therefor.
Line 21, Delete "2-[4-(4amino" and insert -- 2-[4-(4-amino --, therefor.
Line 32, Delete "sting" and insert -- stirring --, therefor.
Line 39, Delete "quinolin4-amine" and insert -- quinolin-4-amine --, therefor.
Line 59, Delete "(ni," and insert -- (m, --, therefor.

Column 179
Line 7, Delete "oxinme" and insert -- oxime --, therefor.
Line 45, Delete "aniino]" and insert -- amino] --, therefor.
Line 48, Delete "nitroquinolin4-yl)ammo]" and insert -- nitroquinolin-4-yl)amino] --, therefor.

Column 180
Line 20, Delete "imlidazo" and insert -- imidazo --, therefor.
Line 44, Delete "(2H1)" and insert -- (2H) --, therefor.
Line 61, Delete "irnol)" and insert -- mmol) --, therefor.

Column 181
Line 17, Delete "CM+H)$^+$;" and insert -- (M+H)$^+$; --, therefor.

Column 184
Line 62, Delete "methy" and insert -- methyl --, therefor.

Column 225
Line 47, Delete "ethoxyrnethyl" and insert -- ethoxymethyl --, therefor.

Column 237
Line 27, Delete "hImunoassay" and insert -- Immunoassay --, therefor.

In the Claims
Column 239
Line 34-44,
In Claim 9, delete " 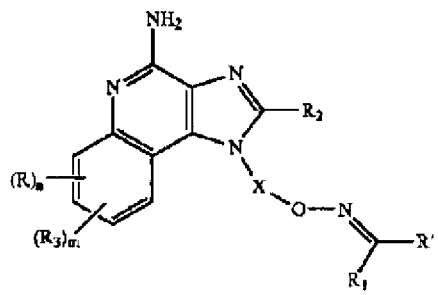 " and
insert -- 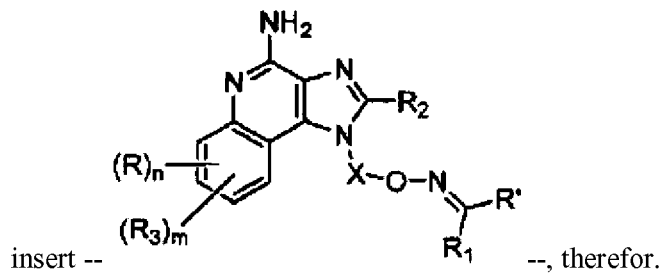 --, therefor.
Column 240
Line 66, In Claim 12, delete "heteroayl," and insert -- heteroaryl, --, therefor.
Column 241
Line 21-31,
In Claim 17, delete " 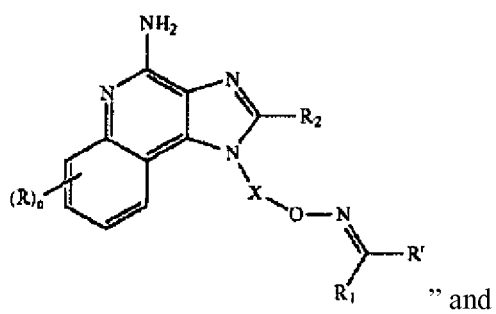 " and
insert -- 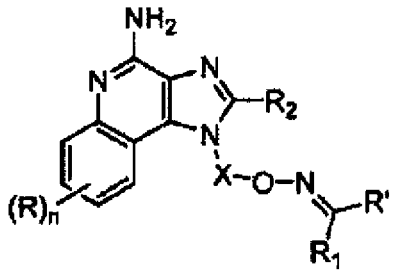 --, therefor.